United States Patent [19]

Huse

[11] Patent Number: 5,770,434
[45] Date of Patent: Jun. 23, 1998

[54] SOLUBLE PEPTIDES HAVING CONSTRAINED, SECONDARY CONFORMATION IN SOLUTION AND METHOD OF MAKING SAME

[75] Inventor: William D. Huse, Del Mar, Calif.

[73] Assignee: IXSYS Incorporated, San Diego, Calif.

[21] Appl. No.: 440,787

[22] Filed: May 15, 1995

Related U.S. Application Data

[63] Continuation of Ser. No. 978,893, Nov. 10, 1992, abandoned, which is a continuation-in-part of Ser. No. 767,436, Sep. 27, 1991, abandoned, which is a continuation-in-part of Ser. No. 590,664, Sep. 28, 1990, abandoned.

[51] Int. Cl.$^6$ .............................. C12N 1/21; C12N 15/63; C12N 15/70
[52] U.S. Cl. ................................. 435/252.33; 435/172.3; 435/320.1
[58] Field of Search .................................. 435/69.1, 69.7, 435/69.8, 172.3, 235.1, 320.1, 22, 31, 73, 5, 6, 252.33; 530/300; 536/22.1, 23.1, 23.4, 23.72, 25.3

[56] References Cited

U.S. PATENT DOCUMENTS

| | | | |
|---|---|---|---|
| 4,458,066 | 7/1984 | Caruthers et al. | 536/25.34 |
| 4,771,000 | 9/1988 | Verrips et al. | 435/69.1 |
| 5,185,147 | 2/1993 | Papsidero | 424/188.1 |
| 5,223,409 | 6/1993 | Ladner et al. | 435/69.7 |
| 5,270,163 | 12/1993 | Gold et al. | 435/6 |
| 5,403,484 | 4/1995 | Ladner et al. | 435/235.1 |
| 5,427,908 | 6/1995 | Dower et al. | 435/5 |
| 5,432,018 | 7/1995 | Dower et al. | 435/5 |

FOREIGN PATENT DOCUMENTS 383620  6/1990  European Pat. Off. .

OTHER PUBLICATIONS

Fieser (1987) PNAS, USA 84, 8568–8572.
Schulze–Gahmen (1985). EMBO 4(7), 1731–1737.
McCormick et al (1987) J. Immunol. 139(8), 2615–2619.
Jemmerson, Ronald and Hutchinson, Robert M. "Fiine Manipulation of Antibody Affinity for Synthetic Epitopes by Altering Peptide Structure: Antibody Binding to Looped Peptides." Eur. J. Immunol. 20:579–585 (1990).
Zuckermann, Ronald N. et al. "Identification of Highest–Affinity Ligands by Affinity Selection From Equimolar Peptide Mixtures Generated by Robotic Synthesis." Proc. Natl. Acad. Sci. USA. 89:4505–4509 (1992).
Jaynes et al., "Construction and Expression of Synthetic DNA Fragments Coding for Polypeptides with Elevated Levels of Essential Amino Acids". Appl. Microbiol. Biotechnol. 21:200–205 (1985).

Oliphant et al., "Cloning of Random–Sequence Oligodeoxynucleotides". Gene 44:177–183 (1986).
Winnaker, Ernst–Ludwig, "From Genes to Clones: Introduction to Gene Technology", Translated by Horst Ibelhaufts. Weinheim, New York, VCH, 1987.
Marvin and Wachtel, "Structure and Assembly of Filamentous Bacterial Viruses". Nature 253:19–23 (1975).
Smith, G., "Filamentous Fusion Phage: Novel Expression Vectors that Display Cloned Antigens on the Virion Surface". Science 228:1315–1317 (1985).
Parmley and Smith, "Antibody–selectable Filamentous FD Phage Vectors: Affinity Purfication of Target Genes". Gene 73:305–318 (1988).
Scott and Smith, "Searching for Peptide Ligands with an Epitope Library". Science 249:386–390 (1990).
Devlin et al., "Random Peptide Libraries: a Source of Specific Protein Binding Molecules". Science 249:404–406 (1990).
Cwirla et al., "Peptides on Phage: a Vast Library of Peptides for Identifying Ligands". Proc. Natl. Acad. Sci. USA 87:6378–6382 (1990).
Olivera, Baldomero et al., "Conotoxins." J. Biol. Chem. 266:22067–22070 (1991).
Gallusser, Andreas and Kuhn, Andreas, Initial Steps in Protein membrane Insertion. Bacterophage M13 Procoat Protein Binds to the Membrane Surface by Electrostatic Interaction. EMBO J. 9:2723–2729.
Akiyama,Yoshinori and Ito, Koreaki The SecY Membrane Component of the Bacterial Protein Export Machinery: Analysis by New Electrophoretic Methods for Integral Membrane Proteins. EMBO J. 4:3351–3356 (1985).
Lill, Roland et al., "The Trigger Factor Cycle Includes Ribosomes, Prescretory Proteins, and the Plasma Membrane." Cell 54:1013–1018 (1988).
Wolfe, Paul B. et al., "Effects of Two *sec Genes* on Protein Assembly into the Plasma Membrane of *Escherichia coli*." 260:1836–1841 (1985).
Kuhn, Andreas "alterations in the Extracellular Domain of M13 Procoat Protein Make its Membrane Insertion Dependent on secA and SecY." Eur. J. Biochem. 177:267–271 (1988).

*Primary Examiner*—Nancy Degen
*Assistant Examiner*—Robert Schwartzman
*Attorney, Agent, or Firm*—Campbell & Flores LLP

[57] ABSTRACT

A method of synthesizing isolated, soluble peptides having constrained secondary structure in solution is described herein. The peptides are encoded by expressible oligonucleotides having a desirable bias of random codon sequences.

37 Claims, 28 Drawing Sheets

```
         |   10       |   20       |   30       |   40       |   50       |   60
   1 AATGCTACTA CTATTAGTAG AATTGATGCC ACCTTTTCAG CTCGCGCCCC AAATGAAAAT 60
  61 ATAGCTAAAC AGGTTATTGA CCATTTGCGA ATGTATCTA  ATGGTCAAAC TAAATCTACT 120
 121 CGTTCGCAGA ATTGGGAATC AACTGTTACA TGGAATGAAA CTTCCAGACA CCGTACTTTA 180
 181 GTTGCATATT TAAAACATGT TGAGCTACAG CACCAGATTC AGCAATTAAG CTCTAAGCCA 240
 241 TCTGCAAAAA TGACCTCTTA TCAAAAGGAG CAATTAAAGG TACTCTCTAA TCCTGACCTG 300
 301 TTGGAGTTTG CTTCCGGTCT GGTTCGCTTT GAAGCTCGAA TTAAAACGCG ATATTTGAAG 360
 361 TCTTTCGGGC TTCCTCTTAA TCTTTTTGAT GCAATCCGCT TTGCTTCTGA CTATAATAGT 420
 421 CAGGGTAAAG ACCTGATTTT TGATTTATGG TCATTCTCGT TTTCTGAACT GTTTAAAGCA 480
 481 TTTGAGGGGG ATTCAATGAA TATTTATGAC GATTCCGCAG TATTGGACGC TATCCAGTCT 540
 541 AAACATTTTA CTATTACCCC CTCTGGCAAA ACTTCTTTTG CAAAAGCCTC TCGCTATTTT 600
 601 GGTTTTTATC GTCGTCTGGT AAACGAGGGT TATGATAGTG TTGCTCTTAC TATGCCTCGT 660
 661 AATTCCTTTT GGCGTTATGT ATCTGCATTA GTTGAATGTG GTATTCCTAA ATCTCAACTG 720
 721 ATGAATCTTT CTACCTGTAA TAATGTTGTT CCGTTAGTTC GTTTTATTAA CGTAGATTTT 780
 781 TCTTCCCAAC GTCCTGACTG GTATAATGAG CCAGTTCTTA AAATCGCATA AGGTAATTCA 840
 841 CAATGATTAA AGTTGAAATT AAACCATCTC AAGCCCAATT TACTACTCGT TCTGGTGTTT 900
 901 CTCGTCAGGG CAAGCCTTAT TCACTGAATG AGCAGCTTTG TTACGTTGAT TTGGGTAATG 960
 961 AATATCCGGT TCTTGTCAAG ATTACTCTTG ATGAAGGTCA GCCAGCCTAT GCGCCTGGTC 1020
1021 TGTACACCGT TCATCTGTCC TCTTTCAAAG TTGGTCAGTT CGGTTCCCTT ATGATTGACC 1080
1081 GTCTGCGCCT CGTTCCGGCT AAGTAACATG GAGCAGGTCG CGGATTTCGA CACAATTTAT 1140
1141 CAGGCGATGA TACAAATCTC CGTTGTACTT TGTTTCGCGC TTGGTATAAT CGCTGGGGGT 1200
1201 CAAAGATGAG TGTTTTAGTG TATTCTTTCG CCTCTTTCGT TTTAGGTTGG TGCCTTCGTA 1260
1261 GTGGCATTAC GTATTTTACC CGTTTAATGG AAACTTCCTC ATGAAAAAGT CTTTAGTCCT 1320
1321 CAAAGCCTCT GTAGCCGTTG CTACCCTCGT TCCGATGCTG TCTTTCGCTG CTGAGGGTGA 1380
1381 CGATCCCGCA AAAGCGGCCT TTAACTCCCT GCAAGCCTCA GCGACCGAAT ATATCGGTTA 1440
1441 TGCGTGGGCG ATGGTTGTTG TCATTGTCGG CGCAACTATC GGTATCAAGC TGTTTAAGAA 1500
1501 ATTCACCTCG AAAGCAAGCT GATAAACCGA TACAATTAAA GGCTCCTTTT GGAGCCTTTT 1560
1561 TTTTTGGAGA TTTTCAACGT GAAAAAATTA TTATTCGCAA TTCCTTTAGT TGTTCCTTTC 1620
1621 TATTCTCACT CCGCTGAAAC TGTTGAAAGT TGTTTAGCAA AACCCCATAC AGAAAATTCA 1680
1681 TTTACTAACG TCTGGAAAGA CGACAAAACT TTAGATCGTT ACGCTAACTA TGAGGGTTGT 1740
```

FIG. 5A

```
1741 CTGTGGAATG CTACAGGCGT TGTAGTTTGT ACTGGTGACG AAACTCAGTG TTACGGTACA 1800
1801 TGGGTTCCTA TTGGGCTTGC TATCCCTGAA AATGAGGGTG GTGGCTCTGA GGGTGGCGGT 1860
1861 TCTGAGGGTG GCGGTTCTGA GGGTGGCGGT ACTAAACCTC CTGAGTACGG TGATACACCT 1920
1921 ATTCCGGGCT ATACTTATAT CAACCCTCTC GACGGCACTT ATCCGCCTGG TACTGAGCAA 1980
1981 AACCCCGCTA ATCCTAATCC TTCTCTTGAG GAGTCTCAGC CTCTTAATAC TTTCATGTTT 2040
2041 CAGAATAATA GGTTCCGAAA TAGGCAGGGG GCATTAACTG TTTATACGGG CACTGTTACT 2100
2101 CAAGGCACTG ACCCCGTTAA AACTTATTAC CAGTACACTC CTGTATCATC AAAAGCCATG 2160
2161 TATGACGCTT ACTGGAACGG TAAATTCAGA GACTGCGCTT TCCATTCTGG CTTTAATGAA 2220
2221 GATCCATTCG TTTGTGAATA TCAAGGCCAA TCGTCTGACC TGCCTCAACC TCCTGTCAAT 2280
2281 GCTGGCGGCG GCTCTGGTGG TGGTTCTGGT GGCGGCTCTG AGGGTGGTGG CTCTGAGGGT 2340
2341 GGCGGTTCTG AGGGTGGCGG CTCTGAGGGA GGCGGTTCCG GTGGTGGCTC TGGTTCCGGT 2400
2401 GATTTTGATT ATGAAAAGAT GGCAAACGCT AATAAGGGGG CTATGACCGA AAATGCCGAT 2460
2461 GAAAACGCGC TACAGTCTGA CGCTAAAGGC AAACTTGATT CTGTCGCTAC TGATTACGGT 2520
2521 GCTGCTATCG ATGGTTTCAT TGGTGACGTT TCCGGCCTTG CTAATGGTAA TGGTGCTACT 2580
2581 GGTGATTTTG CTGGCTCTAA TTCCCAAATG GCTCAAGTCG GTGACGGTGA TAATTCACCT 2640
2641 TTAATGAATA ATTTCCGTCA ATATTTACCT TCCCTCCCTC AATCGGTTGA ATGTCGCCCT 2700
2701 TTTGTCTTTA GCGCTGGTAA ACCATATGAA TTTTCTATTG ATTGTGACAA AATAAACTTA 2760
2761 TTCCGTGGTG TCTTTGCGTT TCTTTTATAT GTTGCCACCT TTATGTATGT ATTTTCTACG 2820
2821 TTTGCTAACA TACTGCGTAA TAAGGAGTCT TAATCATGCC AGTTCTTTTG GGTATTCCGT 2880
2881 TATTATTGCG TTTCCTCGGT TTCCTTCTGG TAACTTTGTT CGGCTATCTG CTTACTTTTC 2940
2941 TTAAAAAGGG CTTCGGTAAG ATAGCTATTG CTATTTCATT GTTTCTTGCT CTTATTATTG 3000
3001 GGCTTAACTC AATTCTTGTG GGTTATCTCT CTGATATTAG CGCTCAATTA CCCTCTGACT 3060
3061 TTGTTCAGGG TGTTCAGTTA ATTCTCCCGT CTAATGCGCT TCCCTGTTTT TATGTTATTC 3120
3121 TCTCTGTAAA GGCTGCTATT TTCATTTTTG ACGTTAAACA AAAAATCGTT TCTTATTTGG 3180
3181 ATTGGGATAA ATAATATGGC TGTTTATTTT GTAACTGGCA AATTAGGCTC TGGAAAGACG 3240
3241 CTCGTTAGCG TTGGTAAGAT TCAGGATAAA ATTGTAGCTG GGTGCAAAAT AGCAACTAAT 3300
3301 CTTGATTTAA GGCTTCAAAA CCTCCCGCAA GTCGGGAGGT TCGCTAAAAC GCCTCGCGTT 3360
3361 CTTAGAATAC CGGATAAGCC TTCTATATCT GATTTGCTTG CTATTGGGCG CGGTAATGAT 3420
3421 TCCTACGATG AAAATAAAAA CGGCTTGCTT GTTCTCGATG AGTGCGGTAC TTGGTTTAAT 3480
3481 ACCCGTTCTT GGAATGATAA GGAAAGACAG CCGATTATTG ATTGGTTTCT ACATGCTCGT 3540
3541 AAATTAGGAT GGGATATTAT CTTCCTTGTT CAGGACTTAT CTATTGTTGA TAAACAGGCG 3600
3601 CGTTCTGCAT TAGCTGAACA TGTTGTTTAT TGTCGTCGTC TGGACAGAAT TACTTTACCT 3660
```

FIG. 5B

```
3661 TTTGTCGGTA CTTTATATTC TCTTATTACT GGCTCGAAAA TGCCTCTGCC TAAATTACAT 3720
3721 GTTGGCGTTG TTAAATATGG CGATTCTCAA TTAAGCCCTA CTGTTGAGCG TTGGCTTTAT 3780
3781 ACTGGTAAGA ATTTGTATAA CGCATATGAT ACTAAACAGG CTTTTTCTAG TAATTATGAT 3840
3841 TCCGGTGTTT ATTCTTATTT AACGCCTTAT TTATCACACG GTCGGTATTT CAAACCATTA 3900
3901 AATTTAGGTC AGAAGATGAA GCTTACTAAA ATATATTTGA AAAGTTTTC ACGCGTTCTT 3960
3961 TGTCTTGCGA TTGGATTTGC ATCAGCATTT ACATATAGTT ATATAACCCA ACCTAAGCCG 4020
4021 GAGGTTAAAA AGGTAGTCTC TCAGACCTAT GATTTTGATA AATTCACTAT TGACTCTTCT 4080
4081 CAGCGTCTTA ATCTAAGCTA TCGCTATGTT TTCAAGGATT CTAAGGGAAA ATTAATTAAT 4140
4141 AGCGACGATT TACAGAAGCA AGGTTATTCA CTCACATATA TTGATTTATG TACTGTTTCC 4200
4201 ATTAAAAAGG TAATTCAAAT GAAATTGTTA AATGTAATTA ATTTTGTTTT CTTGATGTTT 4260
4261 GTTTCATCAT CTTCTTTTGC TCAGGTAATT GAAATGAATA ATTCGCCTCT GCGCGATTTT 4320
4321 GTAACTTGGT ATTCAAAGCA ATCAGGCGAA TCCGTTATTG TTTCTCCCGA TGTAAAAGGT 4380
4381 ACTGTTACTG TATATTCATC TGACGTTAAA CCTGAAAATC TACGCAATTT CTTTATTTCT 4440
4441 GTTTTACGTG CTAATAATTT TGATATGGTT GGTTCAATTC CTTCCATTAT TTAGAAGTAT 4500
4501 AATCCAAACA ATCAGGATTA TATTGATGAA TTGCCATCAT CTGATAATCA GGAATATGAT 4560
4561 GATAATTCCG CTCCTTCTGG TGGTTTCTTT GTTCCGCAAA ATGATAATGT TACTCAAACT 4620
4621 TTTAAAATTA ATAACGTTCG GGCAAAGGAT TTAATACGAG TTGTCGAATT GTTTGTAAAG 4680
4601 TCTAATACTT CTAAATCCTC AAATGTATTA TCTATTGACG GCTCTAATCT ATTAGTTGTT 4740
4741 AGTGCACCTA AAGATATTTT AGATAACCTT CCTCAATTCC TTTCTACTGT TGATTTGCCA 4800
4801 ACTGACCAGA TATTGATTGA GGGTTTGATA TTTGAGGTTC AGCAAGGTGA TGCTTTAGAT 4860
4861 TTTTCATTTG CTGCTGGCTC TCAGCGTGGC ACTGTTGCAG GCGGTGTTAA TACTGACCGC 4920
4921 CTCACCTCTG TTTTATCTTC TGCTGGTGGT TCGTTCGGTA TTTTTAATGG CGATGTTTTA 4980
4981 GGGCTATCAG TTCGCGCATT AAAGACTAAT AGCCATTCAA AAATATTGTC TGTGCCACGT 5040
5041 ATTCTTACGC TTTCAGGTCA GAAGGGTTCT ATCTCTGTTG GCCAGAATGT CCCTTTTATT 5100
5101 ACTGGTCGTG TGACTGGTGA ATCTGCCAAT GTAAATAATC CATTTCAGAC GATTGAGCGT 5160
5161 CAAAATGTAG GTATTTCCAT GAGCGTTTTT CCTGTTGCAA TGGCTGGCGG TAATATTGTT 5220
5221 CTGGATATTA CCAGCAAGGC CGATAGTTTG AGTTCTTCTA CTCAGGCAAG TGATGTTATT 5280
5281 ACTAATCAAA GAAGTATTGC TACAACGGTT AATTTGCGTG ATGGACAGAC TCTTTTACTC 5340
5341 GGTGGCCTCA CTGATTATAA AAACACTTCT CAAGATTCTG GCGTACCGTT CCTGTCTAAA 5400
5401 ATCCCTTTAA TCGGCCTCCT GTTTAGCTCC CGCTCTGATT CCAACGAGGA AAGCACGTTA 5460
5461 TACGTGCTCG TCAAAGCAAC CATAGTACGC GCCCTGTAGC GGCGCATTAA GCGCGGCGGG 5520
5521 TGTGGTGGTT ACGCGCAGCG TGACCGCTAC ACTTGCCAGC GCCCTAGCGC CCGCTCCTTT 5580
```

FIG. 5C

```
5581 CGCTTTCTTC CCTTCCTTTC TCGCCACGTT CGCCGGCTTT CCCCGTCAAG CTCTAAATCG 5640
5641 GGGGCTCCCT TTAGGGTTCC GATTTAGTGC TTTACGGCAC CTCGACCCCA AAAAACTTGA 5700
5701 TTTGGGTGAT GGTTCACGTA GTGGGCCATC GCCCTGATAG ACGGTTTTTC GCCCTTTGAC 5760
5761 GTTGGAGTCC ACGTTCTTTA ATAGTGGACT CTTGTTCCAA ACTGGAACAA CACTCAACCC 5820
5821 TATCTCGGGC TATTCTTTTG ATTTATAAGG GATTTTGCCG ATTTCGGAAC CACCATCAAA 5880
5881 CAGGATTTTC GCCTGCTGGG GCAAACCAGC GTGGACCGCT TGCTGCAACT CTCTCAGGGC 5940
5941 CAGGCGGTGA AGGGCAATCA GCTGTTGCCC GTCTCGCTGG TGAAAAGAAA AACCACCCTG 6000
6001 GCGCCCAATA CGCAAACCGC CTCTCCCCGC GCGTTGGCCG ATTCATTAAT GCAGCTGGCA 6060
6061 CGACAGGTTT CCCGACTGGA AAGCGGGCAG TGAGCGCAAC GCAATTAATG TGAGTTAGCT 6120
6121 CACTCATTAG GCACCCCAGG CTTTACACTT TATGCTTCCG GCTCGTATGT TGTGTGGAAT 6180
6181 TGTGAGCGGA TAACAATTTC ACACAGGAAA CAGCTATGAC CAGGATGTAC GAATTCGCAG 6240
6241 GTAGGAGAGC TCGGCGGATC CTAGGCTGAA GGCGATGACC CTGCTAAGGC TGCATTCAAT 6300
6301 AGTTTACAGG CAAGTGCTAC TGAGTACATT GGCTACGCTT GGGCTATGGT AGTAGTTATA 6360
6361 GTTGGTGCTA CCATAGGGAT TAAATTATTC AAAAAGTTTA CGAGCAAGGC TTCTTAACCA 6420
6421 GCTGGCGTAA TAGCGAAGAG GCCCGCACCG ATCGCCCTTC CCAACAGTTG CGCAGCCTGA 6480
6481 ATGGCGAATG GCGCTTTGCC TGGTTTCCGG CACCAGAAGC GGTGCCGGAA AGCTGGCTGG 6540
6541 AGTGCGATCT TCCTGAGGCC GATACGGTCG TCGTCCCCTC AAACTGGCAG ATGCACGGTT 6600
6601 ACGATGCGCC CATCTACACC AACGTAACCT ATCCCATTAC GGTCAATCCG CCGTTTGTTC 6660
6661 CCACGGAGAA TCCGACGGGT TGTTACTCGC TCACATTTAA TGTTGATGAA AGCTGGCTAC 6720
6721 AGGAAGGCCA GACGCGAATT ATTTTTGATG GCGTTCCTAT TGGTTAAAAA ATGAGCTGAT 6780
6781 TTAACAAAAA TTTAACGCGA ATTTTAACAA AATATTAACG TTTACAATTT AAATATTTGC 6840
6841 TTATACAATC TTCCTGTTTT TGGGGCTTTT CTGATTATCA ACCGGGGTAC ATATGATTGA 6900
6901 CATGCTAGTT TTACGATTAC CGTTCATCGA TTCTCTTGTT TGCTCCAGAC TCTCAGGCAA 6960
6961 TGACCTGATA GCCTTTGTAG ATCTCTCAAA AATAGCTACC CTCTCCGGCA TTAATTTATC 7020
7021 AGCTAGAACG GTTGAATATC ATATTGATGG TGATTTGACT GTCTCCGGCC TTTCTCACCC 7080
7081 TTTTGAATCT TTACCTACAC ATTACTCAGG CATTGCATTT AAAATATATG AGGGTTCTAA 7140
7141 AAATTTTTAT CCTTGCGTTG AAATAAAGGC TTCTCCCGCA AAGTATTAC AGGGTCATAA 7200
7201 TGTTTTTGGT ACAACCGATT TAGCTTTATG CTCTGAGGCT TTATTGCTTA ATTTTGCTAA 7260
7261 TTCTTTGCCT TGCCTGTATG ATTTATTGGA CGTT                          7294
         |    10   |    20   |    30   |   40    |    50   |    60
```

FIG. 5D

```
         |   10      |   20      |   30      |   40      |   50      |   60
   1 AATGCTACTA CTATTAGTAG AATTGATGCC ACCTTTTCAG CTCGCGCCCC AAATGAAAAT 60
  61 ATAGCTAAAC AGGTTATTGA CCATTTGCGA AATGTATCTA ATGGTCAAAC TAAATCTACT 120
 121 CGTTCGCAGA ATTGGGAATC AACTGTTACA TGGAATGAAA CTTCCAGACA CCGTACTTTA 180
 181 GTTGCATATT TAAAACATGT TGAGCTACAG CACCAGATTC AGCAATTAAG CTCTAAGCCA 240
 241 TCTGCAAAAA TGACCTCTTA TCAAAGGAG CAATTAAAGG TACTCTCTAA TCCTGACCTG 300
 301 TTGGAGTTTG CTTCCGGTCT GGTTCGCTTT GAAGCTCGAA TTAAAACGCG ATATTTGAAG 360
 361 TCTTTCGGGC TTCCTCTTAA TCTTTTTGAT GCAATCCGCT TTGCTTCTGA CTATAATAGT 420
 421 CAGGGTAAAG ACCTGATTTT TGATTTATGG TCATTCTCGT TTTCTGAACT GTTTAAAGCA 480
 481 TTTGAGGGGG ATTCAATGAA TATTTATGAC GATTCCGCAG TATTGGACGC TATCCAGTCT 540
 541 AAACATTTTA CTATTACCCC CTCTGGCAAA ACTTCTTTTG CAAAAGCCTC TCGCTATTTT 600
 601 GGTTTTTATC GTCGTCTGGT AAACGAGGGT TATGATAGTG TTGCTCTTAC TATGCCTCGT 660
 661 AATTCCTTTT GGCGTTATGT ATCTGCATTA GTTGAATGTG GTATTCCTAA ATCTCAACTG 720
 721 ATGAATCTTT CTACCTGTAA TAATGTTGTT CCGTTAGTTC GTTTTATTAA CGTAGATTTT 780
 781 TCTTCCCAAC GTCCTGACTG GTATAATGAG CCAGTTCTTA AAATCGCATA AGGTAATTCA 840
 841 CAATGATTAA AGTTGAAATT AAACCATCTC AAGCCCAATT TACTACTCGT TCTGGTGTTT 900
 901 CTCGTCAGGG CAAGCCTTAT TCACTGAATG AGCAGCTTTG TTACGTTGAT TTGGGTAATG 960
 961 AATATCCGGT TCTTGTCAAG ATTACTCTTG ATGAAGGTCA GCCAGCCTAT GCGCCTGGTC 1020
1021 TGTACACCGT TCATCTGTCC TCTTTCAAAG TTGGTCAGTT CGGTTCCCTT ATGATTGACC 1080
1081 GTCTGCGCCT CGTTCCGGCT AAGTAACATG GAGCAGGTCG CGGATTTCGA CACAATTTAT 1140
1141 CAGGCGATGA TACAAATCTC CGTTGTACTT TGTTTCGCGC TTGGTATAAT CGCTGGGGGT 1200
1201 CAAAGATGAG TGTTTTAGTG TATTCTTTCG CCTCTTTCGT TTTAGGTTGG TGCCTTCGTA 1260
1261 GTGGCATTAC GTATTTTACC CGTTTAATGG AAACTTCCTC ATGAAAAAGT CTTTAGTCCT 1320
1321 CAAAGCCTCT GTAGCCGTTG CTACCCTCGT TCCGATGCTG TCTTTCGCTG CTGAGGGTGA 1380
1381 CGATCCCGCA AAAGCGGCCT TTAACTCCCT GCAAGCCTCA GCGACCGAAT ATATCGGTTA 1440
1441 TGCGTGGGCG ATGGTTGTTG TCATTGTCGG CGCAACTATC GGTATCAAGC TGTTTAAGAA 1500
1501 ATTCACCTCG AAAGCAAGCT GATAAACCGA TACAATTAAA GGCTCCTTTT GGAGCCTTTT 1560
1561 TTTTTGGAGA TTTTCAACGT GAAAAAATTA TTATTCGCAA TTCCTTTAGT TGTTCCTTTC 1620
1621 TATTCTCACT CCGCTGAAAC TGTTGAAAGT TGTTTAGCAA AACCCCATAC AGAAAATTCA 1680
1681 TTTACTAACG TCTGGAAAGA CGACAAAACT TTAGATCGTT ACGCTAACTA TGAGGGTTGT 1740
1741 CTGTGGAATG CTACAGGCGT TGTAGTTTGT ACTGGTGACG AAACTCAGTG TTACGGTACA 1800
1801 TGGGTTCCTA TTGGGCTTGC TATCCCTGAA AATGAGGGTG GTGGCTCTGA GGGTGGCGGT 1860
```

FIG. 6A

1861 TCTGAGGGTG GCGGTTCTGA GGGTGGCGGT ACTAAACCTC CTGAGTACGG TGATACACCT 1920
1921 ATTCCGGGCT ATACTTATAT CAACCCTCTC GACGGCACTT ATCCGCCTGG TACTGAGCAA 1980
1981 AACCCCGCTA ATCCTAATCC TTCTCTTGAG GAGTCTCAGC CTCTTAATAC TTTCATGTTT 2040
2041 CAGAATAATA GGTTCCGAAA TAGGCAGGGG GCATTAACTG TTTATACGGG CACTGTTACT 2100
2101 CAAGGCACTG ACCCCGTTAA AACTTATTAC CAGTACACTC CTGTATCATC AAAAGCCATG 2160
2161 TATGACGCTT ACTGGAACGG TAAATTCAGA GACTGCGCTT TCCATTCTGG CTTTAATGAA 2220
2221 GATCCATTCG TTTGTGAATA TCAAGGCCAA TCGTCTGACC TGCCTCAACC TCCTGTCAAT 2280
2281 GCTGGCGGCG GCTCTGGTGG TGGTTCTGGT GGCGGCTCTG AGGGTGGTGG CTCTGAGGGT 2340
2341 GGCGGTTCTG AGGGTGGCGG CTCTGAGGGA GGCGGTTCCG GTGGTGGCTC TGGTTCCGGT 2400
2401 GATTTTGATT ATGAAAAGAT GGCAAACGCT AATAAGGGGG CTATGACCGA AAATGCCGAT 2460
2461 GAAAACGCGC TACAGTCTGA CGCTAAAGGC AAACTTGATT CTGTCGCTAC TGATTACGGT 2520
2521 GCTGCTATCG ATGGTTTCAT TGGTGACGTT TCCGGCCTTG CTAATGGTAA TGGTGCTACT 2580
2581 GGTGATTTTG CTGGCTCTAA TTCCCAAATG GCTCAAGTCG GTGACGGTGA TAATTCACCT 2640
2641 TTAATGAATA ATTTCCGTCA ATATTTACCT TCCCTCCCTC AATCGGTTGA ATGTCGCCCT 2700
2701 TTTGTCTTTA GCGCTGGTAA ACCATATGAA TTTTCTATTG ATTGTGACAA AATAAACTTA 2760
2761 TTCCGTGGTG TCTTTGCGTT TCTTTTATAT GTTGCCACCT TTATGTATGT ATTTTCTACG 2820
2821 TTTGCTAACA TACTGCGTAA TAAGGAGTCT TAATCATGCC AGTTCTTTTG GGTATTCCGT 2880
2881 TATTATTGCG TTTCCTCGGT TTCCTTCTGG TAACTTTGTT CGGCTATCTG CTTACTTTTC 2940
2941 TTAAAAAGGG CTTCGGTAAG ATAGCTATTG CTATTTCATT GTTTCTTGCT CTTATTATTG 3000
3001 GGCTTAACTC AATTCTTGTG GGTTATCTCT CTGATATTAG CGCTCAATTA CCCTCTGACT 3060
3061 TTGTTCAGGG TGTTCAGTTA ATTCTCCCGT CTAATGCGCT TCCCTGTTTT TATGTTATTC 3120
3121 TCTCTGTAAA GGCTGCTATT TTCATTTTTG ACGTTAAACA AAAAATCGTT TCTTATTTGG 3180
3181 ATTGGGATAA ATAATATGGC TGTTTATTTT GTAACTGGCA AATTAGGCTC TGGAAAGACG 3240
3241 CTCGTTAGCG TTGGTAAGAT TAGGATAAA ATTGTAGCTG GGTGCAAAAT AGCAACTAAT 3300
3301 CTTGATTTAA GGCTTCAAAA CCTCCCGCAA GTCGGGAGGT TCGCTAAAAC GCCTCGCGTT 3360
3361 CTTAGAATAC CGGATAAGCC TTCTATATCT GATTTGCTTG CTATTGGGCG CGGTAATGAT 3420
3421 TCCTACGATG AAAATAAAAA CGGCTTGCTT GTTCTCGATG AGTGCGGTAC TTGGTTTAAT 3480
3481 ACCCGTTCTT GGAATGATAA GGAAAGACAG CCGATTATTG ATTGGTTTCT ACATGCTCGT 3540
3541 AAATTAGGAT GGGATATTAT CTTCCTTGTT CAGGACTTAT CTATTGTTGA TAAACAGGCG 3600
3601 CGTTCTGCAT TAGCTGAACA TGTTGTTTAT TGTCGTCGTC TGGACAGAAT TACTTTACCT 3660
3661 TTTGTCGGTA CTTTATATTC TCTTATTACT GGCTCGAAAA TGCCTCTGCC TAAATTACAT 3720
3721 GTTGGCGTTG TTAAATATGG CGATTCTCAA TTAAGCCCTA CTGTTGAGCG TTGGCTTTAT 3780

FIG. 6B

```
3781 ACTGGTAAGA ATTTGTATAA CGCATATGAT ACTAAACAGG CTTTTTCTAG TAATTATGAT 3840
3841 TCCGGTGTTT ATTCTTATTT AACGCCTTAT TTATCACACG GTCGGTATTT CAAACCATTA 3900
3901 AATTTAGGTC AGAAGATGAA ATTAACTAAA ATATATTTGA AAAAGTTTTC TCGCGTTCTT 3960
3961 TGTCTTGCGA TTGGATTTGC ATCAGCATTT ACATATAGTT ATATAACCCA ACCTAAGCCG 4020
4021 GAGGTTAAAA AGGTAGTCTC TCAGACCTAT GATTTTGATA AATTCACTAT TGACTCTTCT 4080
4081 CAGCGTCTTA ATCTAAGCTA TCGCTATGTT TTCAAGGATT CTAAGGGAAA ATTAATTAAT 4140
4141 AGCGACGATT TACAGAAGCA AGGTTATTCA CTCACATATA TTGATTTATG TACTGTTTCC 4200
4201 ATTAAAAAAG GTAATTCAAA TGAAATTGTT AAATGTAATT AATTTTGTTT TCTTGATGTT 4260
4261 TGTTTCATCA TCTTCTTTTG CTCAGGTAAT TGAAATGAAT AATTCGCCTC TGCGCGATTT 4320
4321 TGTAACTTGG TATTCAAAGC AATCAGGCGA ATCCGTTATT GTTTCTCCCG ATGTAAAAGG 4380
4381 TACTGTTACT GTATATTCAT CTGACGTTAA ACCTGAAAAT CTACGCAATT TCTTTATTTC 4440
4441 TGTTTTACGT GCTAATAATT TTGATATGGT TGGTTCAATT CCTTCCATAA TTCAGAAGTA 4500
4501 TAATCCAAAC AATCAGGATT ATATTGATGA ATTGCCATCA TCTGATAATC AGGAATATGA 4560
4561 TGATAATTCC GCTCCTTCTG GTGGTTTCTT TGTTCCGCAA AATGATAATG TTACTCAAAC 4620
4621 TTTTAAAATT AATAACGTTC GGGCAAAGGA TTTAATACGA GTTGTCGAAT GTTTGTAAA 4680
4681 GTCTAATACT TCTAAATCCT CAAATGTATT ATCTATTGAC GGCTCTAATC TATTAGTTGT 4740
4741 TAGTGCACCT AAAGATATTT TAGATAACCT TCCTCAATTC CTTTCTACTG TTGATTTGCC 4800
4801 AACTGACCAG ATATTGATTG AGGGTTTGAT ATTGAGGTT CAGCAAGGTG ATGCTTTAGA 4860
4861 TTTTTCATTT GCTGCTGGCT CTCAGCGTGG CACTGTTGCA GGCGGTGTTA ATACTGACCG 4920
4921 CCTCACCTCT GTTTTATCTT CTGCTGGTGG TTCGTTCGGT ATTTTTAATG GCGATGTTTT 4980
4981 AGGGCTATCA GTTCGCGCAT TAAAGACTAA TAGCCATTCA AAAATATTGT CTGTGCCACG 5040
5041 TATTCTTACG CTTTCAGGTC AGAAGGGTTC TATCTCTGTT GGCCAGAATG TCCCTTTTAT 5100
5101 TACTGGTCGT GTGACTGGTG AATCTGCCAA TGTAAATAAT CCATTTCAGA CGATTGAGCG 5160
5161 TCAAAATGTA GGTATTTCCA TGAGCGTTTT TCCTGTTGCA ATGGCTGGCG GTAATATTGT 5220
5221 TCTGGATATT ACCAGCAAGG CCGATAGTTT GAGTTCTTCT ACTCAGGCAA GTGATGTTAT 5280
5281 TACTAATCAA AGAAGTATTG CTACAACGGT TAATTTGCGT GATGGACAGA CTCTTTTACT 5340
5341 CGGTGGCCTC ACTGATTATA AAAACACTTC TCAAGATTCT GGCGTACCGT TCCTGTCTAA 5400
5401 AATCCCTTTA ATCGGCCTCC TGTTTAGCTC CCGCTCTGAT TCCAACGAGG AAAGCACGTT 5460
5461 ATACGTGCTC GTCAAAGCAA CCATAGTACG CGCCCTGTAG CGGCGCATTA AGCGCGGCGG 5520
5521 GTGTGGTGGT TACGCGCAGC GTGACCGCTA CACTTGCCAG CGCCCTAGCG CCCGCTCCTT 5580
5581 TCGCTTTCTT CCCTTCCTTT CTCGCCACGT TCGCCGGCTT TCCCCGTCAA GCTCTAAATC 5640
5641 GGGGGCTCCC TTTAGGGTTC CGATTTAGTG CTTTACGGCA CCTCGACCCC AAAAAACTTG 5700
```

FIG. 6C

```
5701 ATTTGGGTGA TGGTTCACGT AGTGGGCCAT CGCCCTGATA GACGGTTTTT CGCCCTTTGA 5760
5761 CGTTGGAGTC CACGTTCTTT AATAGTGGAC TCTTGTTCCA AACTGGAACA ACACTCAACC 5820
5821 CTATCTCGGG CTATTCTTTT GATTTATAAG GGATTTTGCC GATTTCGGAA CCACCATCAA 5880
5881 ACAGGATTTT CGCCTGCTGG GGCAAACCAG CGTGGACCGC TTGCTGCAAC TCTCTCAGGG 5940
5941 CCAGGCGGTG AAGGGCAATC AGCTGTTGCC CGTCTCGCTG GTGAAAAGAA AAACCACCCT 6000
6001 GGCGCCCAAT ACGCAAACCG CCTCTCCCCG CGCGTTGGCC GATTCATTAA TGCAGCTGGC 6060
6061 ACGACAGGTT TCCCGACTGG AAAGCGGGCA GTGAGCGCAA CGCAATTAAT GTGAGTTAGC 6120
6121 TCACTCATTA GGCACCCCAG GCTTTACACT TTATGCTTCC GGCTCGTATG TTGTGTGGAA 6180
6181 TTGTGAGCGG ATAACAATTT CACACGCCAA GGAGACAGTC ATAATGAAAT ACCTATTGCC 6240
6241 TACGGCAGCC GCTGGATTGT TATTACTCGC TGCCCAACCA GCCATGGCCG AGCTCGTGAT 6300
6301 GACCCAGACT CCAGAATTCC ATCCGGAATG AGTGTTAATT CTAGAACGCG TAAGCTTGGC 6360
6361 ACTGGCCGTC GTTTTACAAC GTCGTGACTG GGAAAACCCT GGCGTTACCC AACTTAATCG 6420
6421 CCTTGCAGCA CACCCCCCTT TCGCCAGCTG GCGTAATAGC GAAGAGGCCC GCACCGATCG 6480
6481 CCCTTCCCAA CAGTTGCGCA GCCTGAATGG CGAATGGCGC TTTGCCTGGT TTCCGGCACC 6540
6541 AGAAGCGGTG CCGGAAAGCT GGCTGGAGTG CGATCTTCCT GAGGCCGATA CGGTCGTCGT 6600
6601 CCCCTCAAAC TGGCAGATGC ACGGTTACGA TGCGCCCATC TACACCAACG TAACCTATCC 6660
6661 CATTACGGTC AATCCGCCGT TGTTCCCAC GGAGAATCCG ACGGGTTGTT ACTCGCTCAC 6720
6721 ATTTAATGTT GATGAAAGCT GGCTACAGGA AGGCCAGACG CGAATTATTT TTGATGGCGT 6780
6781 TCCTATTGGT TAAAAAATGA GCTGATTTAA CAAAAATTTA ACGCGAATTT TAACAAAATA 6840
6841 TTAACGTTTA CAATTTAAAT ATTTGCTTAT ACAATCTTCC TGTTTTTGGG GCTTTTCTGA 6900
6901 TTATCAACCG GGGTACATAT GATTGACATG CTAGTTTTAC GATTACCGTT CATCGATTCT 6960
6961 CTTGTTTGCT CCAGACTCTC AGGCAATGAC CTGATAGCCT TTGTAGATCT CTCAAAAATA 7020
7021 GCTACCCTCT CCGGCATTAA TTTATCAGCT AGAACGGTTG AATATCATAT TGATGGTGAT 7080
7081 TTGACTGTCT CCGGCCTTTC TCACCCTTTT GAATCTTTAC CTACACATTA CTCAGGCATT 7140
7141 GCATTTAAAA TATATGAGGG TTCTAAAAAT TTTTATCCTT GCGTTGAAAT AAAGGCTTCT 7200
7201 CCCGCAAAAG TATTACAGGG TCATAATGTT TTTGGTACAA CCGATTTAGC TTTATGCTCT 7260
7261 GAGGCTTTAT TGCTTAATTT TGCTAATTCT TTGCCTTGCC TGTATGATTT ATTGGACGTT 7320
             |  10     |  20     |  30     |  40     |  50     |  60
```

FIG. 6D

```
      |   10       |   20       |   30       |   40       |   50       |   60
   1  AATGCTACTA  CTATTAGTAG  AATTGATGCC  ACCTTTTCAG  CTCGCGCCCC  AAATGAAAAT    60
  61  ATAGCTAAAC  AGGTTATTGA  CCATTTGCGA  AATGTATCTA  ATGGTCAAAC  TAAATCTACT   120
 121  CGTTCGCAGA  ATTGGGAATC  AACTGTTACA  TGGAATGAAA  CTTCCAGACA  CCGTACTTTA   180
 181  GTTGCATATT  TAAAACATGT  TGAGCTACAG  CACCAGATTC  AGCAATTAAG  CTCTAAGCCA   240
 241  TCTGCAAAAA  TGACCTCTTA  TCAAAGGAG   CAATTAAAGG  TACTCTCTAA  TCCTGACCTG   300
 301  TTGGAGTTTG  CTTCCGGTCT  GGTTCGCTTT  GAAGCTCGAA  TTAAAACGCG  ATATTTGAAG   360
 361  TCTTTCGGGC  TTCCTCTTAA  TCTTTTTGAT  GCAATCCGCT  TTGCTTCTGA  CTATAATAGT   420
 421  CAGGGTAAAG  ACCTGATTTT  TGATTTATGG  TCATTCTCGT  TTTCTGAACT  GTTAAAGCA    480
 481  TTTGAGGGGG  ATTCAATGAA  TATTTATGAC  GATTCCGCAG  TATTGGACGC  TATCCAGTCT   540
 541  AAACATTTTA  CTATTACCCC  CTCTGGCAAA  ACTTCTTTTG  CAAAAGCCTC  TCGCTATTTT   600
 601  GGTTTTTATC  GTCGTCTGGT  AAACGAGGGT  TATGATAGTG  TTGCTCTTAC  TATGCCTCGT   660
 661  AATTCCTTTT  GGCGTTATGT  ATCTGCATTA  GTTGAATGTG  GTATTCCTAA  ATCTCAACTG   720
 721  ATGAATCTTT  CTACCTGTAA  TAATGTTGTT  CCGTTAGTTC  GTTTTATTAA  CGTAGATTTT   780
 781  TCTTCCCAAC  GTCCTGACTG  GTATAATGAG  CCAGTTCTTA  AAATCGCATA  AGGTAATTCA   840
 841  CAATGATTAA  AGTTGAAATT  AAACCATCTC  AAGCCCAATT  TACTACTCGT  TCTGGTGTTT   900
 901  CTCGTCAGGG  CAAGCCTTAT  TCACTGAATG  AGCAGCTTTG  TTACGTTGAT  TTGGGTAATG   960
 961  AATATCCGGT  TCTTGTCAAG  ATTACTCTTG  ATGAAGGTCA  GCCAGCCTAT  GCGCCTGGTC  1020
1021  TGTACACCGT  TCATCTGTCC  TCTTTCAAAG  TTGGTCAGTT  CGGTTCCCTT  ATGATTGACC  1080
1081  GTCTGCGCCT  CGTTCCGGCT  AAGTAACATG  GAGCAGGTCG  CGGATTTCGA  CACAATTTAT  1140
1141  CAGGCGATGA  TACAAATCTC  CGTTGTACTT  TGTTTCGCGC  TTGGTATAAT  CGCTGGGGGT  1200
1201  CAAAGATGAG  TGTTTTAGTG  TATTCTTTCG  CCTCTTTCGT  TTTAGGTTGG  TGCCTTCGTA  1260
1261  GTGGCATTAC  GTATTTTACC  CGTTTAATGG  AAACTTCCTC  ATGAAAAAGT  CTTTAGTCCT  1320
1321  CAAAGCCTCT  GTAGCCGTTG  CTACCCTCGT  TCCGATGCTG  TCTTTCGCTG  CTGAGGGTGA  1380
1381  CGATCCCGCA  AAAGCGGCCT  TTAACTCCCT  GCAAGCCTCA  GCGACCGAAT  ATATCGGTTA  1440
1441  TGCGTGGGCG  ATGGTTGTTG  TCATTGTCGG  CGCAACTATC  GGTATCAAGC  TGTTTAAGAA  1500
1501  ATTCACCTCG  AAAGCAAGCT  GATAAACCGA  TACAATTAAA  GGCTCCTTTT  GGAGCCTTTT  1560
1561  TTTTTGGAGA  TTTTCAACGT  GAAAAAATTA  TTATTCGCAA  TTCCTTTAGT  TGTTCCTTTC  1620
1621  TATTCTCACT  CCGCTGAAAC  TGTTGAAAGT  TGTTTAGCAA  AACCCCATAC  AGAAAATTCA  1680
1681  TTTACTAACG  TCTGGAAAGA  CGACAAAACT  TTAGATCGTT  ACGCTAACTA  TGAGGGTTGT  1740
```

FIG. 7A

```
1741 CTGTGGAATG CTACAGGCGT TGTAGTTTGT ACTGGTGACG AAACTCAGTG TTACGGTACA 1800
1801 TGGGTTCCTA TTGGGCTTGC TATCCCTGAA AATGAGGGTG GTGGCTCTGA GGGTGGCGGT 1860
1861 TCTGAGGGTG GCGGTTCTGA GGGTGGCGGT ACTAAACCTC CTGAGTACGG TGATACACCT 1920
1921 ATTCCGGGCT ATACTTATAT CAACCCTCTC GACGGCACTT ATCCGCCTGG TACTGAGCAA 1980
1981 AACCCCGCTA ATCCTAATCC TTCTCTTGAG GAGTCTCAGC CTCTTAATAC TTTCATGTTT 2040
2041 CAGAATAATA GGTTCCGAAA TAGGCAGGGG GCATTAACTG TTTATACGGG CACTGTTACT 2100
2101 CAAGGCACTG ACCCCGTTAA AACTTATTAC CAGTACACTC CTGTATCATC AAAAGCCATG 2160
2161 TATGACGCTT ACTGGAACGG TAAATTCAGA GACTGCGCTT TCCATTCTGG CTTTAATGAA 2220
2221 GATCCATTCG TTTGTGAATA TCAAGGCCAA TCGTCTGACC TGCCTCAACC TCCTGTCAAT 2280
2281 GCTGGCGGCG GCTCTGGTGG TGGTTCTGGT GGCGGCTCTG AGGGTGGTGG CTCTGAGGGT 2340
2341 GGCGGTTCTG AGGGTGGCGG CTCTGAGGGA GGCGGTTCCG GTGGTGGCTC TGGTTCCGGT 2400
2401 GATTTTGATT ATGAAAAGAT GGCAAACGCT AATAAGGGGG CTATGACCGA AAATGCCGAT 2460
2461 GAAAACGCGC TACAGTCTGA CGCTAAAGGC AAACTTGATT CTGTCGCTAC TGATTACGGT 2520
2521 GCTGCTATCG ATGGTTTCAT TGGTGACGTT TCCGGCCTTG CTAATGGTAA TGGTGCTACT 2580
2581 GGTGATTTTG CTGGCTCTAA TTCCCAAATG GCTCAAGTCG GTGACGGTGA TAATTCACCT 2640
2641 TTAATGAATA ATTTCCGTCA ATATTTACCT TCCCTCCCTC AATCGGTTGA ATGTCGCCCT 2700
2701 TTTGTCTTTA GCGCTGGTAA ACCATATGAA TTTTCTATTG ATTGTGACAA AATAAACTTA 2760
2761 TTCCGTGGTG TCTTTGCGTT TCTTTTATAT GTTGCCACCT TTATGTATGT ATTTTCTACG 2820
2821 TTTGCTAACA TACTGCGTAA TAAGGAGTCT TAATCATGCC AGTTCTTTTG GGTATTCCGT 2880
2881 TATTATTGCG TTTCCTCGGT TTCCTTCTGG TAACTTTGTT CGGCTATCTG CTTACTTTTC 2940
2941 TTAAAAAGGG CTTCGGTAAG ATAGCTATTG CTATTTCATT GTTTCTTGCT CTTATTATTG 3000
3001 GGCTTAACTC AATTCTTGTG GGTTATCTCT CTGATATTAG CGCTCAATTA CCCTCTGACT 3060
3061 TTGTTCAGGG TGTTCAGTTA ATTCTCCCGT CTAATGCGCT TCCCTGTTTT TATGTTATTC 3120
3121 TCTCTGTAAA GGCTGCTATT TTCATTTTTG ACGTTAAACA AAAAATCGTT TCTTATTTGG 3180
3181 ATTGGGATAA ATAATATGGC TGTTTATTTT GTAACTGGCA AATTAGGCTC TGGAAAGACG 3240
3241 CTCGTTAGCG TTGGTAAGAT TCAGGATAAA ATTGTAGCTG GGTGCAAAAT AGCAACTAAT 3300
3301 CTTGATTTAA GGCTTCAAAA CCTCCCGCAA GTCGGGAGGT TCGCTAAAAC GCCTCGCGTT 3360
3361 CTTAGAATAC CGGATAAGCC TTCTATATCT GATTTGCTTG CTATTGGGCG CGGTAATGAT 3420
3421 TCCTACGATG AAAATAAAAA CGGCTTGCTT GTTCTCGATG AGTGCGGTAC TTGGTTTAAT 3480
3481 ACCCGTTCTT GGAATGATAA GGAAAGACAG CCGATTATTG ATTGGTTTCT ACATGCTCGT 3540
3541 AAATTAGGAT GGGATATTAT TTTTCTTGTT CAGGACTTAT CTATTGTTGA TAAACAGGCG 3600
3601 CGTTCTGCAT TAGCTGAACA TGTTGTTTAT TGTCGTCGTC TGGACAGAAT TACTTTACCT 3660
```

FIG. 7B

```
3661 TTTGTCGGTA CTTTATATTC TCTTATTACT GGCTCGAAAA TGCCTCTGCC TAAATTACAT 3720
3421 GTTGGCGTTG TTAAATATGG CGATTCTCAA TTAAGCCCTA CTGTTGAGCG TTGGCTTTAT 3780
3781 ACTGGTAAGA ATTTGTATAA CGCATATGAT ACTAAACAGG CTTTTTCTAG TAATTATGAT 3840
3841 TCCGGTGTTT ATTCTTATTT AACGCCTTAT TTATCACACG GTCGGTATTT CAAACCATTA 3900
3901 AATTTAGGTC AGAAGATGAA GCTTACTAAA ATATATTTGA AAAGTTTTC ACGCGTTCTT 3960
3961 TGTCTTGCGA TTGGATTTGC ATCAGCATTT ACATATAGTT ATATAACCCA ACCTAAGCCG 4020
4021 GAGGTTAAAA AGGTAGTCTC TCAGACCTAT GATTTTGATA AATTCACTAT TGACTCTTCT 4080
4081 CAGCGTCTTA ATCTAAGCTA TCGCTATGTT TTCAAGGATT CTAAGGGAAA ATTAATTAAT 4140
4141 AGCGACGATT TACAGAAGCA AGGTTATTCA CTCACATATA TTGATTTATG TACTGTTTCC 4200
4201 ATTAAAAAAG GTAATTCAAA TGAAATTGTT AAATGTAATT AATTTTGTTT CTTGATGTT 4260
4261 TGTTTCATCA TCTTCTTTTG CTCAGGTAAT TGAAATGAAT AATTCGCCTC TGCGCGATTT 4320
4321 TGTAACTTGG TATTCAAAGC AATCAGGCGA ATCCGTTATT GTTTCTCCCG ATGTAAAAGG 4380
4381 TACTGTTACT GTATATTCAT CTGACGTTAA ACCTGAAAAT CTACGCAATT TCTTTATTTC 4440
4441 TGTTTTACGT GCTAATAATT TTGATATGGT TGGTTCAATT CCTTCCATAA TTCAGAAGTA 4500
4501 TAATCCAAAC AATCAGGATT ATATTGATGA ATTGCCATCA TCTGATAATC AGGAATATGA 4560
4561 TGATAATTCC GCTCCTTCTG GTGGTTTCTT TGTTCCGCAA AATGATAATG TTACTCAAAC 4620
4621 TTTTAAAATT AATAACGTTC GGGCAAAGGA TTTAATACGA GTTGTCGAAT TGTTTGTAAA 4680
4681 GTCTAATACT TCTAAATCCT CAAATGTATT ATCTATTGAC GGCTCTAATC TATTAGTTGT 4740
4741 TAGTGCACCT AAAGATATTT TAGATAACCT TCCTCAATTC CTTTCTACTG TTGATTTGCC 4800
4801 AACTGACCAG ATATTGATTG AGGGTTTGAT ATTTGAGGTT CAGCAAGGTG ATGCTTTAGA 4860
4861 TTTTTCATTT GCTGCTGGCT CTCAGCGTGG CACTGTTGCA GGCGGTGTTA ATACTGACCG 4920
4921 CCTCACCTCT GTTTTATCTT CTGCTGGTGG TTCGTTCGGT ATTTTTAATG GCGATGTTTT 4980
4981 AGGGCTATCA GTTCGCGCAT TAAAGACTAA TAGCCATTCA AAAATATTGT CTGTGCCACG 5040
5041 TATTCTTACG CTTTCAGGTC AGAAGGGTTC TATCTCTGTT GGCCAGAATG TCCCTTTTAT 5100
5101 TACTGGTCGT GTGACTGGTG AATCTGCCAA TGTAAATAAT CCATTTCAGA CGATTGAGCG 5160
5161 TCAAAATGTA GGTATTTCCA TGAGCGTTTT TCCTGTTGCA ATGGCTGGCG GTAATATTGT 5220
5221 TCTGGATATT ACCAGCAAGG CCGATAGTTT GAGTTCTTCT ACTCAGGCAA GTGATGTTAT 5280
5281 TACTAATCAA GAAGTATTG CTACAACGGT TAATTTGCGT GATGGACAGA CTCTTTTACT 5340
5341 CGGTGGCCTC ACTGATTATA AAAACACTTC TCAAGATTCT GGCGTACCGT TCCTGTCTAA 5400
5401 AATCCCTTTA ATCGGCCTCC TGTTTAGCTC CCGCTCTGAT TCCAACGAGG AAAGCACGTT 5460
5461 ATACGTGCTC GTCAAAGCAA CCATAGTACG CGCCCTGTAG CGGCGCATTA AGCGCGGCGG 5520
5521 GTGTGGTGGT TACGCGCAGC GTGACCGCTA CACTTGCCAG CGCCCTAGCG CCCGCTCCTT 5580
```

FIG. 7C

```
5581 TCGCTTTCTT CCCTTCCTTT CTCGCCACGT TCGCCGGCTT TCCCCGTCAA GCTCTAAATC 5640
5641 GGGGGCTCCC TTTAGGGTTC CGATTTAGTG CTTTACGGCA CCTCGACCCC AAAAAACTTG 5700
5701 ATTTGGGTGA TGGTTCACGT AGTGGGCCAT CGCCCTGATA GACGGTTTTT CGCCCTTTGA 5760
5761 CGTTGGAGTC CACGTTCTTT AATAGTGGAC TCTTGTTCCA AACTGGAACA ACACTCAACC 5820
5821 CTATCTCGGG CTATTCTTTT GATTTATAAG GGATTTTGCC GATTTCGGAA CCACCATCAA 5880
5881 ACAGGATTTT CGCCTGCTGG GGCAAACCAG CGTGGACCGC TTGCTGCAAC TCTCTCAGGG 5940
5941 CCAGGCGGTG AAGGGCAATC AGCTGTTGCC CGTCTCGCTG GTGAAAAGAA AAACCACCCT 6000
6001 GGCGCCCAAT ACGCAAACCG CCTCTCCCCG CGCGTTGGCC GATTCATTAA TGCAGCTGGC 6060
6061 ACGACAGGTT TCCCGACTGG AAAGCGGGCA GTGAGCGCAA CGCAATTAAT GTGAGTTAGC 6120
6121 TCACTCATTA GGCACCCCAG GCTTTACACT TTATGCTTCC GGCTCGTATG TTGTGTGGAA 6180
6181 TTGTGAGCGG ATAACAATTT CACACGCGTC ACTTGGCACT GGCCGTCGTT TTACAACGTC 6240
6241 GTGACTGGGA AAACCCTGGC GTTACCCAAG CTTTGTACAT GGAGAAAATA AAGTGAAACA 6300
6301 AAGCACTATT GCACTGGCAC TCTTACCGTT ACCGTTACTG TTTACCCCTG TGACAAAAGC 6360
6361 CGCCCAGGTC CAGCTGCTCG AGTCAGGCCT ATTGTGCCCA GGGGATTGTA CTAGTGGATC 6420
6421 CTAGGCTGAA GGCGATGACC CTGCTAAGGC TGCATTCAAT AGTTTACAGG CAAGTGCTAC 6480
6481 TGAGTACATT GGCTACGCTT GGGCTATGGT AGTAGTTATA GTTGGTGCTA CCATAGGGAT 6540
6541 TAAATTATTC AAAAAGTTTA CGAGCAAGGC TTCTTAAGCA ATAGCGAAGA GGCCCGCACC 6600
6601 GATCGCCCTT CCCAACAGTT GCGCAGCCTG AATGGCGAAT GGCGCTTTGC CTGGTTTCCG 6660
6661 GCACCAGAAG CGGTGCCGGA AAGCTGGCTG GAGTGCGATC TTCCTGAGGC CGATACGGTC 6720
6721 GTCGTCCCCT CAAACTGGCA GATGCACGGT TACGATGCGC CCATCTACAC CAACGTAACC 6780
6781 TATCCCATTA CGGTCAATCC GCCGTTTGTT CCCACGGAGA ATCCGACGGG TTGTTACTCG 6840
6841 CTCACATTTA ATGTTGATGA AAGCTGGCTA CAGGAAGGCC AGACGCGAAT TATTTTTGAT 6900
6901 GGCGTTCCTA TTGGTTAAAA AATGAGCTGA TTTAACAAAA ATTTAACGCG AATTTTAACA 6960
6961 AAATATTAAC GTTTACAATT TAAATATTTG CTTATACAAT CTTCCTGTTT TTGGGGCTTT 7020
7021 TCTGATTATC AACCGGGGTA CATATGATTG ACATGCTAGT TTTACGATTA CCGTTCATCG 7080
7081 ATTCTCTTGT TTGCTCCAGA CTCTCAGGCA ATGACCTGAT AGCCTTTGTA GATCTCTCAA 7140
7141 AAATAGCTAC CCTCTCCGGC ATTAATTTAT CAGCTAGAAC GGTTGAATAT CATATTGATG 7200
7201 GTGATTTGAC TGTCTCCGGC CTTTCTCACC CTTTTGAATC TTTACCTACA CATTACTCAG 7260
7261 GCATTGCATT TAAAATATAT GAGGGTTCTA AAAATTTTTA TCCTTGCGTT GAAATAAAGG 7320
7321 CTTCTCCCGC AAAAGTATTA CAGGGTCATA ATGTTTTTGG TACAACCGAT TTAGCTTTAT 7380
7381 GCTCTGAGGC TTTATTGCTT AATTTTGCTA ATTCTTTGCC TTGCCTGTAT GATTTATTGG 7440
7441 ACGTT                                                              7445
        |   10    |   20    |   30    |   40    |   50    |   60
```

FIG. 7D

|  | 10 |  | 20 |  | 30 |  | 40 |  | 50 |  | 60 |  |
|---|---|---|---|---|---|---|---|---|---|---|---|---|
| 1 | AATGCTACTA | CTATTAGTAG | AATTGATGCC | ACCTTTTCAG | CTCGCGCCCC | AAATGAAAAT | 60 |
| 61 | ATAGCTAAAC | AGGTTATTGA | CCATTTGCGA | AATGTATCTA | ATGGTCAAAC | TAAATCTACT | 120 |
| 121 | CGTTCGCAGA | ATTGGGAATC | AACTGTTACA | TGGAATGAAA | CTTCCAGACA | CCGTACTTTA | 180 |
| 181 | GTTGCATATT | TAAAACATGT | TGAGCTACAG | CACCAGATTC | AGCAATTAAG | CTCTAAGCCA | 240 |
| 241 | TCTGCAAAAA | TGACCTCTTA | TCAAAAGGAG | CAATTAAAGG | TACTCTCTAA | TCCTGACCTG | 300 |
| 301 | TTGGAGTTTG | CTTCCGGTCT | GGTTCGCTTT | GAAGCTCGAA | TTAAAACGCG | ATATTTGAAG | 360 |
| 361 | TCTTTCGGGC | TTCCTCTTAA | TCTTTTTGAT | GCAATCCGCT | TGCTTCTGA | CTATAATAGT | 420 |
| 421 | CAGGGTAAAG | ACCTGATTTT | TGATTTATGG | TCATTCTCGT | TTTCTGAACT | GTTTAAAGCA | 480 |
| 481 | TTTGAGGGGG | ATTCAATGAA | TATTTATGAC | GATTCCGCAG | TATTGGACGC | TATCCAGTCT | 540 |
| 541 | AAACATTTTA | CTATTACCCC | CTCTGGCAAA | ACTTCTTTTG | CAAAAGCCTC | TCGCTATTTT | 600 |
| 301 | GGTTTTATC | GTCGTCTGGT | AAACGAGGGT | TATGATAGTG | TTGCTCTTAC | TATGCCTCGT | 660 |
| 661 | AATTCCTTTT | GGCGTTATGT | ATCTGCATTA | GTTGAATGTG | GTATTCCTAA | ATCTCAACTG | 720 |
| 721 | ATGAATCTTT | CTACCTGTAA | TAATGTTGTT | CCGTTAGTTC | GTTTATTAA | CGTAGATTTT | 780 |
| 781 | TCTTCCCAAC | GTCCTGACTG | GTATAATGAG | CCAGTTCTTA | AAATCGCATA | AGGTAATTCA | 840 |
| 841 | CAATGATTAA | AGTTGAAATT | AAACCATCTC | AAGCCCAATT | TACTACTCGT | TCTGGTGTTT | 900 |
| 901 | CTCGTCAGGG | CAAGCCTTAT | TCACTGAATG | AGCAGCTTTG | TTACGTTGAT | TTGGGTAATG | 960 |
| 961 | AATATCCGGT | TCTTGTCAAG | ATTACTCTTG | ATGAAGGTCA | GCCAGCCTAT | GCGCCTGGTC | 1020 |
| 1021 | TGTACACCGT | TCATCTGTCC | TCTTTCAAAG | TTGGTCAGTT | CGGTTCCCTT | ATGATTGACC | 1080 |
| 1081 | GTCTGCGCCT | CGTTCCGGCT | AAGTAACATG | GAGCAGGTCG | CGGATTTCGA | CACAATTTAT | 1140 |
| 1141 | CAGGCGATGA | TACAAATCTC | CGTTGTACTT | TGTTTCGCGC | TTGGTATAAT | CGCTGGGGGT | 1200 |
| 1201 | CAAAGATGAG | TGTTTTAGTG | TATTCTTTCG | CCTCTTTCGT | TTTAGGTTGG | TGCCTTCGTA | 1260 |
| 1261 | GTGGCATTAC | GTATTTTACC | CGTTTAATGG | AAACTTCCTC | ATGAAAAAGT | CTTTAGTCCT | 1320 |
| 1321 | CAAAGCCTCT | GTAGCCGTTG | CTACCCTCGT | TCCGATGCTG | TCTTTCGCTG | CTGAGGGTGA | 1380 |
| 1381 | CGATCCCGCA | AAAGCGGCCT | TTAACTCCCT | GCAAGCCTCA | GCGACCGAAT | ATATCGGTTA | 1440 |
| 1441 | TGCGTGGGCG | ATGGTTGTTG | TCATTGTCGG | CGCAACTATC | GGTATCAAGC | TGTTTAAGAA | 1500 |
| 1501 | ATTCACCTCG | AAAGCAAGCT | GATAAACCGA | TACAATTAAA | GGCTCCTTTT | GGAGCCTTTT | 1560 |
| 1561 | TTTTTGGAGA | TTTTCAACGT | GAAAAAATTA | TTATTCGCAA | TTCCTTTAGT | TGTTCCTTTC | 1620 |
| 1621 | TATTCTCACT | CCGCTGAAAC | TGTTGAAAGT | TGTTTAGCAA | AACCCCATAC | AGAAAATTCA | 1680 |
| 1681 | TTTACTAACG | TCTGGAAAGA | CGACAAAACT | TTAGATCGTT | ACGCTAACTA | TGAGGGTTGT | 1740 |

FIG. 8A

```
1741 CTGTGGAATG CTACAGGCGT TGTAGTTTGT ACTGGTGACG AAACTCAGTG TTACGGTACA 1800
1801 TGGGTTCCTA TTGGGCTTGC TATCCCTGAA AATGAGGGTG GTGGCTCTGA GGGTGGCGGT 1860
1861 TCTGAGGGTG GCGGTTCTGA GGGTGGCGGT ACTAAACCTC CTGAGTACGG TGATACACCT 1920
1921 ATTCCGGGCT ATACTTATAT CAACCCTCTC GACGGCACTT ATCCGCCTGG TACTGAGCAA 1980
1981 AACCCCGCTA ATCCTAATCC TTCTCTTGAG GAGTCTCAGC CTCTTAATAC TTTCATGTTT 2040
2041 CAGAATAATA GGTTCCGAAA TAGGCAGGGG GCATTAACTG TTTATACGGG CACTGTTACT 2100
2101 CAAGGCACTG ACCCCGTTAA AACTTATTAC CAGTACACTC CTGTATCATC AAAAGCCATG 2160
2161 TATGACGCTT ACTGGAACGG TAAATTCAGA GACTGCGCTT TCCATTCTGG CTTTAATGAA 2220
2221 GATCCATTCG TTTGTGAATA TCAAGGCCAA TCGTCTGACC TGCCTCAACC TCCTGTCAAT 2280
2281 GCTGGCGGCG GCTCTGGTGG TGGTTCTGGT GGCGGCTCTG AGGGTGGTGG CTCTGAGGGT 2340
2341 GGCGGTTCTG AGGGTGGCGG CTCTGAGGGA GGCGGTTCCG GTGGTGGCTC TGGTTCCGGT 2400
2401 GATTTTGATT ATGAAAAGAT GGCAAACGCT AATAAGGGGG CTATGACCGA AAATGCCGAT 2460
2461 GAAAACGCGC TACAGTCTGA CGCTAAAGGC AAACTTGATT CTGTCGCTAC TGATTACGGT 2520
2521 GCTGCTATCG ATGGTTTCAT TGGTGACGTT TCCGGCCTTG CTAATGGTAA TGGTGCTACT 2580
2581 GGTGATTTTG CTGGCTCTAA TTCCCAAATG GCTCAAGTCG GTGACGGTGA TAATTCACCT 2640
2641 TTAATGAATA ATTTCCGTCA ATATTTACCT TCCCTCCCTC AATCGGTTGA ATGTCGCCCT 2700
2701 TTTGTCTTTA GCGCTGGTAA ACCATATGAA TTTTCTATTG ATTGTGACAA AATAAACTTA 2760
2761 TTCCGTGGTG TCTTTGCGTT TCTTTTATAT GTTGCCACCT TTATGTATGT ATTTTCTACG 2820
2821 TTTGCTAACA TACTGCGTAA TAAGGAGTCT TAATCATGCC AGTTCTTTTG GGTATTCCGT 2880
2881 TATTATTGCG TTTCCTCGGT TTCCTTCTGG TAACTTTGTT CGGCTATCTG CTTACTTTTC 2940
2941 TTAAAAAGGG CTTCGGTAAG ATAGCTATTG CTATTTCATT GTTTCTTGCT CTTATTATTG 3000
3001 GGCTTAACTC AATTCTTGTG GGTTATCTCT CTGATATTAG CGCTCAATTA CCCTCTGACT 3060
3061 TTGTTCAGGG TGTTCAGTTA ATTCTCCCGT CTAATGCGCT TCCCTGTTTT TATGTTATTC 3120
3121 TCTCTGTAAA GGCTGCTATT TTCATTTTTG ACGTTAAACA AAAAATCGTT TCTTATTTGG 3180
3181 ATTGGGATAA ATAATATGGC TGTTTATTTT GTAACTGGCA AATTAGGCTC TGGAAAGACG 3240
3241 CTCGTTAGCG TTGGTAAGAT TCAGGATAAA ATTGTAGCTG GGTGCAAAAT AGCAACTAAT 3300
3301 CTTGATTTAA GGCTTCAAAA CCTCCCGCAA GTCGGGAGGT TCGCTAAAAC GCCTCGCGTT 3360
3361 CTTAGAATAC CGGATAAGCC TTCTATATCT GATTTGCTTG CTATTGGGCG CGGTAATGAT 3420
3421 TCCTACGATG AAAATAAAAA CGGCTTGCTT GTTCTCGATG AGTGCGGTAC TTGGTTTAAT 3480
3481 ACCCGTTCTT GGAATGATAA GGAAAGACAG CCGATTATTG ATTGGTTTCT ACATGCTCGT 3540
3541 AAATTAGGAT GGGATATTAT TTTTCTTGTT CAGGACTTAT CTATTGTTGA TAAACAGGCG 3600
3601 CGTTCTGCAT TAGCTGAACA TGTTGTTTAT TGTCGTCGTC TGGACAGAAT TACTTTACCT 3660
```

FIG. 8B

```
3661 TTTGTCGGTA CTTTATATTC TCTTATTACT GGCTCGAAAA TGCCTCTGCC TAAATTACAT 3720
3721 GTTGGCGTTG TTAAATATGG CGATTCTCAA TTAAGCCCTA CTGTTGAGCG TTGGCTTTAT 3780
3781 ACTGGTAAGA ATTTGTATAA CGCATATGAT ACTAAACAGG CTTTTTCTAG TAATTATGAT 3840
3841 TCCGGTGTTT ATTCTTATTT AACGCCTTAT TTATCACACG GTCGGTATTT CAAACCATTA 3900
3901 AATTTAGGTC AGAAGATGAA GCTTACTAAA ATATATTTGA AAAGTTTTC ACGCGTTCTT 3960
3961 TGTCTTGCGA TTGGATTTGC ATCAGCATTT ACATATAGTT ATATAACCCA ACCTAAGCCG 4020
4021 GAGGTTAAAA AGGTAGTCTC TCAGACCTAT GATTTTGATA AATTCACTAT TGACTCTTCT 4080
4081 CAGCGTCTTA ATCTAAGCTA TCGCTATGTT TTCAAGGATT CTAAGGGAAA ATTAATTAAT 4140
4141 AGCGACGATT TACAGAAGCA AGGTTATTCA CTCACATATA TTGATTTATG TACTGTTTCC 4200
4201 ATTAAAAAAG GTAATTCAAA TGAAATTGTT AAATGTAATT AATTTTGTTT CTTGATGTTT 4260
4261 TGTTTCATCA TCTTCTTTTG CTCAGGTAAT TGAAATGAAT AATTCGCCTC TGCGCGATTT 4320
4321 TGTAACTTGG TATTCAAAGC AATCAGGCGA ATCCGTTATT GTTTCTCCCG ATGTAAAAGG 4380
4381 TACTGTTACT GTATATTCAT CTGACGTTAA ACCTGAAAAT CTACGCAATT TCTTTATTTC 4440
4441 TGTTTTACGT GCTAATAATT TTGATATGGT TGGTTCAATT CCTTCCATAA TTCAGAAGTA 4500
4501 TAATCCAAAC AATCAGGATT ATATTGATGA ATTGCCATCA TCTGATAATC AGGAATATGA 4560
4561 TGATAATTCC GCTCCTTCTG GTGGTTTCTT TGTTCCGCAA AATGATAATG TTACTCAAAC 4620
4621 TTTTAAAATT AATAACGTTC GGGCAAAGGA TTTAATACGA GTTGTCGAAT TGTTTGTAAA 4680
4681 GTCTAATACT TCTAAATCCT CAAATGTATT ATCTATTGAC GGCTCTAATC TATTAGTTGT 4740
4741 TAGTGCACCT AAAGATATTT TAGATAACCT TCCTCAATTC CTTTCTACTG TTGATTTGCC 4800
4801 AACTGACCAG ATATTGATTG AGGGTTTGAT ATTTGAGGTT CAGCAAGGTG ATGCTTTAGA 4860
4861 TTTTTCATTT GCTGCTGGCT CTCAGCGTGG CACTGTTGCA GGCGGTGTTA ATACTGACCG 4920
4921 CCTCACCTCT GTTTTATCTT CTGCTGGTGG TTCGTTCGGT ATTTTTAATG GCGATGTTTT 4980
4981 AGGGCTATCA GTTCGCGCAT TAAAGACTAA TAGCCATTCA AAAATATTGT CTGTGCCACG 5040
5041 TATTCTTACG CTTTCAGGTC AGAAGGGTTC TATCTCTGTT GGCCAGAATG TCCCTTTTAT 5100
5101 TACTGGTCGT GTGACTGGTG AATCTGCCAA TGTAAATAAT CCATTTCAGA CGATTGAGCG 5160
5161 TCAAAATGTA GGTATTTCCA TGAGCGTTTT TCCTGTTGCA ATGGCTGGCG GTAATATTGT 5220
5221 TCTGGATATT ACCAGCAAGG CCGATAGTTT GAGTTCTTCT ACTCAGGCAA GTGATGTTAT 5280
5281 TACTAATCAA GAAGTATTG CTACAACGGT TAATTTGCGT GATGGACAGA CTCTTTTACT 5340
5341 CGGTGGCCTC ACTGATTATA AAAACACTTC TCAAGATTCT GGCGTACCGT TCCTGTCTAA 5400
5401 AATCCCTTTA ATCGGCCTCC TGTTTAGCTC CCGCTCTGAT TCCAACGAGG AAAGCACGTT 5460
5461 ATACGTGCTC GTCAAAGCAA CCATAGTACG CGCCCTGTAG CGGCGCATTA AGCGCGGCGG 5520
5521 GTGTGGTGGT TACGCGCAGC GTGACCGCTA CACTTGCCAG CGCCCTAGCG CCCGCTCCTT 5580
```

FIG. 8C

```
5581 TCGCTTTCTT CCCTTCCTTT CTCGCCACGT TCGCCGGCTT TCCCCGTCAA GCTCTAAATC 5640
5641 GGGGGCTCCC TTTAGGGTTC CGATTTAGTG CTTTACGGCA CCTCGACCCC AAAAAACTTG 5700
5701 ATTTGGGTGA TGGTTCACGT AGTGGGCCAT CGCCCTGATA GACGGTTTTT CGCCCTTTGA 5760
5761 CGTTGGAGTC CACGTTCTTT AATAGTGGAC TCTTGTTCCA AACTGGAACA ACACTCAACC 5820
5821 CTATCTCGGG CTATTCTTTT GATTTATAAG GGATTTTGCC GATTCGGAA CCACCATCAA 5880
5881 ACAGGATTTT CGCCTGCTGG GGCAAACCAG CGTGGACCGC TTGCTGCAAC TCTCTCAGGG 5940
5941 CCAGGCGGTG AAGGGCAATC AGCTGTTGCC CGTCTCGCTG GTGAAAAGAA AAACCACCCT 6000
6001 GGCGCCCAAT ACGCAAACCG CCTCTCCCCG CGCGTTGGCC GATTCATTAA TGCAGCTGGC 6060
6061 ACGACAGGTT TCCCGACTGG AAAGCGGGCA GTGAGCGCAA CGCAATTAAT GTGAGTTAGC 6120
6121 TCACTCATTA GGCACCCCAG GCTTTACACT TTATGCTTCC GGCTCGTATG TTGTGTGGAA 6180
6181 TTGTGAGCGG ATAACAATTT CACACGCGTC ACTTGGCACT GGCCGTCGTT TTACAACGTC 6240
6241 GTGACTGGGA AAACCCTGGC GTTACCCAAG CTTTGTACAT GGAGAAAATA AAGTGAAACA 6300
6301 AAGCACTATT GCACTGGCAC TCTTACCGTT ACTGTTTACC CCTGTGGCAA AAGCCTATGG 6360
6361 GGGGTTTATG ACTTCTGAGG GATCCGGAGC TGAAGGCGAT GACCCTGCTA AGGCTGCATT 6420
6421 CAATAGTTTA CAGGCAAGTG CTACTGAGTA CATTGGCTAC GCTTGGGCTA TGGTAGTAGT 6480
6481 TATAGTTGGT GCTACCATAG GGATTAAATT ATTCAAAAAG TTTACGAGCA AGGCTTCTTA 6540
6541 AGCAATAGCG AAGAGGCCCG CACCGATCGC CCTTCCCAAC AGTTGCGCAG CCTGAATGGC 6600
6601 GAATGGCGCT TTGCCTGGTT TCCGGCACCA GAAGCGGTGC CGGAAAGCTG GCTGGAGTGC 6660
6661 GATCTTCCTG AGGCCGATAC GGTCGTCGTC CCCTCAAACT GGCAGATGCA CGGTTACGAT 6720
6721 GCGCCCATCT ACACCAACGT AACCTATCCC ATTACGGTCA ATCCGCCGTT TGTTCCCACG 6780
6781 GAGAATCCGA CGGGTTGTTA CTCGCTCACA TTTAATGTTG ATGAAAGCTG GCTACAGGAA 6840
6841 GGCCAGACGC GAATTATTTT TGATGGCGTT CCTATTGGTT AAAAAATGAG CTGATTTAAC 6900
6901 AAAAATTTAA CGCGAATTTT AACAAAATAT TAACGTTTAC AATTTAAATA TTTGCTTATA 6960
6961 CAATCTTCCT GTTTTTGGGG CTTTTCTGAT TATCAACCGG GGTACATATG ATTGACATGC 7020
7021 TAGTTTTACG ATTACCGTTC ATCGATTCTC TTGTTTGCTC CAGACTCTCA GGCAATGACC 7080
7081 TGATAGCCTT TGTAGATCTC TCAAAAATAG CTACCCTCTC CGGCATTAAT TTATCAGCTA 7140
7141 GAACGGTTGA ATATCATATT GATGGTGATT TGACTGTCTC CGGCCTTTCT CACCCTTTTG 7200
7201 AATCTTTACC TACACATTAC TCAGGCATTG CATTTAAAAT ATATGAGGGT TCTAAAAATT 7260
7261 TTTATCCTTG CGTTGAAATA AAGGCTTCTC CCGCAAAAGT ATTACAGGGT CATAATGTTT 7320
7321 TTGGTACAAC CGATTTAGCT TTATGCTCTG AGGCTTTATT GCTTAATTTT GCTAATTCTT 7380
7381 TGCCTTGCCT GTATGATTTA TTGGACGTT                                    7409
        | 10       | 20       | 30       | 40       | 50       | 60
```

FIG. 8D

```
        |  10        |  20        |  30        |  40        |  50        |  60
    1 AATGCTACTA CTATTAGTAG AATTGATGCC ACCTTTTCAG CTCGCGCCCC AAATGAAAAT 60
   61 ATAGCTAAAC AGGTTATTGA CCATTTGCGA AATGTATCTA ATGGTCAAAC TAAATCTACT 120
  121 CGTTCGCAGA ATTGGAATC AACTGTTACA TGGAATGAAA CTTCCAGACA CCGTACTTTA 180
  181 GTTGCATATT TAAAACATGT TGAGCTACAG CACCAGATTC AGCAATTAAG CTCTAAGCCA 240
  241 TCTGCAAAAA TGACCTCTTA TCAAAGGAG CAATTAAAGG TACTCTCTAA TCCTGACCTG 300
  301 TTGGAGTTTG CTTCCGGTCT GGTTCGCTTT GAAGCTCGAA TTAAAACGCG ATATTTGAAG 360
  361 TCTTTCGGGC TTCCTCTTAA TCTTTTTGAT GCAATCCGCT TTGCTTCTGA CTATAATAGT 420
  421 CAGGGTAAAG ACCTGATTTT TGATTTATGG TCATTCTCGT TTTCTGAACT GTTTAAAGCA 480
  481 TTTGAGGGGG ATTCAATGAA TATTTATGAC GATTCCGCAG TATTGGACGC TATCCAGTCT 540
  541 AAACATTTTA CTATTACCCC CTCTGGCAAA ACTTCTTTTG CAAAAGCCTC TCGCTATTTT 600
  601 GGTTTTTATC GTCGTCTGGT AAACGAGGGT TATGATAGTG TTGCTCTTAC TATGCCTCGT 660
  661 AATTCCTTTT GGCGTTATGT ATCTGCATTA GTTAATGTG GTATTCCTAA ATCTCAACTG 720
  721 ATGAATCTTT CTACCTGTAA TAATGTTGTT CCGTTAGTTC GTTTTATTAA CGTAGATTTT 780
  781 TCTTCCCAAC GTCCTGACTG GTATAATGAG CCAGTTCTTA AAATCGCATA AGGTAATTCA 840
  841 CAATGATTAA AGTTGAAATT AAACCATCTC AAGCCCAATT TACTACTCGT TCTGGTGTTT 900
  901 CTCGTCAGGG CAAGCCTTAT TCACTGAATG AGCAGCTTTG TTACGTTGAT TTGGGTAATG 960
  961 AATATCCGGT TCTTGTCAAG ATTACTCTTG ATGAAGGTCA GCCAGCCTAT GCGCCTGGTC 1020
 1021 TGTACACCGT TCATCTGTCC TCTTTCAAAG TTGGTCAGTT CGGTTCCCTT ATGATTGACC 1080
 1081 GTCTGCGCCT CGTTCCGGCT AAGTAACATG GAGCAGGTCG CGGATTTCGA CACAATTTAT 1140
 1141 CAGGCGATGA TACAAATCTC CGTTGTACTT TGTTTCGCGC TTGGTATAAT CGCTGGGGGT 1200
 1201 CAAAGATGAG TGTTTTAGTG TATTCTTTCG CCTCTTTCGT TTTAGGTTGG TGCCTTCGTA 1260
 1261 GTGGCATTAC GTATTTTACC CGTTTAATGG AAACTTCCTC ATGAAAAAGT CTTTAGTCCT 1320
 1321 CAAAGCCTCT GTAGCCGTTG CTACCCTCGT TCCGATGCTG TCTTTCGCTG CTGAGGGTGA 1380
 1381 CGATCCCGCA AAAGCGGCCT TTAACTCCCT GCAAGCCTCA GCGACCGAAT ATATCGGTTA 1440
 1441 TGCGTGGGCG ATGGTTGTTG TCATTGTCGG CGCAACTATC GGTATCAAGC TGTTTAAGAA 1500
 1501 ATTCACCTCG AAAGCAAGCT GATAAACCGA TACAATTAAA GGCTCCTTTT GGAGCCTTTT 1560
 1561 TTTTTGGAGA TTTTCAACGT GAAAAATTA TTATTCGCAA TTCCTTTAGT TGTTCCTTTC 1620
 1621 TATTCTCACT CCGCTGAAAC TGTTGAAAGT TGTTTAGCAA AACCCCATAC AGAAAATTCA 1680
 1681 TTTACTAACG TCTGGAAAGA CGACAAAACT TTAGATCGTT ACGCTAACTA TGAGGGTTGT 1740
 1741 CTGTGGAATG CTACAGGCGT TGTAGTTTGT ACTGGTGACG AAACTCAGTG TTACGGTACA 1800
```

FIG. 9A

1801 TGGGTTCCTA TTGGGCTTGC TATCCCTGAA AATGAGGGTG GTGGCTCTGA GGGTGGCGGT 1860

1861 TCTGAGGGTG GCGGTTCTGA GGGTGGCGGT ACTAAACCTC CTGAGTACGG TGATACACCT 1920

1921 ATTCCGGGCT ATACTTATAT CAACCCTCTC GACGGCACTT ATCCGCCTGG TACTGAGCAA 1980

1981 AACCCCGCTA ATCCTAATCC TTCTCTTGAG GAGTCTCAGC CTCTTAATAC TTTCATGTTT 2040

2041 CAGAATAATA GGTTCCGAAA TAGGCAGGGG CATTAACTG TTTATACGGG CACTGTTACT 2100

2101 CAAGGCACTG ACCCCGTTAA AACTTATTAC CAGTACACTC CTGTATCATC AAAAGCCATG 2160

2161 TATGACGCTT ACTGGAACGG TAAATTCAGA GACTGCGCTT TCCATTCTGG CTTTAATGAA 2220

2221 GATCCATTCG TTTGTGAATA TCAAGGCCAA TCGTCTGACC TGCCTCAACC TCCTGTCAAT 2280

2281 GCTGGCGGCG GCTCTGGTGG TGGTTCTGGT GGCGGCTCTG AGGGTGGTGG CTCTGAGGGT 2340

2341 GGCGGTTCTG AGGGTGGCGG CTCTGAGGGA GGCGGTTCCG GTGGTGGCTC TGGTTCCGGT 2400

2401 GATTTTGATT ATGAAAAGAT GGCAAACGCT AATAAGGGGG CTATGACCGA AAATGCCGAT 2460

2461 GAAAACGCGC TACAGTCTGA CGCTAAAGGC AAACTTGATT CTGTCGCTAC TGATTACGGT 2520

2521 GCTGCTATCG ATGGTTTCAT TGGTGACGTT TCCGGCCTTG CTAATGGTAA TGGTGCTACT 2580

2581 GGTGATTTTG CTGGCTCTAA TTCCCAAATG GCTCAAGTCG GTGACGGTGA TAATTCACCT 2640

2641 TTAATGAATA ATTTCCGTCA ATATTTACCT TCCCTCCCTC AATCGGTTGA ATGTCGCCCT 2700

2701 TTTGTCTTTA GCGCTGGTAA ACCATATGAA TTTTCTATTG ATTGTGACAA AATAAACTTA 2760

2761 TTCCGTGGTG TCTTTGCGTT TCTTTTATAT GTTGCCACCT TTATGTATGT ATTTTCTACG 2820

2821 TTTGCTAACA TACTGCGTAA TAAGGAGTCT TAATCATGCC AGTTCTTTTG GGTATTCCGT 2880

2881 TATTATTGCG TTTCCTCGGT TTCCTTCTGG TAACTTTGTT CGGCTATCTG CTTACTTTTC 2940

2941 TTAAAAAGGG CTTCGGTAAG ATAGCTATTG CTATTTCATT GTTTCTTGCT CTTATTATTG 3000

3001 GGCTTAACTC AATTCTTGTG GGTTATCTCT CTGATATTAG CGCTCAATTA CCCTCTGACT 3060

3061 TTGTTCAGGG TGTTCAGTTA ATTCTCCCGT CTAATGCGCT TCCCTGTTTT TATGTTATTC 3120

3121 TCTCTGTAAA GGCTGCTATT TTCATTTTTG ACGTTAAACA AAAAATCGTT TCTTATTTGG 3180

3181 ATTGGGATAA ATAATATGGC TGTTTATTTT GTAACTGGCA AATTAGGCTC TGGAAAGACG 3240

3241 CTCGTTAGCG TTGGTAAGAT TCAGGATAAA ATTGTAGCTG GGTGCAAAAT AGCAACTAAT 3300

3301 CTTGATTTAA GGCTTCAAAA CCTCCCGCAA GTCGGGAGGT TCGCTAAAAC GCCTCGCGTT 3360

3361 CTTAGAATAC CGGATAAGCC TTCTATATCT GATTTGCTTG CTATTGGGCG CGGTAATGAT 3420

3421 TCCTACGATG AAAATAAAAA CGGCTTGCTT GTTCTCGATG AGTGCGGTAC TTGGTTTAAT 3480

3481 ACCCGTTCTT GGAATGATAA GGAAAGACAG CCGATTATTG ATTGGTTTCT ACATGCTCGT 3540

3541 AAATTAGGAT GGGATATTAT CTTCCTTGTT CAGGACTTAT CTATTGTTGA TAAACAGGCG 3600

3601 CGTTCTGCAT TAGCTGAACA TGTTGTTTAT TGTCGTCGTC TGGACAGAAT TACTTTACCT 3660

3661 TTTGTCGGTA CTTTATATTC TCTTATTACT GGCTCGAAAA TGCCTCTGCC TAAATTACAT 3720

FIG. 9B

```
3721 GTTGGCGTTG TTAAATATGG CGATTCTCAA TTAAGCCCTA CTGTTGAGCG TTGGCTTTAT 3780
3781 ACTGGTAAGA ATTTGTATAA CGCATATGAT ACTAAACAGG CTTTTTCTAG TAATTATGAT 3840
3841 TCCGGTGTTT ATTCTTATTT AACGCCTTAT TTATCACACG GTCGGTATTT CAAACCATTA 3900
3901 AATTTAGGTC AGAAGATGAA GCTTACTAAA ATATATTTGA AAAAGTTTTC ACGCGTTCTT 3960
3961 TGTCTTGCGA TTGGATTTGC ATCAGCATTT ACATATAGTT ATATAACCCA ACCTAAGCCG 4020
4021 GAGGTTAAAA AGGTAGTCTC TCAGACCTAT GATTTTGATA AATTCACTAT TGACTCTTCT 4080
4081 CAGCGTCTTA ATCTAAGCTA TCGCTATGTT TTCAAGGATT CTAAGGGAAA ATTAATTAAT 4140
4141 AGCGACGATT TACAGAAGCA AGGTTATTCA CTCACATATA TTGATTTATG TACTGTTTCC 4200
4201 ATTAAAAAGG TAATTCAAAT GAAATTGTTA AATGTAATTA ATTTTGTTTT CTTGATGTTT 4260
4261 GTTTCATCAT CTTCTTTTGC TCAGGTAATT GAAATGAATA ATTCGCCTCT GCGCGATTTT 4320
4321 GTAACTTGGT ATTCAAAGCA ATCAGGCGAA TCCGTTATTG TTTCTCCCGA TGTAAAAGGT 4380
4381 ACTGTTACTG TATATTCATC TGACGTTAAA CCTGAAAATC TACGCAATTT CTTTATTTCT 4440
4441 GTTTTACGTG CTAATAATTT TGATATGGTT GGTTCAATTC CTTCCATTAT TTAGAAGTAT 4500
4501 AATCCAAACA ATCAGGATTA TATTGATGAA TTGCCATCAT CTGATAATCA GGAATATGAT 4560
4561 GATAATTCCG CTCCTTCTGG TGGTTTCTTT GTTCCGCAAA ATGATAATGT TACTCAAACT 4620
4621 TTTAAAATTA ATAACGTTCG GGCAAAGGAT TTAATACGAG TTGTCGAATT GTTTGTAAAG 4680
4681 TCTAATACTT CTAAATCCTC AAATGTATTA TCTATTGACG GCTCTAATCT ATTAGTTGTT 4740
4741 AGTGCACCTA AAGATATTTT AGATAACCTT CCTCAATTCC TTTCTACTGT TGATTTGCCA 4800
4801 ACTGACCAGA TATTGATTGA GGGTTTGATA TTTGAGGTTC AGCAAGGTGA TGCTTTAGAT 4860
4861 TTTTCATTTG CTGCTGGCTC TCAGCGTGGC ACTGTTGCAG GCGGTGTTAA TACTGACCGC 4920
4921 CTCACCTCTG TTTTATCTTC TGCTGGTGGT TCGTTCGGTA TTTTTAATGG CGATGTTTTA 4980
4981 GGGCTATCAG TTCGCGCATT AAAGACTAAT AGCCATTCAA AAATATTGTC TGTGCCACGT 5040
5041 ATTCTTACGC TTTCAGGTCA GAAGGGTTCT ATCTCTGTTG GCCAGAATGT CCCTTTTATT 5100
5101 ACTGGTCGTG TGACTGGTGA ATCTGCCAAT GTAAATAATC CATTTCAGAC GATTGAGCGT 5160
5161 CAAAATGTAG GTATTTCCAT GAGCGTTTTT CCTGTTGCAA TGGCTGGCGG TAATATTGTT 5220
5221 CTGGATATTA CCAGCAAGGC CGATAGTTTG AGTTCTTCTA CTCAGGCAAG TGATGTTATT 5280
5281 ACTAATCAAA GAAGTATTGC TACAACGGTT AATTTGCGTG ATGGACAGAC TCTTTTACTC 5340
5341 GGTGGCCTCA CTGATTATAA AAACACTTCT CAAGATTCTG GCGTACCGTT CCTGTCTAAA 5400
5401 ATCCCTTTAA TCGGCCTCCT GTTTAGCTCC CGCTCTGATT CCAACGAGGA AAGCACGTTA 5460
5461 TACGTGCTCG TCAAAGCAAC CATAGTACGC GCCCTGTAGC GGCGCATTAA GCGCGGCGGG 5520
5521 TGTGGTGGTT ACGCGCAGCG TGACCGCTAC ACTTGCCAGC GCCCTAGCGC CCGCTCCTTT 5580
5581 CGCTTTCTTC CCTTCCTTTC TCGCCACGTT CGCCGGCTTT CCCCGTCAAG CTCTAAATCG 5640
```

FIG. 9C

```
5641 GGGGCTCCCT TTAGGGTTCC GATTTAGTGC TTTACGGCAC CTCGACCCCA AAAAACTTGA 5700
5701 TTTGGGTGAT GGTTCACGTA GTGGGCCATC GCCCTGATAG ACGGTTTTTC GCCCTTTGAC 5760
5761 GTTGGAGTCC ACGTTCTTTA ATAGTGGACT CTTGTTCCAA ACTGGAACAA CACTCAACCC 5820
5821 TATCTCGGGC TATTCTTTTG ATTTATAAGG GATTTTGCCG ATTTCGGAAC CACCATCAAA 5880
5881 CAGGATTTTC GCCTGCTGGG GCAAACCAGC GTGGACCGCT TGCTGCAACT CTCTCAGGGC 5940
5941 CAGGCGGTGA AGGGCAATCA GCTGTTGCCC GTCTCGCTGG TGAAAAGAAA AACCACCCTG 6000
6001 GCGCCCAATA CGCAAACCGC CTCTCCCCGC GCGTTGGCCG ATTCATTAAT GCAGCTGGCA 6060
6061 CGACAGGTTT CCCGACTGGA AAGCGGGCAG TGAGCGCAAC GCAATTAATG TGAGTTAGCT 6120
6121 CACTCATTAG GCACCCCAGG CTTTACACTT TATGCTTCCG GCTCGTATGT TGTGTGGAAT 6180
6181 TGTGAGCGGA TAACAATTTC ACACAGGAAA CAGCTATGAC CAGGATGTAC GAATTCGCAG 6240
6241 GTAGGAGAGC TCGGCGGATC CGAGGCTGAA GGCGATGACC CTGCTAAGGC TGCATTCAAT 6300
6301 AGTTTACAGG CAAGTGCTAC TGAGTACATT GGCTACGCTT GGGCTATGGT AGTAGTTATA 6360
6361 GTTGGTGCTA CCATAGGGAT TAAATTATTC AAAAAGTTTA CGAGCAAGGC TTCTTAACCA 6420
6421 GCTGGCGTAA TAGCGAAGAG GCCCGCACCG ATCGCCCTTC CAACAGTTG CGCAGCCTGA 6480
6481 ATGGCGAATG GCGCTTTGCC TGGTTTCCGG CACCAGAAGC GGTGCCGGAA AGCTGGCTGG 6540
6541 AGTGCGATCT TCCTGAGGCC GATACGGTCG TCGTCCCCTC AAACTGGCAG ATGCACGGTT 6600
6601 ACGATGCGCC CATCTACACC AACGTAACCT ATCCCATTAC GGTCAATCCG CCGTTTGTTC 6660
6661 CCACGGAGAA TCCGACGGGT TGTTACTCGC TCACATTTAA TGTTGATGAA AGCTGGCTAC 6720
6721 AGGAAGGCCA GACGCGAATT ATTTTTGATG GCGTTCCTAT TGGTTAAAAA ATGAGCTGAT 6780
6781 TTAACAAAAA TTTAACGCGA ATTTTAACAA AATATTAACG TTTACAATTT AAATATTTGC 6840
6841 TTATACAATC TTCCTGTTTT TGGGGCTTTT CTGATTATCA ACCGGGGTAC ATATGATTGA 6900
6901 CATGCTAGTT TTACGATTAC CGTTCATCGA TTCTCTTGTT TGCTCCAGAC TCTCAGGCAA 6960
6961 TGACCTGATA GCCTTTGTAG ATCTCTCAAA AATAGCTACC CTCTCCGGCA TTAATTTATC 7020
7021 AGCTAGAACG GTTGAATATC ATATTGATGG TGATTTGACT GTCTCCGGCC TTTCTCACCC 7080
7081 TTTTGAATCT TTACCTACAC ATTACTCAGG CATTGCATTT AAAATATATG AGGGTTCTAA 7140
7141 AAATTTTTAT CCTTGCGTTG AAATAAAGGC TTCTCCCGCA AAGTATTAC AGGGTCATAA 7200
7201 TGTTTTTGGT ACAACCGATT TAGCTTTATG CTCTGAGGCT TTATTGCTTA ATTTTGCTAA 7260
7261 TTCTTTGCCT TGCCTGTATG ATTTATTGGA CGTT                             7294
         |    10    |    20    |    30    |    40    |    50    |    60
```

FIG. 9D

```
           |   10       |   20       |   30       |   40       |   50       |   60
   1  AATGCTACTA CTATTAGTAG AATTGATGCC ACCTTTTCAG CTCGCGCCCC AAATGAAAAT  60
  61  ATAGCTAAAC AGGTTATTGA CCATTTGCGA AATGTATCTA ATGGTCAAAC TAAATCTACT  120
 121  CGTTCGCAGA ATTGGGAATC AACTGTTACA TGGAATGAAA CTTCCAGACA CCGTACTTTA  180
 181  GTTGCATATT TAAAACATGT TGAGCTACAG CACCAGATTC AGCAATTAAG CTCTAAGCCA  240
 241  TCTGCAAAAA TGACCTCTTA TCAAAGGAG CAATTAAAGG TACTCTCTAA TCCTGACCTG  300
 301  TTGGAGTTTG CTTCCGGTCT GGTTCGCTTT GAAGCTCGAA TTAAAACGCG ATATTTGAAG  360
 361  TCTTTCGGGC TTCCTCTTAA TCTTTTTGAT GCAATCCGCT TTGCTTCTGA CTATAATAGT  420
 421  CAGGGTAAAG ACCTGATTTT TGATTTATGG TCATTCTCGT TTTCTGAACT GTTTAAAGCA  480
 481  TTTGAGGGGG ATTCAATGAA TATTTATGAC GATTCCGCAG TATTGGACGC TATCCAGTCT  540
 541  AAACATTTTA CTATTACCCC CTCTGGCAAA ACTTCTTTTG CAAAAGCCTC TCGCTATTTT  600
 601  GGTTTTTATC GTCGTCTGGT AAACGAGGGT TATGATAGTG TTGCTCTTAC TATGCCTCGT  660
 661  AATTCCTTTT GGCGTTATGT ATCTGCATTA GTTAATGTG GTATTCCTAA ATCTCAACTG  720
 721  ATGAATCTTT CTACCTGTAA TAATGTTGTT CCGTTAGTTC GTTTTATTAA CGTAGATTTT  780
 781  TCTTCCCAAC GTCCTGACTG GTATAATGAG CCAGTTCTTA AAATCGCATA AGGTAATTCA  840
 841  CAATGATTAA AGTTGAAATT AAACCATCTC AAGCCCAATT TACTACTCGT TCTGGTGTTT  900
 901  CTCGTCAGGG CAAGCCTTAT TCACTGAATG AGCAGCTTTG TTACGTTGAT TTGGGTAATG  960
 961  AATATCCGGT TCTTGTCAAG ATTACTCTTG ATGAAGGTCA GCCAGCCTAT GCGCCTGGTC  1020
1021  TGTACACCGT TCATCTGTCC TCTTTCAAAG TTGGTCAGTT CGGTTCCCTT ATGATTGACC  1080
1081  GTCTGCGCCT CGTTCCGGCT AAGTAACATG GAGCAGGTCG CGGATTTCGA CACAATTTAT  1140
1141  CAGGCGATGA TACAAATCTC CGTTGTACTT TGTTTCGCGC TTGGTATAAT CGCTGGGGGT  1200
1201  CAAAGATGAG TGTTTTAGTG TATTCTTTCG CCTCTTTCGT TTTAGGTTGG TGCCTTCGTA  1260
1261  GTGGCATTAC GTATTTTACC CGTTTAATGG AAACTTCCTC ATGAAAAGT CTTTAGTCCT  1320
1321  CAAAGCCTCT GTAGCCGTTG CTACCCTCGT TCCGATGCTG TCTTTCGCTG CTGAGGGTGA  1380
1381  CGATCCCGCA AAAGCGGCCT TTAACTCCCT GCAAGCCTCA GCGACCGAAT ATATCGGTTA  1440
1441  TGCGTGGGCG ATGGTTGTTG TCATTGTCGG CGCAACTATC GGTATCAAGC TGTTTAAGAA  1500
1501  ATTCACCTCG AAAGCAAGCT GATAAACCGA TACAATTAAA GGCTCCTTTT GGAGCCTTTT  1560
1561  TTTTTGGAGA TTTTCAACGT GAAAAAATTA TTATTCGCAA TTCCTTTAGT TGTTCCTTTC  1620
1621  TATTCTCACT CCGCTGAAAC TGTTGAAAGT TGTTTAGCAA AACCCCATAC AGAAAATTCA  1680
1681  TTTACTAACG TCTGGAAAGA CGACAAAACT TTAGATCGTT ACGCTAACTA TGAGGGTTGT  1740
```

FIG. 10A

```
1741 CTGTGGAATG CTACAGGCGT TGTAGTTTGT ACTGGTGACG AAACTCAGTG TTACGGTACA 1800
1801 TGGGTTCCTA TTGGGCTTGC TATCCCTGAA AATGAGGGTG GTGGCTCTGA GGGTGGCGGT 1860
1861 TCTGAGGGTG GCGGTTCTGA GGGTGGCGGT ACTAAACCTC CTGAGTACGG TGATACACCT 1920
1921 ATTCCGGGCT ATACTTATAT CAACCCTCTC GACGGCACTT ATCCGCCTGG TACTGAGCAA 1980
1981 AACCCCGCTA ATCCTAATCC TTCTCTTGAG GAGTCTCAGC CTCTTAATAC TTTCATGTTT 2040
2041 CAGAATAATA GGTTCCGAAA TAGGCAGGGG GCATTAACTG TTTATACGGG CACTGTTACT 2100
2101 CAAGGCACTG ACCCCGTTAA AACTTATTAC CAGTACACTC CTGTATCATC AAAAGCCATG 2160
2161 TATGACGCTT ACTGGAACGG TAAATTCAGA GACTGCGCTT TCCATTCTGG CTTTAATGAA 2220
2221 GATCCATTCG TTTGTGAATA TCAAGGCCAA TCGTCTGACC TGCCTCAACC TCCTGTCAAT 2280
2281 GCTGGCGGCG GCTCTGGTGG TGGTTCTGGT GGCGGCTCTG AGGGTGGTGG CTCTGAGGGT 2340
2341 GGCGGTTCTG AGGGTGGCGG CTCTGAGGGA GGCGGTTCCG GTGGTGGCTC TGGTTCCGGT 2400
2401 GATTTTGATT ATGAAAAGAT GGCAAACGCT AATAAGGGGG CTATGACCGA AAATGCCGAT 2460
2461 GAAAACGCGC TACAGTCTGA CGCTAAAGGC AAACTTGATT CTGTCGCTAC TGATTACGGT 2520
2521 GCTGCTATCG ATGGTTTCAT TGGTGACGTT TCCGGCCTTG CTAATGGTAA TGGTGCTACT 2580
2581 GGTGATTTTG CTGGCTCTAA TTCCCAAATG GCTCAAGTCG GTGACGGTGA TAATTCACCT 2640
2641 TTAATGAATA ATTTCCGTCA ATATTTACCT TCCCTCCCTC AATCGGTTGA ATGTCGCCCT 2700
2701 TTTGTCTTTA GCGCTGGTAA ACCATATGAA TTTTCTATTG ATTGTGACAA AATAAACTTA 2760
2761 TTCCGTGGTG TCTTTGCGTT TCTTTTATAT GTTGCCACCT TTATGTATGT ATTTTCTACG 2820
2821 TTTGCTAACA TACTGCGTAA TAAGGAGTCT TAATCATGCC AGTTCTTTTG GGTATTCCGT 2880
2881 TATTATTGCG TTTCCTCGGT TTCCTTCTGG TAACTTTGTT CGGCTATCTG CTTACTTTTC 2940
2941 TTAAAAAGGG CTTCGGTAAG ATAGCTATTG CTATTTCATT GTTTCTTGCT CTTATTATTG 3000
3001 GGCTTAACTC AATTCTTGTG GGTTATCTCT CTGATATTAG CGCTCAATTA CCCTCTGACT 3060
3061 TTGTTCAGGG TGTTCAGTTA ATTCTCCCGT CTAATGCGCT TCCCTGTTTT TATGTTATTC 3120
3121 TCTCTGTAAA GGCTGCTATT TTCATTTTTG ACGTTAAACA AAAAATCGTT TCTTATTTGG 3180
3181 ATTGGGATAA ATAATATGGC TGTTTATTTT GTAACTGGCA AATTAGGCTC TGGAAAGACG 3240
3241 CTCGTTAGCG TTGGTAAGAT TCAGGATAAA ATTGTAGCTG GGTGCAAAAT AGCAACTAAT 3300
3301 CTTGATTTAA GGCTTCAAAA CCTCCCGCAA GTCGGGAGGT TCGCTAAAAC GCCTCGCGTT 3360
3361 CTTAGAATAC CGGATAAGCC TTCTATATCT GATTTGCTTG CTATTGGGCG CGGTAATGAT 3420
3421 TCCTACGATG AAAATAAAAA CGGCTTGCTT GTTCTCGATG AGTGCGGTAC TTGGTTTAAT 3480
3481 ACCCGTTCTT GGAATGATAA GGAAAGACAG CCGATTATTG ATTGGTTTCT ACATGCTCGT 3540
3541 AAATTAGGAT GGGATATTAT TTTTCTTGTT CAGGACTTAT CTATTGTTGA TAAACAGGCG 3600
3601 CGTTCTGCAT TAGCTGAACA TGTTGTTTAT TGTCGTCGTC TGGACAGAAT TACTTTACCT 3660
```

FIG. 10B

```
3661 TTTGTCGGTA CTTTATATTC TCTTATTACT GGCTCGAAAA TGCCTCTGCC TAAATTACAT 3720
3721 GTTGGCGTTG TTAAATATGG CGATTCTCAA TTAAGCCCTA CTGTTGAGCG TTGGCTTTAT 3780
3781 ACTGGTAAGA ATTTGTATAA CGCATATGAT ACTAAACAGG CTTTTTCTAG TAATTATGAT 3840
3841 TCCGGTGTTT ATTCTTATTT AACGCCTTAT TTATCACACG GTCGGTATTT CAAACCATTA 3900
3901 AATTTAGGTC AGAAGATGAA GCTTACTAAA ATATATTTGA AAAGTTTTC ACGCGTTCTT 3960
3961 TGTCTTGCGA TTGGATTTGC ATCAGCATTT ACATATAGTT ATATAACCCA ACCTAAGCCG 4020
4021 GAGGTTAAAA AGGTAGTCTC TCAGACCTAT GATTTTGATA AATTCACTAT TGACTCTTCT 4080
4081 CAGCGTCTTA ATCTAAGCTA TCGCTATGTT TTCAAGGATT CTAAGGGAAA ATTAATTAAT 4140
4141 AGCGACGATT TACAGAAGCA AGGTTATTCA CTCACATATA TTGATTTATG TACTGTTTCC 4200
4201 ATTAAAAAAG GTAATTCAAA TGAAATTGTT AAATGTAATT AATTTTGTTT CTTGATGTT 4260
4261 TGTTTCATCA TCTTCTTTTG CTCAGGTAAT TGAAATGAAT AATTCGCCTC TGCGCGATTT 4320
4321 TGTAACTTGG TATTCAAAGC AATCAGGCGA ATCCGTTATT GTTTCTCCG ATGTAAAAGG 4380
4381 TACTGTTACT GTATATTCAT CTGACGTTAA ACCTGAAAAT CTACGCAATT TCTTTATTTC 4440
4441 TGTTTTACGT GCTAATAATT TTGATATGGT TGGTTCAATT CCTTCCATAA TTCAGAAGTA 4500
4501 TAATCCAAAC AATCAGGATT ATATTGATGA ATTGCCATCA TCTGATAATC AGGAATATGA 4560
4561 TGATAATTCC GCTCCTTCTG GTGGTTTCTT TGTTCCGCAA AATGATAATG TTACTCAAAC 4620
4621 TTTTAAAATT AATAACGTTC GGGCAAAGGA TTTAATACGA GTTGTCGAAT TGTTTGTAAA 4680
4681 GTCTAATACT TCTAAATCCT CAAATGTATT ATCTATTGAC GGCTCTAATC TATTAGTTGT 4740
4741 TAGTGCACCT AAAGATATTT TAGATAACCT TCCTCAATTC CTTTCTACTG TTGATTTGCC 4800
4801 AACTGACCAG ATATTGATTG AGGGTTTGAT ATTTGAGGTT CAGCAAGGTG ATGCTTTAGA 4860
4861 TTTTTCATTT GCTGCTGGCT CTCAGCGTGG CACTGTTGCA GGCGGTGTTA ATACTGACCG 4920
4921 CCTCACCTCT GTTTTATCTT CTGCTGGTGG TTCGTTCGGT ATTTTTAATG GCGATGTTTT 4980
4981 AGGGCTATCA GTTCGCGCAT TAAAGACTAA TAGCCATTCA AAAATATTGT CTGTGCCACG 5040
5041 TATTCTTACG CTTTCAGGTC AGAAGGGTTC TATCTCTGTT GGCCAGAATG TCCCTTTTAT 5100
5101 TACTGGTCGT GTGACTGGTG AATCTGCCAA TGTAAATAAT CCATTTCAGA CGATTGAGCG 5160
5161 TCAAAATGTA GGTATTTCCA TGAGCGTTTT TCCTGTTGCA ATGGCTGGCG GTAATATTGT 5220
5221 TCTGGATATT ACCAGCAAGG CCGATAGTTT GAGTTCTTCT ACTCAGGCAA GTGATGTTAT 5280
5281 TACTAATCAA AGAAGTATTG CTACAACGGT TAATTTGCGT GATGGACAGA CTCTTTTACT 5340
5341 CGGTGGCCTC ACTGATTATA AAAACACTTC TCAAGATTCT GGCGTACCGT TCCTGTCTAA 5400
5401 AATCCCTTTA ATCGGCCTCC TGTTTAGCTC CCGCTCTGAT TCCAACGAGG AAAGCACGTT 5460
5461 ATACGTGCTC GTCAAAGCAA CCATAGTACG CGCCCTGTAG CGGCGCATTA AGCGCGGCGG 5520
5521 GTGTGGTGGT TACGCGCAGC GTGACCGCTA CACTTGCCAG CGCCCTAGCG CCCGCTCCTT 5580
```

FIG. 10C

```
5581 TCGCTTTCTT CCCTTCCTTT CTCGCCACGT TCGCCGGCTT TCCCCGTCAA GCTCTAAATC 5640
5641 GGGGGCTCCC TTTAGGGTTC CGATTTAGTG CTTTACGGCA CCTCGACCCC AAAAAACTTG 5700
5701 ATTTGGGTGA TGGTTCACGT AGTGGGCCAT CGCCCTGATA GACGGTTTTT CGCCCTTTGA 5760
5761 CGTTGGAGTC CACGTTCTTT AATAGTGGAC TCTTGTTCCA AACTGGAACA ACACTCAACC 5820
5821 CTATCTCGGG CTATTCTTTT GATTTATAAG GGATTTTGCC GATTTCGGAA CCACCATCAA 5880
5881 ACAGGATTTT CGCCTGCTGG GGCAAACCAG CGTGGACCGC TTGCTGCAAC TCTCTCAGGG 5940
5941 CCAGGCGGTG AAGGGCAATC AGCTGTTGCC CGTCTCGCTG GTGAAAAGAA AAACCACCCT 6000
6001 GGCGCCCAAT ACGCAAACCG CCTCTCCCCG CGCGTTGGCC GATTCATTAA TGCAGCTGGC 6060
6061 ACGACAGGTT TCCCGACTGG AAAGCGGGCA GTGAGCGCAA CGCAATTAAT GTGAGTTAGC 6120
6121 TCACTCATTA GGCACCCCAG GCTTTACACT TTATGCTTCC GGCTCGTATG TTGTGTGGAA 6180
6181 TTGTGAGCGG ATAACAATTT CACACGCGTC ACTTGGCACT GGCCGTCGTT TTACAACGTC 6240
6241 GTGACTGGGA AAACCCTGGC GTTACCCAAG CTTTGTACAT GGAGAAAATA AAGTGAAACA 6300
6301 AAGCACTATT GCACTGGCAC TCTTACCGTT ACTGTTTACC CCTGTGGCAA AGCCCTTCT 6360
6361 GAGGCATCCG GGAGCTGAAG GCGATGACCC TGCTAAGGCT GCATTCAATA GTTTACAGGC 6420
6421 AAGTGCTACT GAGTACATTG CTACGCTTG GCTATGGTA GTAGTTATAG TTGGTGCTAC 6480
6481 CATAGGGATT AAATTATTCA AAAGTTTAC GAGCAAGGCT TCTTAAGCAA TAGCGAAGAG 6540
6541 GCCCGCACCG ATCGCCCTTC CCAACAGTTG CGCAGCCTGA ATGGCGAATG GCGCTTTGCC 6600
6601 TGGTTTCCGG CACCAGAAGC GGTGCCGGAA AGCTGGCTGG AGTGCGATCT TCCTGAGGCC 6660
6661 GATACGGTCG TCGTCCCCTC AAACTGGCAG ATGCACGGTT ACGATGCGCC CATCTACACC 6720
6721 AACGTAACCT ATCCCATTAC GGTCAATCCG CCGTTTGTTC CCACGGAGAA TCCGACGGGT 6780
6781 TGTTACTCGC TCACATTTAA TGTTGATGAA AGCTGGCTAC AGGAAGGCCA GACGCGAATT 6840
6841 ATTTTTGATG GCGTTCCTAT TGGTTAAAAA ATGAGCTGAT TTAACAAAAA TTTAACGCGA 6900
6901 ATTTTAACAA AATATTAACG TTTACAATTT AAATATTTGC TTATACAATC TTCCTGTTTT 6960
6961 TGGGGCTTTT CTGATTATCA ACCGGGGTAC ATATGATTGA CATGCTAGTT TTACGATTAC 7020
7021 CGTTCATCGA TTCTCTTGTT TGCTCCAGAC TCTCAGGCAA TGACCTGATA GCCTTTGTAG 7080
7081 ATCTCTCAAA AATAGCTACC CTCTCCGGCA TTAATTTATC AGCTAGAACG GTTGAATATC 7140
7141 ATATTGATGG TGATTTGACT GTCTCCGGCC TTTCTCACCC TTTTGAATCT TTACCTACAC 7200
7201 ATTACTCAGG CATTGCATTT AAAATATATG AGGGTTCTAA AAATTTTTAT CCTTGCGTTG 7260
7261 AAATAAAGGC TTCTCCCGCA AAAGTATTAC AGGGTCATAA TGTTTTTGGT ACAACCGATT 7320
7321 TAGCTTTATG CTCTGAGGCT TTATTGCTTA ATTTTGCTAA TTCTTTGCCT TGCCTGTATG 7380
7381 ATTTATTGGA CGTT                                                  7394
        |   10    |   20    |   30    |   40    |   50    |   60
```

FIG. 10D

SEQUENCE LISTING ( 1 ) GENERAL INFORMATION:

( i i i ) NUMBER OF SEQUENCES: 174

( 2 ) INFORMATION FOR SEQ ID NO:1:

( i ) SEQUENCE CHARACTERISTICS:
        ( A ) LENGTH: 7294 base pairs
        ( B ) TYPE: nucleic acid
        ( C ) STRANDEDNESS: both
        ( D ) TOPOLOGY: circular ( x i ) SEQUENCE DESCRIPTION: SEQ ID NO:1:

```
AATGCTACTA   CTATTAGTAG   AATTGATGCC   ACCTTTTCAG   CTCGCGCCCC   AAATGAAAAT        60

ATAGCTAAAC   AGGTTATTGA   CCATTTGCGA   AATGTATCTA   ATGGTCAAAC   TAAATCTACT       120

CGTTCGCAGA   ATTGGGAATC   AACTGTTACA   TGGAATGAAA   CTTCCAGACA   CCGTACTTTA       180

GTTGCATATT   TAAAACATGT   TGAGCTACAG   CACCAGATTC   AGCAATTAAG   CTCTAAGCCA       240

TCTGCAAAAA   TGACCTCTTA   TCAAAAGGAG   CAATTAAAGG   TACTCTCTAA   TCCTGACCTG       300
```

| | | | | | |
|---|---|---|---|---|---|
| TTGGAGTTTG | CTTCCGGTCT | GGTTCGCTTT | GAAGCTCGAA | TTAAAACGCG | ATATTTGAAG | 360 |
| TCTTTCGGGC | TTCCTCTTAA | TCTTTTTGAT | GCAATCCGCT | TTGCTTCTGA | CTATAATAGT | 420 |
| CAGGGTAAAG | ACCTGATTTT | TGATTTATGG | TCATTCTCGT | TTTCTGAACT | GTTTAAAGCA | 480 |
| TTTGAGGGGG | ATTCAATGAA | TATTTATGAC | GATTCCGCAG | TATTGGACGC | TATCCAGTCT | 540 |
| AAACATTTTA | CTATTACCCC | CTCTGGCAAA | ACTTCTTTTG | CAAAAGCCTC | TCGCTATTTT | 600 |
| GGTTTTTATC | GTCGTCTGGT | AAACGAGGGT | TATGATAGTG | TTGCTCTTAC | TATGCCTCGT | 660 |
| AATTCCTTTT | GGCGTTATGT | ATCTGCATTA | GTTGAATGTG | GTATTCCTAA | ATCTCAACTG | 720 |
| ATGAATCTTT | CTACCTGTAA | TAATGTTGTT | CCGTTAGTTC | GTTTATTAA | CGTAGATTTT | 780 |
| TCTTCCCAAC | GTCCTGACTG | GTATAATGAG | CCAGTTCTTA | AAATCGCATA | AGGTAATTCA | 840 |
| CAATGATTAA | AGTTGAAATT | AAACCATCTC | AAGCCCAATT | TACTACTCGT | TCTGGTGTTT | 900 |
| CTCGTCAGGG | CAAGCCTTAT | TCACTGAATG | AGCAGCTTTG | TTACGTTGAT | TTGGGTAATG | 960 |
| AATATCCGGT | TCTTGTCAAG | ATTACTCTTG | ATGAAGGTCA | GCCAGCCTAT | GCGCCTGGTC | 1020 |
| TGTACACCGT | TCATCTGTCC | TCTTTCAAAG | TTGGTCAGTT | CGGTTCCCTT | ATGATTGACC | 1080 |
| GTCTGCGCCT | CGTTCCGGCT | AAGTAACATG | GAGCAGGTCG | CGGATTTCGA | CACAATTTAT | 1140 |
| CAGGCGATGA | TACAAATCTC | CGTTGTACTT | TGTTTCGCGC | TTGGTATAAT | CGCTGGGGGT | 1200 |
| CAAAGATGAG | TGTTTTAGTG | TATTCTTTCG | CCTCTTTCGT | TTTAGGTTGG | TGCCTTCGTA | 1260 |
| GTGGCATTAC | GTATTTTACC | CGTTTAATGG | AAACTTCCTC | ATGAAAAGT | CTTTAGTCCT | 1320 |
| CAAAGCCTCT | GTAGCCGTTG | CTACCCTCGT | TCCGATGCTG | TCTTTCGCTG | CTGAGGGTGA | 1380 |
| CGATCCCGCA | AAAGCGGCCT | TTAACTCCCT | GCAAGCCTCA | GCGACCGAAT | ATATCGGTTA | 1440 |
| TGCGTGGGCG | ATGGTTGTTG | TCATTGTCGG | CGCAACTATC | GGTATCAAGC | TGTTTAAGAA | 1500 |
| ATTCACCTCG | AAAGCAAGCT | GATAAACCGA | TACAATTAAA | GGCTCCTTTT | GGAGCCTTTT | 1560 |
| TTTTGGAGA | TTTTCAACGT | GAAAAAATTA | TTATTCGCAA | TTCCTTTAGT | TGTTCCTTTC | 1620 |
| TATTCTCACT | CCGCTGAAAC | TGTTGAAAGT | TGTTTAGCAA | AACCCCATAC | AGAAAATTCA | 1680 |
| TTTACTAACG | TCTGGAAAGA | CGACAAAACT | TTAGATCGTT | ACGCTAACTA | TGAGGGTTGT | 1740 |
| CTGTGGAATG | CTACAGGCGT | TGTAGTTTGT | ACTGGTGACG | AAACTCAGTG | TTACGGTACA | 1800 |
| TGGGTTCCTA | TTGGGCTTGC | TATCCCTGAA | AATGAGGGTG | GTGGCTCTGA | GGGTGGCGGT | 1860 |
| TCTGAGGGTG | GCGGTTCTGA | GGGTGGCGGT | ACTAAACCTC | CTGAGTACGG | TGATACACCT | 1920 |
| ATTCCGGGCT | ATACTTATAT | CAACCCTCTC | GACGGCACTT | ATCCGCCTGG | TACTGAGCAA | 1980 |
| AACCCCGCTA | ATCCTAATCC | TTCTCTTGAG | GAGTCTCAGC | CTCTTAATAC | TTTCATGTTT | 2040 |
| CAGAATAATA | GGTTCCGAAA | TAGGCAGGGG | GCATTAACTG | TTTATACGGG | CACTGTTACT | 2100 |
| CAAGGCACTG | ACCCCGTTAA | AACTTATTAC | CAGTACACTC | CTGTATCATC | AAAAGCCATG | 2160 |
| TATGACGCTT | ACTGGAACGG | TAAATTCAGA | GACTGCGCTT | TCCATTCTGG | CTTTAATGAA | 2220 |
| GATCCATTCG | TTTGTGAATA | TCAAGGCCAA | TCGTCTGACC | TGCCTCAACC | TCCTGTCAAT | 2280 |
| GCTGGCGGCG | GCTCTGGTGG | TGGTTCTGGT | GGCGGCTCTG | AGGGTGGTGG | CTCTGAGGGT | 2340 |
| GGCGGTTCTG | AGGGTGGCGG | CTCTGAGGGA | GGCGGTTCCG | GTGGTGGCTC | TGGTTCCGGT | 2400 |
| GATTTTGATT | ATGAAAAGAT | GGCAAACGCT | AATAAGGGGG | CTATGACCGA | AAATGCCGAT | 2460 |
| GAAAACGCGC | TACAGTCTGA | CGCTAAAGGC | AAACTTGATT | CTGTCGCTAC | TGATTACGGT | 2520 |
| GCTGCTATCG | ATGGTTTCAT | TGGTGACGTT | TCCGGCCTTG | CTAATGGTAA | TGGTGCTACT | 2580 |
| GGTGATTTTG | CTGGCTCTAA | TTCCCAAATG | GCTCAAGTCG | GTGACGGTGA | TAATTCACCT | 2640 |
| TTAATGAATA | ATTTCCGTCA | ATATTTACCT | TCCCTCCCTC | AATCGGTTGA | ATGTCGCCCT | 2700 |

| | | | | | | |
|---|---|---|---|---|---|---|
| TTTGTCTTTA | GCGCTGGTAA | ACCATATGAA | TTTTCTATTG | ATTGTGACAA | AATAAACTTA | 2760 |
| TTCCGTGGTG | TCTTTGCGTT | TCTTTTATAT | GTTGCCACCT | TTATGTATGT | ATTTTCTACG | 2820 |
| TTTGCTAACA | TACTGCGTAA | TAAGGAGTCT | TAATCATGCC | AGTTCTTTTG | GGTATTCCGT | 2880 |
| TATTATTGCG | TTTCCTCGGT | TTCCTTCTGG | TAACTTTGTT | CGGCTATCTG | CTTACTTTTC | 2940 |
| TTAAAAAGGG | CTTCGGTAAG | ATAGCTATTG | CTATTTCATT | GTTTCTTGCT | CTTATTATTG | 3000 |
| GGCTTAACTC | AATTCTTGTG | GGTTATCTCT | CTGATATTAG | CGCTCAATTA | CCCTCTGACT | 3060 |
| TTGTTCAGGG | TGTTCAGTTA | ATTCTCCCGT | CTAATGCGCT | TCCTGTTTT | TATGTTATTC | 3120 |
| TCTCTGTAAA | GGCTGCTATT | TTCATTTTTG | ACGTTAAACA | AAAAATCGTT | TCTTATTTGG | 3180 |
| ATTGGGATAA | ATAATATGGC | TGTTTATTTT | GTAACTGGCA | AATTAGGCTC | TGGAAAGACG | 3240 |
| CTCGTTAGCG | TTGGTAAGAT | TCAGGATAAA | ATTGTAGCTG | GGTGCAAAAT | AGCAACTAAT | 3300 |
| CTTGATTTAA | GGCTTCAAAA | CCTCCCGCAA | GTCGGGAGGT | TCGCTAAAAC | GCCTCGCGTT | 3360 |
| CTTAGAATAC | CGGATAAGCC | TTCTATATCT | GATTTGCTTG | CTATTGGGCG | CGGTAATGAT | 3420 |
| TCCTACGATG | AAAATAAAAA | CGGCTTGCTT | GTTCTCGATG | AGTGCGGTAC | TTGGTTTAAT | 3480 |
| ACCCGTTCTT | GGAATGATAA | GGAAAGACAG | CCGATTATTG | ATTGGTTTCT | ACATGCTCGT | 3540 |
| AAATTAGGAT | GGGATATTAT | CTTCCTTGTT | CAGGACTTAT | CTATTGTTGA | TAAACAGGCG | 3600 |
| CGTTCTGCAT | TAGCTGAACA | TGTTGTTTAT | TGTCGTCGTC | TGGACAGAAT | TACTTTACCT | 3660 |
| TTTGTCGGTA | CTTTATATTC | TCTTATTACT | GGCTCGAAAA | TGCCTCTGCC | TAAATTACAT | 3720 |
| GTTGGCGTTG | TTAAATATGG | CGATTCTCAA | TTAAGCCCTA | CTGTTGAGCG | TTGGCTTTAT | 3780 |
| ACTGGTAAGA | ATTTGTATAA | CGCATATGAT | ACTAAACAGG | CTTTTTCTAG | TAATTATGAT | 3840 |
| TCCGGTGTTT | ATTCTTATTT | AACGCCTTAT | TTATCACACG | GTCGGTATTT | CAAACCATTA | 3900 |
| AATTTAGGTC | AGAAGATGAA | GCTTACTAAA | ATATATTTGA | AAAAGTTTTC | ACGCGTTCTT | 3960 |
| TGTCTTGCGA | TTGGATTTGC | ATCAGCATTT | ACATATAGTT | ATATAACCCA | ACCTAAGCCG | 4020 |
| GAGGTTAAAA | AGGTAGTCTC | TCAGACCTAT | GATTTTGATA | AATTCACTAT | TGACTCTTCT | 4080 |
| CAGCGTCTTA | ATCTAAGCTA | TCGCTATGTT | TTCAAGGATT | CTAAGGGAAA | ATTAATTAAT | 4140 |
| AGCGACGATT | TACAGAAGCA | AGGTTATTCA | CTCACATATA | TTGATTTATG | TACTGTTTCC | 4200 |
| ATTAAAAGG | TAATTCAAAT | GAAATTGTTA | AATGTAATTA | ATTTTGTTTT | CTTGATGTTT | 4260 |
| GTTTCATCAT | CTTCTTTTGC | TCAGGTAATT | GAAATGAATA | ATTCGCCTCT | GCGCGATTTT | 4320 |
| GTAACTTGGT | ATTCAAAGCA | ATCAGGCGAA | TCCGTTATTG | TTTCTCCCGA | TGTAAAAGGT | 4380 |
| ACTGTTACTG | TATATTCATC | TGACGTTAAA | CCTGAAAATC | TACGCAATTT | CTTTATTTCT | 4440 |
| GTTTTACGTG | CTAATAATTT | TGATATGGTT | GGTTCAATTC | CTTCCATTAT | TTAGAAGTAT | 4500 |
| AATCCAAACA | ATCAGGATTA | TATTGATGAA | TTGCCATCAT | CTGATAATCA | GGAATATGAT | 4560 |
| GATAATTCCG | CTCCTTCTGG | TGGTTTCTTT | GTTCCGCAAA | ATGATAATGT | TACTCAAACT | 4620 |
| TTTAAAATTA | ATAACGTTCG | GGCAAAGGAT | TTAATACGAG | TTGTCGAATT | GTTTGTAAAG | 4680 |
| TCTAATACTT | CTAAATCCTC | AAATGTATTA | TCTATTGACG | GCTCTAATCT | ATTAGTTGTT | 4740 |
| AGTGCACCTA | AAGATATTTT | AGATAACCTT | CCTCAATTCC | TTTCTACTGT | TGATTTGCCA | 4800 |
| ACTGACCAGA | TATTGATTGA | GGGTTTGATA | TTTGAGGTTC | AGCAAGGTGA | TGCTTTAGAT | 4860 |
| TTTTCATTTG | CTGCTGGCTC | TCAGCGTGGC | ACTGTTGCAG | GCGGTGTTAA | TACTGACCGC | 4920 |
| CTCACCTCTG | TTTTATCTTC | TGCTGGTGGT | TCGTTCGGTA | TTTTTAATGG | CGATGTTTTA | 4980 |
| GGGCTATCAG | TTCGCGCATT | AAAGACTAAT | AGCCATTCAA | AAATATTGTC | TGTGCCACGT | 5040 |
| ATTCTTACGC | TTTCAGGTCA | GAAGGGTTCT | ATCTCTGTTG | GCCAGAATGT | CCCTTTTATT | 5100 |

| | | | | | | |
|---|---|---|---|---|---|---|
| ACTGGTCGTG | TGACTGGTGA | ATCTGCCAAT | GTAAATAATC | CATTTCAGAC | GATTGAGCGT | 5160 |
| CAAAATGTAG | GTATTTCCAT | GAGCGTTTTT | CCTGTTGCAA | TGGCTGGCGG | TAATATTGTT | 5220 |
| CTGGATATTA | CCAGCAAGGC | CGATAGTTTG | AGTTCTTCTA | CTCAGGCAAG | TGATGTTATT | 5280 |
| ACTAATCAAA | GAAGTATTGC | TACAACGGTT | AATTTGCGTG | ATGGACAGAC | TCTTTTACTC | 5340 |
| GGTGGCCTCA | CTGATTATAA | AAACACTTCT | CAAGATTCTG | GCGTACCGTT | CCTGTCTAAA | 5400 |
| ATCCCTTTAA | TCGGCCTCCT | GTTTAGCTCC | CGCTCTGATT | CCAACGAGGA | AAGCACGTTA | 5460 |
| TACGTGCTCG | TCAAAGCAAC | CATAGTACGC | GCCCTGTAGC | GGCGCATTAA | GCGCGGCGGG | 5520 |
| TGTGGTGGTT | ACGCGCAGCG | TGACCGCTAC | ACTTGCCAGC | GCCCTAGCGC | CCGCTCCTTT | 5580 |
| CGCTTTCTTC | CCTTCCTTTC | TCGCCACGTT | CGCCGGCTTT | CCCCGTCAAG | CTCTAAATCG | 5640 |
| GGGGCTCCCT | TTAGGGTTCC | GATTTAGTGC | TTTACGGCAC | CTCGACCCCA | AAAAACTTGA | 5700 |
| TTTGGGTGAT | GGTTCACGTA | GTGGGCCATC | GCCCTGATAG | ACGTTTTTC | GCCCTTTGAC | 5760 |
| GTTGGAGTCC | ACGTTCTTTA | ATAGTGGACT | CTTGTTCCAA | ACTGGAACAA | CACTCAACCC | 5820 |
| TATCTCGGGC | TATTCTTTTG | ATTTATAAGG | GATTTTGCCG | ATTTCGGAAC | CACCATCAAA | 5880 |
| CAGGATTTTC | GCCTGCTGGG | GCAAACCAGC | GTGGACCGCT | TGCTGCAACT | CTCTCAGGGC | 5940 |
| CAGGCGGTGA | AGGGCAATCA | GCTGTTGCCC | GTCTCGCTGG | TGAAAAGAAA | AACCACCCTG | 6000 |
| GCGCCCAATA | CGCAAACCGC | CTCTCCCCGC | GCGTTGGCCG | ATTCATTAAT | GCAGCTGGCA | 6060 |
| CGACAGGTTT | CCCGACTGGA | AAGCGGGCAG | TGAGCGCAAC | GCAATTAATG | TGAGTTAGCT | 6120 |
| CACTCATTAG | GCACCCCAGG | CTTTACACTT | TATGCTTCCG | GCTCGTATGT | TGTGTGGAAT | 6180 |
| TGTGAGCGGA | TAACAATTTC | ACACAGGAAA | CAGCTATGAC | CAGGATGTAC | GAATTCGCAG | 6240 |
| GTAGGAGAGC | TCGGCGGATC | CTAGGCTGAA | GGCGATGACC | CTGCTAAGGC | TGCATTCAAT | 6300 |
| AGTTTACAGG | CAAGTGCTAC | TGAGTACATT | GGCTACGCTT | GGGCTATGGT | AGTAGTTATA | 6360 |
| GTTGGTGCTA | CCATAGGGAT | TAAATTATTC | AAAAAGTTTA | CGAGCAAGGC | TTCTTAACCA | 6420 |
| GCTGGCGTAA | TAGCGAAGAG | GCCCGCACCG | ATCGCCCTTC | CCAACAGTTG | CGCAGCCTGA | 6480 |
| ATGGCGAATG | GCGCTTTGCC | TGGTTTCCGG | CACCAGAAGC | GGTGCCGGAA | AGCTGGCTGG | 6540 |
| AGTGCGATCT | TCCTGAGGCC | GATACGGTCG | TCGTCCCCTC | AAACTGGCAG | ATGCACGGTT | 6600 |
| ACGATGCGCC | CATCTACACC | AACGTAACCT | ATCCATTAC | GGTCAATCCG | CCGTTTGTTC | 6660 |
| CCACGGAGAA | TCCGACGGGT | TGTTACTCGC | TCACATTTAA | TGTTGATGAA | AGCTGGCTAC | 6720 |
| AGGAAGGCCA | GACGCGAATT | ATTTTTGATG | GCGTTCCTAT | TGGTTAAAAA | ATGAGCTGAT | 6780 |
| TTAACAAAAA | TTTAACGCGA | ATTTTAACAA | AATATTAACG | TTTACAATTT | AAATATTTGC | 6840 |
| TTATACAATC | TTCCTGTTTT | TGGGGCTTTT | CTGATTATCA | ACCGGGGTAC | ATATGATTGA | 6900 |
| CATGCTAGTT | TTACGATTAC | CGTTCATCGA | TTCTCTTGTT | TGCTCCAGAC | TCTCAGGCAA | 6960 |
| TGACCTGATA | GCCTTTGTAG | ATCTCTCAAA | AATAGCTACC | CTCTCCGGCA | TTAATTTATC | 7020 |
| AGCTAGAACG | GTTGAATATC | ATATTGATGG | TGATTTGACT | GTCTCCGGCC | TTTCTCACCC | 7080 |
| TTTTGAATCT | TTACCTACAC | ATTACTCAGG | CATTGCATTT | AAAATATATG | AGGGTTCTAA | 7140 |
| AAATTTTTAT | CCTTGCGTTG | AAATAAAGGC | TTCTCCCGCA | AAAGTATTAC | AGGGTCATAA | 7200 |
| TGTTTTTGGT | ACAACCGATT | TAGCTTTATG | CTCTGAGGCT | TTATTGCTTA | ATTTTGCTAA | 7260 |
| TTCTTTGCCT | TGCCTGTATG | ATTTATTGGA | CGTT | | | 7294 |

( 2 ) INFORMATION FOR SEQ ID NO:2:

( i ) SEQUENCE CHARACTERISTICS:
        ( A ) LENGTH: 7320 base pairs
        ( B ) TYPE: nucleic acid ( C ) STRANDEDNESS: both
( D ) TOPOLOGY: circular ( x i ) SEQUENCE DESCRIPTION: SEQ ID NO:2:

```
AATGCTACTA CTATTAGTAG AATTGATGCC ACCTTTTCAG CTCGCGCCCC AAATGAAAAT      60
ATAGCTAAAC AGGTTATTGA CCATTTGCGA AATGTATCTA ATGGTCAAAC TAAATCTACT     120
CGTTCGCAGA ATTGGGAATC AACTGTTACA TGGAATGAAA CTTCCAGACA CCGTACTTTA     180
GTTGCATATT TAAAACATGT TGAGCTACAG CACCAGATTC AGCAATTAAG CTCTAAGCCA     240
TCTGCAAAAA TGACCTCTTA TCAAAGGAG  CAATTAAAGG TACTCTCTAA TCCTGACCTG     300
TTGGAGTTTG CTTCCGGTCT GGTTCGCTTT GAAGCTCGAA TTAAAACGCG ATATTTGAAG     360
TCTTTCGGGC TTCCTCTTAA TCTTTTTGAT GCAATCCGCT TTGCTTCTGA CTATAATAGT     420
CAGGGTAAAG ACCTGATTTT TGATTTATGG TCATTCTCGT TTTCTGAACT GTTTAAAGCA     480
TTTGAGGGGG ATTCAATGAA TATTTATGAC GATTCCGCAG TATTGGACGC TATCCAGTCT     540
AAACATTTTA CTATTACCCC CTCTGGCAAA ACTTCTTTTG CAAAAGCCTC TCGCTATTTT     600
GGTTTTTATC GTCGTCTGGT AAACGAGGGT TATGATAGTG TTGCTCTTAC TATGCCTCGT     660
AATTCCTTTT GGCGTTATGT ATCTGCATTA GTTGAATGTG GTATTCCTAA ATCTCAACTG     720
ATGAATCTTT CTACCTGTAA TAATGTTGTT CCGTTAGTTC GTTTTATTAA CGTAGATTTT     780
TCTTCCCAAC GTCCTGACTG GTATAATGAG CCAGTTCTTA AAATCGCATA AGGTAATTCA     840
CAATGATTAA AGTTGAAATT AAACCATCTC AAGCCCAATT TACTACTCGT TCTGGTGTTT     900
CTCGTCAGGG CAAGCCTTAT TCACTGAATG AGCAGCTTTG TTACGTTGAT TTGGGTAATG     960
AATATCCGGT TCTTGTCAAG ATTACTCTTG ATGAAGGTCA GCCAGCCTAT GCGCCTGGTC    1020
TGTACACCGT TCATCTGTCC TCTTTCAAAG TTGGTCAGTT CGGTTCCCTT ATGATTGACC    1080
GTCTGCGCCT CGTTCCGGCT AAGTAACATG GAGCAGGTCG CGGATTTCGA CACAATTTAT    1140
CAGGCGATGA TACAAATCTC CGTTGTACTT TGTTTCGCGC TTGGTATAAT CGCTGGGGGT    1200
CAAAGATGAG TGTTTTAGTG TATTCTTTCG CCTCTTTCGT TTTAGGTTGG TGCCTTCGTA    1260
GTGGCATTAC GTATTTTACC CGTTTAATGG AAACTTCCTC ATGAAAAGT  CTTTAGTCCT    1320
CAAAGCCTCT GTAGCCGTTG CTACCCTCGT TCCGATGCTG TCTTTCGCTG CTGAGGGTGA    1380
CGATCCCGCA AAAGCGGCCT TTAACTCCCT GCAAGCCTCA GCGACCGAAT ATATCGGTTA    1440
TGCGTGGGCG ATGGTTGTTG TCATTGTCGG CGCAACTATC GGTATCAAGC TGTTTAAGAA    1500
ATTCACCTCG AAAGCAAGCT GATAAACCGA TACAATTAAA GGCTCCTTTT GGAGCCTTTT    1560
TTTTTGGAGA TTTTCAACGT GAAAAAATTA TTATTCGCAA TTCCTTTAGT TGTTCCTTTC    1620
TATTCTCACT CCGCTGAAAC TGTTGAAAGT TGTTTAGCAA ACCCCATAC  AGAAAATTCA    1680
TTTACTAACG TCTGGAAAGA CGACAAAACT TTAGATCGTT ACGCTAACTA TGAGGGTTGT    1740
CTGTGGAATG CTACAGGCGT TGTAGTTTGT ACTGGTGACG AAACTCAGTG TTACGGTACA    1800
TGGGTTCCTA TTGGGCTTGC TATCCCTGAA AATGAGGGTG GTGGCTCTGA GGGTGGCGGT    1860
TCTGAGGGTG GCGGTTCTGA GGGTGGCGGT ACTAAACCTC CTGAGTACGG TGATACACCT    1920
ATTCCGGGCT ATACTTATAT CAACCCTCTC GACGGCACTT ATCCGCCTGG TACTGAGCAA    1980
AACCCCGCTA ATCCTAATCC TTCTCTTGAG GAGTCTCAGC CTCTTAATAC TTTCATGTTT    2040
CAGAATAATA GGTTCCGAAA TAGGCAGGGG GCATTAACTG TTTATACGGG CACTGTTACT    2100
CAAGGCACTG ACCCCGTTAA AACTTATTAC CAGTACACTC CTGTATCATC AAAAGCCATG    2160
TATGACGCTT ACTGGAACGG TAAATTCAGA GACTGCGCTT TCCATTCTGG CTTTAATGAA    2220
GATCCATTCG TTTGTGAATA TCAAGGCCAA TCGTCTGACC TGCCTCAACC TCCTGTCAAT    2280
```

| | | | | | |
|---|---|---|---|---|---|
| GCTGGCGGCG | GCTCTGGTGG | TGGTTCTGGT | GGCGGCTCTG | AGGGTGGTGG | CTCTGAGGGT 2340 |
| GGCGGTTCTG | AGGGTGGCGG | CTCTGAGGGA | GGCGGTTCCG | GTGGTGGCTC | TGGTTCCGGT 2400 |
| GATTTTGATT | ATGAAAAGAT | GGCAAACGCT | AATAAGGGGG | CTATGACCGA | AAATGCCGAT 2460 |
| GAAAACGCGC | TACAGTCTGA | CGCTAAAGGC | AAACTTGATT | CTGTCGCTAC | TGATTACGGT 2520 |
| GCTGCTATCG | ATGGTTTCAT | TGGTGACGTT | TCCGGCCTTG | CTAATGGTAA | TGGTGCTACT 2580 |
| GGTGATTTTG | CTGGCTCTAA | TTCCCAAATG | GCTCAAGTCG | GTGACGGTGA | TAATTCACCT 2640 |
| TTAATGAATA | ATTTCCGTCA | ATATTTACCT | TCCCTCCCTC | AATCGGTTGA | ATGTCGCCCT 2700 |
| TTTGTCTTTA | GCGCTGGTAA | ACCATATGAA | TTTTCTATTG | ATTGTGACAA | AATAAACTTA 2760 |
| TTCCGTGGTG | TCTTTGCGTT | TCTTTTATAT | GTTGCCACCT | TTATGTATGT | ATTTTCTACG 2820 |
| TTTGCTAACA | TACTGCGTAA | TAAGGAGTCT | TAATCATGCC | AGTTCTTTTG | GGTATTCCGT 2880 |
| TATTATTGCG | TTTCCTCGGT | TTCCTTCTGG | TAACTTTGTT | CGGCTATCTG | CTTACTTTTC 2940 |
| TTAAAAAGGG | CTTCGGTAAG | ATAGCTATTG | CTATTTCATT | GTTCTTGCT | CTTATTATTG 3000 |
| GGCTTAACTC | AATTCTTGTG | GGTTATCTCT | CTGATATTAG | CGCTCAATTA | CCCTCTGACT 3060 |
| TTGTTCAGGG | TGTTCAGTTA | ATTCTCCCGT | CTAATGCGCT | TCCCTGTTTT | TATGTTATTC 3120 |
| TCTCTGTAAA | GGCTGCTATT | TTCATTTTTG | ACGTTAAACA | AAAAATCGTT | TCTTATTTGG 3180 |
| ATTGGGATAA | ATAATATGGC | TGTTTATTTT | GTAACTGGCA | AATTAGGCTC | TGGAAAGACG 3240 |
| CTCGTTAGCG | TTGGTAAGAT | TTAGGATAAA | ATTGTAGCTG | GGTGCAAAAT | AGCAACTAAT 3300 |
| CTTGATTTAA | GGCTTCAAAA | CCTCCCGCAA | GTCGGGAGGT | TCGCTAAAAC | GCCTCGCGTT 3360 |
| CTTAGAATAC | CGGATAAGCC | TTCTATATCT | GATTTGCTTG | CTATTGGGCG | CGGTAATGAT 3420 |
| TCCTACGATG | AAAATAAAAA | CGGCTTGCTT | GTTCTCGATG | AGTGCGGTAC | TTGGTTTAAT 3480 |
| ACCCGTTCTT | GGAATGATAA | GGAAAGACAG | CCGATTATTG | ATTGGTTTCT | ACATGCTCGT 3540 |
| AAATTAGGAT | GGGATATTAT | CTTCCTTGTT | CAGGACTTAT | CTATTGTTGA | TAAACAGGCG 3600 |
| CGTTCTGCAT | TAGCTGAACA | TGTTGTTTAT | TGTCGTCGTC | TGGACAGAAT | TACTTTACCT 3660 |
| TTTGTCGGTA | CTTTATATTC | TCTTATTACT | GGCTCGAAAA | TGCCTCTGCC | TAAATTACAT 3720 |
| GTTGGCGTTG | TTAAATATGG | CGATTCTCAA | TTAAGCCCTA | CTGTTGAGCG | TTGGCTTTAT 3780 |
| ACTGGTAAGA | ATTTGTATAA | CGCATATGAT | ACTAAACAGG | CTTTTTCTAG | TAATTATGAT 3840 |
| TCCGGTGTTT | ATTCTTATTT | AACGCCTTAT | TTATCACACG | GTCGGTATTT | CAAACCATTA 3900 |
| AATTTAGGTC | AGAAGATGAA | ATTAACTAAA | ATATATTTGA | AAAAGTTTTC | TCGCGTTCTT 3960 |
| TGTCTTGCGA | TTGGATTTGC | ATCAGCATTT | ACATATAGTT | ATATAACCCA | ACCTAAGCCG 4020 |
| GAGGTTAAAA | AGGTAGTCTC | TCAGACCTAT | GATTTTGATA | AATTCACTAT | TGACTCTTCT 4080 |
| CAGCGTCTTA | ATCTAAGCTA | TCGCTATGTT | TTCAAGGATT | CTAAGGGAAA | ATTAATTAAT 4140 |
| AGCGACGATT | TACAGAAGCA | AGGTTATTCA | CTCACATATA | TTGATTTATG | TACTGTTTCC 4200 |
| ATTAAAAAAG | GTAATTCAAA | TGAAATTGTT | AAATGTAATT | AATTTTGTTT | TCTTGATGTT 4260 |
| TGTTTCATCA | TCTTCTTTTG | CTCAGGTAAT | TGAAATGAAT | AATTCGCCTC | TGCGCGATTT 4320 |
| TGTAACTTGG | TATTCAAAGC | AATCAGGCGA | ATCCGTTATT | GTTTCTCCCG | ATGTAAAAGG 4380 |
| TACTGTTACT | GTATATTCAT | CTGACGTTAA | ACCTGAAAAT | CTACGCAATT | TCTTTATTTC 4440 |
| TGTTTTACGT | GCTAATAATT | TTGATATGGT | TGGTTCAATT | CCTTCCATAA | TTCAGAAGTA 4500 |
| TAATCCAAAC | AATCAGGATT | ATATTGATGA | ATTGCCATCA | TCTGATAATC | AGGAATATGA 4560 |
| TGATAATTCC | GCTCCTTCTG | GTGGTTTCTT | TGTTCCGCAA | AATGATAATG | TTACTCAAAC 4620 |
| TTTTAAAATT | AATAACGTTC | GGGCAAAGGA | TTTAATACGA | GTTGTCGAAT | TGTTTGTAAA 4680 |

```
GTCTAATACT TCTAAATCCT CAAATGTATT ATCTATTGAC GGCTCTAATC TATTAGTTGT    4740
TAGTGCACCT AAAGATATTT TAGATAACCT TCCTCAATTC CTTTCTACTG TTGATTTGCC    4800
AACTGACCAG ATATTGATTG AGGGTTTGAT ATTTGAGGTT CAGCAAGGTG ATGCTTTAGA    4860
TTTTTCATTT GCTGCTGGCT CTCAGCGTGG CACTGTTGCA GGCGGTGTTA ATACTGACCG    4920
CCTCACCTCT GTTTTATCTT CTGCTGGTGG TTCGTTCGGT ATTTTAATG GCGATGTTTT     4980
AGGGCTATCA GTTCGCGCAT TAAAGACTAA TAGCCATTCA AAATATTGT CTGTGCCACG     5040
TATTCTTACG CTTTCAGGTC AGAAGGGTTC TATCTCTGTT GGCCAGAATG TCCCTTTTAT    5100
TACTGGTCGT GTGACTGGTG AATCTGCCAA TGTAAATAAT CCATTTCAGA CGATTGAGCG    5160
TCAAAATGTA GGTATTTCCA TGAGCGTTTT TCCTGTTGCA ATGGCTGGCG GTAATATTGT    5220
TCTGGATATT ACCAGCAAGG CCGATAGTTT GAGTTCTTCT ACTCAGGCAA GTGATGTTAT    5280
TACTAATCAA AGAAGTATTG CTACAACGGT TAATTTGCGT GATGGACAGA CTCTTTTACT    5340
CGGTGGCCTC ACTGATTATA AAAACACTTC TCAAGATTCT GGCGTACCGT TCCTGTCTAA    5400
AATCCCTTTA ATCGGCCTCC TGTTTAGCTC CCGCTCTGAT TCCAACGAGG AAAGCACGTT    5460
ATACGTGCTC GTCAAAGCAA CCATAGTACG CGCCCTGTAG CGGCGCATTA AGCGCGGCGG    5520
GTGTGGTGGT TACGCGCAGC GTGACCGCTA CACTTGCCAG CGCCCTAGCG CCCGCTCCTT    5580
TCGCTTTCTT CCCTTCCTTT CTCGCCACGT TCGCCGGCTT TCCCCGTCAA GCTCTAAATC    5640
GGGGGCTCCC TTTAGGGTTC CGATTTAGTG CTTTACGGCA CCTCGACCCC AAAAAACTTG    5700
ATTTGGGTGA TGGTTCACGT AGTGGGCCAT CGCCCTGATA GACGGTTTTT CGCCCTTTGA    5760
CGTTGGAGTC CACGTTCTTT AATAGTGGAC TCTTGTTCCA AACTGGAACA ACACTCAACC    5820
CTATCTCGGG CTATTCTTTT GATTTATAAG GGATTTTGCC GATTTCGGAA CCACCATCAA    5880
ACAGGATTTT CGCCTGCTGG GGCAAACCAG CGTGGACCGC TTGCTGCAAC TCTCTCAGGG    5940
CCAGGCGGTG AAGGGCAATC AGCTGTTGCC CGTCTCGCTG GTGAAAAGAA AAACCACCCT    6000
GGCGCCCAAT ACGCAAACCG CCTCTCCCCG CGCGTTGGCC GATTCATTAA TGCAGCTGGC    6060
ACGACAGGTT TCCCGACTGG AAAGCGGGCA GTGAGCGCAA CGCAATTAAT GTGAGTTAGC    6120
TCACTCATTA GGCACCCCAG GCTTTACACT TTATGCTTCC GGCTCGTATG TTGTGTGGAA    6180
TTGTGAGCGG ATAACAATTT CACACGCCAA GGAGACAGTC ATAATGAAAT ACCTATTGCC    6240
TACGGCAGCC GCTGGATTGT TATTACTCGC TGCCCAACCA GCCATGGCCG AGCTCGTGAT    6300
GACCCAGACT CCAGAATTCC ATCCGGAATG AGTGTTAATT CTAGAACGCG TAAGCTTGGC    6360
ACTGGCCGTC GTTTTACAAC GTCGTGACTG GGAAAACCCT GGCGTTACCC AACTTAATCG    6420
CCTTGCAGCA CACCCCCCTT TCGCCAGCTG GCGTAATAGC GAAGAGGCCC GCACCGATCG    6480
CCCTTCCCAA CAGTTGCGCA GCCTGAATGG CGAATGGCGC TTTGCCTGGT TCCGGCACC     6540
AGAAGCGGTG CCGGAAAGCT GGCTGGAGTG CGATCTTCCT GAGGCCGATA CGGTCGTCGT    6600
CCCCTCAAAC TGGCAGATGC ACGGTTACGA TGCGCCCATC TACACCAACG TAACCTATCC    6660
CATTACGGTC AATCCGCCGT TTGTTCCCAC GGAGAATCCG ACGGGTTGTT ACTCGCTCAC    6720
ATTTAATGTT GATGAAAGCT GGCTACAGGA AGGCCAGACG CGAATTATTT TTGATGGCGT    6780
TCCTATTGGT TAAAAAATGA GCTGATTTAA CAAAAATTTA ACGCGAATTT TAACAAAATA    6840
TTAACGTTTA CAATTTAAAT ATTTGCTTAT ACAATCTTCC TGTTTTTGGG GCTTTTCTGA    6900
TTATCAACCG GGGTACATAT GATTGACATG CTAGTTTTAC GATTACCGTT CATCGATTCT    6960
CTTGTTTGCT CCAGACTCTC AGGCAATGAC CTGATAGCCT TTGTAGATCT CTCAAAAATA    7020
GCTACCCTCT CCGGCATTAA TTTATCAGCT AGAACGGTTG AATATCATAT TGATGGTGAT    7080
```

| | | | | | |
|---|---|---|---|---|---|
| TTGACTGTCT | CCGGCCTTTC | TCACCCTTTT | GAATCTTTAC | CTACACATTA | CTCAGGCATT | 7140
| GCATTTAAAA | TATATGAGGG | TTCTAAAAAT | TTTTATCCTT | GCGTTGAAAT | AAAGGCTTCT | 7200
| CCCGCAAAAG | TATTACAGGG | TCATAATGTT | TTTGGTACAA | CCGATTAGC | TTTATGCTCT | 7260
| GAGGCTTTAT | TGCTTAATTT | TGCTAATTCT | TTGCCTTGCC | TGTATGATTT | ATTGGACGTT | 7320

(2) INFORMATION FOR SEQ ID NO:3:

(i) SEQUENCE CHARACTERISTICS:
        (A) LENGTH: 7445 base pairs
        (B) TYPE: nucleic acid
        (C) STRANDEDNESS: both
        (D) TOPOLOGY: circular (xi) SEQUENCE DESCRIPTION: SEQ ID NO:3:

| | | | | | |
|---|---|---|---|---|---|
| AATGCTACTA | CTATTAGTAG | AATTGATGCC | ACCTTTTCAG | CTCGCGCCCC | AAATGAAAAT | 60
| ATAGCTAAAC | AGGTTATTGA | CCATTTGCGA | AATGTATCTA | ATGGTCAAAC | TAAATCTACT | 120
| CGTTCGCAGA | ATTGGGAATC | AACTGTTACA | TGGAATGAAA | CTTCCAGACA | CCGTACTTTA | 180
| GTTGCATATT | TAAAACATGT | TGAGCTACAG | CACCAGATTC | AGCAATTAAG | CTCTAAGCCA | 240
| TCTGCAAAAA | TGACCTCTTA | TCAAAGGAG | CAATTAAAGG | TACTCTCTAA | TCCTGACCTG | 300
| TTGGAGTTTG | CTTCCGGTCT | GGTTCGCTTT | GAAGCTCGAA | TTAAAACGCG | ATATTTGAAG | 360
| TCTTTCGGGC | TTCCTCTTAA | TCTTTTTGAT | GCAATCCGCT | TTGCTTCTGA | CTATAATAGT | 420
| CAGGGTAAAG | ACCTGATTTT | TGATTATGG | TCATTCTCGT | TTTCTGAACT | GTTTAAAGCA | 480
| TTTGAGGGGG | ATTCAATGAA | TATTTATGAC | GATTCCGCAG | TATTGGACGC | TATCCAGTCT | 540
| AAACATTTTA | CTATTACCCC | CTCTGGCAAA | ACTTCTTTTG | CAAAAGCCTC | TCGCTATTTT | 600
| GGTTTTTATC | GTCGTCTGGT | AAACGAGGGT | TATGATAGTG | TTGCTCTTAC | TATGCCTCGT | 660
| AATTCCTTTT | GGCGTTATGT | ATCTGCATTA | GTTGAATGTG | GTATTCCTAA | ATCTCAACTG | 720
| ATGAATCTTT | CTACCTGTAA | TAATGTTGTT | CCGTTAGTTC | GTTTTATTAA | CGTAGATTTT | 780
| TCTTCCCAAC | GTCCTGACTG | GTATAATGAG | CCAGTTCTTA | AAATCGCATA | AGGTAATTCA | 840
| CAATGATTAA | AGTTGAAATT | AAACCATCTC | AAGCCCAATT | TACTACTCGT | TCTGGTGTTT | 900
| CTCGTCAGGG | CAAGCCTTAT | TCACTGAATG | AGCAGCTTTG | TTACGTTGAT | TGGGTAATG | 960
| AATATCCGGT | TCTTGTCAAG | ATTACTCTTG | ATGAAGGTCA | GCCAGCCTAT | GCGCCTGGTC | 1020
| TGTACACCGT | TCATCTGTCC | TCTTTCAAAG | TTGGTCAGTT | CGGTTCCCTT | ATGATTGACC | 1080
| GTCTGCGCCT | CGTTCCGGCT | AAGTAACATG | GAGCAGGTCG | CGGATTTCGA | CACAATTTAT | 1140
| CAGGCGATGA | TACAAATCTC | CGTTGTACTT | TGTTTCGCGC | TTGGTATAAT | CGCTGGGGGT | 1200
| CAAAGATGAG | TGTTTTAGTG | TATTCTTTCG | CCTCTTTCGT | TTAGGTTGG | TGCCTTCGTA | 1260
| GTGGCATTAC | GTATTTTACC | CGTTTAATGG | AAACTTCCTC | ATGAAAAGT | CTTTAGTCCT | 1320
| CAAAGCCTCT | GTAGCCGTTG | CTACCCTCGT | TCCGATGCTG | TCTTTCGCTG | CTGAGGGTGA | 1380
| CGATCCCGCA | AAAGCGGCCT | TTAACTCCCT | GCAAGCCTCA | GCGACCGAAT | ATATCGGTTA | 1440
| TGCGTGGGCG | ATGGTTGTTG | TCATTGTCGG | CGCAACTATC | GGTATCAAGC | TGTTTAAGAA | 1500
| ATTCACCTCG | AAAGCAAGCT | GATAAACCGA | TACAATTAAA | GGCTCCTTTT | GGAGCCTTTT | 1560
| TTTTGGAGA | TTTTCAACGT | GAAAAAATTA | TTATTCGCAA | TTCCTTAGT | TGTTCCTTTC | 1620
| TATTCTCACT | CCGCTGAAAC | TGTTGAAAGT | TGTTTAGCAA | AACCCCATAC | AGAAAATTCA | 1680
| TTTACTAACG | TCTGGAAAGA | CGACAAAACT | TTAGATCGTT | ACGCTAACTA | TGAGGGTTGT | 1740
| CTGTGGAATG | CTACAGGCGT | TGTAGTTTGT | ACTGGTGACG | AAACTCAGTG | TTACGGTACA | 1800

```
TGGGTTCCTA TTGGGCTTGC TATCCCTGAA AATGAGGGTG GTGGCTCTGA GGGTGGCGGT    1860
TCTGAGGGTG GCGGTTCTGA GGGTGGCGGT ACTAAACCTC CTGAGTACGG TGATACACCT    1920
ATTCCGGGCT ATACTTATAT CAACCCTCTC GACGGCACTT ATCCGCCTGG TACTGAGCAA    1980
AACCCCGCTA ATCCTAATCC TTCTCTTGAG GAGTCTCAGC CTCTTAATAC TTTCATGTTT    2040
CAGAATAATA GGTTCCGAAA TAGGCAGGGG GCATTAACTG TTTATACGGG CACTGTTACT    2100
CAAGGCACTG ACCCGTTAA  AACTTATTAC CAGTACACTC CTGTATCATC AAAAGCCATG    2160
TATGACGCTT ACTGGAACGG TAAATTCAGA GACTGCGCTT TCCATTCTGG CTTTAATGAA    2220
GATCCATTCG TTTGTGAATA TCAAGGCCAA TCGTCTGACC TGCCTCAACC TCCTGTCAAT    2280
GCTGGCGGCG GCTCTGGTGG TGGTTCTGGT GGCGGCTCTG AGGGTGGTGG CTCTGAGGGT    2340
GGCGGTTCTG AGGGTGGCGG CTCTGAGGGA GGCGGTTCCG GTGGTGGCTC TGGTTCCGGT    2400
GATTTTGATT ATGAAAAGAT GGCAAACGCT AATAAGGGGG CTATGACCGA AAATGCCGAT    2460
GAAAACGCGC TACAGTCTGA CGCTAAAGGC AAACTTGATT CTGTCGCTAC TGATTACGGT    2520
GCTGCTATCG ATGGTTTCAT TGGTGACGTT TCCGGCCTTG CTAATGGTAA TGGTGCTACT    2580
GGTGATTTTG CTGGCTCTAA TTCCCAAATG GCTCAAGTCG GTGACGGTGA TAATTCACCT    2640
TTAATGAATA ATTTCCGTCA ATATTTACCT TCCCTCCCTC AATCGGTTGA ATGTCGCCCT    2700
TTTGTCTTTA GCGCTGGTAA ACCATATGAA TTTTCTATTG ATTGTGACAA AATAAACTTA    2760
TTCCGTGGTG TCTTTGCGTT TCTTTTATAT GTTGCCACCT TTATGTATGT ATTTTCTACG    2820
TTTGCTAACA TACTGCGTAA TAAGGAGTCT TAATCATGCC AGTTCTTTTG GGTATTCCGT    2880
TATTATTGCG TTTCCTCGGT TTCCTTCTGG TAACTTTGTT CGGCTATCTG CTTACTTTTC    2940
TTAAAAAGGG CTTCGGTAAG ATAGCTATTG CTATTTCATT GTTTCTTGCT CTTATTATTG    3000
GGCTTAACTC AATTCTTGTG GGTTATCTCT CTGATATTAG CGCTCAATTA CCCTCTGACT    3060
TTGTTCAGGG TGTTCAGTTA ATTCTCCCGT CTAATGCGCT TCCCTGTTTT TATGTTATTC    3120
TCTCTGTAAA GGCTGCTATT TTCATTTTTG ACGTTAAACA AAAAATCGTT TCTTATTTGG    3180
ATTGGGATAA ATAATATGGC TGTTTATTTT GTAACTGGCA AATTAGGCTC TGGAAAGACG    3240
CTCGTTAGCG TTGGTAAGAT TCAGGATAAA ATTGTAGCTG GGTGCAAAAT AGCAACTAAT    3300
CTTGATTTAA GGCTTCAAAA CCTCCCGCAA GTCGGGAGGT TCGCTAAAAC GCCTCGCGTT    3360
CTTAGAATAC CGGATAAGCC TTCTATATCT GATTTGCTTG CTATTGGGCG CGGTAATGAT    3420
TCCTACGATG AAAATAAAAA CGGCTTGCTT GTTCTCGATG AGTGCGGTAC TTGGTTTAAT    3480
ACCCGTTCTT GGAATGATAA GGAAAGACAG CCGATTATTG ATTGGTTTCT ACATGCTCGT    3540
AAATTAGGAT GGGATATTAT TTTTCTTGTT CAGGACTTAT CTATTGTTGA TAAACAGGCG    3600
CGTTCTGCAT TAGCTGAACA TGTTGTTTAT TGTCGTCGTC TGGACAGAAT TACTTTACCT    3660
TTTGTCGGTA CTTTATATTC TCTTATTACT GGCTCGAAAA TGCCTCTGCC TAAATTACAT    3720
GTTGGCGTTG TTAAATATGG CGATTCTCAA TTAAGCCCTA CTGTTGAGCG TTGGCTTTAT    3780
ACTGGTAAGA ATTTGTATAA CGCATATGAT ACTAAACAGG CTTTTTCTAG TAATTATGAT    3840
TCCGGTGTTT ATTCTTATTT AACGCCTTAT TTATCACACG GTCGGTATTT CAAACCATTA    3900
AATTTAGGTC AGAAGATGAA GCTTACTAAA ATATATTTGA AAAAGTTTTC ACGCGTTCTT    3960
TGTCTTGCGA TTGGATTTGC ATCAGCATTT ACATATAGTT ATATAACCCA ACCTAAGCCG    4020
GAGGTTAAAA AGGTAGTCTC TCAGACCTAT GATTTTGATA AATTCACTAT TGACTCTTCT    4080
CAGCGTCTTA ATCTAAGCTA TCGCTATGTT TTCAAGGATT CTAAGGGAAA ATTAATTAAT    4140
AGCGACGATT TACAGAAGCA AGGTTATTCA CTCACATATA TTGATTTATG TACTGTTTCC    4200
```

```
ATTAAAAAAG GTAATTCAAA TGAAATTGTT AAATGTAATT AATTTTGTTT TCTTGATGTT    4260
TGTTTCATCA TCTTCTTTTG CTCAGGTAAT TGAAATGAAT AATTCGCCTC TGCGCGATTT    4320
TGTAACTTGG TATTCAAAGC AATCAGGCGA ATCCGTTATT GTTTCTCCCG ATGTAAAGG     4380
TACTGTTACT GTATATTCAT CTGACGTTAA ACCTGAAAAT CTACGCAATT TCTTTATTTC    4440
TGTTTTACGT GCTAATAATT TTGATATGGT TGGTTCAATT CCTTCCATAA TTCAGAAGTA    4500
TAATCCAAAC AATCAGGATT ATATTGATGA ATTGCCATCA TCTGATAATC AGGAATATGA    4560
TGATAATTCC GCTCCTTCTG GTGGTTTCTT TGTTCCGCAA AATGATAATG TTACTCAAAC    4620
TTTTAAAATT AATAACGTTC GGGCAAAGGA TTTAATACGA GTTGTCGAAT TGTTTGTAAA    4680
GTCTAATACT TCTAAATCCT CAAATGTATT ATCTATTGAC GGCTCTAATC TATTAGTTGT    4740
TAGTGCACCT AAAGATATTT TAGATAACCT TCCTCAATTC CTTTCTACTG TTGATTTGCC    4800
AACTGACCAG ATATTGATTG AGGGTTTGAT ATTTGAGGTT CAGCAAGGTG ATGCTTTAGA    4860
TTTTTCATTT GCTGCTGGCT CTCAGCGTGG CACTGTTGCA GGCGGTGTTA ATACTGACCG    4920
CCTCACCTCT GTTTTATCTT CTGCTGGTGG TTCGTTCGGT ATTTTTAATG GCGATGTTTT    4980
AGGGCTATCA GTTCGCGCAT TAAAGACTAA TAGCCATTCA AAAATATTGT CTGTGCCACG    5040
TATTCTTACG CTTTCAGGTC AGAAGGGTTC TATCTCTGTT GGCCAGAATG TCCCTTTTAT    5100
TACTGGTCGT GTGACTGGTG AATCTGCCAA TGTAAATAAT CCATTTCAGA CGATTGAGCG    5160
TCAAAATGTA GGTATTTCCA TGAGCGTTTT TCCTGTTGCA ATGGCTGGCG GTAATATTGT    5220
TCTGGATATT ACCAGCAAGG CCGATAGTTT GAGTTCTTCT ACTCAGGCAA GTGATGTTAT    5280
TACTAATCAA AGAAGTATTG CTACAACGGT TAATTTGCGT GATGGACAGA CTCTTTTACT    5340
CGGTGGCCTC ACTGATTATA AAAACACTTC TCAAGATTCT GGCGTACCGT TCCTGTCTAA    5400
AATCCCTTTA ATCGGCCTCC TGTTTAGCTC CCGCTCTGAT TCCAACGAGG AAAGCACGTT    5460
ATACGTGCTC GTCAAAGCAA CCATAGTACG CGCCCTGTAG CGGCGCATTA AGCGCGGCGG    5520
GTGTGGTGGT TACGCGCAGC GTGACCGCTA CACTTGCCAG CGCCCTAGCG CCCGCTCCTT    5580
TCGCTTTCTT CCCTTCCTTT CTCGCCACGT TCGCCGGCTT TCCCCGTCAA GCTCTAAATC    5640
GGGGGCTCCC TTTAGGGTTC CGATTTAGTG CTTTACGGCA CCTCGACCCC AAAAAACTTG    5700
ATTTGGGTGA TGGTTCACGT AGTGGGCCAT CGCCCTGATA GACGGTTTTT CGCCCTTTGA    5760
CGTTGGAGTC CACGTTCTTT AATAGTGGAC TCTTGTTCCA AACTGGAACA ACACTCAACC    5820
CTATCTCGGG CTATTCTTTT GATTTATAAG GGATTTTGCC GATTTCGGAA CCACCATCAA    5880
ACAGGATTTT CGCCTGCTGG GGCAAACCAG CGTGGACCGC TTGCTGCAAC TCTCTCAGGG    5940
CCAGGCGGTG AAGGGCAATC AGCTGTTGCC CGTCTCGCTG GTGAAAAGAA AAACCACCCT    6000
GGCGCCCAAT ACGCAAACCG CCTCTCCCCG CGCGTTGGCC GATTCATTAA TGCAGCTGGC    6060
ACGACAGGTT TCCCGACTGG AAAGCGGGCA GTGAGCGCAA CGCAATTAAT GTGAGTTAGC    6120
TCACTCATTA GGCACCCCAG GCTTTACACT TTATGCTTCC GGCTCGTATG TTGTGTGGAA    6180
TTGTGAGCGG ATAACAATTT CACACGCGTC ACTTGGCACT GGCCGTCGTT TTACAACGTC    6240
GTGACTGGGA AAACCCTGGC GTTACCCAAG CTTTGTACAT GGAGAAAATA AAGTGAAACA    6300
AAGCACTATT GCACTGGCAC TCTTACCGTT ACCGTTACTG TTTACCCCTG TGACAAAAGC    6360
CGCCCAGGTC CAGCTGCTCG AGTCAGGCCT ATTGTGCCCA GGGGATTGTA CTAGTGGATC    6420
CTAGGCTGAA GGCGATGACC CTGCTAAGGC TGCATTCAAT AGTTTACAGG CAAGTGCTAC    6480
TGAGTACATT GGCTACGCTT GGGCTATGGT AGTAGTTATA GTTGGTGCTA CCATAGGGAT    6540
TAAATTATTC AAAAAGTTTA CGAGCAAGGC TTCTTAAGCA ATAGCGAAGA GGCCCGCACC    6600
```

| | | | | | | |
|---|---|---|---|---|---|---|
| GATCGCCCTT | CCCAACAGTT | GCGCAGCCTG | AATGGCGAAT | GGCGCTTTGC | CTGGTTTCCG | 6660 |
| GCACCAGAAG | CGGTGCCGGA | AAGCTGGCTG | GAGTGCGATC | TTCCTGAGGC | CGATACGGTC | 6720 |
| GTCGTCCCCT | CAAACTGGCA | GATGCACGGT | TACGATGCGC | CCATCTACAC | CAACGTAACC | 6780 |
| TATCCCATTA | CGGTCAATCC | GCCGTTTGTT | CCCACGGAGA | ATCCGACGGG | TTGTTACTCG | 6840 |
| CTCACATTTA | ATGTTGATGA | AAGCTGGCTA | CAGGAAGGCC | AGACGCGAAT | TATTTTTGAT | 6900 |
| GGCGTTCCTA | TTGGTTAAAA | AATGAGCTGA | TTAACAAAA | ATTTAACGCG | AATTTTAACA | 6960 |
| AAATATTAAC | GTTACAATT | TAAATATTTG | CTTATACAAT | CTTCCTGTTT | TGGGGCTTT | 7020 |
| TCTGATTATC | AACCGGGGTA | CATATGATTG | ACATGCTAGT | TTTACGATTA | CCGTTCATCG | 7080 |
| ATTCTCTTGT | TTGCTCCAGA | CTCTCAGGCA | ATGACCTGAT | AGCCTTTGTA | GATCTCTCAA | 7140 |
| AAATAGCTAC | CCTCTCCGGC | ATTAATTTAT | CAGCTAGAAC | GGTTGAATAT | CATATTGATG | 7200 |
| GTGATTTGAC | TGTCTCCGGC | CTTTCTCACC | CTTTTGAATC | TTTACCTACA | CATTACTCAG | 7260 |
| GCATTGCATT | TAAAATATAT | GAGGGTTCTA | AAAATTTTA | TCCTTGCGTT | GAAATAAAGG | 7320 |
| CTTCTCCCGC | AAAAGTATTA | CAGGGTCATA | ATGTTTTGG | TACAACCGAT | TTAGCTTTAT | 7380 |
| GCTCTGAGGC | TTTATTGCTT | AATTTGCTA | ATTCTTTGCC | TTGCCTGTAT | GATTTATTGG | 7440 |
| ACGTT | | | | | | 7445 |

( 2 ) INFORMATION FOR SEQ ID NO:4:

( i ) SEQUENCE CHARACTERISTICS:
        ( A ) LENGTH: 7409 base pairs
        ( B ) TYPE: nucleic acid
        ( C ) STRANDEDNESS: both
        ( D ) TOPOLOGY: circular ( x i ) SEQUENCE DESCRIPTION: SEQ ID NO:4:

| | | | | | | |
|---|---|---|---|---|---|---|
| AATGCTACTA | CTATTAGTAG | AATTGATGCC | ACCTTTTCAG | CTCGCGCCCC | AAATGAAAAT | 60 |
| ATAGCTAAAC | AGGTTATTGA | CCATTTGCGA | AATGTATCTA | ATGGTCAAAC | TAAATCTACT | 120 |
| CGTTCGCAGA | ATTGGGAATC | AACTGTTACA | TGGAATGAAA | CTTCCAGACA | CCGTACTTTA | 180 |
| GTTGCATATT | TAAAACATGT | TGAGCTACAG | CACCAGATTC | AGCAATTAAG | CTCTAAGCCA | 240 |
| TCTGCAAAAA | TGACCTCTTA | TCAAAGGAG | CAATTAAAGG | TACTCTCTAA | TCCTGACCTG | 300 |
| TTGGAGTTTG | CTTCCGGTCT | GGTTCGCTTT | GAAGCTCGAA | TTAAAACGCG | ATATTTGAAG | 360 |
| TCTTTCGGGC | TTCCTCTTAA | TCTTTTTGAT | GCAATCCGCT | TTGCTTCTGA | CTATAATAGT | 420 |
| CAGGGTAAAG | ACCTGATTTT | TGATTATGG | TCATTCTCGT | TTTCTGAACT | GTTTAAAGCA | 480 |
| TTTGAGGGGG | ATTCAATGAA | TATTTATGAC | GATTCCGCAG | TATTGGACGC | TATCCAGTCT | 540 |
| AAACATTTTA | CTATTACCCC | CTCTGGCAAA | ACTTCTTTTG | CAAAAGCCTC | TCGCTATTTT | 600 |
| GGTTTTTATC | GTCGTCTGGT | AAACGAGGGT | TATGATAGTG | TTGCTCTTAC | TATGCCTCGT | 660 |
| AATTCCTTTT | GGCGTTATGT | ATCTGCATTA | GTTGAATGTG | GTATTCCTAA | ATCTCAACTG | 720 |
| ATGAATCTTT | CTACCTGTAA | TAATGTTGTT | CCGTTAGTTC | GTTTTATTAA | CGTAGATTTT | 780 |
| TCTTCCCAAC | GTCCTGACTG | GTATAATGAG | CCAGTTCTTA | AAATCGCATA | AGGTAATTCA | 840 |
| CAATGATTAA | AGTTGAAATT | AAACCATCTC | AAGCCCAATT | TACTACTCGT | TCTGGTGTTT | 900 |
| CTCGTCAGGG | CAAGCCTTAT | TCACTGAATG | AGCAGCTTTG | TTACGTTGAT | TTGGGTAATG | 960 |
| AATATCCGGT | TCTTGTCAAG | ATTACTCTTG | ATGAAGGTCA | GCCAGCCTAT | GCGCCTGGTC | 1020 |
| TGTACACCGT | TCATCTGTCC | TCTTTCAAAG | TTGGTCAGTT | CGGTTCCCTT | ATGATTGACC | 1080 |
| GTCTGCGCCT | CGTTCCGGCT | AAGTAACATG | GAGCAGGTCG | CGGATTTCGA | CACAATTTAT | 1140 |
| CAGGCGATGA | TACAAATCTC | CGTTGTACTT | TGTTTCGCGC | TTGGTATAAT | CGCTGGGGGT | 1200 |

```
CAAAGATGAG TGTTTTAGTG TATTCTTTCG CCTCTTTCGT TTTAGGTTGG TGCCTTCGTA   1260
GTGGCATTAC GTATTTTACC CGTTTAATGG AAACTTCCTC ATGAAAAAGT CTTTAGTCCT   1320
CAAAGCCTCT GTAGCCGTTG CTACCCTCGT TCCGATGCTG TCTTTCGCTG CTGAGGGTGA   1380
CGATCCCGCA AAAGCGGCCT TAACTCCCT GCAAGCCTCA GCGACCGAAT ATATCGGTTA   1440
TGCGTGGGCG ATGGTTGTTG TCATTGTCGG CGCAACTATC GGTATCAAGC TGTTTAAGAA   1500
ATTCACCTCG AAAGCAAGCT GATAAACCGA TACAATTAAA GGCTCCTTTT GGAGCCTTTT   1560
TTTTTGGAGA TTTTCAACGT GAAAAATTA TTATTCGCAA TTCCTTTAGT TGTTCCTTTC    1620
TATTCTCACT CCGCTGAAAC TGTTGAAAGT TGTTTAGCAA AACCCCATAC AGAAAATTCA   1680
TTTACTAACG TCTGGAAAGA CGACAAAACT TTAGATCGTT ACGCTAACTA TGAGGGTTGT   1740
CTGTGGAATG CTACAGGCGT TGTAGTTTGT ACTGGTGACG AAACTCAGTG TTACGGTACA   1800
TGGGTTCCTA TTGGGCTTGC TATCCCTGAA AATGAGGGTG GTGGCTCTGA GGGTGGCGGT   1860
TCTGAGGGTG GCGGTTCTGA GGGTGGCGGT ACTAAACCTC CTGAGTACGG TGATACACCT   1920
ATTCCGGGCT ATACTTATAT CAACCCTCTC GACGGCACTT ATCCGCCTGG TACTGAGCAA   1980
AACCCCGCTA ATCCTAATCC TTCTCTTGAG GAGTCTCAGC CTCTTAATAC TTTCATGTTT   2040
CAGAATAATA GGTTCCGAAA TAGGCAGGGG GCATTAACTG TTTATACGGG CACTGTTACT   2100
CAAGGCACTG ACCCGTTAA AACTTATTAC CAGTACACTC CTGTATCATC AAAAGCCATG    2160
TATGACGCTT ACTGGAACGG TAAATTCAGA GACTGCGCTT TCCATTCTGG CTTTAATGAA   2220
GATCCATTCG TTTGTGAATA TCAAGGCCAA TCGTCTGACC TGCCTCAACC TCCTGTCAAT   2280
GCTGGCGGCG GCTCTGGTGG TGGTTCTGGT GGCGGCTCTG AGGGTGGTGG CTCTGAGGGT   2340
GGCGGTTCTG AGGGTGGCGG CTCTGAGGGA GGCGGTTCCG GTGGTGGCTC TGGTTCCGGT   2400
GATTTTGATT ATGAAAAGAT GGCAAACGCT AATAAGGGGG CTATGACCGA AAATGCCGAT   2460
GAAAACGCGC TACAGTCTGA CGCTAAAGGC AAACTTGATT CTGTCGCTAC TGATTACGGT   2520
GCTGCTATCG ATGGTTTCAT TGGTGACGTT TCCGGCCTTG CTAATGGTAA TGGTGCTACT   2580
GGTGATTTTG CTGGCTCTAA TTCCCAAATG GCTCAAGTCG GTGACGGTGA TAATTCACCT   2640
TTAATGAATA ATTTCCGTCA ATATTTACCT TCCCTCCCTC AATCGGTTGA ATGTCGCCCT   2700
TTTGTCTTTA GCGCTGGTAA ACCATATGAA TTTTCTATTG ATTGTGACAA AATAAACTTA   2760
TTCCGTGGTG TCTTTGCGTT TCTTTTATAT GTTGCCACCT TTATGTATGT ATTTTCTACG   2820
TTTGCTAACA TACTGCGTAA TAAGGAGTCT TAATCATGCC AGTTCTTTTG GGTATTCCGT   2880
TATTATTGCG TTTCCTCGGT TTCCTTCTGG TAACTTTGTT CGGCTATCTG CTTACTTTTC   2940
TTAAAAAGGG CTTCGGTAAG ATAGCTATTG CTATTTCATT GTTTCTTGCT CTTATTATTG   3000
GGCTTAACTC AATTCTTGTG GGTTATCTCT CTGATATTAG CGCTCAATTA CCCTCTGACT   3060
TTGTTCAGGG TGTTCAGTTA ATTCTCCCGT CTAATGCGCT TCCCTGTTTT TATGTTATTC   3120
TCTCTGTAAA GGCTGCTATT TTCATTTTTG ACGTTAAACA AAAAATCGTT TCTTATTTGG   3180
ATTGGGATAA ATAATATGGC TGTTTATTTT GTAACTGGCA AATTAGGCTC TGGAAAGACG   3240
CTCGTTAGCG TTGGTAAGAT TCAGGATAAA ATTGTAGCTG GGTGCAAAAT AGCAACTAAT   3300
CTTGATTTAA GGCTTCAAAA CCTCCCGCAA GTCGGGAGGT TCGCTAAAAC GCCTCGCGTT   3360
CTTAGAATAC CGGATAAGCC TTCTATATCT GATTTGCTTG CTATTGGGCG CGGTAATGAT   3420
TCCTACGATG AAAATAAAAA CGGCTTGCTT GTTCTCGATG AGTGCGGTAC TTGGTTTAAT   3480
ACCCGTTCTT GGAATGATAA GGAAAGACAG CCGATTATTG ATTGGTTTCT ACATGCTCGT   3540
AAATTAGGAT GGGATATTAT TTTTCTTGTT CAGGACTTAT CTATTGTTGA TAAACAGGCG   3600
```

```
CGTTCTGCAT TAGCTGAACA TGTTGTTTAT TGTCGTCGTC TGGACAGAAT TACTTTACCT   3660
TTTGTCGGTA CTTTATATTC TCTTATTACT GGCTCGAAAA TGCCTCTGCC TAAATTACAT   3720
GTTGGCGTTG TTAAATATGG CGATTCTCAA TTAAGCCCTA CTGTTGAGCG TTGGCTTTAT   3780
ACTGGTAAGA ATTTGTATAA CGCATATGAT ACTAAACAGG CTTTTTCTAG TAATTATGAT   3840
TCCGGTGTTT ATTCTTATTT AACGCCTTAT TTATCACACG GTCGGTATTT CAAACCATTA   3900
AATTTAGGTC AGAAGATGAA GCTTACTAAA ATATATTTGA AAAGTTTTC ACGCGTTCTT    3960
TGTCTTGCGA TTGGATTTGC ATCAGCATTT ACATATAGTT ATATAACCCA ACCTAAGCCG   4020
GAGGTTAAAA AGGTAGTCTC TCAGACCTAT GATTTTGATA AATTCACTAT TGACTCTTCT   4080
CAGCGTCTTA ATCTAAGCTA TCGCTATGTT TTCAAGGATT CTAAGGGAAA ATTAATTAAT   4140
AGCGACGATT TACAGAAGCA AGGTTATTCA CTCACATATA TTGATTTATG TACTGTTTCC   4200
ATTAAAAAAG GTAATTCAAA TGAAATTGTT AAATGTAATT AATTTTGTTT CTTGATGTT    4260
TGTTTCATCA TCTTCTTTTG CTCAGGTAAT TGAAATGAAT AATTCGCCTC TGCGCGATTT   4320
TGTAACTTGG TATTCAAAGC AATCAGGCGA ATCCGTTATT GTTTCTCCCG ATGTAAAAGG   4380
TACTGTTACT GTATATTCAT CTGACGTTAA ACCTGAAAAT CTACGCAATT TCTTTATTTC   4440
TGTTTTACGT GCTAATAATT TTGATATGGT TGGTTCAATT CCTTCCATAA TTCAGAAGTA   4500
TAATCCAAAC AATCAGGATT ATATTGATGA ATTGCCATCA TCTGATAATC AGGAATATGA   4560
TGATAATTCC GCTCCTTCTG GTGGTTTCTT TGTTCCGCAA AATGATAATG TTACTCAAAC   4620
TTTTAAAATT AATAACGTTC GGGCAAAGGA TTTAATACGA GTTGTCGAAT TGTTTGTAAA   4680
GTCTAATACT TCTAAATCCT CAAATGTATT ATCTATTGAC GGCTCTAATC TATTAGTTGT   4740
TAGTGCACCT AAAGATATTT TAGATAACCT TCCTCAATTC CTTTCTACTG TTGATTTGCC   4800
AACTGACCAG ATATTGATTG AGGGTTTGAT ATTTGAGGTT CAGCAAGGTG ATGCTTTAGA   4860
TTTTTCATTT GCTGCTGGCT CTCAGCGTGG CACTGTTGCA GGCGGTGTTA ATACTGACCG   4920
CCTCACCTCT GTTTTATCTT CTGCTGGTGG TTCGTTCGGT ATTTTTAATG GCGATGTTTT   4980
AGGGCTATCA GTTCGCGCAT TAAAGACTAA TAGCCATTCA AAAATATTGT CTGTGCCACG   5040
TATTCTTACG CTTTCAGGTC AGAAGGGTTC TATCTCTGTT GGCCAGAATG TCCCTTTTAT   5100
TACTGGTCGT GTGACTGGTG AATCTGCCAA TGTAAATAAT CCATTTCAGA CGATTGAGCG   5160
TCAAAATGTA GGTATTTCCA TGAGCGTTTT TCCTGTTGCA ATGGCTGGCG GTAATATTGT   5220
TCTGGATATT ACCAGCAAGG CCGATAGTTT GAGTTCTTCT ACTCAGGCAA GTGATGTTAT   5280
TACTAATCAA AGAAGTATTG CTACAACGGT TAATTTGCGT GATGGACAGA CTCTTTTACT   5340
CGGTGGCCTC ACTGATTATA AAAACACTTC TCAAGATTCT GGCGTACCGT TCCTGTCTAA   5400
AATCCCTTTA ATCGGCCTCC TGTTTAGCTC CCGCTCTGAT TCCAACGAGG AAAGCACGTT   5460
ATACGTGCTC GTCAAAGCAA CCATAGTACG CGCCCTGTAG CGGCGCATTA AGCGCGGCGG   5520
GTGTGGTGGT TACGCGCAGC GTGACCGCTA CACTTGCCAG CGCCCTAGCG CCCGCTCCTT   5580
TCGCTTTCTT CCCTTCCTTT CTCGCCACGT TCGCCGGCTT TCCCCGTCAA GCTCTAAATC   5640
GGGGGCTCCC TTTAGGGTTC CGATTTAGTG CTTTACGGCA CCTCGACCCC AAAAAACTTG   5700
ATTTGGGTGA TGGTTCACGT AGTGGGCCAT CGCCCTGATA GACGGTTTTT CGCCCTTTGA   5760
CGTTGGAGTC CACGTTCTTT AATAGTGGAC TCTTGTTCCA AACTGGAACA ACACTCAACC   5820
CTATCTCGGG CTATTCTTTT GATTTATAAG GGATTTTGCC GATTTCGGAA CCACCATCAA   5880
ACAGGATTTT CGCCTGCTGG GGCAAACCAG CGTGGACCGC TTGCTGCAAC TCTCTCAGGG   5940
CCAGGCGGTG AAGGGCAATC AGCTGTTGCC CGTCTCGCTG GTGAAAAGAA AAACCACCCT   6000
```

| | | | | | |
|---|---|---|---|---|---|
| GGCGCCCAAT | ACGCAAACCG | CCTCTCCCCG | CGCGTTGGCC | GATTCATTAA | TGCAGCTGGC | 6060
| ACGACAGGTT | TCCCGACTGG | AAAGCGGGCA | GTGAGCGCAA | CGCAATTAAT | GTGAGTTAGC | 6120
| TCACTCATTA | GGCACCCCAG | GCTTTACACT | TTATGCTTCC | GGCTCGTATG | TTGTGTGGAA | 6180
| TTGTGAGCGG | ATAACAATTT | CACACGCGTC | ACTTGGCACT | GGCCGTCGTT | TTACAACGTC | 6240
| GTGACTGGGA | AAACCCTGGC | GTTACCCAAG | CTTTGTACAT | GGAGAAAATA | AAGTGAAACA | 6300
| AAGCACTATT | GCACTGGCAC | TCTTACCGTT | ACTGTTTACC | CCTGTGGCAA | AAGCCTATGG | 6360
| GGGGTTTATG | ACTTCTGAGG | GATCCGGAGC | TGAAGGCGAT | GACCCTGCTA | AGGCTGCATT | 6420
| CAATAGTTTA | CAGGCAAGTG | CTACTGAGTA | CATTGGCTAC | GCTTGGGCTA | TGGTAGTAGT | 6480
| TATAGTTGGT | GCTACCATAG | GGATTAAATT | ATTCAAAAAG | TTTACGAGCA | AGGCTTCTTA | 6540
| AGCAATAGCG | AAGAGGCCCG | CACCGATCGC | CCTTCCCAAC | AGTTGCGCAG | CCTGAATGGC | 6600
| GAATGGCGCT | TTGCCTGGTT | TCCGGCACCA | GAAGCGGTGC | CGGAAAGCTG | GCTGGAGTGC | 6660
| GATCTTCCTG | AGGCCGATAC | GGTCGTCGTC | CCCTCAAACT | GGCAGATGCA | CGGTTACGAT | 6720
| GCGCCCATCT | ACACCAACGT | AACCTATCCC | ATTACGGTCA | ATCCGCCGTT | TGTTCCCACG | 6780
| GAGAATCCGA | CGGGTTGTTA | CTCGCTCACA | TTTAATGTTG | ATGAAAGCTG | GCTACAGGAA | 6840
| GGCCAGACGC | GAATTATTTT | TGATGGCGTT | CCTATTGGTT | AAAAAATGAG | CTGATTTAAC | 6900
| AAAATTTAA | CGCGAATTTT | AACAAATAT | TAACGTTTAC | AATTTAAATA | TTTGCTTATA | 6960
| CAATCTTCCT | GTTTTTGGGG | CTTTTCTGAT | TATCAACCGG | GGTACATATG | ATTGACATGC | 7020
| TAGTTTTACG | ATTACCGTTC | ATCGATTCTC | TTGTTTGCTC | CAGACTCTCA | GGCAATGACC | 7080
| TGATAGCCTT | TGTAGATCTC | TCAAAAATAG | CTACCCTCTC | CGGCATTAAT | TTATCAGCTA | 7140
| GAACGGTTGA | ATATCATATT | GATGGTGATT | TGACTGTCTC | CGGCCTTTCT | CACCCTTTTG | 7200
| AATCTTTACC | TACACATTAC | TCAGGCATTG | CATTTAAAAT | ATATGAGGGT | TCTAAAAATT | 7260
| TTTATCCTTG | CGTTGAAATA | AAGGCTTCTC | CCGCAAAAGT | ATTACAGGGT | CATAATGTTT | 7320
| TTGGTACAAC | CGATTTAGCT | TTATGCTCTG | AGGCTTTATT | GCTTAATTTT | GCTAATTCTT | 7380
| TGCCTTGCCT | GTATGATTTA | TTGGACGTT | | | | 7409

( 2 ) INFORMATION FOR SEQ ID NO:5:

( i ) SEQUENCE CHARACTERISTICS:
        ( A ) LENGTH: 7294 base pairs
        ( B ) TYPE: nucleic acid
        ( C ) STRANDEDNESS: both
        ( D ) TOPOLOGY: circular ( x i ) SEQUENCE DESCRIPTION: SEQ ID NO:5:

| | | | | | |
|---|---|---|---|---|---|
| AATGCTACTA | CTATTAGTAG | AATTGATGCC | ACCTTTTCAG | CTCGCGCCCC | AAATGAAAAT | 60
| ATAGCTAAAC | AGGTTATTGA | CCATTTGCGA | AATGTATCTA | ATGGTCAAAC | TAAATCTACT | 120
| CGTTCGCAGA | ATTGGGAATC | AACTGTTACA | TGGAATGAAA | CTTCCAGACA | CCGTACTTTA | 180
| GTTGCATATT | TAAAACATGT | TGAGCTACAG | CACCAGATTC | AGCAATTAAG | CTCTAAGCCA | 240
| TCTGCAAAAA | TGACCTCTTA | TCAAAGGAG | CAATTAAAGG | TACTCTCTAA | TCCTGACCTG | 300
| TTGGAGTTTG | CTTCCGGTCT | GGTTCGCTTT | GAAGCTCGAA | TTAAAACGCG | ATATTTGAAG | 360
| TCTTTCGGGC | TTCCTCTTAA | TCTTTTTGAT | GCAATCCGCT | TTGCTTCTGA | CTATAATAGT | 420
| CAGGGTAAAG | ACCTGATTTT | TGATTTATGG | TCATTCTCGT | TTTCTGAACT | GTTTAAAGCA | 480
| TTTGAGGGGG | ATTCAATGAA | TATTTATGAC | GATTCCGCAG | TATTGGACGC | TATCCAGTCT | 540
| AAACATTTTA | CTATTACCCC | CTCTGGCAAA | ACTTCTTTTG | CAAAAGCCTC | TCGCTATTTT | 600

| | | | | | |
|---|---|---|---|---|---|
| GGTTTTTATC | GTCGTCTGGT | AAACGAGGGT | TATGATAGTG | TTGCTCTTAC | TATGCCTCGT | 660 |
| AATTCCTTTT | GGCGTTATGT | ATCTGCATTA | GTTGAATGTG | GTATTCCTAA | ATCTCAACTG | 720 |
| ATGAATCTTT | CTACCTGTAA | TAATGTTGTT | CCGTTAGTTC | GTTTTATTAA | CGTAGATTTT | 780 |
| TCTTCCCAAC | GTCCTGACTG | GTATAATGAG | CCAGTTCTTA | AAATCGCATA | AGGTAATTCA | 840 |
| CAATGATTAA | AGTTGAAATT | AAACCATCTC | AAGCCCAATT | TACTACTCGT | TCTGGTGTTT | 900 |
| CTCGTCAGGG | CAAGCCTTAT | TCACTGAATG | AGCAGCTTTG | TTACGTTGAT | TGGGTAATG | 960 |
| AATATCCGGT | TCTTGTCAAG | ATTACTCTTG | ATGAAGGTCA | GCCAGCCTAT | GCGCCTGGTC | 1020 |
| TGTACACCGT | TCATCTGTCC | TCTTTCAAAG | TTGGTCAGTT | CGGTTCCCTT | ATGATTGACC | 1080 |
| GTCTGCGCCT | CGTTCCGGCT | AAGTAACATG | GAGCAGGTCG | CGGATTTCGA | CACAATTTAT | 1140 |
| CAGGCGATGA | TACAAATCTC | CGTTGTACTT | TGTTTCGCGC | TTGGTATAAT | CGCTGGGGGT | 1200 |
| CAAAGATGAG | TGTTTTAGTG | TATTCTTTCG | CCTCTTTCGT | TTTAGGTTGG | TGCCTTCGTA | 1260 |
| GTGGCATTAC | GTATTTACC | CGTTTAATGG | AAACTTCCTC | ATGAAAAGT | CTTTAGTCCT | 1320 |
| CAAAGCCTCT | GTAGCCGTTG | CTACCCTCGT | TCCGATGCTG | TCTTTCGCTG | CTGAGGGTGA | 1380 |
| CGATCCCGCA | AAAGCGGCCT | TTAACTCCCT | GCAAGCCTCA | GCGACCGAAT | ATATCGGTTA | 1440 |
| TGCGTGGGCG | ATGGTTGTTG | TCATTGTCGG | CGCAACTATC | GGTATCAAGC | TGTTTAAGAA | 1500 |
| ATTCACCTCG | AAAGCAAGCT | GATAAACCGA | TACAATTAAA | GGCTCCTTTT | GGAGCCTTTT | 1560 |
| TTTTGGAGA | TTTTCAACGT | GAAAAAATTA | TTATTCGCAA | TTCCTTTAGT | TGTTCCTTTC | 1620 |
| TATTCTCACT | CCGCTGAAAC | TGTTGAAAGT | TGTTTAGCAA | AACCCCATAC | AGAAAATTCA | 1680 |
| TTTACTAACG | TCTGGAAAGA | CGACAAAACT | TTAGATCGTT | ACGCTAACTA | TGAGGGTTGT | 1740 |
| CTGTGGAATG | CTACAGGCGT | TGTAGTTTGT | ACTGGTGACG | AAACTCAGTG | TTACGGTACA | 1800 |
| TGGGTTCCTA | TTGGGCTTGC | TATCCCTGAA | AATGAGGGTG | GTGGCTCTGA | GGGTGGCGGT | 1860 |
| TCTGAGGGTG | GCGGTTCTGA | GGGTGGCGGT | ACTAAACCTC | CTGAGTACGG | TGATACACCT | 1920 |
| ATTCCGGGCT | ATACTTATAT | CAACCCTCTC | GACGGCACTT | ATCCGCCTGG | TACTGAGCAA | 1980 |
| AACCCCGCTA | ATCCTAATCC | TTCTCTTGAG | GAGTCTCAGC | CTCTTAATAC | TTTCATGTTT | 2040 |
| CAGAATAATA | GGTTCCGAAA | TAGGCAGGGG | GCATTAACTG | TTTATACGGG | CACTGTTACT | 2100 |
| CAAGGCACTG | ACCCCGTTAA | AACTTATTAC | CAGTACACTC | CTGTATCATC | AAAAGCCATG | 2160 |
| TATGACGCTT | ACTGGAACGG | TAAATTCAGA | GACTGCGCTT | TCCATTCTGG | CTTTAATGAA | 2220 |
| GATCCATTCG | TTTGTGAATA | TCAAGGCCAA | TCGTCTGACC | TGCCTCAACC | TCCTGTCAAT | 2280 |
| GCTGGCGGCG | GCTCTGGTGG | TGGTTCTGGT | GGCGGCTCTG | AGGGTGGTGG | CTCTGAGGGT | 2340 |
| GGCGGTTCTG | AGGGTGGCGG | CTCTGAGGGA | GGCGGTTCCG | GTGGTGGCTC | TGGTTCCGGT | 2400 |
| GATTTTGATT | ATGAAAAGAT | GGCAAACGCT | AATAAGGGGG | CTATGACCGA | AAATGCCGAT | 2460 |
| GAAAACGCGC | TACAGTCTGA | CGCTAAAGGC | AAACTTGATT | CTGTCGCTAC | TGATTACGGT | 2520 |
| GCTGCTATCG | ATGGTTTCAT | TGGTGACGTT | TCCGGCCTTG | CTAATGGTAA | TGGTGCTACT | 2580 |
| GGTGATTTTG | CTGGCTCTAA | TTCCCAAATG | GCTCAAGTCG | GTGACGGTGA | TAATTCACCT | 2640 |
| TTAATGAATA | ATTTCCGTCA | ATATTTACCT | TCCCTCCCTC | AATCGGTTGA | ATGTCGCCCT | 2700 |
| TTTGTCTTTA | GCGCTGGTAA | ACCATATGAA | TTTTCTATTG | ATTGTGACAA | AATAAACTTA | 2760 |
| TTCCGTGGTG | TCTTTGCGTT | TCTTTTATAT | GTTGCCACCT | TATGTATGT | ATTTTCTACG | 2820 |
| TTTGCTAACA | TACTGCGTAA | TAAGGAGTCT | TAATCATGCC | AGTTCTTTTG | GGTATTCCGT | 2880 |
| TATTATTGCG | TTTCCTCGGT | TTCCTTCTGG | TAACTTTGTT | CGGCTATCTG | CTTACTTTTC | 2940 |
| TTAAAAAGGG | CTTCGGTAAG | ATAGCTATTG | CTATTTCATT | GTTTCTTGCT | CTTATTATTG | 3000 |

| | | | | | |
|---|---|---|---|---|---|
| GGCTTAACTC | AATTCTTGTG | GGTTATCTCT | CTGATATTAG | CGCTCAATTA | CCCTCTGACT | 3060 |
| TTGTTCAGGG | TGTTCAGTTA | ATTCTCCCGT | CTAATGCGCT | TCCCTGTTTT | TATGTTATTC | 3120 |
| TCTCTGTAAA | GGCTGCTATT | TTCATTTTTG | ACGTTAAACA | AAAAATCGTT | TCTTATTTGG | 3180 |
| ATTGGGATAA | ATAATATGGC | TGTTTATTTT | GTAACTGGCA | AATTAGGCTC | TGGAAAGACG | 3240 |
| CTCGTTAGCG | TTGGTAAGAT | TCAGGATAAA | ATTGTAGCTG | GGTGCAAAAT | AGCAACTAAT | 3300 |
| CTTGATTTAA | GGCTTCAAAA | CCTCCCGCAA | GTCGGGAGGT | TCGCTAAAAC | GCCTCGCGTT | 3360 |
| CTTAGAATAC | CGGATAAGCC | TTCTATATCT | GATTTGCTTG | CTATTGGGCG | CGGTAATGAT | 3420 |
| TCCTACGATG | AAAATAAAAA | CGGCTTGCTT | GTTCTCGATG | AGTGCGGTAC | TTGGTTTAAT | 3480 |
| ACCCGTTCTT | GGAATGATAA | GGAAAGACAG | CCGATTATTG | ATTGGTTTCT | ACATGCTCGT | 3540 |
| AAATTAGGAT | GGGATATTAT | CTTCCTTGTT | CAGGACTTAT | CTATTGTTGA | TAAACAGGCG | 3600 |
| CGTTCTGCAT | TAGCTGAACA | TGTTGTTTAT | TGTCGTCGTC | TGGACAGAAT | TACTTTACCT | 3660 |
| TTTGTCGGTA | CTTTATATTC | TCTTATTACT | GGCTCGAAAA | TGCCTCTGCC | TAAATTACAT | 3720 |
| GTTGGCGTTG | TTAAATATGG | CGATTCTCAA | TTAAGCCCTA | CTGTTGAGCG | TTGGCTTTAT | 3780 |
| ACTGGTAAGA | ATTTGTATAA | CGCATATGAT | ACTAAACAGG | CTTTTTCTAG | TAATTATGAT | 3840 |
| TCCGGTGTTT | ATTCTTATTT | AACGCCTTAT | TTATCACACG | GTCGGTATTT | CAAACCATTA | 3900 |
| AATTTAGGTC | AGAAGATGAA | GCTTACTAAA | ATATATTTGA | AAAGTTTTC | ACGCGTTCTT | 3960 |
| TGTCTTGCGA | TTGGATTTGC | ATCAGCATTT | ACATATAGTT | ATATAACCCA | ACCTAAGCCG | 4020 |
| GAGGTTAAAA | AGGTAGTCTC | TCAGACCTAT | GATTTTGATA | AATTCACTAT | TGACTCTTCT | 4080 |
| CAGCGTCTTA | ATCTAAGCTA | TCGCTATGTT | TTCAAGGATT | CTAAGGGAAA | ATTAATTAAT | 4140 |
| AGCGACGATT | TACAGAAGCA | AGGTTATTCA | CTCACATATA | TTGATTTATG | TACTGTTTCC | 4200 |
| ATTAAAAGG | TAATTCAAAT | GAAATTGTTA | AATGTAATTA | ATTTTGTTTT | CTTGATGTTT | 4260 |
| GTTTCATCAT | CTTCTTTTGC | TCAGGTAATT | GAAATGAATA | ATTCGCCTCT | GCGCGATTTT | 4320 |
| GTAACTTGGT | ATTCAAAGCA | ATCAGGCGAA | TCCGTTATTG | TTTCTCCCGA | TGTAAAAGGT | 4380 |
| ACTGTTACTG | TATATTCATC | TGACGTTAAA | CCTGAAAATC | TACGCAATTT | CTTTATTTCT | 4440 |
| GTTTTACGTG | CTAATAATTT | TGATATGGTT | GGTTCAATTC | CTTCCATTAT | TTAGAAGTAT | 4500 |
| AATCCAAACA | ATCAGGATTA | TATTGATGAA | TTGCCATCAT | CTGATAATCA | GGAATATGAT | 4560 |
| GATAATTCCG | CTCCTTCTGG | TGGTTTCTTT | GTTCCGCAAA | ATGATAATGT | TACTCAAACT | 4620 |
| TTTAAAATTA | ATAACGTTCG | GGCAAAGGAT | TTAATACGAG | TTGTCGAATT | GTTTGTAAAG | 4680 |
| TCTAATACTT | CTAAATCCTC | AAATGTATTA | TCTATTGACG | GCTCTAATCT | ATTAGTTGTT | 4740 |
| AGTGCACCTA | AAGATATTTT | AGATAACCTT | CCTCAATTCC | TTTCTACTGT | TGATTTGCCA | 4800 |
| ACTGACCAGA | TATTGATTGA | GGGTTTGATA | TTTGAGGTTC | AGCAAGGTGA | TGCTTTAGAT | 4860 |
| TTTTCATTTG | CTGCTGGCTC | TCAGCGTGGC | ACTGTTGCAG | GCGGTGTTAA | TACTGACCGC | 4920 |
| CTCACCTCTG | TTTTATCTTC | TGCTGGTGGT | TCGTTCGGTA | TTTTTAATGG | CGATGTTTTA | 4980 |
| GGGCTATCAG | TTCGCGCATT | AAAGACTAAT | AGCCATTCAA | AAATATTGTC | TGTGCCACGT | 5040 |
| ATTCTTACGC | TTTCAGGTCA | GAAGGGTTCT | ATCTCTGTTG | GCCAGAATGT | CCCTTTTATT | 5100 |
| ACTGGTCGTG | TGACTGGTGA | ATCTGCCAAT | GTAAATAATC | CATTTCAGAC | GATTGAGCGT | 5160 |
| CAAAATGTAG | GTATTTCCAT | GAGCGTTTTT | CCTGTTGCAA | TGGCTGGCGG | TAATATTGTT | 5220 |
| CTGGATATTA | CCAGCAAGGC | CGATAGTTTG | AGTTCTTCTA | CTCAGGCAAG | TGATGTTATT | 5280 |
| ACTAATCAAA | GAAGTATTGC | TACAACGGTT | AATTTGCGTG | ATGGACAGAC | TCTTTTACTC | 5340 |
| GGTGGCCTCA | CTGATTATAA | AAACACTTCT | CAAGATTCTG | GCGTACCGTT | CCTGTCTAAA | 5400 |

| | | | | | | |
|---|---|---|---|---|---|---|
| ATCCCTTTAA | TCGGCCTCCT | GTTTAGCTCC | CGCTCTGATT | CCAACGAGGA | AAGCACGTTA | 5460 |
| TACGTGCTCG | TCAAAGCAAC | CATAGTACGC | GCCCTGTAGC | GGCGCATTAA | GCGCGGCGGG | 5520 |
| TGTGGTGGTT | ACGCGCAGCG | TGACCGCTAC | ACTTGCCAGC | GCCCTAGCGC | CCGCTCCTTT | 5580 |
| CGCTTTCTTC | CCTTCCTTTC | TCGCCACGTT | CGCCGGCTTT | CCCCGTCAAG | CTCTAAATCG | 5640 |
| GGGGCTCCCT | TTAGGGTTCC | GATTTAGTGC | TTTACGGCAC | CTCGACCCCA | AAAAACTTGA | 5700 |
| TTTGGGTGAT | GGTTCACGTA | GTGGGCCATC | GCCCTGATAG | ACGGTTTTC | GCCCTTTGAC | 5760 |
| GTTGGAGTCC | ACGTTCTTTA | ATAGTGGACT | CTTGTTCCAA | ACTGGAACAA | CACTCAACCC | 5820 |
| TATCTCGGGC | TATTCTTTTG | ATTTATAAGG | GATTTGCCG | ATTTCGGAAC | CACCATCAAA | 5880 |
| CAGGATTTTC | GCCTGCTGGG | GCAAACCAGC | GTGGACCGCT | TGCTGCAACT | CTCTCAGGGC | 5940 |
| CAGGCGGTGA | AGGGCAATCA | GCTGTTGCCC | GTCTCGCTGG | TGAAAAGAAA | AACCACCCTG | 6000 |
| GCGCCCAATA | CGCAAACCGC | CTCTCCCCGC | GCGTTGGCCG | ATTCATTAAT | GCAGCTGGCA | 6060 |
| CGACAGGTTT | CCCGACTGGA | AAGCGGGCAG | TGAGCGCAAC | GCAATTAATG | TGAGTTAGCT | 6120 |
| CACTCATTAG | GCACCCCAGG | CTTTACACTT | TATGCTTCCG | GCTCGTATGT | TGTGTGGAAT | 6180 |
| TGTGAGCGGA | TAACAATTTC | ACACAGGAAA | CAGCTATGAC | CAGGATGTAC | GAATTCGCAG | 6240 |
| GTAGGAGAGC | TCGGCGGATC | CGAGGCTGAA | GGCGATGACC | CTGCTAAGGC | TGCATTCAAT | 6300 |
| AGTTTACAGG | CAAGTGCTAC | TGAGTACATT | GGCTACGCTT | GGGCTATGGT | AGTAGTTATA | 6360 |
| GTTGGTGCTA | CCATAGGGAT | TAAATTATTC | AAAAAGTTTA | CGAGCAAGGC | TTCTTAACCA | 6420 |
| GCTGGCGTAA | TAGCGAAGAG | GCCCGCACCG | ATCGCCCTTC | CCAACAGTTG | CGCAGCCTGA | 6480 |
| ATGGCGAATG | GCGCTTTGCC | TGGTTTCCGG | CACCAGAAGC | GGTGCCGGAA | AGCTGGCTGG | 6540 |
| AGTGCGATCT | TCCTGAGGCC | GATACGGTCG | TCGTCCCCTC | AAACTGGCAG | ATGCACGGTT | 6600 |
| ACGATGCGCC | CATCTACACC | AACGTAACCT | ATCCCATTAC | GGTCAATCCG | CCGTTTGTTC | 6660 |
| CCACGGAGAA | TCCGACGGGT | TGTTACTCGC | TCACATTTAA | TGTTGATGAA | AGCTGGCTAC | 6720 |
| AGGAAGGCCA | GACGCGAATT | ATTTTTGATG | GCGTTCCTAT | TGGTTAAAAA | ATGAGCTGAT | 6780 |
| TTAACAAAAA | TTTAACGCGA | ATTTTAACAA | AATATTAACG | TTTACAATTT | AAATATTTGC | 6840 |
| TTATACAATC | TTCCTGTTTT | TGGGGCTTTT | CTGATTATCA | ACCGGGGTAC | ATATGATTGA | 6900 |
| CATGCTAGTT | TTACGATTAC | CGTTCATCGA | TTCTCTTGTT | TGCTCCAGAC | TCTCAGGCAA | 6960 |
| TGACCTGATA | GCCTTTGTAG | ATCTCTCAAA | AATAGCTACC | CTCTCCGGCA | TTAATTTATC | 7020 |
| AGCTAGAACG | GTTGAATATC | ATATTGATGG | TGATTTGACT | GTCTCCGGCC | TTTCTCACCC | 7080 |
| TTTTGAATCT | TTACCTACAC | ATTACTCAGG | CATTGCATTT | AAAATATATG | AGGGTTCTAA | 7140 |
| AAATTTTTAT | CCTTGCGTTG | AAATAAAGGC | TTCTCCCGCA | AAAGTATTAC | AGGGTCATAA | 7200 |
| TGTTTTTGGT | ACAACCGATT | TAGCTTTATG | CTCTGAGGCT | TTATTGCTTA | ATTTGCTAA | 7260 |
| TTCTTTGCCT | TGCCTGTATG | ATTTATTGGA | CGTT | | | 7294 |

( 2 ) INFORMATION FOR SEQ ID NO:6:

( i ) SEQUENCE CHARACTERISTICS:
  ( A ) LENGTH: 7394 base pairs
  ( B ) TYPE: nucleic acid
  ( C ) STRANDEDNESS: both
  ( D ) TOPOLOGY: circular ( x i ) SEQUENCE DESCRIPTION: SEQ ID NO:6:

| | | | | | | |
|---|---|---|---|---|---|---|
| AATGCTACTA | CTATTAGTAG | AATTGATGCC | ACCTTTTCAG | CTCGCGCCCC | AAATGAAAAT | 60 |
| ATAGCTAAAC | AGGTTATTGA | CCATTTGCGA | AATGTATCTA | ATGGTCAAAC | TAAATCTACT | 120 |
| CGTTCGCAGA | ATTGGGAATC | AACTGTTACA | TGGAATGAAA | CTTCCAGACA | CCGTACTTTA | 180 |

| | | | | | |
|---|---|---|---|---|---|
| GTTGCATATT | TAAAACATGT | TGAGCTACAG | CACCAGATTC | AGCAATTAAG | CTCTAAGCCA | 240 |
| TCTGCAAAAA | TGACCTCTTA | TCAAAGGAG | CAATTAAAGG | TACTCTCTAA | TCCTGACCTG | 300 |
| TTGGAGTTTG | CTTCCGGTCT | GGTTCGCTTT | GAAGCTCGAA | TTAAAACGCG | ATATTTGAAG | 360 |
| TCTTTCGGGC | TTCCTCTTAA | TCTTTTTGAT | GCAATCCGCT | TTGCTTCTGA | CTATAATAGT | 420 |
| CAGGGTAAAG | ACCTGATTTT | TGATTATGG | TCATTCTCGT | TTTCTGAACT | GTTTAAAGCA | 480 |
| TTTGAGGGGG | ATTCAATGAA | TATTTATGAC | GATTCCGCAG | TATTGGACGC | TATCCAGTCT | 540 |
| AAACATTTTA | CTATTACCCC | CTCTGGCAAA | ACTTCTTTTG | CAAAAGCCTC | TCGCTATTTT | 600 |
| GGTTTTTATC | GTCGTCTGGT | AAACGAGGGT | TATGATAGTG | TTGCTCTTAC | TATGCCTCGT | 660 |
| AATTCCTTTT | GGCGTTATGT | ATCTGCATTA | GTTGAATGTG | GTATTCCTAA | ATCTCAACTG | 720 |
| ATGAATCTTT | CTACCTGTAA | TAATGTTGTT | CCGTTAGTTC | GTTTATTAA | CGTAGATTTT | 780 |
| TCTTCCCAAC | GTCCTGACTG | GTATAATGAG | CCAGTTCTTA | AAATCGCATA | AGGTAATTCA | 840 |
| CAATGATTAA | AGTTGAAATT | AAACCATCTC | AAGCCCAATT | TACTACTCGT | TCTGGTGTTT | 900 |
| CTCGTCAGGG | CAAGCCTTAT | TCACTGAATG | AGCAGCTTTG | TTACGTTGAT | TTGGGTAATG | 960 |
| AATATCCGGT | TCTTGTCAAG | ATTACTCTTG | ATGAAGGTCA | GCCAGCCTAT | GCGCCTGGTC | 1020 |
| TGTACACCGT | TCATCTGTCC | TCTTTCAAAG | TTGGTCAGTT | CGGTTCCCTT | ATGATTGACC | 1080 |
| GTCTGCGCCT | CGTTCCGGCT | AAGTAACATG | GAGCAGGTCG | CGGATTTCGA | CACAATTTAT | 1140 |
| CAGGCGATGA | TACAAATCTC | CGTTGTACTT | TGTTTCGCGC | TTGGTATAAT | CGCTGGGGGT | 1200 |
| CAAAGATGAG | TGTTTTAGTG | TATTCTTTCG | CCTCTTTCGT | TTTAGGTTGG | TGCCTTCGTA | 1260 |
| GTGGCATTAC | GTATTTTACC | CGTTTAATGG | AAACTTCCTC | ATGAAAAAGT | CTTTAGTCCT | 1320 |
| CAAAGCCTCT | GTAGCCGTTG | CTACCCTCGT | TCCGATGCTG | TCTTTCGCTG | CTGAGGGTGA | 1380 |
| CGATCCCGCA | AAAGCGGCCT | TTAACTCCCT | GCAAGCCTCA | GCGACCGAAT | ATATCGGTTA | 1440 |
| TGCGTGGGCG | ATGGTTGTTG | TCATTGTCGG | CGCAACTATC | GGTATCAAGC | TGTTTAAGAA | 1500 |
| ATTCACCTCG | AAAGCAAGCT | GATAAACCGA | TACAATTAAA | GGCTCCTTTT | GGAGCCTTTT | 1560 |
| TTTTGGAGA | TTTTCAACGT | GAAAAAATTA | TTATTCGCAA | TTCCTTAGT | TGTTCCTTTC | 1620 |
| TATTCTCACT | CCGCTGAAAC | TGTTGAAAGT | TGTTTAGCAA | AACCCCATAC | AGAAAATTCA | 1680 |
| TTTACTAACG | TCTGGAAAGA | CGACAAAACT | TTAGATCGTT | ACGCTAACTA | TGAGGGTTGT | 1740 |
| CTGTGGAATG | CTACAGGCGT | TGTAGTTTGT | ACTGGTGACG | AAACTCAGTG | TTACGGTACA | 1800 |
| TGGGTTCCTA | TTGGGCTTGC | TATCCCTGAA | AATGAGGGTG | GTGGCTCTGA | GGGTGGCGGT | 1860 |
| TCTGAGGGTG | GCGGTTCTGA | GGGTGGCGGT | ACTAAACCTC | CTGAGTACGG | TGATACACCT | 1920 |
| ATTCCGGGCT | ATACTTATAT | CAACCCTCTC | GACGGCACTT | ATCCGCCTGG | TACTGAGCAA | 1980 |
| AACCCCGCTA | ATCCTAATCC | TTCTCTTGAG | GAGTCTCAGC | CTCTTAATAC | TTTCATGTTT | 2040 |
| CAGAATAATA | GGTTCCGAAA | TAGGCAGGGG | GCATTAACTG | TTTATACGGG | CACTGTTACT | 2100 |
| CAAGGCACTG | ACCCCGTTAA | AACTTATTAC | CAGTACACTC | CTGTATCATC | AAAAGCCATG | 2160 |
| TATGACGCTT | ACTGGAACGG | TAAATTCAGA | GACTGCGCTT | TCCATTCTGG | CTTTAATGAA | 2220 |
| GATCCATTCG | TTTGTGAATA | TCAAGGCCAA | TCGTCTGACC | TGCCTCAACC | TCCTGTCAAT | 2280 |
| GCTGGCGGCG | GCTCTGGTGG | TGGTTCTGGT | GGCGGCTCTG | AGGGTGGTGG | CTCTGAGGGT | 2340 |
| GGCGGTTCTG | AGGGTGGCGG | CTCTGAGGGA | GGCGGTTCCG | GTGGTGGCTC | TGGTTCCGGT | 2400 |
| GATTTTGATT | ATGAAAAGAT | GGCAAACGCT | AATAAGGGGG | CTATGACCGA | AAATGCCGAT | 2460 |
| GAAAACGCGC | TACAGTCTGA | CGCTAAAGGC | AAACTTGATT | CTGTCGCTAC | TGATTACGGT | 2520 |
| GCTGCTATCG | ATGGTTTCAT | TGGTGACGTT | TCCGGCCTTG | CTAATGGTAA | TGGTGCTACT | 2580 |

| | | | | | |
|---|---|---|---|---|---|
| GGTGATTTTG | CTGGCTCTAA | TTCCCAAATG | GCTCAAGTCG | GTGACGGTGA | TAATTCACCT | 2640 |
| TTAATGAATA | ATTTCCGTCA | ATATTTACCT | TCCCTCCCTC | AATCGGTTGA | ATGTCGCCCT | 2700 |
| TTTGTCTTTA | GCGCTGGTAA | ACCATATGAA | TTTTCTATTG | ATTGTGACAA | AATAAACTTA | 2760 |
| TTCCGTGGTG | TCTTTGCGTT | TCTTTTATAT | GTTGCCACCT | TTATGTATGT | ATTTTCTACG | 2820 |
| TTTGCTAACA | TACTGCGTAA | TAAGGAGTCT | TAATCATGCC | AGTTCTTTTG | GGTATTCCGT | 2880 |
| TATTATTGCG | TTTCCTCGGT | TTCCTTCTGG | TAACTTTGTT | CGGCTATCTG | CTTACTTTTC | 2940 |
| TTAAAAGGG | CTTCGGTAAG | ATAGCTATTG | CTATTTCATT | GTTTCTTGCT | CTTATTATTG | 3000 |
| GGCTTAACTC | AATTCTTGTG | GGTTATCTCT | CTGATATTAG | CGCTCAATTA | CCCTCTGACT | 3060 |
| TTGTTCAGGG | TGTTCAGTTA | ATTCTCCGT | CTAATGCGCT | TCCCTGTTTT | TATGTTATTC | 3120 |
| TCTCTGTAAA | GGCTGCTATT | TTCATTTTTG | ACGTTAAACA | AAAAATCGTT | TCTTATTTGG | 3180 |
| ATTGGGATAA | ATAATATGGC | TGTTTATTTT | GTAACTGGCA | AATTAGGCTC | TGGAAAGACG | 3240 |
| CTCGTTAGCG | TTGGTAAGAT | TTAGGATAAA | ATTGTAGCTG | GGTGCAAAAT | AGCAACTAAT | 3300 |
| CTTGATTTAA | GGCTTCAAAA | CCTCCCGCAA | GTCGGGAGGT | TCGCTAAAAC | GCCTCGCGTT | 3360 |
| CTTAGAATAC | CGGATAAGCC | TTCTATATCT | GATTTGCTTG | CTATTGGGCG | CGGTAATGAT | 3420 |
| TCCTACGATG | AAAATAAAAA | CGGCTTGCTT | GTTCTCGATG | AGTGCGGTAC | TTGGTTTAAT | 3480 |
| ACCCGTTCTT | GGAATGATAA | GGAAAGACAG | CCGATTATTG | ATTGGTTTCT | ACATGCTCGT | 3540 |
| AAATTAGGAT | GGGATATTAT | TTTTCTTGTT | CAGGACTTAT | CTATTGTTGA | TAAACAGGCG | 3600 |
| CGTTCTGCAT | TAGCTGAACA | TGTTGTTTAT | TGTCGTCGTC | TGGACAGAAT | TACTTTACCT | 3660 |
| TTTGTCGGTA | CTTTATATTC | TCTTATTACT | GGCTCGAAAA | TGCCTCTGCC | TAAATTACAT | 3720 |
| GTTGGCGTTG | TTAAATATGG | CGATTCTCAA | TTAAGCCCTA | CTGTTGAGCG | TTGGCTTTAT | 3780 |
| ACTGGTAAGA | ATTTGTATAA | CGCATATGAT | ACTAAACAGG | CTTTTTCTAG | TAATTATGAT | 3840 |
| TCCGGTGTTT | ATTCTTATTT | AACGCCTTAT | TTATCACACG | GTCGGTATTT | CAAACCATTA | 3900 |
| AATTTAGGTC | AGAAGATGAA | GCTTACTAAA | ATATATTTGA | AAAAGTTTTC | ACGCGTTCTT | 3960 |
| TGTCTTGCGA | TTGGATTTGC | ATCAGCATTT | ACATATAGTT | ATATAACCCA | ACCTAAGCCG | 4020 |
| GAGGTTAAAA | AGGTAGTCTC | TCAGACCTAT | GATTTTGATA | AATTCACTAT | TGACTCTTCT | 4080 |
| CAGCGTCTTA | ATCTAAGCTA | TCGCTATGTT | TTCAAGGATT | CTAAGGGAAA | ATTAATTAAT | 4140 |
| AGCGACGATT | TACAGAAGCA | AGGTTATTCA | CTCACATATA | TTGATTTATG | TACTGTTTCC | 4200 |
| ATTAAAAAAG | GTAATTCAAA | TGAAATTGTT | AAATGTAATT | AATTTTGTTT | TCTTGATGTT | 4260 |
| TGTTTCATCA | TCTTCTTTTG | CTCAGGTAAT | TGAAATGAAT | AATTCGCCTC | TGCGCGATTT | 4320 |
| TGTAACTTGG | TATTCAAAGC | AATCAGGCGA | ATCCGTTATT | GTTTCTCCCG | ATGTAAAAGG | 4380 |
| TACTGTTACT | GTATATTCAT | CTGACGTTAA | ACCTGAAAAT | CTACGCAATT | TCTTTATTTC | 4440 |
| TGTTTTACGT | GCTAATAATT | TTGATATGGT | TGGTTCAATT | CCTTCCATAA | TTCAGAAGTA | 4500 |
| TAATCCAAAC | AATCAGGATT | ATATTGATGA | ATTGCCATCA | TCTGATAATC | AGGAATATGA | 4560 |
| TGATAATTCC | GCTCCTTCTG | GTGGTTTCTT | TGTTCCGCAA | AATGATAATG | TTACTCAAAC | 4620 |
| TTTTAAAATT | AATAACGTTC | GGGCAAAGGA | TTTAATACGA | GTTGTCGAAT | TGTTTGTAAA | 4680 |
| GTCTAATACT | TCTAAATCCT | CAAATGTATT | ATCTATTGAC | GGCTCTAATC | TATTAGTTGT | 4740 |
| TAGTGCACCT | AAAGATATTT | TAGATAACCT | TCCTCAATTC | CTTTCTACTG | TTGATTTGCC | 4800 |
| AACTGACCAG | ATATTGATTG | AGGGTTTGAT | ATTTGAGGTT | CAGCAAGGTG | ATGCTTTAGA | 4860 |
| TTTTTCATTT | GCTGCTGGCT | CTCAGCGTGG | CACTGTTGCA | GGCGGTGTTA | ATACTGACCG | 4920 |
| CCTCACCTCT | GTTTTATCTT | CTGCTGGTGG | TTCGTTCGGT | ATTTTTAATG | GCGATGTTTT | 4980 |

```
AGGGCTATCA GTTCGCGCAT TAAAGACTAA TAGCCATTCA AAAATATTGT CTGTGCCACG    5040
TATTCTTACG CTTTCAGGTC AGAAGGGTTC TATCTCTGTT GGCCAGAATG TCCCTTTTAT    5100
TACTGGTCGT GTGACTGGTG AATCTGCCAA TGTAAATAAT CCATTTCAGA CGATTGAGCG    5160
TCAAAATGTA GGTATTTCCA TGAGCGTTTT TCCTGTTGCA ATGGCTGGCG GTAATATTGT    5220
TCTGGATATT ACCAGCAAGG CCGATAGTTT GAGTTCTTCT ACTCAGGCAA GTGATGTTAT    5280
TACTAATCAA AGAAGTATTG CTACAACGGT TAATTTGCGT GATGGACAGA CTCTTTTACT    5340
CGGTGGCCTC ACTGATTATA AAAACACTTC TCAAGATTCT GGCGTACCGT TCCTGTCTAA    5400
AATCCCTTTA ATCGGCCTCC TGTTTAGCTC CCGCTCTGAT TCCAACGAGG AAAGCACGTT    5460
ATACGTGCTC GTCAAAGCAA CCATAGTACG CGCCCTGTAG CGGCGCATTA AGCGCGGCGG    5520
GTGTGGTGGT TACGCGCAGC GTGACCGCTA CACTTGCCAG CGCCCTAGCG CCCGCTCCTT    5580
TCGCTTTCTT CCCTTCCTTT CTCGCCACGT TCGCCGGCTT TCCCCGTCAA GCTCTAAATC    5640
GGGGGCTCCC TTTAGGGTTC CGATTTAGTG CTTTACGGCA CCTCGACCCC AAAAAACTTG    5700
ATTTGGGTGA TGGTTCACGT AGTGGGCCAT CGCCCTGATA GACGGTTTTT CGCCCTTTGA    5760
CGTTGGAGTC CACGTTCTTT AATAGTGGAC TCTTGTTCCA AACTGGAACA ACACTCAACC    5820
CTATCTCGGG CTATTCTTTT GATTTATAAG GGATTTTGCC GATTTCGGAA CCACCATCAA    5880
ACAGGATTTT CGCCTGCTGG GGCAAACCAG CGTGGACCGC TTGCTGCAAC TCTCTCAGGG    5940
CCAGGCGGTG AAGGGCAATC AGCTGTTGCC CGTCTCGCTG GTGAAAAGAA AAACCACCCT    6000
GGCGCCCAAT ACGCAAACCG CCTCTCCCCG CGCGTTGGCC GATTCATTAA TGCAGCTGGC    6060
ACGACAGGTT TCCCGACTGG AAAGCGGGCA GTGAGCGCAA CGCAATTAAT GTGAGTTAGC    6120
TCACTCATTA GGCACCCCAG GCTTTACACT TTATGCTTCC GGCTCGTATG TTGTGTGGAA    6180
TTGTGAGCGG ATAACAATTT CACACGCGTC ACTTGGCACT GGCCGTCGTT TTACAACGTC    6240
GTGACTGGGA AAACCCTGGC GTTACCCAAG CTTTGTACAT GGAGAAAATA AAGTGAAACA    6300
AAGCACTATT GCACTGGCAC TCTTACCGTT ACTGTTTACC CCTGTGGCAA AAGCCCTTCT    6360
GAGGCATCCG GGAGCTGAAG GCGATGACCC TGCTAAGGCT GCATTCAATA GTTTACAGGC    6420
AAGTGCTACT GAGTACATTG GCTACGCTTG GGCTATGGTA GTAGTTATAG TTGGTGCTAC    6480
CATAGGGATT AAATTATTCA AAAAGTTTAC GAGCAAGGCT TCTTAAGCAA TAGCGAAGAG    6540
GCCCGCACCG ATCGCCCTTC CCAACAGTTG CGCAGCCTGA ATGGCGAATG GCGCTTTGCC    6600
TGGTTTCCGG CACCAGAAGC GGTGCCGGAA AGCTGGCTGG AGTGCGATCT TCCTGAGGCC    6660
GATACGGTCG TCGTCCCCTC AAACTGGCAG ATGCACGGTT ACGATGCGCC CATCTACACC    6720
AACGTAACCT ATCCCATTAC GGTCAATCCG CCGTTTGTTC CCACGGAGAA TCCGACGGGT    6780
TGTTACTCGC TCACATTTAA TGTTGATGAA AGCTGGCTAC AGGAAGGCCA GACGCGAATT    6840
ATTTTTGATG GCGTTCCTAT TGGTTAAAAA ATGAGCTGAT TTAACAAAAA TTTAACGCGA    6900
ATTTTAACAA AATATTAACG TTTACAATTT AAATATTTGC TTATACAATC TTCCTGTTTT    6960
TGGGGCTTTT CTGATTATCA ACCGGGGTAC ATATGATTGA CATGCTAGTT TTACGATTAC    7020
CGTTCATCGA TTCTCTTGTT TGCTCCAGAC TCTCAGGCAA TGACCTGATA GCCTTTGTAG    7080
ATCTCTCAAA AATAGCTACC CTCTCCGGCA TTAATTTATC AGCTAGAACG GTTGAATATC    7140
ATATTGATGG TGATTTGACT GTCTCCGGCC TTTCTCACCC TTTTGAATCT TTACCTACAC    7200
ATTACTCAGG CATTGCATTT AAAATATATG AGGGTTCTAA AATTTTTAT CCTTGCGTTG    7260
AAATAAAGGC TTCTCCCGCA AAAGTATTAC AGGGTCATAA TGTTTTTGGT ACAACCGATT    7320
TAGCTTTATG CTCTGAGGCT TTATTGCTTA ATTTTGCTAA TTCTTTGCCT TGCCTGTATG    7380
```

ATTTATTGGA CGTT 7394

( 2 ) INFORMATION FOR SEQ ID NO:7:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

GATCCTAGGC TGAAGGCGAT GACCCTGCTA AGGCTGC 37

( 2 ) INFORMATION FOR SEQ ID NO:8:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

ATTCAATAGT TTACAGGCAA GTGCTACTGA GTACA 35

( 2 ) INFORMATION FOR SEQ ID NO:9:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

TTGGCTACGC TTGGGCTATG GTAGTAGTTA TAGTT 35

( 2 ) INFORMATION FOR SEQ ID NO:10:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

GGTGCTACCA TAGGGATTAA ATTATTCAAA AAGTT 35

( 2 ) INFORMATION FOR SEQ ID NO:11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

TACGAGCAAG GCTTCTTA 18

( 2 ) INFORMATION FOR SEQ ID NO:12:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

AGCTTAAGAA GCCTTGCTCG TAAACTTTTT GAATAATTT 39

( 2 ) INFORMATION FOR SEQ ID NO:13:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

AATCCCTATG GTAGCACCAA CTATAACTAC TACCAT    36

( 2 ) INFORMATION FOR SEQ ID NO:14:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

AGCCCAAGCG TAGCCAATGT ACTCAGTAGC ACTTG    35

( 2 ) INFORMATION FOR SEQ ID NO:15:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

CCTGTAAACT ATTGAATGCA GCCTTAGCAG GGTC    34

( 2 ) INFORMATION FOR SEQ ID NO:16:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

ATCGCCTTCA GCCTAG    16

( 2 ) INFORMATION FOR SEQ ID NO:17:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

CTCGAATTCG TACATCCTGG TCATAGC    27

( 2 ) INFORMATION FOR SEQ ID NO:18:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

CATTTTTGCA GATGGCTTAG A    21

( 2 ) INFORMATION FOR SEQ ID NO:19:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

TAGCATTAAC GTCCAATA        18

( 2 ) INFORMATION FOR SEQ ID NO:20:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

ATATATTTTA GTAAGCTTCA TCTTCT        26

( 2 ) INFORMATION FOR SEQ ID NO:21:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

GACAAAGAAC GCGTGAAAAC TTT        23

( 2 ) INFORMATION FOR SEQ ID NO:22:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

GCGGGCCTCT TCGCTATTGC TTAAGAAGCC TTGCT        35

( 2 ) INFORMATION FOR SEQ ID NO:23:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

TTCAGCCTAG GATCCGCCGA GCTCTCCTAC CTGCGAATTC GTACATCC        48

( 2 ) INFORMATION FOR SEQ ID NO:24:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

TGGATTATAC TTCTAAATAA TGGA        24

( 2 ) INFORMATION FOR SEQ ID NO:25:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:25:

TAACACTCAT TCCGGATGGA ATTCTGGAGT CTGGGT    36

( 2 ) INFORMATION FOR SEQ ID NO:26:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:26:

AATTCGCCAA GGAGACAGTC AT    22

( 2 ) INFORMATION FOR SEQ ID NO:27:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:27:

AATGAAATAC CTATTGCCTA CGGCAGCCGC TGGATTGTT    39

( 2 ) INFORMATION FOR SEQ ID NO:28:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:28:

ATTACTCGCT GCCCAACCAG CCATGGCCGA GCTCGTGAT    39

( 2 ) INFORMATION FOR SEQ ID NO:29:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:29:

GACCCAGACT CCAGATATCC AACAGGAATG AGTGTTAAT    39

( 2 ) INFORMATION FOR SEQ ID NO:30:

( i ) SEQUENCE CHARACTERISTICS:
    ( A ) LENGTH: 13 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:30:

TCTAGAACGC GTC    13

( 2 ) INFORMATION FOR SEQ ID NO:31:

( i ) SEQUENCE CHARACTERISTICS:
    ( A ) LENGTH: 35 base pairs ( B ) TYPE: nucleic acid
        ( C ) STRANDEDNESS: single
        ( D ) TOPOLOGY: linear ( x i ) SEQUENCE DESCRIPTION: SEQ ID NO:31:

ACGTGACGCG TTCTAGAATT AACACTCATT CCTGT    35

( 2 ) INFORMATION FOR SEQ ID NO:32:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

TGGATATCTG GAGTCTGGGT CATCACGAGC TCGGCCATG    39

( 2 ) INFORMATION FOR SEQ ID NO:33:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

GCTGGTTGGG CAGCGAGTAA TAACAATCCA GCGGCTGCC    39

( 2 ) INFORMATION FOR SEQ ID NO:34:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

GTAGGCAATA GGTATTTCAT TATGACTGTC CTTGGCG    37

( 2 ) INFORMATION FOR SEQ ID NO:35:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:35:

TGACTGTCTC CTTGGCGTGT GAAATTGTTA    30

( 2 ) INFORMATION FOR SEQ ID NO:36:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:36:

TAACACTCAT TCCGGATGGA ATTCTGGAGT CTGGGT    36

( 2 ) INFORMATION FOR SEQ ID NO:37:

( i ) SEQUENCE CHARACTERISTICS:
        ( A ) LENGTH: 25 base pairs
        ( B ) TYPE: nucleic acid
        ( C ) STRANDEDNESS: single ( D ) TOPOLOGY: linear ( x i ) SEQUENCE DESCRIPTION: SEQ ID NO:37:

CAATTTTATC CTAAATCTTA CCAAC                                                                         25

( 2 ) INFORMATION FOR SEQ ID NO:38:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:38:

CATTTTTGCA GATGGCTTAG A                                                                             21

( 2 ) INFORMATION FOR SEQ ID NO:39:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:39:

CGAAAGGGGG GTGTGCTGCA A                                                                             21

( 2 ) INFORMATION FOR SEQ ID NO:40:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:40:

TAGCATTAAC GTCCAATA                                                                                 18

( 2 ) INFORMATION FOR SEQ ID NO:41:

( i ) SEQUENCE CHARACTERISTICS:
            ( A ) LENGTH: 43 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:41:

AAACGACGGC CAGTGCCAAG TGACGCGTGT GAAATTGTTA TCC                                                      43

( 2 ) INFORMATION FOR SEQ ID NO:42:

( i ) SEQUENCE CHARACTERISTICS:
            ( A ) LENGTH: 43 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:42:

GGCGAAAGGG AATTCTGCAA GGCGATTAAG CTTGGGTAAC GCC                                                      43

( 2 ) INFORMATION FOR SEQ ID NO:43:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:43:

GGCGTTACCC AAGCTTTGTA CATGGAGAAA ATAAAG  36

( 2 ) INFORMATION FOR SEQ ID NO:44:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:44:

TGAAACAAAG CACTATTGCA CTGGCACTCT TACCGTTACC GT  42

( 2 ) INFORMATION FOR SEQ ID NO:45:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:45:

TACTGTTTAC CCCTGTGACA AAAGCCGCCC AGGTCCAGCT GC  42

( 2 ) INFORMATION FOR SEQ ID NO:46:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:46:

TCGAGTCAGG CCTATTGTGC CCAGGGATTG TACTAGTGGA TCCG  44

( 2 ) INFORMATION FOR SEQ ID NO:47:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:47:

TGGCGAAAGG GAATTCGGAT CCACTAGTAC AATCCCTG  38

( 2 ) INFORMATION FOR SEQ ID NO:48:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:48:

GGCACAATAG GCCTGACTCG AGCAGCTGGA CCAGGGCGGC TT  42

( 2 ) INFORMATION FOR SEQ ID NO:49:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:49:

TTGTCACAGG GGTAAACAGT AACGGTAACG GTAAGTGTGC CA 42

( 2 ) INFORMATION FOR SEQ ID NO:50:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:50:

GTGCAATAGT GCTTTGTTTC ACTTTATTTT CTCCATGTAC AA 42

( 2 ) INFORMATION FOR SEQ ID NO:51:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:51:

TAACGGTAAG AGTGCCAGTG C 21

( 2 ) INFORMATION FOR SEQ ID NO:52:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(25, "")
        ( D ) OTHER INFORMATION: /note= ""M represents an equal
            mixture of A and C at this location and at
            locations 28, 31, 34, 37, 40, 43, 46 & 49""

( x i ) SEQUENCE DESCRIPTION: SEQ ID NO:52:

AGCTCCCGGA TGCCTCAGAA GATGMNNMNN MNMNNMNNM NNMNNMNNMN NGGCTTTTGC 60

CACAGGGG 68

( 2 ) INFORMATION FOR SEQ ID NO:53:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(17, "")
        ( D ) OTHER INFORMATION: /note= ""M represents an equal
            mixture of A and C at this location and at
            locations 20, 23, 26, 29, 32, 35, 38, 41, 44 &

( x i ) SEQUENCE DESCRIPTION: SEQ ID NO:53:

CAGCCTCGGA TCCGCCMNNM NNMNNMNNMN NMNNMNNMNN MNMNNATGM GAAT 54

( 2 ) INFORMATION FOR SEQ ID NO:54:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:54:

GGTAAACAGT AACGGTAAGA GTGCCAG 27

(2) INFORMATION FOR SEQ ID NO:55:

(i) SEQUENCE CHARACTERISTICS:
  (A) LENGTH: 19 base pairs
  (B) TYPE: nucleic acid
  (C) STRANDEDNESS: single
  (D) TOPOLOGY: linear (xi) SEQUENCE DESCRIPTION: SEQ ID NO:55:

GGGCTTTTGC CACAGGGGT 19

(2) INFORMATION FOR SEQ ID NO:56:

(i) SEQUENCE CHARACTERISTICS:
  (A) LENGTH: 63 base pairs
  (B) TYPE: nucleic acid
  (C) STRANDEDNESS: single
  (D) TOPOLOGY: linear (xi) SEQUENCE DESCRIPTION: SEQ ID NO:56:

AGGGTCATCG CCTTCAGCTC CGGATCCCTC AGAAGTCATA AACCCCCAT AGGCTTTTGC 60

CAC 63

(2) INFORMATION FOR SEQ ID NO:57:

(i) SEQUENCE CHARACTERISTICS:
  (A) LENGTH: 47 base pairs
  (B) TYPE: nucleic acid
  (C) STRANDEDNESS: single
  (D) TOPOLOGY: linear (xi) SEQUENCE DESCRIPTION: SEQ ID NO:57:

TCGCCTTCAG CTCCGGATG CCTCAGAAGC ATGAACCCCC CATAGGC 47

(2) INFORMATION FOR SEQ ID NO:58:

(i) SEQUENCE CHARACTERISTICS:
  (A) LENGTH: 25 base pairs
  (B) TYPE: nucleic acid
  (C) STRANDEDNESS: single
  (D) TOPOLOGY: linear (xi) SEQUENCE DESCRIPTION: SEQ ID NO:58:

CAATTTTATC CTAAATCTTA CCAAC 25

(2) INFORMATION FOR SEQ ID NO:59:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (xi) SEQUENCE DESCRIPTION: SEQ ID NO:59:

GCCTTCAGCC TCGGATCCGC C 21

(2) INFORMATION FOR SEQ ID NO:60:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (xi) SEQUENCE DESCRIPTION: SEQ ID NO:60:

CGGATGCCTC AGAAGCCCCN N          21

( 2 ) INFORMATION FOR SEQ ID NO:61:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:61:

CGGATGCCTC AGAAGGGCTT TTGCCACAGG          30

( 2 ) INFORMATION FOR SEQ ID NO:62:

( i ) SEQUENCE CHARACTERISTICS:
        ( A ) LENGTH: 22 amino acids
        ( B ) TYPE: amino acid
        ( D ) TOPOLOGY: circular ( i i ) MOLECULE TYPE: peptide ( x i ) SEQUENCE DESCRIPTION: SEQ ID NO:62:

Thr Gln Ser Lys Cys Ser Thr Asp His Trp Leu Gly Tyr Ile Glu Tyr
1               5                   10                  15

Phe Ile Met Cys Thr Tyr
            20

( 2 ) INFORMATION FOR SEQ ID NO:63:

( i ) SEQUENCE CHARACTERISTICS:
        ( A ) LENGTH: 22 amino acids
        ( B ) TYPE: amino acid
        ( D ) TOPOLOGY: circular ( i i ) MOLECULE TYPE: peptide ( x i ) SEQUENCE DESCRIPTION: SEQ ID NO:63:

Cys Asp Asp Gln Tyr Tyr Thr Asp His Glu Gln Gly Lys Cys Glu Val
1               5                   10                  15

Ala Leu Tyr Tyr Thr Gly
            20

( 2 ) INFORMATION FOR SEQ ID NO:64:

( i ) SEQUENCE CHARACTERISTICS:
        ( A ) LENGTH: 24 amino acids
        ( B ) TYPE: amino acid
        ( D ) TOPOLOGY: both ( i i ) MOLECULE TYPE: peptide ( x i ) SEQUENCE DESCRIPTION: SEQ ID NO:64:

Thr Gln Ser Lys Cys Ser Thr Asp His Trp Leu Gly Tyr Ile Glu Tyr
1               5                   10                  15

Phe Ile Met Cys Thr Tyr Arg Arg
            20

( 2 ) INFORMATION FOR SEQ ID NO:65:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:65:

AATTCTTTTA 10

( 2 ) INFORMATION FOR SEQ ID NO:66:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:66:

AATTCTGTTA 10

( 2 ) INFORMATION FOR SEQ ID NO:67:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:67:

AATTCGTTTA 10

( 2 ) INFORMATION FOR SEQ ID NO:68:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:68:

AATTCGGTTA 10

( 2 ) INFORMATION FOR SEQ ID NO:69:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:69:

AATTCTTCTA 10

( 2 ) INFORMATION FOR SEQ ID NO:70:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:70:

AATTCTCCTA 10

( 2 ) INFORMATION FOR SEQ ID NO:71:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:71:

AATTCGTCTA 10

( 2 ) INFORMATION FOR SEQ ID NO:72:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:72:

AATTCGCCTA  10

( 2 ) INFORMATION FOR SEQ ID NO:73:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:73:

AATTCTTATA  10

( 2 ) INFORMATION FOR SEQ ID NO:74:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:74:

AATTCTCATA  10

( 2 ) INFORMATION FOR SEQ ID NO:75:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:75:

AATTCGTATA  10

( 2 ) INFORMATION FOR SEQ ID NO:76:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:76:

AATTCGCATA  10

( 2 ) INFORMATION FOR SEQ ID NO:77:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:77:

AATTCTTGTA  10

( 2 ) INFORMATION FOR SEQ ID NO:78:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:78:

AATTCTCGTA    10

( 2 ) INFORMATION FOR SEQ ID NO:79:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:79:

AATTCGTGTA    10

( 2 ) INFORMATION FOR SEQ ID NO:80:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:80:

AATTCGCGTA    10

( 2 ) INFORMATION FOR SEQ ID NO:81:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:81:

AATTCTCTGA    10

( 2 ) INFORMATION FOR SEQ ID NO:82:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:82:

AATTCTATGA    10

( 2 ) INFORMATION FOR SEQ ID NO:83:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:83:

AATTCGCTGA    10

( 2 ) INFORMATION FOR SEQ ID NO:84:

( i ) SEQUENCE CHARACTERISTICS:
  ( A ) LENGTH: 10 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:84:

AATTCGATGA 10

( 2 ) INFORMATION FOR SEQ ID NO:85:

( i ) SEQUENCE CHARACTERISTICS:
  ( A ) LENGTH: 10 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:85:

AATTCTCAGA 10

( 2 ) INFORMATION FOR SEQ ID NO:86:

( i ) SEQUENCE CHARACTERISTICS:
  ( A ) LENGTH: 10 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:86:

AATTCTGAGA 10

( 2 ) INFORMATION FOR SEQ ID NO:87:

( i ) SEQUENCE CHARACTERISTICS:
  ( A ) LENGTH: 10 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:87:

AATTCGCAGA 10

( 2 ) INFORMATION FOR SEQ ID NO:88:

( i ) SEQUENCE CHARACTERISTICS:
  ( A ) LENGTH: 10 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:88:

AATTCGGAGA 10

( 2 ) INFORMATION FOR SEQ ID NO:89:

( i ) SEQUENCE CHARACTERISTICS:
  ( A ) LENGTH: 10 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:89:

AATTCTACTA 10

( 2 ) INFORMATION FOR SEQ ID NO:90:

( i ) SEQUENCE CHARACTERISTICS:
  ( A ) LENGTH: 10 base pairs ( B ) TYPE: nucleic acid
        ( C ) STRANDEDNESS: single
        ( D ) TOPOLOGY: linear ( x i ) SEQUENCE DESCRIPTION: SEQ ID NO:90:

AATTCTGCTA                                                                                                            10

( 2 ) INFORMATION FOR SEQ ID NO:91:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:91:

AATTCGACTA                                                                                                            10

( 2 ) INFORMATION FOR SEQ ID NO:92:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:92:

AATTCGGCTA                                                                                                            10

( 2 ) INFORMATION FOR SEQ ID NO:93:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:93:

AATTCTAATA                                                                                                            10

( 2 ) INFORMATION FOR SEQ ID NO:94:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:94:

AATTCTGATA                                                                                                            10

( 2 ) INFORMATION FOR SEQ ID NO:95:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:95:

AATTCGAATA                                                                                                            10

( 2 ) INFORMATION FOR SEQ ID NO:96:

( i ) SEQUENCE CHARACTERISTICS:
        ( A ) LENGTH: 10 base pairs
        ( B ) TYPE: nucleic acid
        ( C ) STRANDEDNESS: single (D) TOPOLOGY: linear (xi) SEQUENCE DESCRIPTION: SEQ ID NO:96:

AATTCGGATA 10

(2) INFORMATION FOR SEQ ID NO:97:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:97:

AATTCTTGGA 10

(2) INFORMATION FOR SEQ ID NO:98:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:98:

AATTCTGGGA 10

(2) INFORMATION FOR SEQ ID NO:99:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:99:

AATTCGTGGA 10

(2) INFORMATION FOR SEQ ID NO:100:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:100:

AATTCGGGGA 10

(2) INFORMATION FOR SEQ ID NO:101:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:101:

AATTCTATAA 10

(2) INFORMATION FOR SEQ ID NO:102:

(i) SEQUENCE CHARACTERISTICS:
        (A) LENGTH: 10 base pairs
        (B) TYPE: nucleic acid
        (C) STRANDEDNESS: single
        (D) TOPOLOGY: linear ( x i ) SEQUENCE DESCRIPTION: SEQ ID NO:102:

AATTCTAAAA                                                                                                                       10

( 2 ) INFORMATION FOR SEQ ID NO:103:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:103:

AATTCGATAA                                                                                                                       10

( 2 ) INFORMATION FOR SEQ ID NO:104:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:104:

AATTCGAAAA                                                                                                                       10

( 2 ) INFORMATION FOR SEQ ID NO:105:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 13..14
        ( D ) OTHER INFORMATION: /note= "N = X (used in Table VI),
            which represents an equal mixture of all four
            nucleotides."

( x i ) SEQUENCE DESCRIPTION: SEQ ID NO:105:

AATTCCATAA AANNA                                                                                                                 15

( 2 ) INFORMATION FOR SEQ ID NO:106:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 13..14
        ( D ) OTHER INFORMATION: /note= "N = X (used in Table VI),
            which represents an equal mixture of all four
            nucleotides."

( x i ) SEQUENCE DESCRIPTION: SEQ ID NO:106:

AATTCCATAA ACNNA                                                                                                                 15

( 2 ) INFORMATION FOR SEQ ID NO:107:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:

(A) NAME/KEY: misc_feature
(B) LOCATION: 13..14
(D) OTHER INFORMATION: /note= "N = X (used in Table VI), which represents an equal mixture of all four nucleotides."

(xi) SEQUENCE DESCRIPTION: SEQ ID NO:107:

AATTCCATAA CANNA 15

(2) INFORMATION FOR SEQ ID NO:108:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: misc_feature
(B) LOCATION: 13..14
(D) OTHER INFORMATION: /note= "N = X (used in Table VI), which represents an equal mixture of all four nucleotides."

(xi) SEQUENCE DESCRIPTION: SEQ ID NO:108:

AATTCCATAA CCNNA 15

(2) INFORMATION FOR SEQ ID NO:109:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: misc_feature
(B) LOCATION: 13..14
(D) OTHER INFORMATION: /note= "N = X (used in Table VI), which represents an equal mixture of all four nucleotides."

(xi) SEQUENCE DESCRIPTION: SEQ ID NO:109:

AATTCCATAG AANNA 15

(2) INFORMATION FOR SEQ ID NO:110:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: misc_feature
(B) LOCATION: 13..14
(D) OTHER INFORMATION: /note= "N = X (used in Table VI), which represents an equal mixture of all four nucleotides."

(xi) SEQUENCE DESCRIPTION: SEQ ID NO:110:

AATTCCATAG ACNNA 15

(2) INFORMATION FOR SEQ ID NO:111:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:

(A) NAME/KEY: misc_feature
(B) LOCATION: 13..14
(D) OTHER INFORMATION: /note= "N = X (used in Table VI), which represents an equal mixture of all four nucleotides."

(xi) SEQUENCE DESCRIPTION: SEQ ID NO:111:

AATTCCATAG GANNA 15

(2) INFORMATION FOR SEQ ID NO:112:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: misc_feature
(B) LOCATION: 13..14
(D) OTHER INFORMATION: /note= "N = X (used in Table VI), which represents an equal mixture of all four nucleotides."

(xi) SEQUENCE DESCRIPTION: SEQ ID NO:112:

AATTCCATAG GCNNA 15

(2) INFORMATION FOR SEQ ID NO:113:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: misc_feature
(B) LOCATION: 13..14
(D) OTHER INFORMATION: /note= "N = X (used in Table VI), which represents an equal mixture of all four nucleotides."

(xi) SEQUENCE DESCRIPTION: SEQ ID NO:113:

AATTCCATAT AANNA 15

(2) INFORMATION FOR SEQ ID NO:114:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: misc_feature
(B) LOCATION: 13..14
(D) OTHER INFORMATION: /note= "N = X (used in Table VI), which represents an equal mixture of all four nucleotides."

(xi) SEQUENCE DESCRIPTION: SEQ ID NO:114:

AATTCCATAT ACNNA 15

(2) INFORMATION FOR SEQ ID NO:115:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:

(A) NAME/KEY: misc_feature
(B) LOCATION: 13..14
(D) OTHER INFORMATION: /note= "N = X (used in Table VI), which represents an equal mixture of all four nucleotides."

(xi) SEQUENCE DESCRIPTION: SEQ ID NO:115:

AATTCCATAT GANNA 15

(2) INFORMATION FOR SEQ ID NO:116:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: misc_feature
(B) LOCATION: 13..14
(D) OTHER INFORMATION: /note= "N = X (used in Table VI), which represents an equal mixture of all four nucleotides."

(xi) SEQUENCE DESCRIPTION: SEQ ID NO:116:

AATTCCATAT GCNNA 15

(2) INFORMATION FOR SEQ ID NO:117:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: misc_feature
(B) LOCATION: 13..14
(D) OTHER INFORMATION: /note= "N = X (used in Table VI), which represents an equal mixture of all four nucleotides."

(xi) SEQUENCE DESCRIPTION: SEQ ID NO:117:

AATTCCATAC AANNA 15

(2) INFORMATION FOR SEQ ID NO:118:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: misc_feature
(B) LOCATION: 13..14
(D) OTHER INFORMATION: /note= "N = X (used in Table VI), which represents an equal mixture of all four nucleotides."

(xi) SEQUENCE DESCRIPTION: SEQ ID NO:118:

AATTCCATAC ACNNA 15

(2) INFORMATION FOR SEQ ID NO:119:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:

(A) NAME/KEY: misc_feature
                (B) LOCATION: 13..14
                (D) OTHER INFORMATION: /note= "N = X (used in Table VI),
                    which represents an equal mixture of all four
                    nucleotides."

(xi) SEQUENCE DESCRIPTION: SEQ ID NO:119:

AATTCCATAC GANNA                                                                15

(2) INFORMATION FOR SEQ ID NO:120:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (ix) FEATURE:
                (A) NAME/KEY: misc_feature
                (B) LOCATION: 13..14
                (D) OTHER INFORMATION: /note= "N = X (used in Table VI),
                    which represents an equal mixture of all four
                    nucleotides."

(xi) SEQUENCE DESCRIPTION: SEQ ID NO:120:

AATTCCATAC GCNNA                                                                15

(2) INFORMATION FOR SEQ ID NO:121:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (ix) FEATURE:
                (A) NAME/KEY: misc_feature
                (B) LOCATION: 13..14
                (D) OTHER INFORMATION: /note= "N = X (used in Table VI),
                    which represents an equal mixture of all four
                    nucleotides."

(xi) SEQUENCE DESCRIPTION: SEQ ID NO:121:

AATTCCATCA GANNA                                                                15

(2) INFORMATION FOR SEQ ID NO:122:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (ix) FEATURE:
                (A) NAME/KEY: misc_feature
                (B) LOCATION: 13..14
                (D) OTHER INFORMATION: /note= "N = X (used in Table VI),
                    which represents an equal mixture of all four
                    nucleotides."

(xi) SEQUENCE DESCRIPTION: SEQ ID NO:122:

AATTCCATCA GCNNA                                                                15

(2) INFORMATION FOR SEQ ID NO:123:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (ix) FEATURE:

(A) NAME/KEY: misc_feature
(B) LOCATION: 13..14
(D) OTHER INFORMATION: /note= "N = X (used in Table VI), which represents an equal mixture of all four nucleotides."

(xi) SEQUENCE DESCRIPTION: SEQ ID NO:123:

AATTCCATCA TANNA 15

(2) INFORMATION FOR SEQ ID NO:124:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: misc_feature
(B) LOCATION: 13..14
(D) OTHER INFORMATION: /note= "N = X (used in Table VI), which represents an equal mixture of all four nucleotides."

(xi) SEQUENCE DESCRIPTION: SEQ ID NO:124:

AATTCCATCA TCNNA 15

(2) INFORMATION FOR SEQ ID NO:125:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: misc_feature
(B) LOCATION: 13..14
(D) OTHER INFORMATION: /note= "N = X (used in Table VI), which represents an equal mixture of all four nucleotides."

(xi) SEQUENCE DESCRIPTION: SEQ ID NO:125:

AATTCCATCT GANNA 15

(2) INFORMATION FOR SEQ ID NO:126:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: misc_feature
(B) LOCATION: 13..14
(D) OTHER INFORMATION: /note= "N = X (used in Table VI), which represents an equal mixture of all four nucleotides."

(xi) SEQUENCE DESCRIPTION: SEQ ID NO:126:

AATTCCATCT GCNNA 15

(2) INFORMATION FOR SEQ ID NO:127:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:

(A) NAME/KEY: misc_feature
(B) LOCATION: 13..14
(D) OTHER INFORMATION: /note= "N = X (used in Table VI), which represents an equal mixture of all four nucleotides."

(xi) SEQUENCE DESCRIPTION: SEQ ID NO:127:

AATTCCATCT CANNA 15

(2) INFORMATION FOR SEQ ID NO:128:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: misc_feature
(B) LOCATION: 13..14
(D) OTHER INFORMATION: /note= "N = X (used in Table VI), which represents an equal mixture of all four nucleotides."

(xi) SEQUENCE DESCRIPTION: SEQ ID NO:128:

AATTCCATCT CCNNA 15

(2) INFORMATION FOR SEQ ID NO:129:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: misc_feature
(B) LOCATION: 13..14
(D) OTHER INFORMATION: /note= "N = X (used in Table VI), which represents an equal mixture of all four nucleotides."

(xi) SEQUENCE DESCRIPTION: SEQ ID NO:129:

AATTCCATAG TANNA 15

(2) INFORMATION FOR SEQ ID NO:130:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: misc_feature
(B) LOCATION: 13..14
(D) OTHER INFORMATION: /note= "N = X (used in Table VI), which represents an equal mixture of all four nucleotides."

(xi) SEQUENCE DESCRIPTION: SEQ ID NO:130:

AATTCCATAG TCNNA 15

(2) INFORMATION FOR SEQ ID NO:131:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:

(A) NAME/KEY: misc_feature
(B) LOCATION: 13..14
(D) OTHER INFORMATION: /note= "N = X (used in Table VI), which represents an equal mixture of all four nucleotides."

(xi) SEQUENCE DESCRIPTION: SEQ ID NO:131:

AATTCCATAG CANNA 15

(2) INFORMATION FOR SEQ ID NO:132:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: misc_feature
(B) LOCATION: 13..14
(D) OTHER INFORMATION: /note= "N = X (used in Table VI), which represents an equal mixture of all four nucleotides."

(xi) SEQUENCE DESCRIPTION: SEQ ID NO:132:

AATTCCATAG CCNNA 15

(2) INFORMATION FOR SEQ ID NO:133:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: misc_feature
(B) LOCATION: 13..14
(D) OTHER INFORMATION: /note= "N = X (used in Table VI), which represents an equal mixture of all four nucleotides."

(xi) SEQUENCE DESCRIPTION: SEQ ID NO:133:

AATTCCATAT TANNA 15

(2) INFORMATION FOR SEQ ID NO:134:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: misc_feature
(B) LOCATION: 13..14
(D) OTHER INFORMATION: /note= "N = X (used in Table VI), which represents an equal mixture of all four nucleotides."

(xi) SEQUENCE DESCRIPTION: SEQ ID NO:134:

AATTCCATAT TCNNA 15

(2) INFORMATION FOR SEQ ID NO:135:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:

( A ) NAME/KEY: misc_feature
( B ) LOCATION: 13..14
( D ) OTHER INFORMATION: /note= "N = X (used in Table VI), which represents an equal mixture of all four nucleotides."

( x i ) SEQUENCE DESCRIPTION: SEQ ID NO:135:

AATTCCATAT CANNA                                                                 15

( 2 ) INFORMATION FOR SEQ ID NO:136:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i x ) FEATURE:
( A ) NAME/KEY: misc_feature
( B ) LOCATION: 13..14
( D ) OTHER INFORMATION: /note= "N = X (used in Table VI), which represents an equal mixture of all four nucleotides."

( x i ) SEQUENCE DESCRIPTION: SEQ ID NO:136:

AATTCCATAT CCNNA                                                                 15

( 2 ) INFORMATION FOR SEQ ID NO:137:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i x ) FEATURE:
( A ) NAME/KEY: misc_feature
( B ) LOCATION: 13..14
( D ) OTHER INFORMATION: /note= "N = X (used in Table VI), which represents an equal mixture of all four nucleotides."

( x i ) SEQUENCE DESCRIPTION: SEQ ID NO:137:

AATTCCATCC AANNA                                                                 15

( 2 ) INFORMATION FOR SEQ ID NO:138:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i x ) FEATURE:
( A ) NAME/KEY: misc_feature
( B ) LOCATION: 13..14
( D ) OTHER INFORMATION: /note= "N = X (used in Table VI), which represents an equal mixture of all four nucleotides."

( x i ) SEQUENCE DESCRIPTION: SEQ ID NO:138:

AATTCCATCC ACNNA                                                                 15

( 2 ) INFORMATION FOR SEQ ID NO:139:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i x ) FEATURE:

(A) NAME/KEY: misc_feature
(B) LOCATION: 13..14
(D) OTHER INFORMATION: /note= "N = X (used in Table VI), which represents an equal mixture of all four nucleotides."

(xi) SEQUENCE DESCRIPTION: SEQ ID NO:139:

AATTCCATCC CANNA 15

(2) INFORMATION FOR SEQ ID NO:140:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: misc_feature
(B) LOCATION: 13..14
(D) OTHER INFORMATION: /note= "N = X (used in Table VI), which represents an equal mixture of all four nucleotides."

(xi) SEQUENCE DESCRIPTION: SEQ ID NO:140:

AATTCCATCC CCNNA 15

(2) INFORMATION FOR SEQ ID NO:141:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: misc_feature
(B) LOCATION: 13..14
(D) OTHER INFORMATION: /note= "N = X (used in Table VI), which represents an equal mixture of all four nucleotides."

(xi) SEQUENCE DESCRIPTION: SEQ ID NO:141:

AATTCCATTA TANNA 15

(2) INFORMATION FOR SEQ ID NO:142:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: misc_feature
(B) LOCATION: 13..14
(D) OTHER INFORMATION: /note= "N = X (used in Table VI), which represents an equal mixture of all four nucleotides."

(xi) SEQUENCE DESCRIPTION: SEQ ID NO:142:

AATTCCATTA TCNNA 15

(2) INFORMATION FOR SEQ ID NO:143:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:

(A) NAME/KEY: misc_feature
(B) LOCATION: 13..14
(D) OTHER INFORMATION: /note= "N = X (used in Table VI), which represents an equal mixture of all four nucleotides."

(xi) SEQUENCE DESCRIPTION: SEQ ID NO:143:

AATTCCATTT TANNA                                                                         15

(2) INFORMATION FOR SEQ ID NO:144:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (ix) FEATURE:
    (A) NAME/KEY: misc_feature
    (B) LOCATION: 13..14
    (D) OTHER INFORMATION: /note= "N = X (used in Table VI), which represents an equal mixture of all four nucleotides."

(xi) SEQUENCE DESCRIPTION: SEQ ID NO:144:

AATTCCATTT TCNNA                                                                         15

(2) INFORMATION FOR SEQ ID NO:145:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (xi) SEQUENCE DESCRIPTION: SEQ ID NO:145:

AAMGGTTGGT CGGTACCGG                                                                     19

(2) INFORMATION FOR SEQ ID NO:146:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (xi) SEQUENCE DESCRIPTION: SEQ ID NO:146:

AGRGGTTGGT CGGTACCGG                                                                     19

(2) INFORMATION FOR SEQ ID NO:147:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (xi) SEQUENCE DESCRIPTION: SEQ ID NO:147:

ATRGGTTGGT CGGTACCGG                                                                     19

(2) INFORMATION FOR SEQ ID NO:148:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (xi) SEQUENCE DESCRIPTION: SEQ ID NO:148:

ACRGGTTGGT CGGTACCGG                                                                 19

( 2 ) INFORMATION FOR SEQ ID NO:149:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:149:

CAKGGTTGGT CGGTACCGG                                                                 19

( 2 ) INFORMATION FOR SEQ ID NO:150:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:150:

CTSGGTTGGT CGGTACCGG                                                                 19

( 2 ) INFORMATION FOR SEQ ID NO:151:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:151:

AGYGGTTGGT CGGTACCGG                                                                 19

( 2 ) INFORMATION FOR SEQ ID NO:152:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:152:

ATYGGTTGGT CGGTACCGG                                                                 19

( 2 ) INFORMATION FOR SEQ ID NO:153:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:153:

CCMGGTTGGT CGGTACCGG                                                                 19

( 2 ) INFORMATION FOR SEQ ID NO:154:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:154:

TWTGGTTGGT CGGTACCGG                                                                 19

( 2 ) INFORMATION FOR SEQ ID NO:155:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:155:

AGGATCCGCC GAGCTCAAMA     20

( 2 ) INFORMATION FOR SEQ ID NO:156:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:156:

AGGATCCGCC GAGCTCAGRA     20

( 2 ) INFORMATION FOR SEQ ID NO:157:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:157:

AGGATCCGCC GAGCTCATRA     20

( 2 ) INFORMATION FOR SEQ ID NO:158:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:158:

AGGATCCGCC GAGCTCACRA     20

( 2 ) INFORMATION FOR SEQ ID NO:159:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:159:

AGGATCCGCC GAGCTCCAKA     20

( 2 ) INFORMATION FOR SEQ ID NO:160:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:160:

AGGATCCGCC GAGCTCCTSA     20

( 2 ) INFORMATION FOR SEQ ID NO:161:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:161:

AGGATCCGCC GAGCTCAGYA 20

( 2 ) INFORMATION FOR SEQ ID NO:162:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:162:

AGGATCCGCC GAGCTCATYA 20

( 2 ) INFORMATION FOR SEQ ID NO:163:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:163:

AGGATCCGCC GAGCTCCCMA 20

( 2 ) INFORMATION FOR SEQ ID NO:164:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:164:

AGGATCCGCC GAGCTCTWTA 20

( 2 ) INFORMATION FOR SEQ ID NO:165:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:165:

AAMGGCTTTT GCCACAGG 18

( 2 ) INFORMATION FOR SEQ ID NO:166:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:166:

AGRGGCTTTT GCCACAGG 18

( 2 ) INFORMATION FOR SEQ ID NO:167:

( i ) SEQUENCE CHARACTERISTICS:

( A ) LENGTH: 18 base pairs
             ( B ) TYPE: nucleic acid
             ( C ) STRANDEDNESS: single
             ( D ) TOPOLOGY: linear ( x i ) SEQUENCE DESCRIPTION: SEQ ID NO:167:

ATRGGCTTTT GCCACAGG                                                                              18

( 2 ) INFORMATION FOR SEQ ID NO:168:

( i ) SEQUENCE CHARACTERISTICS:
             ( A ) LENGTH: 18 base pairs
             ( B ) TYPE: nucleic acid
             ( C ) STRANDEDNESS: single
             ( D ) TOPOLOGY: linear ( x i ) SEQUENCE DESCRIPTION: SEQ ID NO:168:

ACRGGCTTTT GCCACAGG                                                                              18

( 2 ) INFORMATION FOR SEQ ID NO:169:

( i ) SEQUENCE CHARACTERISTICS:
             ( A ) LENGTH: 18 base pairs
             ( B ) TYPE: nucleic acid
             ( C ) STRANDEDNESS: single
             ( D ) TOPOLOGY: linear ( x i ) SEQUENCE DESCRIPTION: SEQ ID NO:169:

CAKGGCTTTT GCCACAGG                                                                              18

( 2 ) INFORMATION FOR SEQ ID NO:170:

( i ) SEQUENCE CHARACTERISTICS:
             ( A ) LENGTH: 18 base pairs
             ( B ) TYPE: nucleic acid
             ( C ) STRANDEDNESS: single
             ( D ) TOPOLOGY: linear ( x i ) SEQUENCE DESCRIPTION: SEQ ID NO:170:

CTSGGCTTTT GCCACAGG                                                                              18

( 2 ) INFORMATION FOR SEQ ID NO:171:

( i ) SEQUENCE CHARACTERISTICS:
             ( A ) LENGTH: 18 base pairs
             ( B ) TYPE: nucleic acid
             ( C ) STRANDEDNESS: single
             ( D ) TOPOLOGY: linear ( x i ) SEQUENCE DESCRIPTION: SEQ ID NO:171:

AGYGGCTTTT GCCACAGG                                                                              18

( 2 ) INFORMATION FOR SEQ ID NO:172:

( i ) SEQUENCE CHARACTERISTICS:
             ( A ) LENGTH: 18 base pairs
             ( B ) TYPE: nucleic acid
             ( C ) STRANDEDNESS: single
             ( D ) TOPOLOGY: linear ( x i ) SEQUENCE DESCRIPTION: SEQ ID NO:172:

ATYGGCTTTT GCCACAGG                                                                              18

( 2 ) INFORMATION FOR SEQ ID NO:173:

( i ) SEQUENCE CHARACTERISTICS:
             ( A ) LENGTH: 18 base pairs
             ( B ) TYPE: nucleic acid

```
        ( C ) STRANDEDNESS: single
        ( D ) TOPOLOGY: linear ( x i ) SEQUENCE DESCRIPTION: SEQ ID NO:173:

CCMGGCTTTT GCCACAGG                                                                           18

( 2 ) INFORMATION FOR SEQ ID NO:174:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:174:

TWTGGCTTTT GCCACAGG                                                                           18
```

SOLUBLE PEPTIDES HAVING CONSTRAINED, SECONDARY CONFORMATION IN SOLUTION AND METHOD OF MAKING SAME

This application is a continuation of application Ser. No. 07/978,893, filed Nov. 10, 1992, abandoned, which is a continuation-in-part of application Ser. No. 07/767,436, filed Sep. 27, 1991, abandoned, which is a continuation-in-part of U.S. Ser. No. 07/590,664, filed on Sep. 28, 1990, now abandoned, the contents of each is hereby incorporated by reference into the present disclosure.

BACKGROUND OF THE INVENTION

The biological function of a peptide depends upon its direct, physical interaction with another molecule. The peptide or protein is termed the ligand.

Peptides are distinguishable by their specificity for certain ligand-binding proteins. The specificity of binding, i.e., the discrimination between closely related ligands, is determined by a peptide's binding affinity. Peptides having useful binding properties are invaluable for chemotherapy and drug design. Therefore, a need exists for the generation of peptides having biologically useful binding affinities and being soluble in solution.

Secondary structure of a peptide is critical for determining its binding affinity. For example, a highly flexible peptide is able to interact with many distinct molecules; however, the peptide-ligand interaction is easily disrupted, or in other words, the binding affinity of the peptide is low. Thus, a peptide having a specific secondary structure is able to bind tightly with only a few or one ligand.

However, if secondary structure of the ligand results from non-covalent interactions, the peptide inevitably is insoluble. Intra-peptide covalent bonds can solve this problem resulting in constrained peptides, i.e., peptides having a stable secondary structure in a solution, that are soluble.

This invention provides a method to synthesize soluble peptides having constrained, secondary conformation in solution, as well as the peptides produced by this method.

This invention also relates generally to methods for synthesizing and expressing oligonucleotides and, more particularly, to methods for expressing oligonucleotides having biased, but random codon sequences.

Oligonucleotide synthesis proceeds via linear coupling of individual monomers in a stepwise reaction. The reactions are generally performed on a solid phase support by first coupling the 3' end of the first monomer to the support. The second monomer is added to the 5' end of the first monomer in a condensation reaction to yield a dinucleotide coupled to the solid support. At the end of each coupling reaction, the by-products and unreacted, free monomers are washed away so that the starting material for the next round of synthesis is the pure oligonucleotide attached to the support. In this reaction scheme, the stepwise addition of individual monomers to a single, growing end of a oligonucleotide ensures accurate synthesis of the desired sequence. Moreover, unwanted side reactions are eliminated, such as the condensation of two oligonucleotides, resulting in high product yields.

In some instances, it is desired that synthetic oligonucleotides have random nucleotide sequences. This result can be accomplished by adding equal proportions of all four nucleotides in the monomer coupling reactions, leading to the random incorporation of all nucleotides and yielding a population of oligonucleotides with random sequences. Since all possible combinations of nucleotide sequences are represented within the population, all possible codon triplets will also be represented. If the objective is ultimately to generate random peptide products, this approach has a severe limitation because the random codons synthesized will bias the amino acids incorporated during translation of the DNA by the cell into polypeptides.

The bias is due to the redundancy of the genetic code. There are four nucleotide monomers which leads to sixty-four possible triplet codons. With only twenty amino acids to specify, many of the amino acids are encoded by multiple codons. Therefore, a population of oligonucleotides synthesized by sequential addition of monomers from a random population will not encode peptides whose amino acid sequence represents all possible combinations of the twenty different amino acids in equal proportions. That is, the frequency of amino acids incorporated into polypeptides will be biased toward those amino acids which are specified by multiple codons.

To alleviate amino acid bias due to the redundancy of the genetic code, the oligonucleotides can be synthesized from nucleotide triplets. Here, a triplet coding for each of the twenty amino acids is synthesized from individual monomers. Once synthesized, the triplets are used in the coupling reactions instead of individual monomers. By mixing equal proportions of the triplets, synthesis of oligonucleotides with random codons can be accomplished. However, this is not possible because of the inefficiency of the coupling, which is less than 3% and the high cost of synthesis.

Amino acid bias can be reduced, however, by synthesizing the degenerate codon sequence NNK where N is a mixture of all four nucleotides and K is a mixture guanine and thymine nucleotides. Each position within an oligonucleotide having this codon sequence will contain a total of 32 codons (12 encoding amino acids being represented once, 5 represented twice, 3 represented three times and one codon being a stop codon). Oligonucleotides expressed with such degenerate codon sequences will produce peptide products whose sequences are biased toward those amino acids being represented more than once. Thus, populations of peptides whose sequences are completely random cannot be obtained from oligonucleotides synthesized from degenerate sequences.

There thus exists a need for a method to express oligonucleotides having a fully random or desirably biased sequence which alleviates genetic redundancy. The present invention satisfies these needs and provides additional advantages as well.

SUMMARY OF THE INVENTION

This invention provides a peptide having constrained, secondary structure in solution as well as methods of synthesizing these peptides.

The invention provides a plurality of procaryotic cells containing a diverse population of expressible oligonucleotides encoding soluble peptides having constrained secondary structure or conformation in solution, the expressible oligonucleotide being operationally linked to expression elements, the expressible oligonucleotides further characterized as having a desirable bias of random codon sequences.

BRIEF DESCRIPTION OF THE DRAWINGS

FIG. 3C shows the joining of vector population from sublibraries to form the functional surface expression vector M13IX. FIG. 3D shows the generation of a surface expression library in a non-suppressor strain and the production of phage. The phage are used to infect a suppressor strain (FIG. 3E) for surface expression and screening of the library.

FIG. 5 is the nucleotide sequence of M13IX42 (SEQ ID NO: 1).

FIG. 6 is the nucleotide sequence of M13IX22 (SEQ ID NO: 2).

FIG. 7 is the nucleotide sequence of M13IX30 (SEQ ID NO: 3).

FIG. 8 is the nucleotide sequence of M13ED03 (SEQ ID NO: 4).

FIG. 9 is the nucleotide sequence of M13IX421 (SEQ ID NO: 5).

FIG. 10 is the nucleotide sequence of M13ED04 (SEQ ID NO: 6).

DETAILED DESCRIPTION OF THE INVENTION

Figure 1:
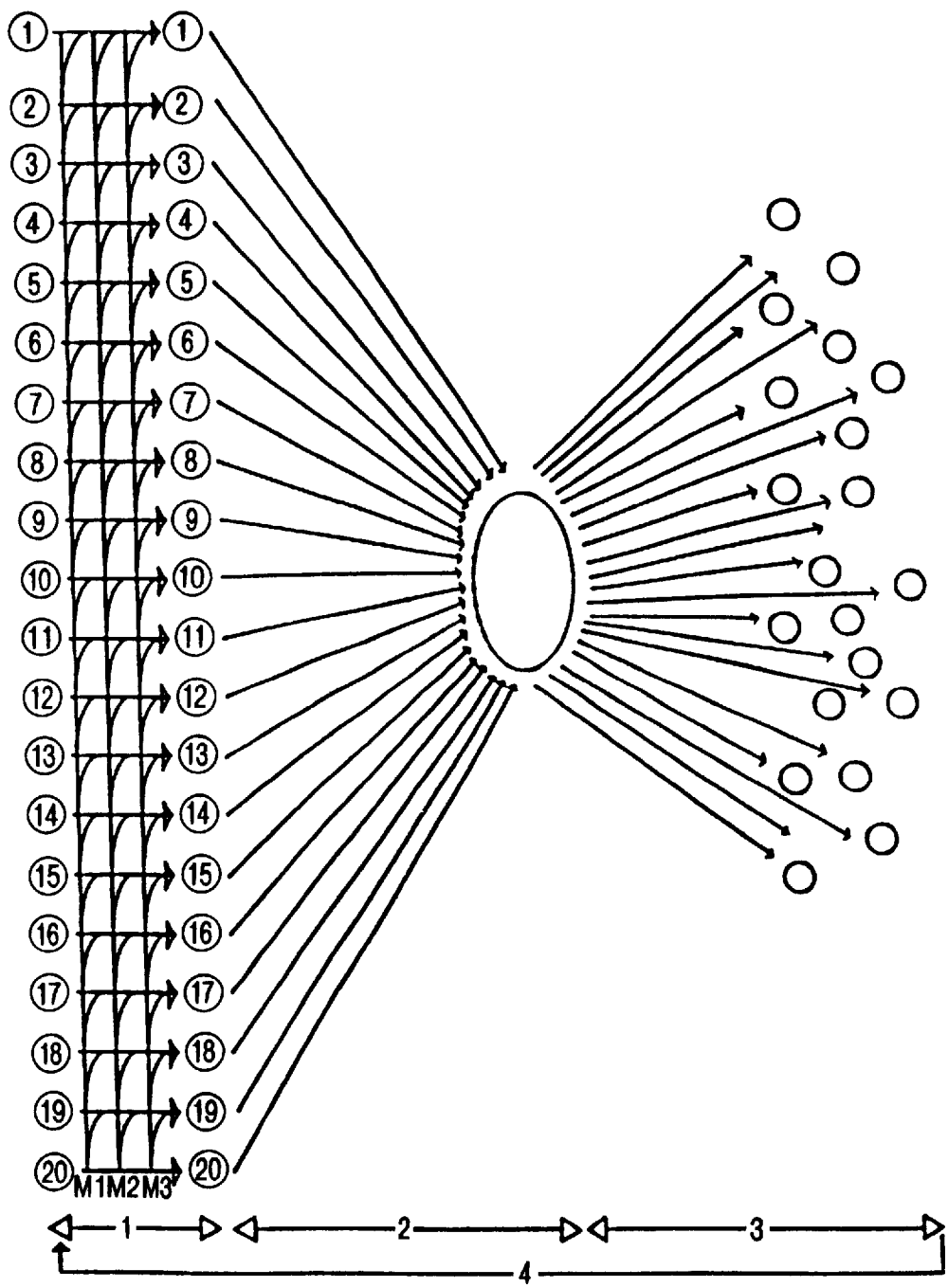
FIG. 1 is a schematic drawing for synthesizing oligonucleotides from nucleotide monomers with random tuplets at each position using twenty reaction vessels.

This invention is directed to a simple and inexpensive method for synthesizing and expressing oligonucleotides having a desirable bias of random codons using individual monomers. The oligonucleotides produced by this method encode soluble peptides having constrained secondary structure in solution. The method is advantageous in that individual monomers are used instead of triplets and by synthesizing only a non-degenerate subset of all triplets, codon redundancy is alleviated. Thus, the oligonucleotides synthesized represent a large proportion of possible random triplet sequences which can be obtained. The oligonucleotides can be expressed, for example, on the surface of filamentous bacteriophage in a form which does not alter phage viability or impose biological selections against certain peptide sequences. The oligonucleotides produced are therefore useful for generating an unlimited number of pharmacological and research products.

This invention entails the sequential coupling of monomers to produce oligonucleotides with a desirable bias of random codons. The coupling reactions for the randomization of twenty codons which specify the amino acids of the genetic code are performed in ten different reaction vessels. Each reaction vessel contains a support on which the monomers for two different codons are coupled in three sequential reactions. One of the reactions couples an equal mixture of two monomers such that the final product has two different codon sequences. The codons are randomized by removing the supports from the reaction vessels and mixing them to produce a single batch of supports containing all twenty codons at a particular position. Synthesis at the next codon position proceeds by equally dividing the mixed batch of supports into ten reaction vessels as before and sequentially coupling the monomers for each pair of codons. The supports are again mixed to randomize the codons at the position just synthesized. The cycle of coupling, mixing and dividing continues until the desired number of codon positions have been randomized. After the last position has been randomized, the oligonucleotides with random codons are cleaved from the support. The random oligonucleotides can then be expressed, for example, on the surface of filamentous bacteriophage as gene VIII-peptide fusion proteins. Alternative genes can be used as well. Using this method, one can randomize oligonucleotides at certain positions and select for specific oligonucleotides at others.

This invention provides a diverse population of synthetic biased oligonucleotides contained in vectors so as to be expressible in cells. In the preferred embodiment of this invention, the oligonucleotides are fully defined in that at least two codons encode amino acids capable of forming a covalent bond. The populations of oligonucleotides can be expressed as fusion products in combination with surface proteins of filamentous bacteriophage, such as M13, as with gene VIII. The vectors can be transfected into a plurality of cells, such as the procaryote *E. coli*.

In one embodiment, the diverse population of oligonucleotides can be formed by randomly combining first and second precursor populations, each or either precursor population having a desirable bias of random codon sequences. Methods of synthesizing and expressing the diverse population of expressible oligonucleotides are also provided.

Two precursor populations of random precursor oligonucleotides are synthesized in one embodiment. The oligonucleotides within each population encode a portion of the final oligonucleotide that is expressed. Oligonucleotides within one precursor population encode the carboxy terminal portion of the expressed oligonucleotides. In one embodiment, these oligonucleotides are cloned in frame with a gene VIII (gVIII) sequence so that translation of the sequence produces peptide fusion proteins. The second population of precursor oligonucleotides are cloned into a separate vector. Each precursor oligonucleotide within this population encodes the anti-sense of the amino terminal portion of the expressed oligonucleotides. This vector also contains the elements necessary for expression. The two vectors containing the random oligonucleotides are combined such that the two precursor oligonucleotide portions are joined together at random to form a population of larger oligonucleotides derived from two smaller portions. The vectors contain selectable markers to ensure maximum efficiency in joining together the two oligonucleotide populations. A mechanism also exists to control the expression of gVIII-peptide fusion proteins during library construction and screening.

As used herein, the term "monomer" or "nucleotide monomer" refers to individual nucleotides used in the chemical synthesis of oligonucleotides. Monomers that can be used include both the ribo- and deoxyribo-forms of each of the five standard nucleotides (derived from the bases adenine (A or dA, respectively), guanine (G or dG), cytosine (C or dC), thymine (T) and uracil (U)). Derivatives and precursors of bases such as inosine which are capable of supporting polypeptide biosynthesis are also included as monomers. Also included are chemically modified nucleotides, for example, one having a reversible blocking agent attached to any of the positions on the purine or pyrimidine bases, the ribose or deoxyribose sugar or the phosphate or hydroxyl moieties of the monomer. Such blocking groups include, for example, dimethoxytrityl, benzoyl, isobutyryl, beta-cyanoethyl and diisopropylamine groups, and are used to protect hydroxyls, exocyclic amines and phosphate moieties. Other blocking agents can also be used and are known to one skilled in the art.

As used herein, the term "tuplet" refers to a group of elements of a definable size. The elements of a tuplet as used herein are nucleotide monomers. For example, a tuplet can be a dinucleotide, a trinucleotide or can also be four or more nucleotides.

As used herein, the term "codon" or "triplet" refers to a tuplet consisting of three adjacent nucleotide monomers which specify one of the twenty naturally occurring amino acids found in polypeptide biosynthesis. The term also includes nonsense, or stop, codons which do not specify any amino acid.

"Random codons" or "randomized codons," as used herein, refers to more than one codon at a position within a collection of oligonucleotides. The number of different codons can be from two to twenty at any particular position. "Randomized oligonucleotides," as used herein, refers to a collection of oligonucleotides with random codons at one or more positions. "Random codon sequences" as used herein means that more than one codon position within a randomized oligonucleotide contains random codons. For example, if randomized oligonucleotides are six nucleotides in length (i.e., two codons) and both the first and second codon positions are randomized to encode all twenty amino acids, then a population of oligonucleotides having random codon sequences with every possible combination of the twenty triplets in the first and second position makes up the above population of randomized oligonucleotides. The number of possible codon combinations is $20^2$. Likewise, if randomized oligonucleotides of fifteen nucleotides in length are synthesized which have random codon sequences at all positions encoding all twenty amino acids, then all triplets coding for each of the twenty amino acids will be found in equal proportions at every position. The population constituting the randomized oligonucleotides will contain $20^{15}$ different possible species of oligonucleotides. "Random tuplets," or "randomized tuplets" are defined analogously.

As used herein, the term "bias" refers to a preference. It is understood that there can be degrees of preference or bias toward codon sequences which encode particular amino acids. For example, an oligonucleotide whose codon sequences do not preferably encode particular amino acids is unbiased and therefore completely random. The oligonucleotide codon sequences can also be biased toward predetermined codon sequences or codon frequencies and while still diverse and random, will exhibit codon sequences biased toward a defined, or preferred, sequence. "A desirable bias of random codon sequences" as used herein, refers to the predetermined degree of bias which can be selected from totally random to essentially, but not totally, defined (or preferred). There must be at least one codon position which is variable, however.

As used herein, the term "support" refers to a solid phase material for attaching monomers for chemical synthesis. Such support is usually composed of materials such as beads of control pore glass but can be other materials known to one skilled in the art. The term is also meant to include one or more monomers coupled to the support for additional oligonucleotide synthesis reactions.

As used herein, the terms "coupling" or "condensing" refers to the chemical reactions for attaching one monomer to a second monomer or to a solid support. Such reactions are known to one skilled in the art and are typically performed on an automated DNA synthesizer such as a MilliGen/Biosearch Cyclone Plus Synthesizer using procedures recommended by the manufacturer. "Sequentially coupling" as used herein, refers to the stepwise addition of monomers.

The term "soluble peptide" means a peptide that is soluble at a concentration equivalent to its affinity to a receptor. The peptide can then be used in aqueous solution without being attached to a cell or phage.

The term "constrained secondary structure in solution" means a peptide having a covalent bond that is not the backbone peptide bond.

A method of synthesizing oligonucleotides having biased random tuplets using individual monomers is described. The method consists of several steps, the first being synthesis of a nucleotide tuplet for each tuplet to be randomized. As described here and below, a nucleotide triplet (i.e., a codon) will be used as a specific example of a tuplet. Any size tuplet will work using the methods disclosed herein, and one skilled in the art would know how to use the methods to randomize tuplets of any size.

If the randomization of codons specifying all twenty amino acids is desired at a position, then twenty different codons are synthesized. Likewise, if randomization of only ten codons at a particular position is desired then those ten codons are synthesized. Randomization of codons from two to sixty-four can be accomplished by synthesizing each desired triplet. Preferably, randomization of from two to twenty codons is used for any one position because of the redundancy of the genetic code. The codons selected at one position do not have to be the same codons selected at the next position. Additionally, the sense or anti-sense sequence oligonucleotide can be synthesized. The process therefore provides for randomization of any desired codon position with any number of codons. In addition, it also allows one to preselect a specified codon to be present at a particular position within a randomized sequence.

Codons to be randomized are synthesized sequentially by coupling the first monomer of each codon to separate supports. The supports for the synthesis of each codon can, for example, be contained in different reaction vessels such that one reaction vessel corresponds to the monomer coupling reactions for one codon. As will be used here and below, if twenty codons are to be randomized, then twenty reaction vessels can be used in independent coupling reactions for the first twenty monomers of each codon. Synthesis proceeds by sequentially coupling the second monomer of each codon to the first monomer to produce a dimer, followed by coupling the third monomer for each codon to each of the above-synthesized dimers to produce a trimer (FIG. 1, step 1, where $M_1$, $M_2$ and $M_3$ represent the first, second and third monomer, respectively, for each codon to be randomized).

Following synthesis of the first codons from individual monomers, the randomization is achieved by mixing the supports from all twenty reaction vessels which contain the individual codons to be randomized. The solid phase support can be removed from its vessel and mixed to achieve a random distribution of all codon species within the population (FIG. 1, step 2). The mixed population of supports, constituting all codon species, are then redistributed into twenty independent reaction vessels (FIG. 1, step 3). The resultant vessels are all identical and contain equal portions of all twenty codons coupled to a solid phase support.

For randomization of the second position codon, synthesis of twenty additional codons is performed in each of the twenty reaction vessels produced in step 3 as the condensing substrates of step 1 (FIG. 1, step 4). Steps 1 and 4 are therefore equivalent except that step 4 uses the supports produced by the previous synthesis cycle (steps 1 through 3) for codon synthesis whereas step 1 is the initial synthesis of the first codon in the oligonucleotide. The supports resulting from step 4 will each have two codons attached to them (i.e., a hexanucleotide) with the codon at the first position being any one of twenty possible codons (i.e., random) and the codon at the second position being one of the twenty possible codons.

For randomization of the codon at the second position and synthesis of the third position codon, steps 2 through 4 are again repeated. This process yields in each vessel a three codon oligonucleotide (i.e., 9 nucleotides) with codon positions 1 and 2 randomized and position three containing one of the twenty possible codons. Steps 2 through 4 are repeated to randomize the third position codon and synthesize the codon at the next position. The process is continued until an oligonucleotide of the desired length is achieved. After the final randomization step, the oligonucleotide can be cleaved from the supports and isolated by methods known to one skilled in the art. Alternatively, the oligonucleotides can remain on the supports for use in methods employing probe hybridization.

The diversity of codon sequences, i.e., the number of different possible oligonucleotides, that can be obtained using the methods of the present invention, is extremely large and only limited by the physical characteristics of available materials. For example, a support composed of beads of about 100 $\mu$m in diameter will be limited to about 10,000 beads/reaction vessel using a 1 $\mu$M reaction vessel containing 25 mg of beads. This size bead can support about $1 \times 10^7$ oligonucleotides per bead. Synthesis using separate reaction vessels for each of the twenty amino acids will produce beads in which all the oligonucleotides attached to an individual bead are identical. The diversity which can be obtained under these conditions is approximately $10^7$ copies of 10,000×20 or 200,000 different random oligonucleotides. The diversity can be increased, however, in several ways without departing from the basic methods disclosed herein. For example, the number of possible sequences can be increased by decreasing the size of the individual beads which make up the support. A bead of about 30 $\mu$m in diameter will increase the number of beads per reaction vessel and therefore the number of oligonucleotides synthesized. Another way to increase the diversity of oligonucleotides with random codons is to increase the volume of the reaction vessel. For example, using the same size bead, a larger volume can contain a greater number of beads than a smaller vessel and therefore support the synthesis of a greater number of oligonucleotides. Increasing the number of codons coupled to a support in a single reaction vessel also increases the diversity of the random oligonucleotides. The total diversity will be the number of codons coupled per vessel raised to the number of codon positions synthesized. For example, using ten reaction vessels, each synthesizing two codons to randomize a total of twenty codons, the number of different oligonucleotides of ten codons in length per 100 $\mu$m bead can be increased where each bead will contain about $2^{10}$ or $1 \times 10^3$ different sequences instead of one. One skilled in the art will know how to modify such parameters to increase the diversity of oligonucleotides with random codons.

A method of synthesizing oligonucleotides having random codons at each position using individual monomers wherein the number of reaction vessels is less than the number of codons to be randomized is also described. For example, if twenty codons are to be randomized at each position within an oligonucleotide population, then ten reaction vessels can be used. The use of a smaller number of reaction vessels than the number of codons to be randomized at each position is preferred because the smaller number of reaction vessels is easier to manipulate and results in a greater number of possible oligonucleotides synthesized.

Figure 2:
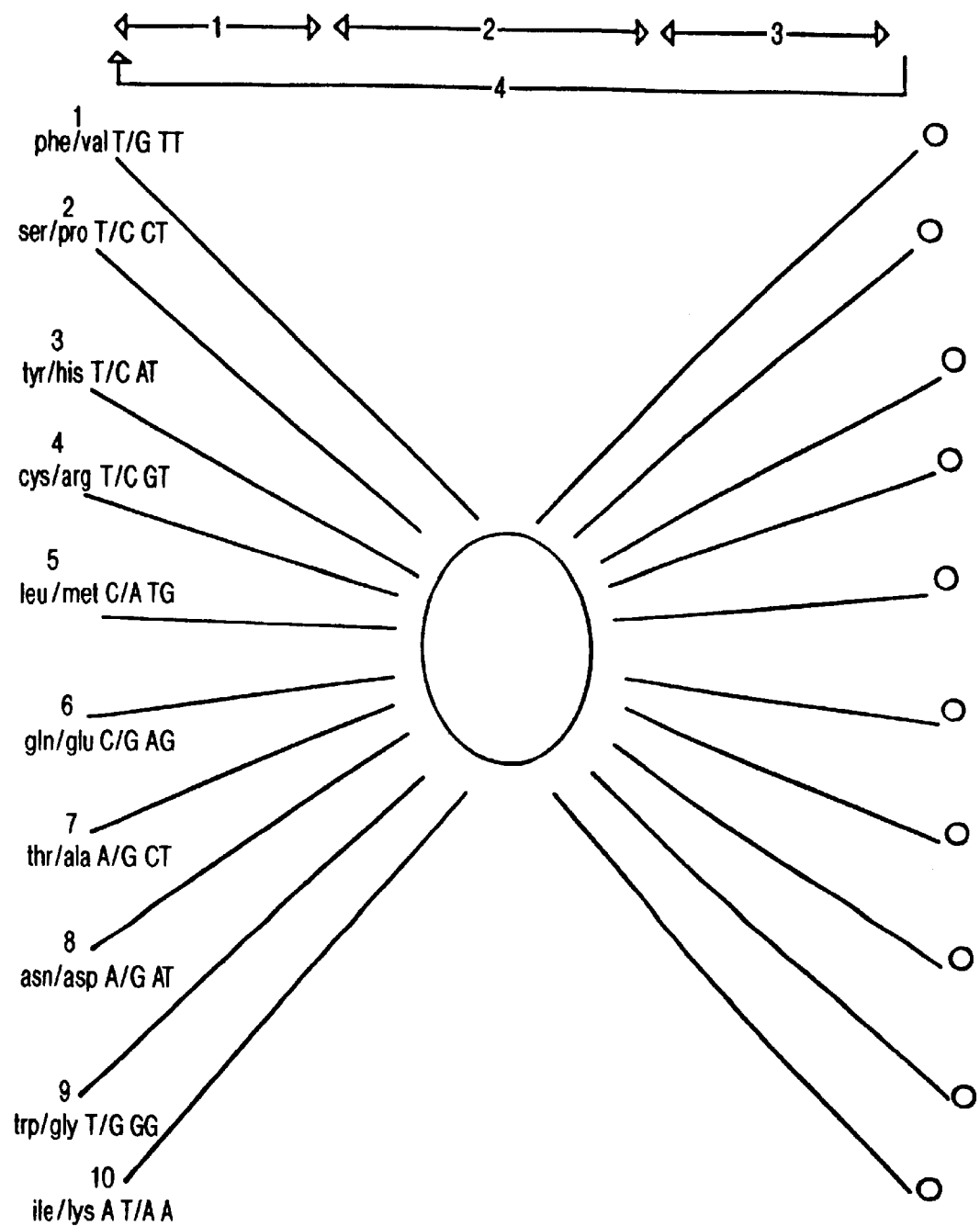
FIG. 2 is a schematic drawing for synthesizing oligonucleotides from nucleotide monomers with random tuplets at each position using ten reaction vessels.

The use of a smaller number of reaction vessels for random synthesis of twenty codons at a desired position within an oligonucleotide is similar to that described above using twenty reaction vessels except that each reaction vessel can contain the synthesis products of more than one codon. For example, step one synthesis using ten reaction vessels proceeds by coupling about two different codons on supports contained in each of ten reaction vessels. This is shown in FIG. 2 where each of the two codons coupled to a different support can consist of the following sequences: (1) (T/G)TT for Phe and Val; (2) (T/C)CT for Ser and Pro; (3) (T/C)AT for Tyr and His; (4) (T/C)GT for Cys and Arg; (5) (C/A)TG for Leu and Met; (6) (C/G)AG for Gln and Glu; (7) (A/G)CT for Thr and Ala; (8) (A/G)AT for Asn and Asp; (9) (T/G)GG for Trp and Gly and (10) A(T/A)A for Ile and Cys. The slash (/) signifies that a mixture of the monomers indicated on each side of the slash are used as if they were a single monomer in the indicated coupling step. The antisense sequence for each of the above codons can be generated by synthesizing the complementary sequence. For example, the antisense for Phe and Val can be AA(C/A). The amino acids encoded by each of the above pairs of sequences are given as the standard three letter nomenclature.

Coupling of the monomers in this fashion will yield codons specifying all twenty of the naturally occurring amino acids attached to supports in ten reaction vessels. However, the number of individual reaction vessels to be used will depend on the number of codons to be randomized at the desired position and can be determined by one skilled in the art. For example, if ten codons are to be randomized, then five reaction vessels can be used for coupling. The codon sequences given above can be used for this synthesis as well. The sequences of the codons can also be changed to incorporate or be replaced by any of the additional forty-four codons which constitutes the genetic code.

The remaining steps of synthesis of oligonucleotides with random codons using a smaller number of reaction vessels are as outlined above for synthesis with twenty reaction vessels except that the mixing and dividing steps are performed with supports from about half the number of reaction vessels. These remaining steps are shown in FIG. 2 (steps 2 through 4).

Oligonucleotides having at least one specified tuplet at a predetermined position and the remaining positions having random tuplets are synthesized using the methods described herein. The synthesis steps are similar to those outlined above using twenty or less reaction vessels except that prior to synthesis of the specified codon position, the dividing of the supports into separate reaction vessels for synthesis of different codons is omitted. For example, if the codon at the second position of the oligonucleotide is to be specified, then following synthesis of random codons at the first position and mixing of the supports, the mixed supports are not divided into new reaction vessels but, instead, are contained in a single reaction vessel to synthesize the specified codon. The specified codon is synthesized sequentially from individual monomers as described above. Thus, the number of reaction vessels is increased or decreased at each step to allow for the synthesis of a specified codon or a desired number of random codons. In the most preferred embodiment of this invention, the specified codons are codons capable of forming covalent bonds, e.g., cysteine, glutamic acid, lysine, leucine and tyrosine.

Following codon synthesis, the mixed supports are divided into individual reaction vessels for synthesis of the next codon to be randomized (FIG. 1, step 3) or can be used without separation for synthesis of a consecutive specified codon. The rounds of synthesis can be repeated for each codon to be added until the desired number of positions with predetermined or randomized codons are obtained.

Synthesis of oligonucleotides with the first position codon being specified can also be synthesized using the above method. In this case, the first position codon is synthesized from the appropriate monomers. The supports are divided into the required number of reaction vessels needed for synthesis of random codons at the second position and the rounds of synthesis, mixing and dividing are performed as described above.

A method of synthesizing oligonucleotides having tuplets which are diverse but biased toward a predetermined sequence is also described herein. This method employs two reaction vessels, one vessel for the synthesis of a predetermined sequence and the second vessel for the synthesis of a random sequence. This method is advantageous to use when a significant number of codon positions, for example, are to be of a specified sequence since it alleviates the use of multiple reaction vessels. Instead, a mixture of four different monomers such as adenine, guanine, cytosine and thymine nucleotides are used for the first and second monomers in the codon. The codon is completed by coupling a mixture of a pair of monomers of either guanine and thymine or cytosine and adenine nucleotides at the third monomer position. In the second vessel, nucleotide monomers are coupled sequentially to yield the predetermined codon sequence. Mixing of the two supports yields a population of oligonucleotides containing both the predetermined codon and the random codons at the desired position. Synthesis can proceed by using this mixture of supports in a single reaction vessel, for example, for coupling additional predetermined codons or, further dividing the mixture into two reaction vessels for synthesis of additional random codons.

The two reaction vessel method can be used for codon synthesis within an oligonucleotide with a predetermined tuplet sequence by dividing the support mixture into two portions at the desired codon position to be randomized. Additionally, this method allows for the extent of randomization to be adjusted. For example, unequal mixing or dividing of the two supports will change the fraction of codons with predetermined sequences compared to those with random codons at the desired position. Unequal mixing and dividing of supports can be useful when there is a need to synthesize random codons at a significant number of positions within an oligonucleotide of a longer or shorter length.

The extent of randomization can also be adjusted by using unequal mixtures of monomers in the first, second and third monomer coupling steps of the random codon position. The unequal mixtures can be in any or all of the coupling steps to yield a population of codons enriched in sequences reflective of the monomer proportions.

Synthesis of randomized oligonucleotides is performed using methods well known to one skilled in the art. Linear coupling of monomers can, for example, be accomplished using phosphoramidite chemistry with a MilliGen/Biosearch Cyclone Plus automated synthesizer as described by the manufacturer (Millipore, Burlington, Mass.). Other chemistries and automated synthesizers can be employed as well and are known to one skilled in the art.

Synthesis of multiple codons can be performed without modification to the synthesizer by separately synthesizing the codons in individual sets of reactions. Alternatively, modification of an automated DNA synthesizer can be performed for the simultaneous synthesis of codons in multiple reaction vessels.

In one embodiment, the invention provides a plurality of procaryotic cells containing a diverse population of expressible oligonucleotides operationally linked to expression elements, the expressible oligonucleotides having a desirable bias of random codon sequences. These oligonucleotides can, in one embodiment, be produced from diverse combinations of first and second precursor oligonucleotides having a desirable bias of random sequences. The invention provides for a method for constructing such a plurality of procaryotic cells as well.

The oligonucleotides synthesized by the above methods can be used to express a plurality of random soluble peptides having constrained secondary structure in solution, diverse but biased toward a predetermined sequence or which contain at least one specified codon at a predetermined position. The need will determine which type of oligonucleotide is to be expressed to give the resultant population of random peptides and is known to one skilled in the art. Expression can be performed in any compatible vector/host system. Such systems include, for example, plasmids or phagemids in procaryotes such as E. coli, yeast systems, and other eucaryotic systems such as mammalian cells, but will be described herein in context with its presently preferred embodiment, i.e. expression on the surface of filamentous bacteriophage. Filamentous bacteriophage can be, for example, M13, f1 and fd. Such phage have circular single-stranded genomes and double strand replicative DNA forms. Additionally, the peptides can also be expressed in soluble or secreted form depending on the need and the vector/host system employed. Furthermore, this invention provides host cells containing the expressible oligonucleotides, the vectors and the isolated soluble, stable peptides produced by growing a host cell described above under conditions favoring expression of the oligonucleotide, and isolating the peptide so produced.

Figure 3:
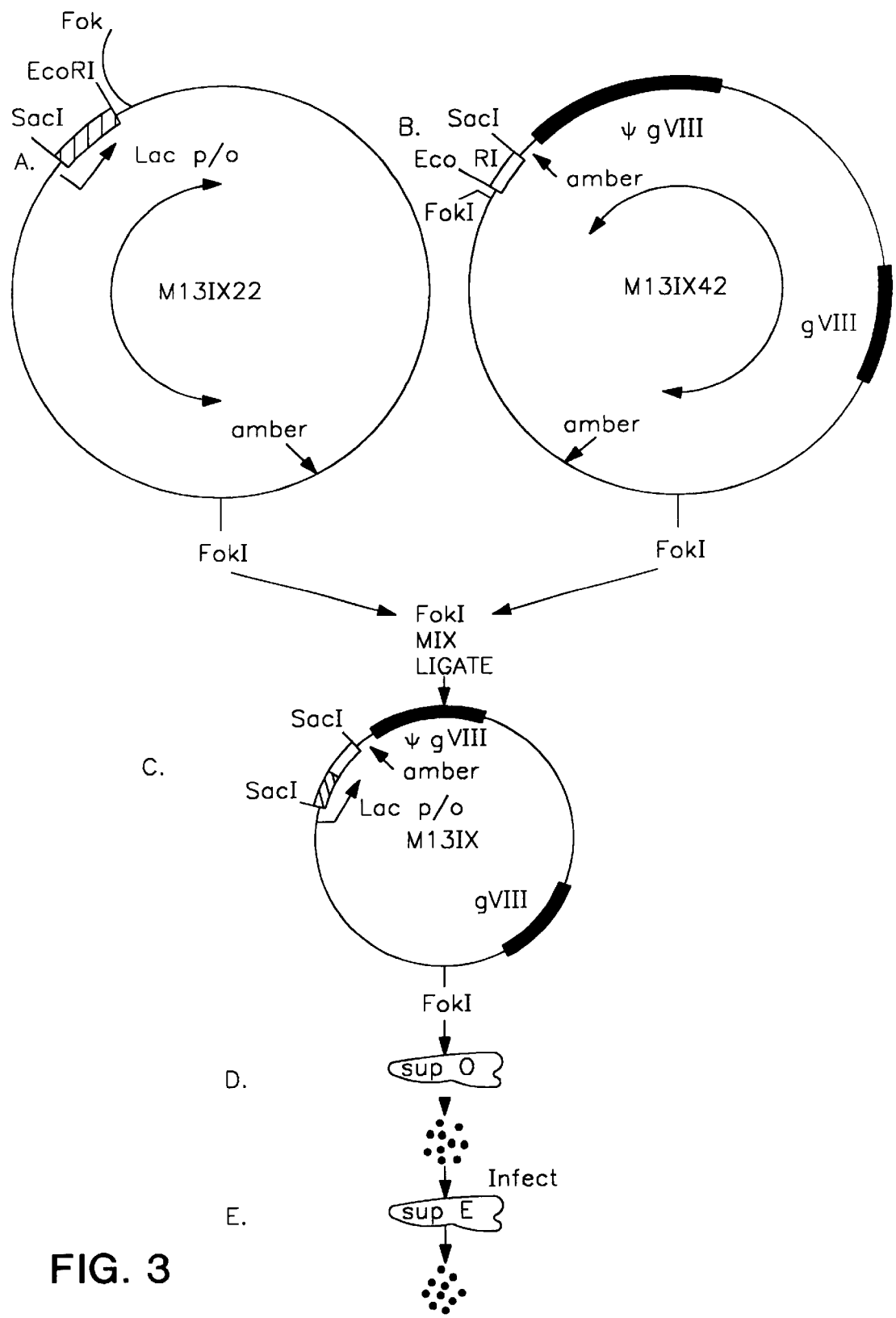
FIGS. 3A–3E show a schematic diagram of the two vectors used for sublibrary and library production from precursor oligonucleotide portions. M13IX22 (FIG. 3A) is the vector used to clone the anti-sense precursor portions (hatched box). The single-headed arrow represents the Lac p/o expression sequences and the double-headed arrow represents the portion of M13IX22 which is to be combined with M13IX42. The amber stop codon for biological selection and relevant restriction sites are also shown. M13IX42 (FIG. 3B) is the vector used to clone the sense precursor portions (open box). Thick lines represent the pseudo-wild type (gVIII) and wild type (gVIII) gene VIII sequences. The double-headed arrow represents the portion of M13IX42 which is to be combined with M13IX22. The two amber stop codons and relevant restriction sites are also shown.

For the purpose of illustration only, expression of random peptides on the surface of M13 can be accomplished, for example, using the vector system shown in FIG. 3. Construction of the vectors enabling one of ordinary skill to make them are explicitly set out in Examples I and II. The complete nucleotide sequences are given in FIGS. 5, 6 and 7 (SEQ ID NOS: 1, 2 and 3, respectively). This system produces random oligonucleotides functionally linked to expression elements and to gVIII by combining two smaller oligonucleotide portions contained in separate vectors into a single vector. The diversity of oligonucleotide species obtained by this system or others described herein can be $5 \times 10^7$ or greater. Diversity of less than $5 \times 10^7$ can also be obtained and will be determined by the need and type of random peptides to be expressed. The random combination of two precursor portions into a larger oligonucleotide increases the diversity of the population several fold and has the added advantage of producing oligonucleotides larger than what can be synthesized by standard methods. Additionally, although the correlation is not known, when the number of possible paths an oligonucleotide can take during synthesis such as described herein is greater than the number of beads, then there will be a correlation between the synthesis path and the sequences obtained. By combining oligonucleotide populations which are synthesized separately, this correlation will be destroyed. Therefore, any bias which may be inherent in the synthesis procedures will be alleviated by joining two precursor portions into a contiguous random oligonucleotide.

Populations of precursor oligonucleotides to be combined into an expressible form are each cloned into separate vectors. The two precursor portions which make up the combined oligonucleotide corresponds to the carboxy and amino terminal portions of the expressed peptide. Each precursor oligonucleotide can encode either the sense or anti-sense and will depend on the orientation of the expression elements and the gene encoding the fusion portion of the protein as well as the mechanism used to join the two precursor oligonucleotides. For the vectors shown in FIG. 3, precursor oligonucleotides corresponding to the carboxy terminal portion of the peptide encode the sense strand. Those corresponding to the amino terminal portion encode the anti-sense strand. Oligonucleotide populations are inserted between the Eco RI and Sac I restriction enzyme sites in M13IX22 and M13IX42 (FIG. 3A and B). M13IX42 (SEQ ID NO: 1) is the vector used for sense strand precursor oligonucleotide portions and M13IX22 (SEQ ID NO: 2) is used for anti-sense precursor portions.

The populations of randomized oligonucleotides inserted into the vectors are synthesized with Eco RI and Sac I recognition sequences flanking opposite ends of the random codon sequences. The sites allow annealing and ligation of these single strand oligonucleotides into a double stranded vector restricted with Eco RI and Sac I. Alternatively, the oligonucleotides can be inserted into the vector by standard mutagenesis methods. In this latter method, single stranded vector DNA is isolated from the phage and annealed with random oligonucleotides having known sequences complementary to vector sequences. The oligonucleotides are extended with DNA polymerase to produce double stranded vectors containing the randomized oligonucleotides.

A vector useful for sense strand oligonucleotide portions, M13IX42 (FIG. 3B) contains down-stream and in frame with the Eco RI and Sac I restriction sites a sequence encoding the pseudo-wild type gVIII product. This gene encodes the wild type M13 gVIII amino acid sequence but has been changed at the nucleotide level to reduce homologous recombination with the wild type gVIII contained on the same vector. The wild type gVIII is present to ensure that at least some functional, non-fusion coat protein will be produced. The inclusion of a wild type gVIII therefore reduces the possibility of non-viable phage production and biological selection against certain peptide fusion proteins. Differential regulation of the two genes can also be used to control the relative ratio of the pseudo and wild type proteins.

Also contained downstream and in frame with the Eco RI and Sac I restriction sites is an amber stop codon. The mutation is located six codons downstream from Sac I and therefore lies between the inserted oligonucleotides and the gVIII sequence. As was the function of the wild type gVIII, the amber stop codon also reduces biological selection when combining precursor portions to produce expressible oligonucleotides. This is accomplished by using a non-suppressor (sup O) host strain because non-suppressor strains will terminate expression after the oligonucleotide sequences but before the pseudo gVIII sequences. Therefore, the pseudo gVIII will never be expressed on the phage surface under these circumstances. Instead, only soluble peptides will be produced. Expression in a non-suppressor strain can be advantageously utilized when one wishes to produce large populations of soluble peptides. Stop codons other than amber, such as opal and ochre, or molecular switches, such as inducible repressor elements, can also be used to unlink peptide expression from surface expression. Additional controls exist as well and are described below.

A vector useful for anti-sense strand oligonucleotide portions, M13IX22, (FIG. 3A), contains the expression elements for the peptide fusion proteins. Upstream and in frame with the Sac I and Eco RI sites in this vector is a leader sequence for surface expression. A ribosome binding site and Lac Z promoter/operator elements are present for transcription and translation of the peptide fusion proteins.

Both vectors contain a pair of Fok I restriction enzyme sites (FIGS. 3A and B) for joining together two precursor oligonucleotide portions and their vector sequences. One site is located at the ends of each precursor oligonucleotide which is to be joined. The second Fok I site within the vectors is located at the end of the vector sequences which are to be joined. The 5' overhang of this second Fok I site has been altered to encode a sequence which is not found in the overhangs produced at the first Fok I site within the oligonucleotide portions. The two sites allow the cleavage of each circular vector into two portions and subsequent ligation of essential components within each vector into a single circular vector where the two oligonucleotide precursor portions form a contiguous sequence (FIG. 3C). Non-compatible overhangs produced at the two Fok I sites allows optimal conditions to be selected for performing concatermization or circularization reactions for joining the two vector portions. Such selection of conditions can be used to govern the reaction order and therefore increase the efficiency of joining.

Fok I is a restriction enzyme whose recognition sequence is distal to the point of cleavage. Distal placement of the recognition sequence in its location to the cleavage point is important since if the two were superimposed within the oligonucleotide portions to be combined, it would lead to an invariant codon sequence at the juncture. To alleviate the formation of invariant codons at the juncture, Fok I recognition sequences can be placed outside of the random codon sequence and still be used to restrict within the random sequence. Subsequent annealing of the single-strand overhangs produced by Fok I and ligation of the two oligonucleotide precursor portions allows the juncture to be formed. A variety of restriction enzymes restrict DNA by this mechanism and can be used instead of Fok I to join precursor oligonucleotides without creating invariant codon sequences. Such enzymes include, for example, Alw I, Bbu I, Bsp MI, Hga I, Hph I, Mbo II, Mnl I, Ple I and Sfa NI. One skilled in the art knows how to substitute Fok I recognition sequences for alternative enzyme recognition sequences such as those above, and use the appropriate enzyme for joining precursor oligonucleotide portions.

Although the sequences of the precursor oligonucleotides are random and will invariably have oligonucleotides within the two precursor populations whose sequences are sufficiently complementary to anneal after cleavage, the efficiency of annealing can be increased by insuring that the single-strand overhangs within one precursor population will have a complementary sequence within the second precursor population. This can be accomplished by synthesizing a non-degenerate series of known sequences at the Fok I cleavage site coding for each of the twenty amino acids. Since the Fok I cleavage site contains a four base overhang, forty different sequences are needed to randomly encode all twenty amino acids. For example, if two precursor populations of ten codons in length are to be combined, then after the ninth codon position is synthesized, the mixed population of supports are divided into forty reaction vessels for each of the populations and complementary sequences for each of the corresponding reaction vessels between populations are independently synthesized. The sequences are shown in Tables III and VI of Example I where the oligonucleotides on columns 1R through 40R form complementary overhangs with the oligonucleotides on the corresponding columns 1L through 40L once cleaved. The degenerate X positions in Table VI are necessary to maintain the reading frame once the precursor oligonucleotide portions are joined. However, use of restriction enzymes which produce a blunt end, such as Mnl I can be alternatively used in place of Fok I to alleviate the degeneracy introduced in maintaining the reading frame.

The last feature exhibited by each of the vectors is an amber stop codon located in an essential coding sequence within the vector portion lost during combining (FIG. 3C). The amber stop codon is present to select for viable phage produced from only the proper combination of precursor oligonucleotides and their vector sequences into a single vector species. Other non-sense mutations or selectable markers can work as well.

The combining step randomly brings together different precursor oligonucleotides within the two populations into a single vector (FIG. 3C; M13IX). For example, the vector sequences donated from each independent vector described above, M13IX22 and M13IX42, are necessary for production of viable phage. Also, since the expression elements are contained in M13IX22 and the gVIII sequences are contained in M13IX42, expression of functional gVIII-peptide fusion proteins cannot be accomplished until the sequences are linked as shown in M13IX.

The combining step is performed by restricting each population of vectors containing randomized oligonucleotides with Fok I, mixing and ligating (FIG. 3C). Any vectors generated which contain an amber stop codon will not produce viable phage when introduced into a non-suppressor strain (FIG. 3D). Therefore, only the sequences which do not contain an amber stop codon will make up the final population of vectors contained in the library. These vector sequences are the sequences required for surface expression of randomized peptides. By analogous methodology, more than two vector portions can be combined into a single vector which expresses random peptides.

Surface expression of the random peptide library is performed in an amber suppressor strain. As described above, the amber stop codon between the random codon sequence and the gVIII sequence unlinks the two components in a non-suppressor strain. Isolating the phage produced from the non-suppressor strain and infecting a suppressor strain will link the random codon sequences to the gVIII sequence during expression (FIG. 3E). Culturing the suppressor strain after infection allows the expression of all peptide species within the library as gVIII-peptide fusion proteins. Alternatively, the DNA can be isolated from the non-suppressor strain and then introduced into a suppressor strain to accomplish the same effect.

The level of expression of gVIII-peptide fusion proteins can additionally be controlled at the transcriptional level. The gVIII-peptide fusion proteins are under the inducible control of the Lac Z promoter/operator system. Other inducible promoters can work as well and are known by one skilled in the art. For high levels of surface expression, the suppressor library is cultured in an inducer of the Lac Z promoter such as isopropylthio-β-galactoside (IPTG). Inducible control is beneficial because biological selection against non-functional gVIII-peptide fusion proteins can be minimized by culturing the library under non-expressing conditions. Expression can then be induced only at the time of screening to ensure that the entire population of oligonucleotides within the library are accurately represented on the phage surface. Also this can be used to control the valency of the peptide on the phage surface.

The surface expression library is screened for specific peptides which bind ligand binding proteins by standard affinity isolation procedures. Such methods include, for example, panning, affinity chromatography and solid phase blotting procedures. Panning as described by Parmley and Smith, Gene 73:305–318 (1988), which is incorporated herein by reference, is preferred because high titers of phage can be screened easily, quickly and in small volumes. Furthermore, this procedure can select minor peptide species within the population, which otherwise would have been undetectable, and amplified to substantially homogenous populations. The selected peptide sequences can be determined by sequencing the nucleic acid encoding such peptides after amplification of the phage population.

The invention provides a plurality of procaryotic cells containing a diverse population of oligonucleotides encoding soluble peptides having constrained secondary structure in solution, the oligonucleotides being operationally linked to expression sequences. The invention provides for methods of constructing such populations of cells as well.

Random oligonucleotides synthesized by any of the methods described previously can also be expressed on the surface of filamentous bacteriophage, such as M13, for example, without the joining together of precursor oligonucleotides. A vector such as that shown in FIG. 4, M13IX30, can be used. This vector exhibits all the functional features of the combined vector shown in FIG. 3C for surface expression of gVIII-peptide fusion proteins. The complete nucleotide sequence for M13IX30 (SEQ ID NO: 3) is shown in FIG. 7.

For example, M13IX30 contains a wild type gVIII for phage viability and a pseudo gVIII sequence for peptide fusions. The vector also contains in frame restriction sites for cloning random peptides. The cloning sites in this vector are Xho I, Stu I and Spe I. Oligonucleotides should therefore be synthesized with the appropriate complementary ends for annealing and ligation or insertional mutagenesis. Alternatively, the appropriate termini can be generated by PCR technology. Between the restriction sites and the pseudo gVIII sequence is an in-frame amber stop codon, again, ensuring complete viability of phage in constructing and manipulating the library. Expression and screening is performed as described above for the surface expression library of oligonucleotides generated from precursor portions.

Thus, peptides can be selected that are capable of being bound by a ligand binding protein from a population of random peptides by (a) operationally linking a diverse population of oligonucleotides having a desirable bias of random codon sequences to expression elements; (b) introducing said population of vectors into a compatible host under conditions sufficient for expressing said population of random peptides; and (c) determining the peptides which bind to said binding protein. Also provided is a method for determining the encoding nucleic acid sequence of such selected peptides.

The following examples are intended to illustrate, but not limit the invention.

EXAMPLE I

Isolation and Characterization of Peptide Ligands Generated From Right and Left Half Random Oligonucleotides This example shows the synthesis of random oligonucleotides and the construction and expression of surface expression libraries of the encoded randomized peptides. The random peptides of this example derive from the mixing and joining together of two random oligonucleotides. Also demonstrated is the isolation and characterization of peptide ligands and their corresponding nucleotide sequence for specific binding proteins.

Synthesis of Random Oligonucleotides

The synthesis of two randomized oligonucleotides which correspond to smaller portions of a larger randomized oligonucleotide is shown below. Each of the two smaller portions make up one-half of the larger oligonucleotide. The population of randomized oligonucleotides constituting each half are designated the right and left half. Each population of right and left halves are ten codons in length with twenty random codons at each position. The right half corresponds to the sense sequence of the randomized oligonucleotides and encode the carboxy terminal half of the expressed peptides. The left half corresponds to the anti-sense sequence of the randomized oligonucleotides and encode the amino terminal half of the expressed peptides. The right and left halves of the randomized oligonucleotide populations are cloned into separate vector species and then mixed and joined so that the right and left halves come together in random combination to produce a single expression vector species which contains a population of randomized oligonucleotides twenty codons in length. Electroporation of the vector population into an appropriate host produces filamentous phage which express the random peptides on their surface.

The reaction vessels for oligonucleotide synthesis were obtained from the manufacturer of the automated synthesizer (Millipore, Burlington, Mass.; supplier of MilliGen/Biosearch Cyclone Plus Synthesizer). The vessels were supplied as packages containing empty reaction columns (1 μmole), frits, crimps and plugs (MilliGen/Biosearch catalog #GEN 860458). Derivatized and underivatized control pore glass, phosphoramidite nucleotides, and synthesis reagents were also obtained from MilliGen/Biosearch. Crimper and decrimper tools were obtained from Fisher Scientific Co., Pittsburgh, Pa. (Catalog numbers 06-406-20 and 06-406-25A, respectively).

Ten reaction columns were used for right half synthesis of random oligonucleotides ten codons in length. The oligonucleotides have 5 monomers at their 3' end of the sequence 5'GAGCT3' and 8 monomers at their 5' end of the sequence 5'AATTCCAT3'. The synthesizer was fitted with a column derivatized with a thymine nucleotide (T-column, MilliGen/Biosearch #0615.50) and was programmed to synthesize the sequences shown in Table I for each of ten columns in independent reaction sets. The sequence of the last three monomers (from right to left since synthesis proceeds 3' to 5') encode the indicated amino acids:

TABLE I

| Column | Sequence (5' to 3') | Amino Acids |
| --- | --- | --- |
| column 1R | (T/G)TTGAGCT | Phe and Val |
| column 2R | (T/C)CTGAGCT | Ser and Pro |
| column 3R | (T/C)ATGAGCT | Tyr and His |
| column 4R | (T/C)GTGAGCT | Cys and Arg |
| column 5R | (C/A)TGGAGCT | Leu and Met |
| column 6R | (C/G)AGGAGCT | Gln and Glu |
| column 7R | (A/G)CTGAGCT | Thr and Ala |
| column 8R | (A/G)ATGAGCT | Asn and Asp |
| column 9R | (T/G)GGGAGCT | Trp and Gly |
| column 1R | A(T/A)AGAGCT | Ile and Cys | where the two monomers in parentheses denote a single monomer position within the codon and indicate that an equal mixture of each monomer was added to the reaction for coupling. The monomer coupling reactions for each of the 10 columns were performed as recommended by the manufacturer (amidite version S1.06, #8400-050990, scale 1 μM). After the last coupling reaction, the columns were washed with acetonitrile and lyophilized to dryness.

Following synthesis, the plugs were removed from each column using a decrimper and the reaction products were poured into a single weigh boat. Initially the bead mass increases, due to the weight of the monomers, however, at later rounds of synthesis material is lost. In either case, the material was equalized with underivatized control pore glass and mixed thoroughly to obtain a random distribution of all twenty codon species. The reaction products were then aliquotted into 10 new reaction columns by removing 25 mg of material at a time and placing it into separate reaction columns. Alternatively, the reaction products can be aliquotted by suspending the beads in a liquid that is dense enough for the beads to remain dispersed, preferably a liquid that is equal in density to the beads, and then aliquoting equal volumes of the suspension into separate reaction columns. The lip on the inside of the columns where the frits rest was cleared of material using vacuum suction with a syringe and 25 G needle. New frits were placed onto the lips, the plugs were fitted into the columns and were crimped into place using a crimper.

Synthesis of the second codon position was achieved using the above 10 columns containing the random mixture of reaction products from the first codon synthesis. The monomer coupling reactions for the second codon position are shown in Table II. An A in the first position means that any monomer can be programmed into the synthesizer. At that position, the first monomer position is not coupled by the synthesizer since the software assumes that the monomer is already attached to the column. An A also denotes that the columns from the previous codon synthesis should be placed on the synthesizer for use in the present synthesis round. Reactions were again sequentially repeated for each column as shown in Table II and the reaction products washed and dried as described above.

TABLE II

| Column | Sequence (5' to 3') | Amino Acids |
| --- | --- | --- |
| column 1R | (T/G)TTA | Phe and Val |

TABLE II-continued

| Column | Sequence (5' to 3') | Amino Acids |
|---|---|---|
| column 2R | (T/C)CTA | Ser and Pro |
| column 3R | (T/C)ATA | Tyr and His |
| column 4R | (T/C)GTA | Cys and Arg |
| column 5R | (C/A)TGA | Leu and Met |
| column 6R | (C/G)AGA | Gln and Glu |
| column 7R | (A/G)CTA | Thr and Ala |
| column 8R | (A/G)ATA | Asn and Asp |
| column 9R | (T/G)GGA | Trp and Gly |
| column 10R | A(T/A)AA | Ile and Cys |

Randomization of the second codon position was achieved by removing the reaction products from each of the columns and thoroughly mixing the material. The material was again divided into new reaction columns and prepared for monomer coupling reactions as described above.

Random synthesis of the next seven codons (positions 3 through 9) proceeded identically to the cycle described above for the second codon position and again used the monomer sequences of Table II. Each of the newly repacked columns containing the random mixture of reaction products from synthesis of the previous codon position was used for the synthesis of the subsequent codon position. After synthesis of the codon at position nine and mixing of the reaction products, the material was divided and repacked into 40 different columns and the monomer sequences shown in Table III (SEQ ID NOS: 65–104, respectively) were coupled to each of the 40 columns in independent reactions. The oligonucleotides from each of the 40 columns were mixed once more and cleaved from the control pore glass as recommended by the manufacturer.

TABLE III

| Column | Sequence (5' to 3') |
|---|---|
| column 1R | AATTCTTTTA |
| column 2R | AATTCTGTTA |
| column 3R | AATTCGTTTA |
| column 4R | AATTCGGTTA |
| column 5R | AATTCTTCTA |
| column 6R | AATTCTCCTA |
| column 7R | AATTCGTCTA |
| column 8R | AATTCGCCTA |
| column 9R | AATTCTTATA |
| column 10R | AATTCTCATA |
| column 11R | AATTCGTATA |
| column 12R | AATTCGCATA |
| column 13R | AATTCTTGTA |
| column 14R | AATTCTCGTA |
| column 15R | AATTCGTGTA |
| column 16R | AATTCGCGTA |
| column 17R | AATTCTCTGA |
| column 18R | AATTCTATGA |
| column 19R | AATTCGCTGA |
| column 20R | AATTCGATGA |
| column 21R | AATTCTCAGA |
| column 22R | AATTCTGAGA |
| column 23R | AATTCGCAGA |
| column 24R | AATTCGGAGA |
| column 25R | AATTCTACTA |
| column 26R | AATTCTGCTA |
| column 27R | AATTCGACTA |
| column 28R | AATTCGGCTA |
| column 29R | AATTCTAATA |
| column 30R | AATTCTGATA |
| column 31R | AATTCGAATA |
| column 32R | AATTCGGATA |
| column 33R | AATTCTTGGA |
| column 34R | AATTCTGGGA |

TABLE III-continued

| Column | Sequence (5' to 3') |
|---|---|
| column 35R | AATTCGTGGA |
| column 36R | AATTCGGGGA |
| column 37R | AATTCTATAA |
| column 38R | AATTCTAAAA |
| column 39R | AATTCGATAA |
| column 40R | AATTCGAAAA |

Left half synthesis of random oligonucleotides proceeded similarly to the right half synthesis. This half of the oligonucleotide corresponds to the anti-sense sequence of the encoded randomized peptides. Thus, the complementary sequence of the codons in Tables I through III are synthesized. The left half oligonucleotides also have 5 monomers at their 3' end of the sequence 5'GAGCT3' and 8 monomers at their 5' end of the sequence 5'AATTCCAT3'. The rounds of synthesis, washing, drying, mixing, and dividing are as described above.

For the first codon position, the synthesizer was fitted with a T-column and programmed to synthesize the sequences shown in Table IV for each of ten columns in independent reaction sets. As with right half synthesis, the sequence of the last three monomers (from right to left) encode the indicated amino acids:

TABLE IV

| Column | Sequence (5' to 3') | Amino Acids |
|---|---|---|
| column 1L | AA(A/C)GAGCT | Phe and Val |
| column 2L | AG(A/G)GAGCT | Ser and Pro |
| column 3L | AT(A/G)GAGCT | Tyr and His |
| column 4L | AC(A/G)GAGCT | Cys and Arg |
| column 5L | CA(G/T)GAGCT | Leu and Met |
| column 6L | CT(G/C)GAGCT | Gln and Glu |
| column 7L | AG(T/C)GAGCT | Thr and Ala |
| column 8L | AT(T/C)GAGCT | Asn and Asp |
| column 9L | CC(A/C)GAGCT | Trp and Gly |
| column 10L | T(A/T)TGAGCT | Ile and Cys |

Following washing and drying, the plugs for each column were removed, mixed and aliquotted into ten new reaction columns as described above. Synthesis of the second codon position was achieved using these ten columns containing the random mixture of reaction products from the first codon synthesis. The monomer coupling reactions for the second codon position are shown in Table V.

TABLE V

| Column | Sequence (5' to 3') | Amino Acids |
|---|---|---|
| column 1L | AA(A/C)A | Phe and Val |
| column 2L | AG(A/G)A | Ser and Pro |
| column 3L | AT(A/G)A | Tyr and His |
| column 4L | AC(A/G)A | Cys and Arg |
| column 5L | CA(G/T)A | Leu and Met |
| column 6L | CT(G/C)A | Gln and Glu |
| column 7L | AG(T/C)A | Thr and Ala |
| column 8L | AT(T/C)A | Asn and Asp |
| column 9L | CC(A/C)A | Trp and Gly |
| column 10L | T(A/T)TA | Ile and Cys |

Again, randomization of the second codon position was achieved by removing the reaction products from each of the columns and thoroughly mixing the beads. The beads were repacked into ten new reaction columns.

Random synthesis of the next seven codon positions proceeded identically to the cycle described above for the second codon position and again used the monomer sequences of Table V. After synthesis of the codon at position nine and mixing of the reaction products, the material was divided and repacked into 40 different columns and the monomer sequences shown in Table VI (SEQ ID NOS: 105–144, respectively) were coupled to each of the 40 columns in independent reactions.

TABLE VI

| Column | Sequence (5' to 3') |
|---|---|
| column 1L | AATTCCATAAAAXXA |
| column 2L | AATTCCATAAACXXA |
| column 3L | AATTCCATAACAXXA |
| column 4L | AATTCCATAACCXXA |
| column 5L | AATTCCATAGAAXXA |
| column 6L | AATTCCATAGACXXA |
| column 7L | AATTCCATAGGAXXA |
| column 8L | AATTCCATAGGCXXA |
| column 9L | AATTCCATATAAXXA |
| column 10L | AATTCCATATACXXA |
| column 11L | AATTCCATATGAXXA |
| column 12L | AATTCCATATGCXXA |
| column 13L | AATTCCATACAAXXA |
| column 14L | AATTCCATACACXXA |
| column 15L | AATTCCATACGAXXA |
| column 16L | AATTCCATACGCXXA |
| column 17L | AATTCCATCAGAXXA |
| column 18L | AATTCCATCAGCXXA |
| column 19L | AATTCCATCATAXXA |
| column 20L | AATTCCATCATCXXA |
| column 21L | AATTCCATCTGAXXA |
| column 22L | AATTCCATCTGCXXA |
| column 23L | AATTCCATCTCAXXA |
| column 24L | AATTCCATCTCCXXA |
| column 25L | AATTCCATAGTAXXA |
| column 26L | AATTCCATAGTCXXA |
| column 27L | AATTCCATAGCAXXA |
| column 28L | AATTCCATAGCCXXA |
| column 29L | AATTCCATATTAXXA |
| column 30L | AATTCCATATTCXXA |
| column 31L | AATTCCATATCAXXA |
| column 32L | AATTCCATATCCXXA |
| column 33L | AATTCCATCCAAXXA |
| column 34L | AATTCCATCCACXXA |
| column 35L | AATTCCATCCCAXXA |
| column 36L | AATTCCATCCCCXXA |
| column 37L | AATTCCATTATAXXA |
| column 38L | AATTCCATTATCXXA |
| column 39L | AATTCCATTTAXXA |
| column 40L | AATTCCATTTTCXXA |

The first two monomers denoted by an "X" represent an equal mixture of all four nucleotides at that position. This is necessary to retain a relatively unbiased codon sequence at the junction between right and left half oligonucleotides. The above right and left half random oligonucleotides were cleaved and purified from the supports and used in constructing the surface expression libraries below.

Vector Construction

Two M13-based vectors, M13IX42 (SEQ ID NO: 1) and M13IX22 (SEQ ID NO: 2), were constructed for the cloning and propagation of right and left half populations of random oligonucleotides, respectively. The vectors were specially constructed to facilitate the random joining and subsequent expression of right and left half oligonucleotide populations. Each vector within the population contains one right and one left half oligonucleotide from the population joined together to form a single contiguous oligonucleotide with random codons which is twenty-two codons in length. The resultant population of vectors are used to construct a surface expression library.

M13IX42, or the right-half vector, was constructed to harbor the right half populations of randomized oligonucleotides. M13mp18 (Pharmacia, Piscataway, N.J.) was the starting vector. This vector was genetically modified to contain, in addition to the encoded wild type M13 gene VIII already present in the vector: (1) a pseudo-wild type M13 gene VIII sequence with a stop codon (amber) placed between it and an Eco RI-Sac I cloning site for randomized oligonucleotides; (2) a pair of Fok I sites to be used for joining with M13IX22, the left-half vector; (3) a second amber stop codon placed on the opposite side of the vector than the portion being combined with the left-half vector; and (4) various other mutations to remove redundant restriction sites and the amino terminal portion of Lac Z.

The pseudo-wild type M13 gene VIII was used for surface expression of random peptides. The pseudo-wild type gene encodes the identical amino acid sequence as that of the wild type gene; however, the nucleotide sequence has been altered so that only 63% identity exists between this gene and the encoded wild type gene VIII. Modification of the gene VIII nucleotide sequence used for surface expression reduces the possibility of homologous recombination with the wild type gene VIII contained on the same vector. Additionally, the wild type M13 gene VIII was retained in the vector system to ensure that at least some functional, non-fusion coat protein would be produced. The inclusion of wild type gene VIII therefore reduces the possibility of non-viable phage production from the random peptide fusion genes.

The pseudo-wild type gene VIII was constructed by chemically synthesizing a series of oligonucleotides which encode both strands of the gene. The oligonucleotides are presented in Table VII (SEQ ID NOS: 7 through 16).

TABLE VII

Pseudo-Wild Type Gene VIII Oligonucleotide Series

Sequence (5' to 3')

| Top Strand Oligonucleotides | |
|---|---|
| VIII 03 | GATCC TAG GCT GAA GGC GAT GAC CCT GCT AAG GCT GC |
| VIII 04 | A TTC AAT AGT TTA CAG GCA AGT GCT ACT GAG TAC A |
| VIII 05 | TT GGC TAC GCT TGG GCT ATG GTA GTA GTT ATA GTT |
| VIII 06 | GGT GCT ACC ATA GGG ATT AAA TTA TTC AAA AAG TT |
| VIII 07 | T ACG AGC AAG GCT TCT TA |

| Bottom Strand Oligonucleotides | |
|---|---|
| VIII 08 | AGC TTA AGA AGC CTT GCT CGT AAA CTT TTT GAA TAA TTT |
| VIII 09 | AAT CCC TAT GGT AGC ACC AAC TAT AAC TAC TAC CAT |
| VIII 10 | AGC CCA AGC GTA GCC AAT GTA CTC AGT AGC ACT TG |
| VIII 11 | C CTG TAA ACT ATT GAA TGC AGC CTT AGC AGG GTC |
| VIII 12 | ATC GCC TTC AGC CTA G |

Except for the terminal oligonucleotides VIII 03 (SEQ ID NO: 7) and VIII 08 (SEQ ID NO: 12), the above oligonucleotides (oligonucleotides VIII 04-VIII 07 and 09–12 (SEQ ID NOS: 8 through 11 and 13 through 16)) were mixed at 200 ng each in 10 µl final volume and phosphorylated with T4 polynucleotide Kinase (Pharmacia, Piscataway, N.J.) with 1 mM ATP at 37° C. for 1 hour. The reaction was stopped at 65° C. for 5 minutes. Terminal oligonucleotides were added to the mixture and annealed into double-stranded form by heating to 65° C. for 5 minutes, followed by cooling to room temperature over a period of 30 minutes.

The annealed oligonucleotides were ligated together with 1.0 U of T4 DNA ligase (BRL). The annealed and ligated oligonucleotides yield a double-stranded DNA flanked by a Bam HI site at its 5' end and by a Hind III site at its 3' end. A translational stop codon (amber) immediately follows the Bam HI site. The gene VIII sequence begins with the codon GAA (Glu) two codons 3' to the stop codon. The double-stranded insert was phosphorylated using T4 DNA Kinase (Pharmacia, Piscataway, N.J.) and ATP (10 mM Tris-HCl, pH 7.5, 10 mM MgCl$_2$) and cloned in frame with the Eco RI and Sac I sites within the M13 polylinker. To do so, M13mp18 was digested with Bam HI (New England Biolabs, Beverley, Mass.) and Hind III (New England Biolabs) and combined at a molar ratio of 1:10 with the double-stranded insert. The ligations were performed at 16° C. overnight in 1×ligase buffer (50 mM Tris-HCl, pH 7.8, 10 mM MgCl$_2$, 20 mM DTT, 1 mM ATP, 50 µg/ml BSA) containing 1.0 U of T4 DNA ligase (New England Biolabs). The ligation mixture was transformed into a host and screened for positive clones using standard procedures in the art.

Several mutations were generated within the right-half vector to yield functional M13IX42. The mutations were generated using the method of Kunkel et al., Meth. Enzymol. 154:367–382 (1987), which is incorporated herein by reference, for site-directed mutagenesis. The reagents, strains and protocols were obtained from a Bio Rad Mutagenesis kit (Bio Rad, Richmond, Calif.) and mutagenesis was performed as recommended by the manufacturer.

A Fok I site used for joining the right and left halves was generated 8 nucleotides 5' to the unique Eco RI site using the oligonucleotide 5'-CTCGAATTCGTACATCCT GGTCATAGC-3' (SEQ ID NO: 17). The second Fok I site retained in the vector is naturally encoded at position 3547; however, the sequence within the overhang was changed to encode CTTC. Two Fok I sites were removed from the vector at positions 239 and 7244 of M13mp18 as well as the Hind III site at the end of the pseudo gene VIII sequence using the mutant oligonucleotides 5'-CATTTTTGCAGATGGCTTAGA-3' (SEQ ID NO: 18) and 5'-TAGCATTAACGTCCAATA-3' (SEQ ID NO: 19), respectively. New Hind III and Mlu I sites were also introduced at position 3919 and 3951 of M13IX42. The oligonucleotides used for this mutagenesis had the sequences 5'-ATATATTTTAGTAAGCTTCATCTTCT-3' (SEQ ID NO: 20) and 5'-GACAAAGAACGCGTGAAAA CTTT-3' (SEQ ID NO: 21), respectively. The amino terminal portion of Lac Z was deleted by oligonucleotide-directed mutagenesis using the mutant oligonucleotide 5'-GCGGGCCTCTTCGCTATTGCTTAAGAAGCCTTG CT-3' (SEQ ID NO: 22). This deletion also removed a third M13mp18 derived Fok I site. The distance between the Eco RI and Sac I sites was increased to ensure complete double digestion by inserting a spacer sequence. The spacer sequence was inserted using the oligonucleotide 5'-TTCAGCCTAGGATCCGCCGAGCTCTCCTACCTGC GAATTCGTACATCC-3' (SEQ ID NO: 23). Finally, an amber stop codon was placed at position 4492 using the mutant oligonucleotide 5'-TGGATTATACTTCTA AATAATGGA-3' (SEQ ID NO: 24). The amber stop codon is used as a biological selection to ensure the proper recombination of vector sequences to bring together right and left halves of the randomized oligonucleotides. In constructing the above mutations, all changes made in a M13 coding region were performed such that the amino acid sequence remained unaltered. It should be noted that several mutations within M13mp18 were found which differed from the published sequence. Where known, these sequence differences are recorded herein as found and therefore may not correspond exactly to the published sequence of M13mp18.

The sequence of the resultant vector, M13IX42, is shown in FIG. 5 (SEQ ID NO: 1). FIG. 3A also shows M13IX42 where each of the elements necessary for producing a surface expression library between right and left half randomized oligonucleotides is marked. The sequence between the two Fok I sites shown by the arrow is the portion of M13IX42 which is to be combined with a portion of the left-half vector to produce random oligonucleotides as fusion proteins of gene VIII.

M13IX22, or the left-half vector, was constructed to harbor the left half populations of randomized oligonucleotides. This vector was constructed from M13mp19 (Pharmacia, Piscataway, N.J.) and contains: (1) Two Fok I sites for mixing with M13IX42 to bring together the left and right halves of the randomized oligonucleotides; (2) sequences necessary for expression such as a promoter and signal sequence and translation initiation signals; (3) an Eco RI-Sac I cloning site for the randomized oligonucleotides; and (4) an amber stop codon for biological selection in bringing together right and left half oligonucleotides.

Of the two Fok I sites used for mixing M13IX22 with M13IX42, one is naturally encoded in M13mp18 and M13mp19 (at position 3547). As with M13IX42, the overhang within this naturally occurring Fok I site was changed to CTTC. The other Fok I site was introduced after construction of the translation initiation signals by site-directed mutagenesis using the oligonucleotide 5'-TAACACTCATTCCGGATGGAATTCTGGAGTCTGG GT-3' (SEQ ID NO: 25).

The translation initiation signals were constructed by annealing of overlapping oligonucleotides as described above to produce a double-stranded insert containing a 5' Eco RI site and a 3' Hind III site. The overlapping oligonucleotides are shown in Table VIII (SEQ ID NOS: 26 through 34) and were ligated as a double-stranded insert between the Eco RI and Hind III sites of M13mp18 as described for the pseudo gene VIII insert. The ribosome binding site (AGGAGAC) is located in oligonucleotide 015 (SEQ ID NO: 26) and the translation initiation codon (ATG) is the first three nucleotides of oligonucleotide 016 (SEQ ID NO: 27).

TABLE VIII

Oligonucleotide Series for Construction of Translation Signals in M13IX22

| Oligonucleotide | Sequence (5' to 3') |
|---|---|
| 015 | AATT C GCC AAG GAG ACA GTC AT |
| 016 | AATG AAA TAC CTA TTG CCT ACG GCA GCC GCT GGA TTG TT |
| 017 | ATTA CTC GCT GCC CAA CCA GCC ATG GCC GAG CTC GTG AT |
| 018 | GACC CAG ACT CCA GATATC CAA CAG GAA TGA GTG TTA AT |
| 019 | TCT AGA ACG CGT C |
| 020 | ACGT G ACG CGT TCT AGA AT TAA CACTCA TTC CTG T |
| 021 | TG GAT ATC TGG AGT CTG GGT CAT CAC GAG CTC GGC CAT G |
| 022 | GC TGG TTG GGC AGC GAG TAA TAA CAA TCC AGC GGC TGC C |
| 023 | GT AGG CAA TAG GTA TTT CAT TAT GAC TGT CCT TGG CG |

Oligonucleotide 017 (SEQ ID NO: 28) contained a Sac I restriction site 67 nucleotides downstream from the ATG codon. The naturally occurring Eco RI site was removed and a new site introduced 25 nucleotides downstream from the Sac I. Oligonucleotides 5'-TGACTGTCTCCTTGGCGTG TGAAATTGTTA-3' (SEQ ID NO: 35) and 5'-TAACACTCATTCCGGATGGAATTCTGGAGTCTGG GT-3' (SEQ ID NO: 36) were used to generate each of the mutations, respectively. An amber stop codon was also introduced at position 3263 of M13mp18 using the oligonucleotide 5'-CAATTTTATCCTAAATCTTACCAAC-3' (SEQ ID NO: 37).

In addition to the above mutations, a variety of other modifications were made to remove certain sequences and redundant restriction sites. The LAC Z ribosome binding site was removed when the original Eco RI site in M13mp18 was mutated. Also, the Fok I sites at positions 239, 6361 and 7244 of M13mp18 were likewise removed with mutant oligonucleotides 5'-CATTTTTGCAGATGGCTTAGA-3' (SEQ ID NO: 38), 5'-CGAAAGGGGGGTGTGCTGCAA-3' (SEQ ID NO: 39) and 5'-TAGCATTAACGTCCAATA-3' (SEQ ID NO: 40), respectively. Again, mutations within the coding region did not alter the amino acid sequence.

The resultant vector, M13IX22, is 7320 base pairs in length, the sequence of which is shown in FIG. 6 (SEQ ID NO: 2). The Sac I and Eco RI cloning sites are at positions 6290 and 6314, respectively. FIG. 3A also shows M13IX22 where each of the elements necessary for producing a surface expression library between right and left half randomized oligonucleotides is marked.

Library Construction

Each population of right and left half randomized oligonucleotides from columns 1R through 40R and columns 1L through 40L are cloned separately into M13IX42 and M13IX22, respectively, to create sublibraries of right and left half randomized oligonucleotides. Therefore, a total of eighty sublibraries are generated. Separately maintaining each population of randomized oligonucleotides until the final screening step is performed to ensure maximum efficiency of annealing of right and left half oligonucleotides. The greater efficiency increases the total number of randomized oligonucleotides which can be obtained. Alternatively, one can combine all forty populations of right half oligonucleotides (columns 1R-40R) into one population and of left half oligonucleotides (columns 1L-40L) into a second population to generate just one sublibrary for each.

For the generation of sublibraries, each of the above populations of randomized oligonucleotides are cloned separately into the appropriate vector. The right half oligonucleotides are cloned into M13IX42 to generate sublibraries M13IX42.1R through M13IX42.40R. The left half oligonucleotides are similarly cloned into M13IX22 to generate sublibraries M13IX22.1L through M13IX22.40L. Each vector contains unique Eco RI and Sac I restriction enzyme sites which produce 5' and 3' single-stranded overhangs, respectively, when digested. The single strand overhangs are used for the annealing and ligation of the complementary single-stranded random oligonucleotides.

The randomized oligonucleotide populations are cloned between the Eco RI and Sac I sites by sequential digestion and ligation steps. Each vector is treated with an excess of Eco RI (New England Biolabs) at 37° C. for 2 hours followed by addition of 4–24 units of calf intestinal alkaline phosphatase (Boehringer Mannheim, Indianapolis, Ind.). Reactions are stopped by phenol/chloroform extraction and ethanol precipitation. The pellets are resuspended in an appropriate amount of distilled or deionized water (dH$_2$O). About 10 pmol of vector is mixed with a 5000-fold molar excess of each population of randomized oligonucleotides in 10 μl of 1×ligase buffer (50 mM Tris-HCl, pH 7.8, 10 mM MgCl$_2$, 20 mM DTT, 1 mM ATP, 50 μg/ml BSA) containing 1.0 U of T4 DNA ligase (BRL, Gaithersburg, Md.). The ligation is incubated at 16° C. for 16 hours. Reactions are stopped by heating at 75° C. for 15 minutes and the DNA is digested with an excess of Sac I (New England Biolabs) for 2 hours. Sac I is inactivated by heating at 75° C. for 15 minutes and the volume of the reaction mixture is adjusted to 300 μl with an appropriate amount of 10×ligase buffer and dH$_2$O. One unit of T4 DNA ligase (BRL) is added and the mixture is incubated overnight at 16° C. The DNA is ethanol precipitated and resuspended in TE (10 mM Tris-HCl, pH 8.0, 1 mM EDTA). DNA from each ligation is electroporated into XL1 Blue™ cells (Stratagene, La Jolla, Calif.), as described below, to generate the sublibraries.

E. coli XL1 Blue™ is electroporated as described by Smith et al., Focus 12:38–40 (1990) which is incorporated herein by reference. The cells are prepared by inoculating a fresh colony of XL1s into 5 mls of SOB without magnesium (20 g bacto-tryptone, 5 g bacto-yeast extract, 0.584 g NaCl, 0.186 g KCl, dH$_2$O to 1,000 mls) and grown with vigorous aeration overnight at 37° C. SOB without magnesium (500 ml) is inoculated at 1:1000 with the overnight culture and grown with vigorous aeration at 37° C. until the OD$_{550}$ is 0.8 (about 2 to 3 h). The cells are harvested by centrifugation at 5,000 rpm (2,600×g) in a GS3 rotor (Sorvall, Newtown, Conn.) at 4° C. for 10 minutes, resuspended in 500 ml of ice-cold 10% (v/v) sterile glycerol and centrifuged and resuspended a second time in the same manner. After a third centrifugation, the cells are resuspended in 10% sterile glycerol at a final volume of about 2 ml, such that the OD$_{550}$ of the suspension is 200 to 300. Usually, resuspension is achieved in the 10% glycerol that remains in the bottle after pouring off the supernate. Cells are frozen in 40 μl aliquots in microcentrifuge tubes using a dry ice-ethanol bath and stored frozen at −70° C.

Frozen cells are electroporated by thawing slowly on ice before use and mixing with about 10 pg to 500 ng of vector per 40 μl of cell suspension. A 40 μl aliquot is placed in an 0.1 cm electroporation chamber (Bio-Rad, Richmond, Calif.) and pulsed once at 0° C. using 200Ω parallel resistor, 25 μF, 1.88 kV, which gives a pulse length (τ) of ~4 ms. A 10 μl aliquot of the pulsed cells are diluted into 1 ml SOC (98 mls SOB plus 1 ml of 2M MgCl$_2$ and 1 ml of 2M glucose) in a 12-×75-mm culture tube, and the culture is shaken at 37° C. for 1 hour prior to culturing in selective media, (see below).

Each of the eighty sublibraries are cultured using methods known to one skilled in the art. Such methods can be found in Sanbrook et al., Molecular Cloning: A Laboratory Manuel, Cold Spring Harbor Laboratory, Cold Spring Harbor, 1989, and in Ausubel et al., Current Protocols in Molecular Biology, John Wiley and Sons, New York, 1989, both of which are incorporated herein by reference. Briefly, the above 1 ml sublibrary cultures were grown up by diluting 50-fold into 2XYT media (16 g tryptone, 10 g yeast extract, 5 g NaCl) and culturing at 37° C. for 5–8 hours. The bacteria were pelleted by centrifugation at 10,000×g. The supernatant containing phage was transferred to a sterile tube and stored at 4° C.

Double strand vector DNA containing right and left half randomized oligonucleotide inserts is isolated from the cell pellet of each sublibrary. Briefly, the pellet is washed in TE (10 mM Tris, pH 8.0, 1 mM EDTA) and recollected by centrifugation at 7,000 rpm for 5' in a Sorval centrifuge (Newtown, Conn.). Pellets are resuspended in 6 mls of 10% Sucrose, 50 mM Tris, pH 8.0. 3.0 ml of 10 mg/μl lysozyne is added and incubated on ice for 20 minutes. 12 mls of 0.2M NaOH, 1% SDS is added followed by 10 minutes on ice. The suspensions are then incubated on ice for 20 minutes after addition of 7.5 mls of 3M NaOAc, pH 4.6. The samples are centrifuged at 15,000 rpm for 15 minutes at 4° C., RNased and extracted with phenol/chloroform, followed by ethanol precipitation. The pellets are resuspended, weighed and an equal weight of $CsCl_2$ is dissolved into each tube until a density of 1.60 g/ml is achieved. EtBr is added to 600 µg/ml and the double-stranded DNA is isolated by equilibrium centrifugation in a TV-1665 rotor (Sorval) at 50,000 rpm for 6 hours. These DNAs from each right and left half sublibrary are used to generate forty libraries in which the right and left halves of the randomized oligonucleotides have been randomly joined together.

Each of the forty libraries are produced by joining together one right half and one left half sublibrary. The two sublibraries joined together corresponded to the same column number for right and left half random oligonucleotide synthesis. For example, sublibrary M13IX42.1R is joined with M13IX22.1L to produce the surface expression library M13IX.1RL. In the alternative situation where only two sublibraries are generated from the combined populations of all right half synthesis and all left half synthesis, only one surface expression library would be produced.

For the random joining of each right and left half oligonucleotide populations into a single surface expression vector species, the DNAs isolated from each sublibrary are digested an excess of Fok I (New England Biolabs). The reactions are stopped by phenol/chloroform extraction, followed by ethanol precipitation. Pellets are resuspended in $dH_2O$. Each surface expression library is generated by ligating equal molar amounts (5–10 pmol) of Fok I digested DNA isolated from corresponding right and left half sublibraries in 10 µl of 1×ligase buffer containing 1.0 U of T4 DNA ligase (Bethesda Research Laboratories, Gaithersburg, Md.). The ligations proceed overnight at 16° C. and are electroporated into the sup O strain MK30-3 (Boehringer Mannheim Biochemical, (BMB), Indianapolis, Ind.) as previously described for XL1 cells. Because MK30-3 is sup O, only the vector portions encoding the randomized oligonucleotides which come together will produce viable phage.

Screening of Surface Expression Libraries

Purified phage are prepared from 50 ml liquid cultures of XL1 Blue™ cells (Stratagene) which are infected at a m.o.i. of 10 from the phage stocks stored at 4° C. The cultures are induced with 2 mM IPTG. Supernatants from all cultures are combined and cleared by two centrifugations, and the phage are precipitated by adding 1/7.5 volumes of PEG solution (25% PEG-8000, 2.5M NaCl), followed by incubation at 4° C. overnight. The precipitate is recovered by centrifugation for 90 minutes at 10,000×g. Phage pellets are resuspended in 25 ml of 0.01M Tris-HCl, pH 7.6, 1.0 mM EDTA, and 0.1% Sarkosyl and then shaken slowly at room temperature for 30 minutes. The solutions are adjusted to 0.5M NaCl and to a final concentration of 5% polyethylene glycol. After 2 hours at 4° C., the precipitates containing the phage are recovered by centrifugation for 1 hour at 15,000×g. The precipitates are resuspended in 10 ml of NET buffer (0.1M NaCl, 1.0 mM EDTA, and 0.01M Tris-HCl, pH 7.6), mixed well, and the phage repelleted by centrifugation at 170,000×g for 3 hours. The phage pellets are subsequently resuspended overnight in 2 ml of NET buffer and subjected to cesium chloride centrifugation for 18 hours at 110,000×g (3.86 g of cesium chloride in 10 ml of buffer). Phage bands are collected, diluted 7-fold with NET buffer, recentrifuged at 170,000×g for 3 hours, resuspended, and stored at 4° C. in 0.3 ml of NET buffer containing 0.1 mM sodium azide.

Ligand binding proteins used for panning on streptavidin coated dishes are first biotinylated and then absorbed against UV-inactivated blocking phage (see below). The biotinylating reagents are dissolved in dimethylformamide at a ratio of 2.4 mg solid NHS-SS-Biotin (sulfosuccinimidyl 2-(biotinamido)ethyl-1,3'-dithiopropionate; Pierce, Rockford, Ill.) to 1 ml solvent and used as recommended by the manufacturer. Small-scale reactions are accomplished by mixing 1 µl dissolved reagent with 43 µl of 1 mg/ml ligand binding protein diluted in sterile bicarbonate buffer (0.1M $NaHCO_3$, pH 8.6). After 2 hours at 25° C., residual biotinylating reagent is reacted with 500 µl 1M ethanolamine (pH adjusted to 9 with HCl) for an additional 2 hours. The entire sample is diluted with 1 ml TBS containing 1 mg/ml BSA, concentrated to about 50 µM on a Centricon 30 ultra-filter (Amicon), and washed on the same filter three times with 2 ml TBS and once with 1 ml TBS containing 0.02% $NaN_3$ and $7\times10^{12}$ UV-inactivated blocking phage (see below); the final retentate (60–80 µl) is stored at 4° C. Ligand binding proteins biotinylated with the NHS-SS-Biotin reagent are linked to biotin via a disulfide-containing chain.

UV-irradiated M13 phage were used for blocking binding proteins which fortuitously bound filamentous phage in general. M13mp8 (Messing and Vieira, Gene 19:262–276 (1982), which is incorporated herein by reference) was chosen because it carries two amber stop codons, which ensure that the few phage surviving irradiation will not grow in the sup O strains used to titer the surface expression libraries. A 5 ml sample containing $5\times10^{13}$ M13mp8 phage, purified as described above, was placed in a small petri plate and irradiated with a germicidal lamp at a distance of two feet for 7 minutes (flux 150 µW/cm$^2$). $NaN_3$ was added to 0.02% and phage particles concentrated to $10^{14}$ particles/ml on a Centricon 30-kDa ultrafilter (Amicon).

For panning, polystyrene petri plates (60×15 mm, Falcon; Becton Dickinson, Lincoln Park, N.J.) are incubated with 1 ml of 1 mg/ml of streptavidin (BMB) in 0.1M $NaHCO_3$ pH 8.6–0.02% $NaN_3$ in a small, air-tight plastic box overnight in a cold room. The next day streptavidin is removed and replaced with at least 10 ml blocking solution (29 mg/ml of BSA; 3 µg/ml of streptavidin; 0.1M $NaHCO_3$ pH 8.6–0.02% $NaN_3$) and incubated at least 1 hour at room temperature. The blocking solution is removed and plates are washed rapidly three times with Tris buffered saline containing 0.5% Tween 20 (TBS-0.5% Tween 20).

Selection of phage expressing peptides bound by the ligand binding proteins is performed with 5 µl (2.7 µg ligand binding protein) of blocked biotinylated ligand binding proteins reacted with a 50 µl portion of each library. Each mixture is incubated overnight at 4° C., diluted with 1 ml TBS-0.5% Tween 20, and transferred to a streptavidin-coated petri plate prepared as described above. After rocking 10 minutes at room temperature, unbound phage are removed and plates washed ten times with TBS-0.5% Tween 20 over a period of 30–90 minutes. Bound phage are eluted from plates with 800 µl sterile elution buffer (1 mg/ml BSA, 0.1M HCl, pH adjusted to 2.2 with glycerol) for 15 minutes and eluates neutralized with 48 µl 2M Tris (pH unadjusted). A 20 µl portion of each eluate is titered on MK30-3 concentrated cells with dilutions of input phage.

A second round of panning is performed by treating 750 µl of first eluate from each library with 5 mM DTT for 10 minutes to break disulfide bonds linking biotin groups to residual biotinylated binding proteins. The treated eluate is concentrated on a Centricon 30 ultrafilter (Amicon), washed three times with TBS-0.5% Tween 20, and concentrated to a final volume of about 50 µl. Final retentate is transferred to a tube containing 5.0 μl (2.7 μg ligand binding protein) blocked biotinylated ligand binding proteins and incubated overnight. The solution is diluted with 1 ml TBS-0.5% Tween 20, panned, and eluted as described above on fresh streptavidin-coated petri plates. The entire second eluate (800 μl) is neutralized with 48 μl 2M Tris, and 20 μl is titered simultaneously with the first eluate and dilutions of the input phage.

Individual phage populations are purified through 2 to 3 rounds of plaque purification. Briefly, the second eluate titer plates are lifted with nitrocellulose filters (Schleicher & Schuell, Inc., Keene, N.H.) and processed by washing for 15 minutes in TBS (10 mM Tris-HCl, pH 7.2, 150 mM NaCl), followed by an incubation with shaking for an additional 1 hour at 37° C. with TBS containing 5% nonfat dry milk (TBS-5% NDM) at 0.5 ml/cm². The wash is discarded and fresh TBS-5% NDM is added (0.1 ml/cm²) containing the ligand binding protein between 1 nM to 100 mM, preferably between 1 to 100 μM. All incubations are carried out in heat-sealable pouches (Sears). Incubation with the ligand binding protein proceeds for 12–16 hours at 4° C. with shaking. The filters are removed from the bags and washed 3 times for 30 minutes at room temperature with 150 mls of TBS containing 0.1% NDM and 0.2% NP-40 (Sigma, St. Louis, MO.). The filters are then incubated for 2 hours at room temperature in antiserum against the ligand binding protein at an appropriate dilution in TBS-0.5% NDM, washed in 3 changes of TBS containing 0.1% NDM and 0.2% NP-40 as described above and incubated in TBS containing 0.1% NDM and 0.2% NP-40 with $1 \times 10^6$ cpm of $^{125}$I-labeled Protein A (specific activity=$2.1 \times 10^7$ cpm/μg). After a washing with TBS containing 0.1% NDM and 0.2% NP-40 as described above, the filters are wrapped in Saran Wrap and exposed to Kodak X-Omat x-ray film (Kodak, Rochester, N.Y.) for 1–12 hours at −70° C. using Dupont Cronex Lightning Plus Intensifying Screens (Dupont, Willmington, Del.).

Positive plaques identified are cored with the large end of a pasteur pipet and placed into 1 ml of SM (5.8 g NaCl, 2 g MgSO$_4$.7H$_2$O, 50 ml 1M Tris-HCl, pH 7.5, 5 mls 2% gelatin, to 1000 mls with dH$_2$O) plus 1–3 drops of CHCl$_3$ and incubated at 37° C. 2–3 hours or overnight at 4° C. The phage are diluted 1:500 in SM and 2 μl are added to 300 μl of XL1 cells plus 3 mls of soft agar per 100 mm² plate. The XL1 cells are prepared for plating by growing a colony overnight in 10 ml LB (10 g bacto-tryptone, 5 g bacto-yeast extract, 10 g NaCl, 1000 ml dH$_2$O) containing 100 μl of 20% maltose and 100 μl of 1M MgSO$_4$. The bacteria are pelletted by centrifugation at 2000×g for 10 minutes and the pellet is resuspended gently in 10 mls of 10 mM MgSO$_4$. The suspension is diluted 4-fold by adding 30 mls of 10 mM MgSO$_4$ to give an OD$_{600}$ of approximately 0.5. The second and third round screens are identical to that described above except that the plaques are cored with the small end of a pasteur pipet and placed into 0.5 mls SM plus a drop of CHCl$_3$ and 1–5 μl of the phage following incubation are used for plating without dilution. At the end of the third round of purification, an individual plaque is picked and the templates prepared for sequencing.

Template Preparation and Sequencing

Templates are prepared for sequencing by inoculating a 1 ml culture of 2XYT containing a 1:100 dilution of an overnight culture of XL1 with an individual plaque. The plaques are picked using a sterile toothpick. The culture is incubated at 37° C. for 5–6 hours with shaking and then transferred to a 1.5 ml microfuge tube. 200 μl of PEG solution is added, followed by vortexing and placed on ice for 10 minutes. The phage precipitate is recovered by centrifugation in a microfuge at 12,000×g for 5 minutes. The supernatant is discarded and the pellet is resuspended in 230 μl of TE (10 mM Tris-HCl, pH 7.5, 1 mM EDTA) by gently pipeting with a yellow pipet tip. Phenol (200 μl) is added, followed by a brief vortex and microfuged to separate the phases. The aqueous phase is transferred to a separate tube and extracted with 200 μl of phenol/chloroform (1:1) as described above for the phenol extraction. A 0.1 volume of 3M NaOAc is added, followed by addition of 2.5 volumes of ethanol and precipitated at −20° C. for 20 minutes. The precipitated templates are recovered by centrifugation in a microfuge at 12,000×g for 8 minutes. The pellet is washed in 70% ethanol, dried and resuspended in 25 μl TE. Sequencing was performed using a Sequenase™ sequencing kit following the protocol supplied by the manufacturer (U.S. Biochemical, Cleveland, Ohio).

EXAMPLE II

Isolation and Characterization of Peptide Ligands Generated From Oligonucleotides Having Random Codons at Two Predetermined Positions This example shows the generation of a surface expression library from a population of oligonucleotides having randomized codons. The oligonucleotides are ten codons in length and are cloned into a single vector species for the generation of a M13 gene VIII-based surface expression library. The example also shows the selection of peptides for a ligand binding protein and characterization of their encoded nucleic acid sequences.

Oligonucleotide Synthesis

Oligonucleotides were synthesized as described in Example I. The synthesizer was programmed to synthesize the sequences shown in Table IX (SEQ ID NOS: 145–154, respectively). These sequences correspond to the first random codon position synthesized and 3' flanking sequences of the oligonucleotide which hybridizes to the leader sequence in the vector. The complementary sequences are used for insertional mutagenesis of the synthesized population of oligonucleotides.

TABLE IX

| Column | Sequence (5' to 3') |
| --- | --- |
| column 1 | AA(A/C)GGTTGGTCGGTACCGG |
| column 2 | AG(A/G)GGTTGGTCGGTACCGG |
| column 3 | AT(A/G)GGTTGGTCGGTACCGG |
| column 4 | AC(A/G)GGTTGGTCGGTACCGG |
| column 5 | CA(G/T)GGTTGGTCGGTACCGG |
| column 6 | CT(G/C)GGTTGGTCGGTACCGG |
| column 7 | AG(T/C)GGTTGGTCGGTACCGG |
| column 8 | AT(T/C)GGTTGGTCGGTACCGG |
| column 9 | CC(A/C)GGTTGGTCGGTACCGG |
| column 10 | T(A/T)TGGTTGGTCGGTACCGG |

The next eight random codon positions were synthesized as described for Table V in Example I. Following the ninth position synthesis, the reaction products were once more combined, mixed and redistributed into 10 new reaction columns. Synthesis of the last random codon position and 5' flanking sequences are shown in Table X (SEQ ID NOS: 155–164, respectively).

TABLE X

| Column | Sequence (5' to 3') |
| --- | --- |
| column 1 | AGGATCCGCCGAGCTCAA(A/C)A |
| column 2 | AGGATCCGCCGAGCTCAG(A/G)A |
| column 3 | AGGATCCGCCGAGCTCAT(A/G)A |
| column 4 | AGGATCCGCCGAGCTCAC(A/G)A |
| column 5 | AGGATCCGCCGAGCTCCA(G/T)A |
| column 6 | AGGATCCGCCGAGCTCCT(G/C)A |
| column 7 | AGGATCCGCCGAGCTCAG(T/C)A |
| column 8 | AGGATCCGCCGAGCTCAT(T/C)A |
| column 9 | AGGATCCGCCGAGCTCCC(A/C)A |
| column 10 | AGGATCCGCCGAGCTCT(A/T)TA |

The reaction products were mixed once more and the oligonucleotides cleaved and purified as recommended by the manufacturer. The purified population of oligonucleotides were used to generate a surface expression library as described below.

Vector Construction

Figure 4:
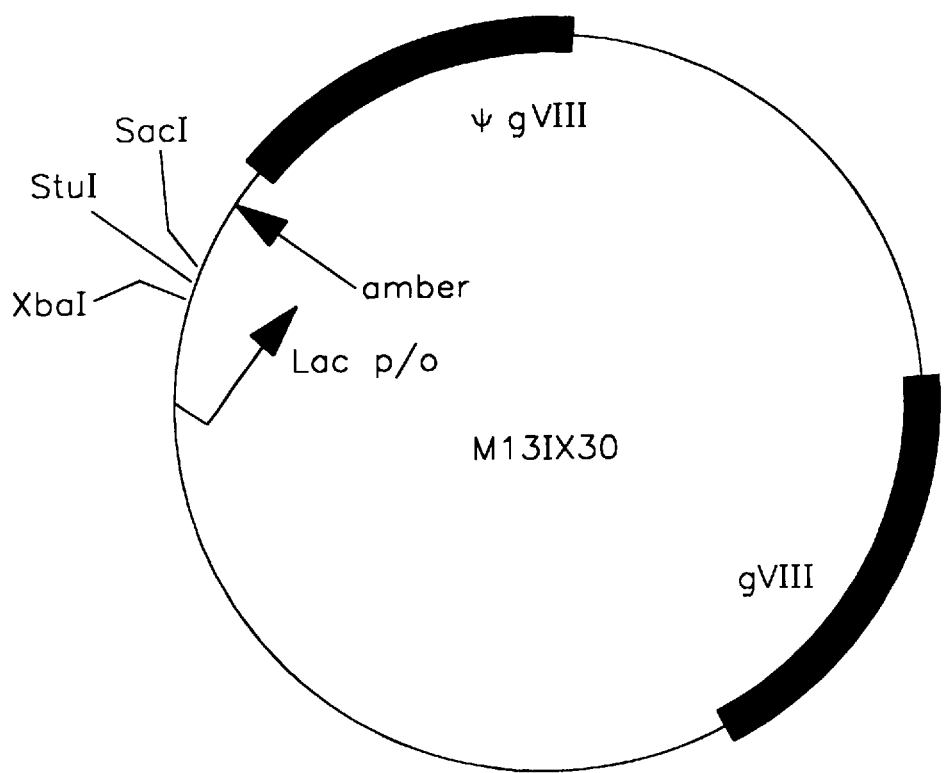
FIG. 4 is a schematic diagram of the vector used for generation of surface expression libraries from random oligonucleotide populations (M13IX30). The symbols are as described for FIG. 3.

The vector used for generating surface expression libraries from a single oligonucleotide population (i.e., without joining together of right and left half oligonucleotides) is described below. The vector is a M13-based expression vector which directs the synthesis of gene VIII-peptide fusion proteins (FIG. 4). This vector exhibits all the functions that the combined right and left half vectors of Example I exhibit.

An M13-based vector was constructed for the cloning and surface expression of populations of random oligonucleotides (FIG. 4, M13IX30), M13mp19 (Pharmacia) was the starting vector. This vector was modified to contain, in addition to the encoded wild type M13 gene VIII: (1) a pseudo-wild type gene, gene VIII sequence with an amber stop codon placed between it and the restriction sites for cloning oligonucleotides; (2) Stu I, Spe I and Xho I restriction sites in frame with the pseudo-wild type gVIII for cloning oligonucleotides; (3) sequences necessary for expression, such as a promoter, signal sequence and translation initiation signals; (4) various other mutations to remove redundant restriction sites and the amino terminal portion of Lac Z.

Construction of M13IX30 was performed in four steps. In the first step, a precursor vector containing the pseudo gene VIII and various other mutations was constructed, M13IX01F. The second step involved the construction of a small cloning site in a separate M13mp18 vector to yield M13IX03. In the third step, expression sequences and cloning sites were constructed in M13IX03 to generate the intermediate vector M13IX04B. The fourth step involved the incorporation of the newly constructed sequences from the intermediate vector into M13IX01F to yield M13IX30. Incorporation of these sequences linked them with the pseudo gene VIII.

Construction of the precursor vector M13IX01F was similar to that of M13IX42 described in Example I except for the following features: (1) M13mp19 was used as the starting vector; (2) the Fok I site 5' to the unique Eco RI site was not incorporated and the overhang at the naturally occurring Fok I site at position 3547 was not changed to 5'-CTTC-3'; (3) the spacer sequence was not incorporated between the Eco RI and Sac I sites; and (4) the amber codon at position 4492 was not incorporated.

In the second step, M13mp18 was mutated to remove the 5' end of Lac Z up to the Lac i binding site and including the Lac Z ribosome binding site and start codon. Additionally, the polylinker was removed and a Mlu I site was introduced in the coding region of Lac Z. A single oligonucleotide was used for these mutagenesis and had the sequence "5'-AAACGACGGCCAGTGCCAAGTGACGCGTGTGAAATTGTTATCC-3'" (SEQ ID NO: 41). Restriction enzyme sites for Hind III and Eco RI were introduced downstream of the MluI site using the oligonucleotide "5'-GGCGAAAGGGAATTCTGCAAGGCGATTAAGCTTGGGTAACGCC-3'" (SEQ ID NO: 42). These modifications of M13mp18 yielded the vector M13IX03.

The expression sequences and cloning sites were introduced into M13IX03 by chemically synthesizing a series of oligonucleotides which encode both strands of the desired sequence. The oligonucleotides are presented in Table XI (SEQ ID NOS: 43 through 50).

TABLE XI

M131X30 Oligonucleotide Series

Sequence (5' to 3')

Top Strand Oligonucleotides

| | |
| --- | --- |
| 084 | GGCGTTACCCAAGCTTTGTACATGGAGAAAATAAAG |
| 027 | TGAAACAAAGCACTATTGCACTGGCACTCTTACCGTTACCGT |
| 028 | TACTGTTTACCCCTGTGACAAAAGCCGCCCAGGTCCAGCTGC |
| 029 | TCGAGTCAGGCCTATTGTGCCCAGGGATTGTACTAGTGGATCCG |

Bottom Oligonucleotides

| | |
| --- | --- |
| 085 | TGGCGAAAGGGAATTCGGATCCACTAGTACAATCCCTG |
| 031 | GGCACAATAGGCCTGACTCGAGCAGCTGGACCAGGGCGGCTT |
| 032 | TTGTCACAGGGGTAAACAGTAACGGTAACGGTAAGTGTGCCA |
| 033 | GTGCAATAGTGCTTTGTTTCACTTTATTTTCTCCATGTACAA |

The above oligonucleotides except for the terminal oligonucleotides 084 (SEQ ID NO: 43) and 085 (SEQ ID NO: 47) of Table XI were mixed, phosphorylated, annealed and ligated to form a double stranded insert as described in Example I. However, instead of cloning directly into the intermediate vector the insert was first amplified by PCR using the terminal oligonucleotides 084 (SEQ ID NO: 43) and 085 (SEQ ID NO: 47) as primers. The terminal oligonucleotide 084 (SEQ ID NO: 43) contains a Hind III site 10 nucleotides internal to its 5' end. Oligonucleotide 085 (SEQ ID NO: 47) has an Eco RI site at its 5' end. Following amplification, the products were restricted with Hind III and Eco RI and ligated as described in Example I into the polylinker of M13mp18 digested with the same two enzymes. The resultant double stranded insert contained a ribosome binding site, a translation initiation codon followed by a leader sequence and three restriction enzyme sites for cloning random oligonucleotides (Xho I, Stu I, Spe I). The vector was named M13IX04.

During cloning of the double-stranded insert, it was found that one of the GCC codons in oligonucleotides 028 and its complement in 031 was deleted. Since this deletion did not affect function, the final construct is missing one of the two GCC codons. Additionally, oligonucleotide 032 contained a GTG codon where a GAG codon was needed. Mutagenesis was performed using the oligonucleotide 5'-TAACGGTAAGAGTGCCAGTGC-3' (SEQ ID NO: 51)

to convert the codon to the desired sequence. The resultant intermediate vector was named M13IX04B.

The fourth step in constructing M13IX30 involved inserting the expression and cloning sequences from M13IX04B upstream of the pseudo-wild type gVIII in M13IX01F. This was accomplished by digesting M13IX04B with Dra III and Ban HI and gel isolating the 700 base pair insert containing the sequences of interest. M13IX01F was likewise digested with Dra III and Bam HI. The insert was combined with the double digested vector at a molar ratio of 3:1 and ligated as described in Example I. It should be noted that all modifications in the vectors described herein were confirmed by sequence analysis. The sequence of the final construct, M13IX30, is shown in FIG. 7 (SEQ ID NO: 3). FIG. 4 also shows M13IX30 where each of the elements necessary for surface expression of randomized oligonucleotides is marked.

Library Construction, Screening and Characterization of Encoded Oligonucleotides Construction of an M13IX30 surface expression library is accomplished identically to that described in Example I for sublibrary construction except the oligonucleotides described above are inserted into M13IX30 by mutagenesis instead of by ligation. The library is constructed and propagated on MK30-3 (BMB) and phage stocks are prepared for infection of XLI cells and screening. The surface expression library is screened and encoding oligonucleotides characterized as described in Example I.

EXAMPLE III

Isolation and Characterization of Peptide Ligands Generated from Right and Left Half Degenerate Oligonucleotides This example shows the construction and expression of a surface expression library of degenerate oligonucleotides. The encoded peptides of this example derive from the mixing and joining together of two separate oligonucleotide populations. Also demonstrated is the isolation and characterization of peptide ligands and their corresponding nucleotide sequence for specific binding proteins.

Synthesis of Oligonucleotide Populations

A population of left half degenerate oligonucleotides and a population of right half degenerate oligonucleotides was synthesized using standard automated procedures as described in Example I.

The degenerate codon sequences for each population of oligonucleotides were generated by sequentially synthesizing the triplet NNG/T where N is an equal mixture of all four nucleotides. The antisense sequence for each population of oligonucleotides was synthesized and each population contained 5' and 3' flanking sequences complementary to the vector sequence. The complementary termini was used to incorporate each population of oligonucleotides into their respective vectors by standard mutagenesis procedures. Such procedures have been described previously in Example I and in the Detailed Description. Synthesis of the antisense sequence of each population was necessary since the single-stranded form of the vectors are obtained only as the sense strand.

The left half oligonucleotide population was synthesized having the following sequence: 5'-AGCTCCCGGATGCCTCAGAAGATG(A/CNN)$_9$GGCTTTTGCCACAGGGG-3' (SEQ ID NO: 52). The right half oligonucleotide population was synthesized having the following sequence: 5'-CAGCCTCGGATCCGCC(A/CNN)$_{10}$ATG(A/C)GAAT-3' (SEQ ID NO: 53). These two oligonucleotide populations when incorporated into their respective vectors and joined together encode a 20 codon oligonucleotide having 19 degenerate positions and an internal predetermined codon sequence.

Vector Construction

Modified forms of the previously described vectors were used for the construction of right and left half sublibraries. The construction of left half sublibraries was performed in an M13-based vector termed M13ED03. This vector is a modified form of the previously described M13IX30 vector and contains all the essential features of both M13IX30 and M13IX22. M13ED03 contains, in addition to a wild type and a pseudo-wild type gene VIII, sequences necessary for expression and two Fok I sites for joining with a right half oligonucleotide sublibrary. Therefore, this vector combines the advantages of both previous vectors in that it can be used for the generation and expression of surface expression libraries from a single oligonucleotide population or it can be joined with a sublibrary to bring together right and left half oligonucleotide populations into a surface expression library.

M13ED03 was constructed in two steps from M13IX30. The first step involved the modification of M13IX30 to remove a redundant sequence and to incorporate a sequence encoding the eight amino-terminal residues of human β-endorphin. The leader sequence was also mutated to increase secretion of the product.

During construction of M13IX04 (an intermediate vector to M13IX30 which is described in Example II), a six nucleotide sequence was duplicated in oligonucleotide 027 (SEQ ID NO: 44) and its complement 032 (SEQ ID NO: 49). This sequence, 5'-TTACCG-3', was deleted by mutagenesis in the construction of M13ED01. The oligonucleotide used for the mutagenesis was 5'-GGTAAACAGTAACGGTAA GAGTGCCAG-3' (SEQ ID NO: 54). The mutation in the leader sequence was generated using the oligonucleotide 5'-GGGCTTTTGCCACAGGGGT-3' (SEQ ID NO: 55). This mutagenesis resulted in the A residue at position 6353 of M13IX30 being changed to a G residue. The resultant vector was designated M13IX32.

To generate M13ED01, the nucleotide sequence encoding β-endorphin (8 amino acid residues of β-endorphin plus 3 extra amino acid residues) was incorporated after the leader sequence by mutagenesis. The oligonucleotide used had the following sequence: 5'-AGGGTCATCGCCTTCAGCTCC GGATCCCTCAGAAGTCATAAACCCCCCATAGGCTTT TGCCAC-3' (SEQ ID NO: 56). This mutagenesis also removed some of the downstream sequences through the Spe I site.

The second step in the construction of M13ED03 involved vector changes which put the β-endorphin sequence in frame with the downstream pseudo-gene VIII sequence and incorporated a Fok I site for joining with a sublibrary of right half oligonucleotides. This vector was designed to incorporate oligonucleotide populations by mutagenesis using sequences complementary to those flanking or overlapping with the encoded β-endorphin sequence. The absence of β-endorphin expression after mutagenesis can therefore be used to measure the mutagenesis frequency. In addition to the above vector changes, M13ED03 was also modified to contain an amber codon at position 3262 for biological selection during joining of right and left half sublibraries.

The mutations were incorporated using standard mutagenesis procedures as described in Example I. The frame shift changes and Fok I site were generated using the oligonucleotide 5'-TCGCCTTCAGCTCCCGGATGCCTCAGAAGCATGA ACCCCCCATAGGC-3' (SEQ ID NO: 57). The amber codon was generated using the oligonucleotide 5'-CAATTTTATCCTAAATCTTACCAAC-3' (SEQ ID NO: 58). The full sequence of the resultant vector, M13ED03, is provided in FIG. 8 (SEQ ID NO: 4).

The construction of right half oligonucleotide sublibraries was performed in a modified form of the M13IX42 vector. The new vector, M13IX421, is identical to M13IX42 except that the amber codon between the Eco RI-SacI cloning site and the pseudo-gene VIII sequence was removed. This change ensures that all expression off of the Lac Z promoter produces a peptide-gene VIII fusion protein. Removal of the amber codon was performed by mutagenesis using the following oligonucleotide: 5'-GCCTTCAGCCTCGGATC CGCC-3' (SEQ ID NO: 59). The full sequence of M13IX421 is shown in FIG. 9 (SEQ ID NO: 5).

Library Construction, Screening and Characterization of Encoded Oligonucleotides A sublibrary was constructed for each of the previously described degenerate populations of oligonucleotides. The left half population of oligonucleotides was incorporated into M13ED03 to generate the sublibrary M13ED03.L and the right half population of oligonucleotides was incorporated into M13IX421 to generate the sublibrary M13IX421.R. Each of the oligonucleotide populations were incorporated into their respective vectors using site-directed mutagenesis as described in Example I. Briefly, the nucleotide sequences flanking the degenerate codon sequences were complementary to the vector at the site of incorporation. The populations of nucleotides were hybridized to single-stranded M13ED03 or M13IX421 vectors and extended with T4 DNA polymerase to generate a double-stranded circular vector. Mutant templates were obtained by uridine selection in vivo, as described by Kunkel et al., supra. Each of the vector populations were electroporated into host cells and propagated as described in Example I.

The random joining of right and left half sublibraries into a single surface expression library was accomplished as described in Example I except that prior to digesting each vector population with Fok I they were first digested with an enzyme that cuts in the unwanted portion of each vector. Briefly, M13ED03.L was digested with Bgl II (cuts at 7094) and M13IX421.R was digested with Hind III (cuts at 3919). Each of the digested populations were further treated with alkaline phosphatase to ensure that the ends would not religate and then digested with an excess of Fok I. Ligations, electroporation and propagation of the resultant library was performed as described in Example I.

The surface expression library was screened for ligand binding proteins using a modified panning procedure. Briefly, 1 ml of the library, about $10^{12}$ phage particles, was added to 1-5 $\mu$g of the ligand binding protein. The ligand binding protein was either an antibody or receptor globulin (Rg) molecule, Aruffo et al., Cell 61:1303–1313 (1990), which is incorporated herein by reference. Phage were incubated shaking with affinity ligand at room temperature for 1 to 3 hours followed by the addition of 200 $\mu$l of 1 $\mu$m latex beads (Biosite, San Diego, Calif.) which were coated with goat-antimouse IgG. This mixture was incubated shaking for an additional 1-2 hours at room temperature. Beads were pelleted for 2 minutes by centrifugation in a microfuge and washed with TBS which can contain 0.1% Tween 20. Three additional washes were performed where the last wash did not contain any Tween 20.

Beads containing bound phage were added to plates at a concentration that produces a suitable density for plaque identification screening and sequencing of positive clones (i.e., plated at confluency for rare clones and 200–500 plaques/plate if pure plaques were needed). Briefly, plaques grown for about 6 hours at 37° C. were overlaid with nitrocellulose filters that had been soaked in 2 mM IPTG and briefly dried. The filters remained on the plaques overnight at room temperature, removed and placed in blocking solution for 1–2 hours. Following blocking, the filters were incubated in 1 $\mu$g/ml ligand binding protein in blocking solution for 1–2 hours at room temperature. Goat antimouse Ig-coupled alkaline phosphatase (Fisher) was added at a 1:1000 dilution and the filters were rapidly washed with 10 mls of TBS or block solution over a glass vacuum filter. Positive plaques were identified after alkaline phosphatase development for detection.

Alternatively, the bound phage were eluted from the beads using 200 $\mu$M 0.1M Glycine-HCl, pH 2.2, for 15 minutes and the beads were removed by centrifugation. The supernatant containing phage (eluate) was removed and phage exhibiting binding to the ligand binding protein were further enriched by one to two more cycles of panning. The eluates were screened by plaque formation, as described above. Typical yields after the first eluate were about $1 \times 10^6$–$5 \times 10^6$ pfu. The second and third eluate generally yielded about $5 \times 10^6$–$2 \times 10^7$ pfu and $5 \times 10^7$–$1 \times 10^{10}$ pfu, respectively.

Screening of the degenerate oligonucleotide library with several different ligand binding proteins resulted in the identification of peptide sequences which bound to each of the ligands. For example, screening with an antibody to β-endorphin resulted in the detection of about 30–40 different clones which essentially all had the core amino acid sequence known to interact with the antibody. The sequences flanking the core sequences were different showing that they were independently derived and not duplicates of the same clone. Screening with an antibody known as 57 gave similar results (i.e., a core consensus sequence was identified but the flanking sequences among the clones were different).

EXAMPLE IV

Generation of a Left Half Random Oligonucleotide Library

This example shows the synthesis and construction of a left half random oligonucleotide library.

A population of random oligonucleotides nine codons in length was synthesized as described in Example I except that different sequences at their 5' and 3' ends were synthesized so that they could be easily inserted into the vector by mutagenesis. Also, the mixing and dividing steps for generating random distributions of reaction products was performed by the alternative method of dispensing equal volumes of bead suspensions. The liquid chosen that was dense enough for the beads to remain dispersed was 100% acetonitrile.

Briefly, each column was prepared for the first coupling reaction by suspending 22 mg (1 $\mu$mole) of 48 $\mu$mol/g capacity beads (Genta, San Diego, Calif.) in 0.5 mls of 100% acetonitrile. These beads are smaller than those described in Example I and are derivatized with a guanine nucleotide. They also do not have a controlled pore size. The bead suspension was then transferred to an empty reaction column. Suspensions were kept relatively dispersed by gently pipetting the suspension during transfer. Columns were plugged and monomer coupling reactions were performed as shown in Table XII (SEQ ID NOS: 165–174, respectively).

TABLE XII

| Column | Sequence (5' to 3') |
| --- | --- |
| column 1L | AA(A/C)GGCTTTTGCCACAGG |
| column 2L | AG(A/G)GGCTTTTGCCACAGG |
| column 3L | AT(A/G)GGCTTTTGCCACAGG |
| column 4L | AC(A/G)GGCTTTTGCCACAGG |
| column 5L | CA(G/T)GGCTTTTGCCACAGG |
| column 6L | CT(G/C)GGCTTTTGCCACAGG |
| column 7L | AG(T/C)GGCTTTTGCCACAGG |
| column 8L | AT(T/C)GGCTTTTGCCACAGG |
| column 9L | CC(A/C)GGCTTTTGCCACAGG |
| column 10L | T(A/T)TGGCTTTTGCCACAGG |

After coupling of the last monomer, the columns were unplugged as described previously and their contents were poured into a 1.5 ml microfuge tube. The columns were rinsed with 100% acetonitrile to recover any remaining beads. The volume used for rinsing was determined so that the final volume of total bead suspension was about 100 µl for each new reaction column that the beads would be aliquoted into. The mixture was vortexed gently to produce a uniformly dispersed suspension and then divided, with constant pipetting of the mixture, into equal volumes. Each mixture of beads was then transferred to an empty reaction column. The empty tubes were washed with a small volume of 100% acetonitrile and also transferred to their respective columns. Random codon positions 2 through 9 were then synthesized as described in Example I where the mixing and dividing steps were performed using a suspension in 100% acetonitrile. The coupling reactions for codon positions 2 through 9 are shown in Table XIII.

TABLE XIII

| Column | Sequence (5' to 3') |
| --- | --- |
| column 1L | AA(A/C)A |
| column 2L | AG(A/G)$\overline{A}$ |
| column 3L | AT(A/G)$\overline{A}$ |
| column 4L | AC(A/G)$\overline{A}$ |
| column 5L | CA(G/T)$\overline{A}$ |
| column 6L | CT(G/C)$\overline{A}$ |
| column 7L | AG(T/C)$\overline{A}$ |
| column 8L | AT(T/C)$\overline{A}$ |
| column 9L | CC(A/C)$\overline{A}$ |
| column 10L | T(A/T)T$\overline{A}$ |

After coupling of the last monomer for the ninth codon position, the reaction products were mixed and a portion was transferred to an empty reaction column. Columns were plugged and the following monomer coupling reactions were performed: 5'-CGGATGCCTCAGAAGCCCCXXA-3' (SEQ ID NO: 60). The resulting population of random oligonucleotides was purified and incorporated by mutagenesis into the left half vector M13ED04.

M13ED04 is a modified version of the M13ED03 vector described in Example III and therefore contains all the features of that vector. The difference between M13ED03 and M13ED04 is that M13ED04 does not contain the five amino acid sequence (Tyr Gly Gly Phe Met) recognized by anti-β-endorphin antibody. This sequence was deleted by mutagenesis using the oligonucleotide 5'-CGGATGCCTCAGAAGGGCTTTTGCCACAGG (SEQ ID NO: 61). The entire nucleotide sequence of this vector is shown in FIG. 10 (SEQ ID NO: 6).

EXAMPLE V

Generation of Soluble, Conformationally-Constrained Random Peptides

This example shows the synthesis and construction of expressible oligonucleotides encoding soluble peptides having a constrained secondary structure in solution.

As noted previously, the binding affinity of a peptide for a ligand-binding protein is a function of the primary and secondary structure of the peptide. The effect of primary structure on affinity may be determined as disclosed in the above examples.

In its broadest form, the disclosed method provides oligonucleotides that are synthesized having a desired bias of predetermined codons such that the oligonucleotides encode peptides having a constrained secondary structure in aqueous solution. In a preferred embodiment, oligonucleotides encoding peptides having a constrained secondary structure are synthesized having a desired bias of predetermined codons such that the predetermined codons are separated by at least one random codon.

Oligonucleotides having more than one tuplet encoding an amino acid capable of forming a covalent bond at a predetermined position and the remaining positions having random tuplets are synthesized using the methods described herein. The synthesis steps are similar to those outlined above using twenty or less reaction vessels except that prior to synthesis of the specified codon position, the dividing of the supports into separate reaction vessels for synthesis of different codons is omitted. For example, if the codon at the second position of the oligonucleotide is to be specified, then following synthesis of random codons at the first position and mixing of the supports, the mixed supports are not divided into new reaction vessels but, instead, are contained in a single reaction vessel to synthesize the specified codon. The specified codon is synthesized sequentially from individual monomers as described above. Thus, the number of reaction vessels is increased or decreased at each step to allow for the synthesis of a specified codon or a desired number of random codons.

Alternatively, a population of random left and right precursor oligonucleotides are synthesized essentially as described in Example I, except that at least one predetermined codon encoding cysteine, lysine, glutamic acid, leucine or tyrosine is incorporated into each oligonucleotide. Combination of right and left oligonucleotides results in a single oligonucleotide containing at least two predetermined codons. Alternatively, a population of random oligonucleotides is synthesized as described in Example II, except that at least two predetermined codons encoding cysteine, lysine, glutamic acid, leucine or tyrosine are incorporated into only one of the two precursor oligonucleotide populations.

Following expression of the oligonucleotides, a peptide having a constrained secondary structure is obtained by allowing the formation of at least one intra-peptide covalent bond. One skilled in the art would know the conditions necessary to allow formation of the particular covalent bond. See, for example, *Proteins, Structures and Molecular Principles*, Creighton, T. E. ed., W. H. Freeman and Co., New York (1984), incorporated herein by reference. Although oligonucleotides can encode peptides capable of forming more than one intra-peptide covalent bond, only one such bond is necessary to form a conformationally-constrained peptide.

The peptide libraries are expressed on the surface of a cell, for example, a bacteriophage. Phage expressing peptide ligands are initially identified by panning, essentially as described in Example I, except that the phage are first incubated in the presence of a ligand-binding protein (in this example, an antibody), then panned in protein A-coated dishes. Individual phage populations are purified through three rounds of plague purification, essentially as described in Example I.

Two phage encoding peptides showing significantly higher ligand binding affinity than the general phage population are isolated, the oligonucleotide sequences are determined and the amino acid sequences deduced. The ligand binds with highest affinity to a twenty-two amino acid peptide having the sequence TQSKCSTDHWLGYIEYFIMCTY (SEQ. ID. NO.: 62). The ligand also binds with high affinity to a peptide having the sequence CDDQYYTDHEQGKCEVALYYTG (SEQ. ID. NO.: 63).

The above-identified peptides are each capable of forming several intra-peptide covalent bonds. For example, a disulfide bond may form between two cysteine residues, a ε(γ-glutamyl)-lysine bond may form between lysine and glutamic acid residues, a lysinonorleucine bond may form between lysine and leucine residues or a dityrosine bond can form between two tyrosine residues (Devlin, Textbook of Biochemistry 3d ed. (1992)). In addition, other peptides can be constructed that contain, for example, four lysine residues, which can form the heterocyclic structure of desmosine.

The nature of the covalent bond in the peptide having the sequence TQSKCSTDHWLGYIEYFIMCTY (SEQ. ID. NO.: 62) is determined by examining the effect of amino acid substitutions on the binding affinity of the ligand, by methods known to those skilled in the art, and described herein. Creighton, supra, pp. 335–396, incorporated herein by reference.

The oligonucleotide encoding this peptide is cloned into a vector that allowed secretion of the expressed peptide. The peptide TQSKCSTDHWLGYIEYFIMCTY (SEQ. ID. NO.: 62) is soluble at a concentration of 4 mg/ml. The same peptide, except containing the substitution of alanine for cysteine is insoluble at this concentration.

EXAMPLE VI

Binding Studies Using Conformationally Constrained Peptides

The association constant ($K_a$), dissociation constant ($K_d$) and affinity constant (K) were determined for the reaction of a monoclonal antibody with the linear or the cyclized form of a peptide, using a BIAcore automated biosensor (Pharmacia Biosensor AB, Uppsala, Sweden), as described by Karlsson et al., J. Immunol. Meth. 145:229–240 (1991). A 24 amino acid peptide, TQSKCSTDHWLGYIEYFIMCTYRR (SEQ. ID. NO.: 64), which is recognized by the J2B9 monoclonal antibody, was used for these experiments. The peptide contains two cysteine residues that form a disulfide bond under oxidizing conditions.

The cyclized form of the peptide was immobilized by its amino terminus to the BIAcore sensor chip and exposed to 0.016, 0.033, 0.066, 0.13 or 2.3 nM solutions of the J2B9 antibody. Changes in refractive index were measured and the formulas described by Karlsson et al., supra, were used to calculate the following rate and affinity constants: $K_a=3.7\times 10^5$ $M^{-1}s^{-1}$; $K_d=4.5\times 10^{-4}$ $sec^{-1}$ and $K=8.4\times 10^8 M$.

After the above-described measurements were obtained, the disulfide bond was reduced by treating the cyclized peptide with 10 mM dithiothreitol, while the peptide was still attached to the BIAcore sensor chip. The dissociation rate of the linear peptide and the J2B9 monoclonal antibody was then determined, as described above.

The dissociation rate of the J2B9 antibody and the linear peptide was calculated to be $1.54\times 10^{-3}$ sec. Thus, the antibody dissociated from the linear peptide three times faster than it dissociated from the cyclized peptide. Reoxidation of the linearized peptide to reform the cyclized peptide resulted in the dissociation rate again decreasing to the $10^{-4}$ range. These results show that a conformationally constrained peptide binds a specific receptor with greater affinity than a peptide with a less stable secondary structure.

Although the invention has been described with reference to the presently preferred embodiment, it should be understood that various modifications can be made without departing from the spirit of the invention. Accordingly, the invention is limited only by the claims.

---

I claim:

1. A composition of matter comprising a plurality of E. coli cells containing a diverse population of expressible oligonucleotides, each of said oligonucleotides encoding a peptide having a desirable bias of predetermined covalent constraints, wherein each of said oligonucleotides is operationally linked to (i) expression elements, (ii) a suppressible stop codon and (iii) a nucleic acid encoding a coat protein contained within an E. coli filamentous bacteriophage vector so as to be expressed as a fusion protein with said coat protein of said E. coli filamentous bacteriophage in a suppressor host or as a secreted peptide in a non-suppressor host, said expressible oligonucleotides having a desirable bias of random codon sequences and wherein said plurality of E. coli cells comprise at least one of said expressible oligonucleotides which encodes a peptide with constrained secondary structure.

2. The composition of claim 1, wherein said oligonucleotides have more than one codon encoding an amino acid capable of forming a covalent bond.

3. The composition of claim 1, wherein said expressible oligonucleotides are expressed as gVIII-fusion proteins on the surface of and E. coli filamentous bacteriophage.

4. The composition of claim 2, wherein said amino acid is an amino acid selected from the group consisting of cysteine, glutamic acid, lysine, leucine and tyrosine.

5. A composition of matter comprising a plurality of E. coli cells containing a diverse population of expressible oligonucleotides, each of said oligonucleotides encoding a peptide having a desirable bias of predetermined covalent constraints, wherein each of said oligonucleotides is operationally linked to expression elements and to a nucleic acid encoding a coat protein contained within an E. coli filamentous bacteriophage vector so as to be expressed as a fusion protein or as a secreted peptide, said expressible oligonucleotides having a desirable bias of random codon sequences produced from random combinations of first and second oligonucleotide precursor populations, each or either of said first and second oligonucleotide precursor populations having a desirable bias of random codon sequences and wherein said plurality of cells comprise at least one of said expressible oligonucleotides which encodes a peptide with constrained secondary structure.

6. The composition of claim 5, wherein said first or second oligonucleotide precursor populations are biased.

7. The composition of claim 5, wherein said first and second oligonucleotide precursor populations are biased.

8. The composition of claim 5, wherein said first or second oligonucleotide precursor populations have more than one codon encoding an amino acid capable of forming a covalent bond.

9. The composition of claim 5, wherein said first and second oligonucleotide precursor populations have at least one codon encoding an amino acid capable of forming a covalent bond.

10. The composition of claim 5, wherein said expressible oligonucleotides are expressed as gVIII-fusion proteins on the surface of an E. coli filamentous bacteriophage.

11. The composition of claim 8 or 9, wherein said amino acid is an amino acid selected from the group consisting of cysteine, glutamic acid, lysine, leucine and tyrosine.

12. A kit for the preparation of vectors for the expression of a peptide:coat protein fusion protein or a secreted peptide from a diverse population of random peptides having a desirable bias of predetermined covalent constraints, wherein at least one of said random peptides in said diverse population is a peptide with constrained secondary structure, said peptides being generated from combined first and second oligonucleotide precursor populations which when combined have a desirable bias of random codon sequences, comprising: two E. coli filamentous bacteriophage vectors, a first filamentous bacteriophage vector having a cloning site for said first precursor oligonucleotides and a pair of restriction sites for operationally combining first precursor oligonucleotides with second precursor oligonucleotides; and a second filamentous bacteriophage vector having a cloning site for said second precursor oligonucleotides and a pair of restriction sites complementary to those on said first vector, one or both vectors containing expression elements capable of being operationally linked to said combined first and second precursor oligonucleotides and to a nucleic acid encoding a coat protein.

13. The kit of claim 12, wherein said filamentous bacteriophage vectors are derived from M13, f1 or fd.

14. The kit of claim 12, wherein said first or second oligonucleotide precursor populations are biased toward a pre-determined sequence.

15. The kit of claim 12, wherein said first and second oligonucleotide precursor populations are biased toward a predetermined sequence.

16. The kit of claim 12, wherein said first or second oligonucleotide precursor populations have more than one codon encoding an amino acid capable of forming a covalent bond.

17. The kit of claim 12, wherein said first and second oligonucleotide precursor populations have at least one codon encoding an amino acid capable of forming a covalent bond.

18. The kit of claim 16 or 17, wherein said amino acid is an amino acid selected from the group consisting of cysteine, glutamic acid, lysine, leucine and tyrosine.

19. A cloning system for expressing as a peptide:coat protein fusion protein or as a secreted peptide a diverse population of oligonucleotides encoding random peptides having a desirable bias of predetermined covalent constraints, wherein at least one of said oligonucleotides within said diverse population encodes a peptide with constrained secondary structure, said oligonucleotides being generated from a desirable bias of random codon sequences, said cloning system comprising an *E. coli* filamentous bacteriophage vector having a pair of restriction sites so as to allow the operational combination of said oligonucleotides into a contiguous oligonucleotide encoding said peptide having constrained secondary structure, said contiguous oligonucleotide being operationally linked to expression elements and to a nucleic acid encoding a coat protein contained within an *E. coli* filamentous bacteriophage so as to be expressed as a peptide:coat protein fusion protein or as a secreted peptide.

20. The cloning system of claim 19, wherein said oligonucleotides have more than one codon encoding an amino acid capable of forming a covalent bond.

21. A cloning system for expressing as a peptide:coat protein fusion protein or as a secreted peptide a diverse population of oligonucleotides encoding random peptides having a desirable bias of predetermined covalent constraints wherein at least one of said oligonucleotides within said diverse population encodes a peptide with constrained secondary structure, said oligonucleotides being generated from diverse populations of combined first and second oligonucleotide precursor populations each or either having a desirable bias of random codon sequences said cloning system, comprising: a set of first filamentous bacteriophage vectors having a diverse population of first precursor oligonucleotides having a desirable bias of random codon sequences and a second set of filamentous bacteriophage vectors having a diverse population of second precursor oligonucleotides having a desirable bias of random codon sequences, said first and second vectors each having a pair of restriction sites so as to allow the operational combination of said oligonucleotides into a contiguous oligonucleotide encoding said peptide having constrained secondary structure and to a nucleic acid encoding a bacteriophage coat protein.

22. The composition of claim 21, wherein said first or second oligonucleotide precursor populations are biased.

23. The composition of claim 21, wherein said first and second oligonucleotide precursor populations are biased.

24. The cloning system of claim 21, wherein said first or second oligonucleotide precursor populations have more than one codon encoding an amino acid capable of forming a covalent bond.

25. The cloning system of claim 21, wherein said first and second oligonucleotide precursor populations have at least one codon encoding an amino acid capable of forming a covalent bond.

26. The cloning system of claim 21, wherein said first and second vectors are combined through a pair of restriction sites.

27. The composition of claim 21, wherein said expressible oligonucleotides are expressed as gVIII-fusion proteins on the surface of an *E. coli* filamentous bacteriophage.

28. An expressible oligonucleotide produced by the cloning system of claim 21.

29. A host cell containing the cloning system of claim 21.

30. The cloning system of claim 24 or 25, wherein said amino acid is an amino acid selected from the group consisting of cysteine, glutamic acid, lysine, leucine and tyrosine.

31. A population of vectors comprising a diverse population of oligonucleotides operationally linked to (i) expression elements, (ii) a suppressible stop codon and (iii) a nucleic acid encoding a coat protein so as to be expressed as a fusion protein with said coat protein of an *E. coli* filamentous bacteriophage in a suppressor host or as a secreted peptide in a non-suppressor host, said oligonucleotides having a desirable bias of random codon sequences, and more than one codon encoding an amino acid capable of forming a covalent bond.

32. A population of vectors of claim 31, wherein said amino acid is an amino acid selected from the group consisting of cysteine, glutamic acid, lysine, leucine and tyrosine.

33. A host cell containing the population of vectors of claim 32.

34. A method of isolating a soluble peptide having a desirable bias of predetermined covalent constraints, comprising growing said host cell of claim 29 or 33 under suitable conditions favoring expression of said peptide, and affinity isolating said peptide so produced.

35. A method of constructing a diverse population of vectors containing combined first and second oligonucleotide precursor populations, wherein each or either precursor oligonucleotides has a desirable bias of random codon sequences, and which express said combined oligonucleotides which encode random peptides having a desirable bias of predetermined covalent constraints, wherein at least one of said peptides exhibits constrained secondary structure, comprising the steps of:

(a) operationally linking sequences from a diverse population of first precursor oligonucleotides having a desirable bias of random codon sequences to a first *E. coli* filamentous bacteriophage vector;

(b) operationally linking sequences from a diverse population of second precursor oligonucleotides having a desirable bias of random codon sequences to a second *E. coli* filamentous bacteriophage vectors, wherein said first or second, or first and second precursor oligonucleotides have at least one codon capable of forming a covalent bond; and (c) combining the vector products of steps (a) and (b) under conditions where said populations of first and second precursor oligonucleotides are joined together into a population of combined vectors which express said random peptides as a fusion with a coat protein or as a secreted peptide.

36. The method of claim 35, wherein said amino acid is an amino acid selected from the group consisting of cysteine, glutamic acid, lysine, leucine and tyrosine.

37. The method of claim 35, wherein steps (a) through (d) are repeated two or more times.

* * * * *